(12) United States Patent
Burns et al.

(10) Patent No.: US 10,399,996 B2
(45) Date of Patent: Sep. 3, 2019

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Bin Liu, Plainsboro, NJ (US); Jiangchao Yao, Princeton, NJ (US); Denis Daigle, Street, MD (US); Steven A. Boyd, Chester Springs, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 15/261,359

(22) Filed: Sep. 9, 2016

(65) Prior Publication Data

US 2017/0073360 A1  Mar. 16, 2017

Related U.S. Application Data

(60) Provisional application No. 62/217,380, filed on Sep. 11, 2015, provisional application No. 62/312,705, filed on Mar. 24, 2016.

(51) Int. Cl.
| | |
|---|---|
| *C07F 5/02* | (2006.01) |
| *A61K 31/69* | (2006.01) |
| *A61K 45/06* | (2006.01) |
| *A61K 31/407* | (2006.01) |
| *A61K 31/546* | (2006.01) |

(52) U.S. Cl.
CPC ............ *C07F 5/025* (2013.01); *A61K 31/407* (2013.01); *A61K 31/546* (2013.01); *A61K 31/69* (2013.01); *A61K 45/06* (2013.01)

(58) Field of Classification Search
CPC .................................................. C07F 5/025
See application file for complete search history.

(56) References Cited

U.S. PATENT DOCUMENTS

| | | | |
|---|---|---|---|
| 4,427,690 | A | 1/1984 | Cole et al. |
| 7,271,186 | B1 | 9/2007 | Shoichet et al. |
| 8,680,136 | B2 | 3/2014 | Hirst |
| 8,912,169 | B2 | 12/2014 | Burns et al. |
| 9,040,504 | B2 | 5/2015 | Burns et al. |
| 9,101,638 | B2 | 8/2015 | Reddy |
| 9,376,454 | B2 | 6/2016 | Burns et al. |
| 9,403,850 | B2 | 8/2016 | Burns et al. |
| 9,422,314 | B2 | 8/2016 | Burns et al. |
| 9,963,467 | B2 | 5/2018 | Reddy et al. |
| 2010/0056478 | A1 | 3/2010 | Desarbre et al. |
| 2010/0120715 | A1 | 5/2010 | Burns et al. |
| 2010/0286092 | A1 | 11/2010 | Burns et al. |
| 2010/0292185 | A1 | 11/2010 | Burns et al. |
| 2010/0317621 | A1 | 12/2010 | Burns et al. |
| 2011/0294777 | A1 | 12/2011 | Blizzard et al. |
| 2014/0194385 | A1 | 7/2014 | Reddy et al. |
| 2015/0094472 | A1 | 4/2015 | Hecker et al. |
| 2015/0361106 | A1 | 12/2015 | Burns et al. |
| 2015/0361107 | A1 | 12/2015 | Trout |
| 2015/0361108 | A1 | 12/2015 | Burns et al. |
| 2016/0024121 | A1 | 1/2016 | Burns et al. |
| 2016/0264598 | A1 | 9/2016 | Burns et al. |
| 2018/0079760 | A1 | 3/2018 | Burns et al. |
| 2018/0194783 | A1 | 7/2018 | Burns et al. |
| 2018/0273552 | A1 | 9/2018 | Burns et al. |
| 2018/0291039 | A1 | 10/2018 | Burns et al. |

FOREIGN PATENT DOCUMENTS

| | | | | |
|---|---|---|---|---|
| CN | 1965838 | A | 5/2007 | |
| CN | 105801610 | A | 7/2016 | |
| RU | 2012107163 | A | 9/2013 | |
| WO | WO-2005004799 | A2 | 1/2005 | |
| WO | WO-2009064413 | A1 | 5/2009 | |
| WO | WO-2009064414 | A1 | 5/2009 | |
| WO | WO-2010056827 | A1 | 5/2010 | |
| WO | WO-2010130708 | A1 | 11/2010 | |
| WO | WO-2012021455 | A1 | 2/2012 | |
| WO | WO-2013014497 | A1 | 1/2013 | |
| WO | WO-2013053372 | A1 | 4/2013 | |
| WO | WO-2013092979 | A1 | 6/2013 | |
| WO | WO-2013122888 | A2 | 8/2013 | |
| WO | WO-2014086664 | A1 * | 6/2014 | ............. C07F 5/025 |
| WO | WO-2014089365 | A1 | 6/2014 | |
| WO | WO-2014107535 | A1 * | 7/2014 | ........... A61K 31/407 |
| WO | WO-2014107536 | A1 | 7/2014 | |
| WO | WO-2014110442 | A1 | 7/2014 | |
| WO | WO-2014151958 | A1 | 9/2014 | |
| WO | WO-2015157618 | A1 | 10/2015 | |
| WO | WO-2015171398 | A1 | 11/2015 | |
| WO | WO-2015171430 | A1 | 11/2015 | |

(Continued)

OTHER PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Watkins, R.R., et al. "Novel β-lactamase inhibitors: a therapeutic hope against the scourge of multi-drug resistance." © Dec. 24, 2013. Accessed Jul. 7, 2018. Available from: < https://www.frontiersin.org/articles/10.3389/fnnicb.2013.00392/full >. (Year: 2013).*
Teitelman, A. "Can Anything Prevent Recurrent Bacterial Vaginosis?" Medscape. © Jan. 4, 2010. Accessed Jul. 7, 2018. Available from: < https://www.medscape.com/viewarticle/714690 >. (Year: 2010).*
Evans, C.T., et al. "Prevention of Clostridium difficile Infection With Probiotics." © Apr. 28, 2015. Accessed Jul. 7, 2018. Available from: < https://academic.oup.com/cid/article/60/suppl_2/S122/379459 >. (Year: 2015).*

(Continued)

*Primary Examiner* — Andrew D Kosar
*Assistant Examiner* — John S Kenyon
(74) *Attorney, Agent, or Firm* — Wilson Sonsini Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

17 Claims, No Drawings

(56) References Cited

FOREIGN PATENT DOCUMENTS

| WO | WO-2015179308 A1 | 11/2015 |
|---|---|---|
| WO | WO-2015191907 A1 | 12/2015 |
| WO | WO-2016003929 A1 | 1/2016 |
| WO | WO-2017100537 A1 | 6/2017 |
| WO | WO-2018027062 A1 | 2/2018 |
| WO | WO-2018165048 A1 | 9/2018 |
| WO | WO-2018218154 A1 | 11/2018 |
| WO | WO-2018218190 A1 | 11/2018 |

OTHER PUBLICATIONS

Bacterial Infection 101. Available at http://www.onhealth.com/content/l/bacterial_infections (34 pgs) (2017).
Co-pending U.S. Appl. No. 15/435,097, filed Feb. 16, 2017.
U.S. Appl. No. 15/194,433 Office Action dated Feb. 9, 2017.
Co-pending U.S. Appl. No. 15/333,049, filed Oct. 24, 2016.
Co-pending U.S. Appl. No. 15/366,769, filed Dec. 1, 2016.
Patani et al. Bioisosterism: A Rational Approach in Drug Design. Chemical Reviews 96:3147-3176 (1996).
PCT/US2016/051076 International Search Report and Written Opinion dated Jan. 17, 2017.
Bodner Research Web. The Chemistry of the Halogens. Available from http://web.archive.org/web/20090414155348/http://chemechem/topicreview/bp/ch10/group3.php (2009).
Bundgaard. Design of Prodrugs. Elsevier. Chapter 1. pp. 1-3 (1985).
Burns et al. CAPLUS AN 2014-1130723 (2014).
Co-pending U.S. Appl. No. 15/194,433, filed Jun. 27, 2016.
Co-pending U.S. Appl. No. 15/212,959, filed Jul. 18, 2016.
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem 47(10):2393-2404 (2004).
Han. Targeted Prodrug Design to Optimize Drug Delivery. AAPS Pharmsci. 2(1)Article 6:1-11 (2000).
Isomer. https://en.wikipedia.org/wiki/Isomer (2015).
Lima et al. Bioisosterism: A Useful Strategy for Molecular Modification and Drug Design. Current Medicinal Chemistry 12:23-49 (2005).

Morandi et al. Structure-based optimization of cephalothin-analogue boronic acids as β- lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-β-lactamase. Biochemistry 39(18):5312-5321 (2000).
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Testa. Prodrug research: futile or fertile? Biochem. Pharm. 68:2097-2106 (2004).
U.S. Appl. No. 14/152,916 Office Action dated Aug. 29, 2014.
U.S. Appl. No. 14/693,318 Office Action dated Sep. 1, 2015.
U.S. Appl. No. 14/759,853 Office Action dated Dec. 11, 2015.
Weston et al. Structure-based enhancement of boronic acid-based inhibitors of AmpC β-lactamase. J. Med. Chem. 41(23):4577-4586 (1998).
Definition of Quinoxaline from PubChem. http://pubchem.ncbi.nlm.nih.gov/compund/quinoxaline#section=information-sources. (24 pgs) (2005).
Definition of Quinoxaline from Wikipedia. http://en.wikipedia.org/wiki/Quinoxaline (3 pgs.) (2016).
Ishikawa et al. Synthesis and antimicrobial activity of 2,3-bis(bromomethyl)quinoxaline derivatives. Bioorg Chem 41-42:1-5 (2012).
Isomer. https://en.wikipedia.org/wiki/Isomer (5 pgs) (2017).
U.S. Appl. No. 90/013,866 Ex Parte Reexam Office Action dated Apr. 20, 2017.
Co-pending U.S. Appl. No. 15/675,253, filed Aug. 11, 2017.
Co-pending U.S. Appl. No. 15/675,262, filed Aug. 11, 2017.
Co-pending U.S. Appl. No. 15/886,490, filed Feb. 1, 2018.
U.S. Appl. No. 15/675,262 Office Action dated Jan. 24, 2018.
U.S. Appl. No. 15/675,262 Office Action dated Sep. 18, 2017.
Co-pending U.S. Appl. No. 16/103,445, filed Aug. 14, 2018.
Co-pending U.S. Appl. No. 16/148,941, filed Oct. 1, 2018.
Winkler et al. Design and exploration of novel boronic acid inhibitors reveals important interactions with a clavulanic acid-resistant sulfhydryl-variable (SHV) β-lactamase. J Med Chem 56:1084-1097 (2013) (Publication Date (Web): Dec. 19, 2012).

* cited by examiner

BETA-LACTAMASE INHIBITORS

CROSS-REFERENCE TO RELATED APPLICATIONS

This application claims the benefit of U.S. Application Ser. No. 62/217,380, filed Sep. 11, 2015, and U.S. Application Ser. No. 62/312,705, filed Mar. 24, 2016, each of which are hereby incorporated by reference in their entireties.

This invention was made with the support of the United States government under Contract numbers R43AI096679 and R44AI096679 by the National Institutes of Health (NIH) and Contract numbers R43AI096613 and R44AI096613 by the National Institutes of Health (NIH). The government has certain rights in the invention.

FIELD OF INVENTION

The present invention relates to boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) are widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections.

In one aspect, provided herein are compounds of Formula (I) or Formula (II), or pharmaceutically acceptable salts, solvates, stereoisomers, tautomers, prodrugs, metabolites, N-oxides, or isomers thereof:

Formula (I)

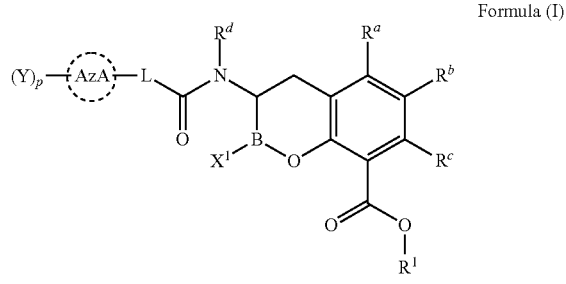

Formula (II)

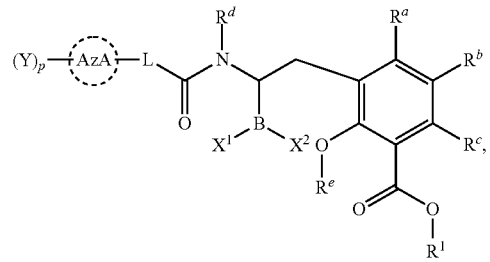

wherein:

L is —(CR$^2$R$^3$)$_n$—;

n is 0, 1, 2, 3, 4, 5, or 6;

p is 0, 1, 2 or 3;

X$^1$ and X$^2$ are independently selected from —OH, —OR$^X$, and F;

AzA is a five-membered heteroaromatic ring system bearing at least one heteroatom from the group consisting of N, O, and S;

each Y is selected from the group consisting of fluoro, chloro, bromo, iodo, boronic acid, optionally substituted boronic ester, optionally substituted C$_1$-C$_6$ alkyl, optionally substituted C$_2$-C$_6$ alkenyl, optionally substituted C$_2$-C$_6$ alkynyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_v$S(O)$_{0,1,2}$NR$^6$R$^7$, —OC(O)R$^{11}$, —OC(O)(CR$^9$R$^{10}$)$_v$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NO$_2$, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)OR$^{11}$, —NR$^6$C(O)R$^{11}$, —NR$^6$C(O)OR$^{11}$, —N(R$^6$)C(O)(CR$^9$R$^{10}$)NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_w$NR$^6$R$^7$, —(CR$^9$R$^{10}$)$_v$N(R$^6$)C(O)(CR$^9$R$^{10}$)$_w$ONR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$S(O)$_{0,1,2}$(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heteroaryl(CR$^9$R$^{10}$)$_v$NR$^6$R$^7$, —(CR$^9$R$^{10}$)$_v$Heterocyclyl-NR$^6$R$^7$, —(CR$^9$R$^{10}$)$_v$Heterocyclyl(CR$^9$R$^{10}$)$_v$NR$^6$R$^7$, —(CR$^9$R$^{10}$)$_v$Heterocyclyl-(NR$^6$R$^7$)$_2$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$O(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion; and
v is 1-4;
w is 2-4;
or two Ys taken together with the atoms to which they are attached form an optionally substituted carbocycle, an optionally substituted heterocycle, or an optionally substituted heteroaryl;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

each R$^x$ are independently optionally substituted C$_1$-C$_6$ alkyl, optionally substituted C$_3$-C$_6$ cycloalkyl, optionally substituted alkoxyalkyl, optionally substituted hydroxyalkyl, optionally substituted aminoalkyl, optionally substituted heterocycle, optionally substituted aryl, optionally substituted heteroaryl, optionally substituted cycloalkylalkyl, optionally substituted heterocyclealkyl, optionally substituted aralkyl, optionally substituted heteroaralkyl, (poly ethylene glycol) ethyl, or an optionally substituted saccharide;

or two R$^x$ taken together with the atom to which they are attached form an optionally substituted heterocycle;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, —NR$^6$R$^7$, —(CR$^9$R$^{10}$)$_v$C(O)NR$^6$R$^7$, —(CR$^9$R$^{10}$)$_v$C(O)OH, —(CR$^9$R$^{10}$)$_v$OH, —(CR$^9$R$^{10}$)$_v$NR$^6$R$^7$, and —(CR$^9$R$^{10}$)$_v$N(R$^6$)C(=NR$^8$)NR$^6$R$^7$;

or R$^2$ and R$^3$ on the same carbon are taken together to form an oxo or optionally substituted oxime;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —CN, —OH, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_nNR^6R^7$, —$(CR^aR^b)_vC(O)NR^6R^7$, —$C(O)NR^6R^7$, —$C(O)OR^{11}$, —C(O)OH, —$NR^6SO_2R^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II), n is 1, 2, 3, 4, 5, or 6; and AzA is a five-membered heteroaromatic ring system bearing at least three heteroatoms from the group consisting of N, O, and S.

In some embodiments of a compound of Formula (I) or Formula (II), AzA is a five-membered heteroaromatic ring system bearing at least three N heteroatoms.

In some embodiments of a compound of Formula (I) or Formula (II), $R^a$, $R^b$, and $R^c$ are independently selected from the group consisting of hydrogen, fluoro, chloro, optionally substituted $C_1$-$C_6$ alkyl, —OH, —$OR^{11}$, —$NR^6R^7$, and —$SR^{11}$.

In some embodiments of a compound of Formula (I) or Formula (II), $R^a$, $R^b$, and $R^c$ are independently selected from the group consisting of hydrogen, fluoro, chloro, —OH, and —$OCH_3$.

In some embodiments of a compound of Formula (I) or Formula (II), $R^a$, $R^b$, $R^c$, and $R^e$ are hydrogen.

In some embodiments of a compound of Formula (I) or Formula (II), $X^1$ is —OH and $X^2$ is —OH when present.

In some embodiments of a compound of Formula (I) or Formula (II), $R^d$ is hydrogen.

In some embodiments of a compound of Formula (I) or Formula (II), n is 1, 2, or 3.

In some embodiments of a compound of Formula (I) or Formula (II), n is 1.

In some embodiments of a compound of Formula (I) or Formula (II), n is 2.

In some embodiments of a compound of Formula (I) or Formula (II), each $R^2$ and $R^3$ are independently selected from the group consisting of hydrogen, fluoro, chloro, bromo, optionally substituted $C_1$-$C_6$ alkyl, and —$CF_3$.

In some embodiments of a compound of Formula (I) or Formula (II), each $R^2$ and $R^3$ are hydrogen.

In some embodiments of a compound of Formula (I) or Formula (II), when n is at least 2, two $R^2$ on adjacent carbons are taken together to form a double bond; or two $R^2$ and two $R^3$ on adjacent carbons are taken together to form a triple bond.

In some embodiments of a compound of Formula (I) or Formula (II), $R^1$ is hydrogen, $R^{31}$, —$R^{30}OC(O)R^{31}$, or —$R^{30}OC(O)OR^{31}$; each $R^{30}$ is independently —$CH_2$—, —$CH(CH_3)$—, or —$C(CH_3)_2$—; and each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl.

In some embodiments of a compound of Formula (I) or Formula (II), $R^1$ is hydrogen.

In some embodiments of a compound of Formula (I) or Formula (II), $R^1$ is $R^{31}$; and $R^{31}$ is optionally substituted $C_1$-$C_{12}$ alkyl.

In some embodiments of a compound of Formula (I) or Formula (II), $R^1$ is $R^{31}$; and $R^{31}$ is methyl, ethyl, propyl, butyl, or isopropyl.

In some embodiments of a compound of Formula (I) or Formula (II), $R^1$ is —$R^{30}OC(O)R^{31}$ or —$R^{30}OC(O)OR^{31}$; each $R^{30}$ is —$CH_2$—, —$CH(CH_3)$—, or —$C(CH_3)_2$—; and each $R^{31}$ is $C_1$-$C_{12}$ alkyl, $C_3$-$C_8$ cycloalkyl, $C_3$-$C_8$ heterocyclyl, or aryl.

In some embodiments of a compound of Formula (I) or Formula (II), $R^1$ is —$R^{30}OC(O)R^{31}$ or —$R^{30}OC(O)OR^{31}$; each $R^{30}$ is —$CH_2$—, or —$CH(CH_3)$—; and each $R^{31}$ is $C_1$-$C_{12}$ alkyl.

In some embodiments of a compound of Formula (I) or Formula (II), AzA is triazolyl, thiadiazolyl, oxadiazolyl, or tetrazolyl.

In some embodiments of a compound of Formula (I) or Formula (II), $(Y)_p$-AzA is selected from:

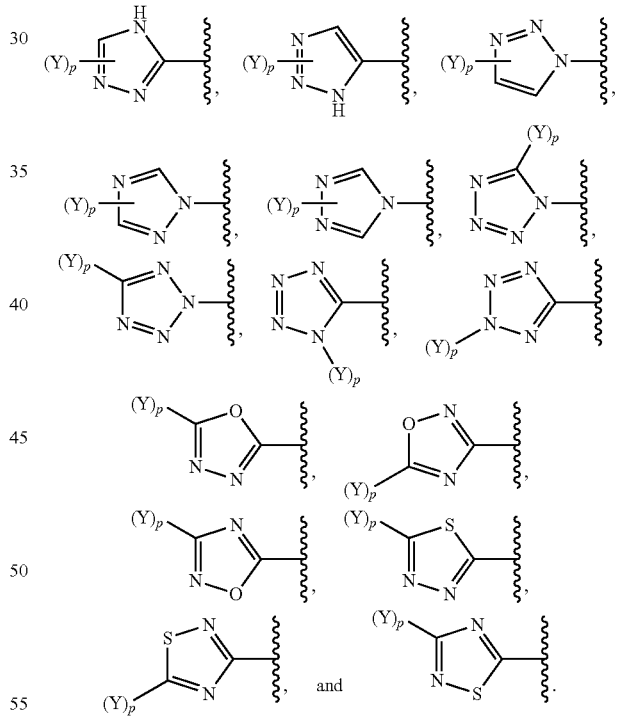

In some embodiments of a compound of Formula (I) or Formula (II), AzA is tetrazolyl.

In some embodiments of a compound of Formula (I) or Formula (II), AzA is C-tetrazolyl.

In some embodiments of a compound of Formula (I) or Formula (II), AzA is N-tetrazolyl.

In some embodiments of a compound of Formula (I) or Formula (II), AzA is triazolyl.

In some embodiments of a compound of Formula (I) or Formula (II), AzA is 1,2,3-triazolyl.

In some embodiments of a compound of Formula (I) or Formula (II), AzA is N-linked 1,2,3-triazolyl or N-linked 1,2,4-triazolyl.

In some embodiments of a compound of Formula (I) or Formula (II), AzA is C-linked 1,2,3-triazolyl or C-linked 1,2,4-triazolyl.

In some embodiments of a compound of Formula (I) or Formula (II), $(Y)_p$-AzA is selected from:

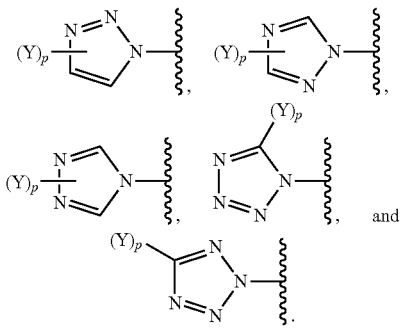

In some embodiments of a compound of Formula (I) or Formula (II), $(Y)_p$-AzA is selected from:

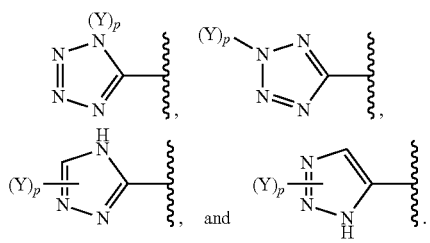

In some embodiments of a compound of Formula (I) or Formula (II), at least one Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_w$OH, —$O(CR^9R^{10})_w OR^{11}$, —$O(CR^9R^{10})_w NR^6R^7$, —$O(CR^9R^{10})_w NR^6C(O)R^{11}$, —$O(CR^9R^{10})_w NR^6C(O)OR^{11}$, —$O(CR^9R^{10})_w NR^6C(O)NR^6R^7$, —$O(CR^9R^{10})_w C(O)NR^6R^7$, —$O(CR^9R^{10})_w NR^6S(O)_{0,1,2}R^{11}$, —$O(CR^9R^{10})_w NR^6S(O)_{0,1,2}NR^6R^7$, —$O(CR^9R^{10})_w S(O)_{0,1,2}R^{11}$, —$O(CR^9R^{10})_w S(O)_{0,1,2}NR^6R^7$, —$O(CR^6R^7)_v C(=NR^8)NR^6R^7$, —$O(CR^9R^{10})_v N(R^6)C(=NR^8)R^{11}$, —$O(CR^9R^{10})_v C(=NR^8)NR^6C(=NR^8)NR^6R^7$, —$O(CR^9R^{10})_w N(R^6)C(=NR^8)NR^6R^7$, —$O(CR^9R^{10})_w S(O)_{0,1,2}R^{11}$, —$O(CR^9R^{10})_w S(O)_{0,1,2}NR^6R^7$, —$OC(O)R^{11}$, —$OC(O)(CR^9R^{10})_w NR^6R^7$, —$OC(O)NR^6R^7$, —$OC(O)OR^{11}$, —$OC(O)NR^6(CR^9R^{10})_w NR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_w NR^6$-Heteroaryl, —$O(CR^9R^{10})_w NR^6$-Heterocyclyl, —$O(CR^9R^{10})_w O$—Heterocyclyl, —$NR^6R^7$, —$NR^6(CR^9R^{10})_w NR^6R^7$, —$NR^6(CR^9R^{10})_w$OH, —$NR^6(CR^9R^{10})_w OR^{11}$, —$NR^6C(O)R^{11}$, —$NR^6C(O)OR^{11}$, —$N(R^6)C(O)(CR^9R^{10})_w NR^6R^7$, —$NR^6C(O)NR^6R^7$, —$NR^6C(O)NR^6(CR^9R^{10})_w NR^6R^7$, —$NR^6(CR^9R^{10})_w S(O)_{0,1,2}R^{11}$, —$NR^6(CR^9R^{10})_w S(O)_{0,1,2}NR^6R^7$, —$NR^6(CR^9R^{10})_w NR^6R^7 S(O)_{0,1,2}R^{11}$, —$NR^6(CR^9R^{10})_w NR^6 S(O)_{0,1,2}NR^6R^6$, —$NR^6C(=NR^8)NR^6R^6$, —$N(R^6)C(=NR^8)R^{11}$, —$NR^6(CR^9R^{10})_w N(R^6)C(=NR^8)R^{11}$, —$NR^6(CR^9R^{10})_w C(=NR^8)NR^6R^7$, —$NR^6(CR^9R^{10})_w N(R^6)C(=NR^8)NR^6R^7$, —$NR^6(CR^9R^{10})_w NR^6C(=O)NR^6R^7$, —$NR^6(CR^9R^{10})_w NR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_w NR^6$-Heteroaryl, —$NR^6(CR^9R^{10})_w NR^6$-Heterocyclyl, —CN, —$(CR^9R^{10})_w CN$, —$(CR^9R^{10})_w NR^6R^7$, —$(CR^9R^{10})_w$OH, —$(CR^9R^{10})_v OR^{11}$, —$(CR^9R^{10})_v OC(O)R^{11}$, —$(CR^9R^{10})_v OC(O)NR^6R^6$, —$(CR^9R^{10})_v O(CR^9R^{10})_v OR^{11}$, —$(CR^9R^{10})_v O(CR^9R^{10})_w OH$, —$(CR^9R^{10})_v O(CR^9R^{10})_w NR^6R^7$, —$(CR^9R^{10})_w NR^6(CR^9R^{10})_w OH$, —$(CR^9R^{10})_w NR^6(CR^9R^{10})_w OR^{11}$, —$(CR^9R^{10})_w C(O)NR^6R^7$, —$(CR^9R^{10})_v C(O)NR^6(CR^9R^{10})_w NR^6R^7$, —$(CR^9R^{10})_v C(O)NR^6(CR^9R^{10})_w OR^{11}$, —$(CR^9R^{10})_w N(R^6)C(O)R^{11}$, —$(CR^9R^{10})_w N(R^6)C(O)OR^{11}$, —$(CR^9R^{10})_w N(R^6)C(O)NR^6R^7$, —$(CR^9R^{10})_w N(R^6)C(O)(CR^9R^{10})_w NR^6R^7$, —$(CR^9R^{10})_w N(R^6)S(O)_{0,1,2}R^{11}$, —$(CR^9R^{10})_w N(R^6)S(O)_{0,1,2}NR^6R^7$—$(CR^9R^{10})_w S(O)_{0,1,2}NR^6R^7$, —$(CR^9R^{10})_w NR^6(CR^9R^{10})_w NR^6R^7$, —$(CR^9R^{10})_w NR^6(CR^9R^{10})_w N(R^6)CH(=NR^8)$, —$(CR^9R^{10})_w N(R^6)C(=NR^8)R^{11}$, —$(CR^9R^{10})_w C(=NR^8)NR^6R^7$, —$(CR^9R^{10})_w N(R^6)C(=NR^8)NR^6R^7$, —$(CR^9R^{10})_w C(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_v$Heteroaryl, —$(CR^9R^{10})_v$Heterocyclyl, —C(O)OH, —$C(O)OR^{11}$, —$C(O)NR^6R^7$, —$C(O)NR^6(CR^9R^{10})_w NR^6R^7$, —$C(O)NR^6(CR^9R^{10})_w OH$, —$C(O)NR^6(CR^9R^{10})_w OR^{11}$, —$C(=NR^8)NR^6R^7$, —$C(=NR^8)NR^6C(O)R^{11}$, —$S(O)_{0,1,2}R^{11}$, —$S(O)_{0,1,2}(CR^9R^{10})_w NR^6R^7$, —$S(O)_{0,1,2}(CR^9R^{10})_w OH$, —$S(O)_{0,1,2}(CR^9R^{10})_w OR^{11}$, —$SO_2NR^6R^7$, —$S(O)_{0,1,2}NR^6(CR^9R^{10})_w NR^6R^7$, —$S(O)_{0,1,2}(CR^9R^{10})_w N(R^6)C(=NR^8)R^{11}$, —$S(O)_{0,1,2}(CR^9R^{10})_w C(=NR^8)NR^6R^7$, —$S(O)_{0,1,2}(CR^9R^{10})_w N(R^6)C(=NR^8)NR^6R^7$, and —$S(O)_{0,1,2}(CR^9R^{10})_v C(=NR^8)NR^6C(=NR^8)NR^6R^7$.

In some embodiments of a compound of Formula (I) or Formula (II), at least one Y is selected from the group consisting of optionally substituted alkyl, optionally substituted heterocycle, optionally substituted heteroaryl, —$NR^6R^7$, —$NR^6(CR^9R^{10})_w NR^6R^7$, —$NR^6C(O)R^{11}$, —$NR^6C(O)OR^{11}$, —$N(R^6)C(O)(CR^9R^{10})_w NR^6R^7$, —$NR^6C(O)NR^6R^7$, —$NR^6C(O)NR^6(CR^9R^{10})_w NR^6R^7$, —$NR^6(CR^9R^{10})_w S(O)_{0,1,2}R^{11}$, —$NR^6(CR^9R^{10})_w S(O)_{0,1,2}NR^6R^7$, —$NR^6(CR^9R^{10})_w NR^6R^7 S(O)_{0,1,2}R^{11}$, —$NR^6(CR^9R^{10})_w NR^6 S(O)_{0,1,2}NR^6R^6$, —$NR^6C(=NR^8)NR^6R^6$, —$N(R^6)C(=NR^8)R^{11}$, —$NR^6(CR^9R^{10})_w N(R^6)C(=NR^8)R^{11}$, —$NR^6(CR^9R^{10})_w C(=NR^8)NR^6R^7$, —$NR^6(CR^9R^{10})_w N(R^6)C(=NR^8)NR^6R^7$, —$NR^6(CR^9R^{10})_w NR^6C(=O)NR^6R^7$, —$NR^6(CR^9R^{10})_w NR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_w NR^6$-Heteroaryl, —$NR^6(CR^9R^{10})_w NR^6$-Heterocyclyl, —CN, —$(CR^9R^{10})_v NR^6R^7$, —$(CR^9R^{10})_v$OH, —$(CR^9R^{10})_v OR^{11}$, —$(CR^9R^{10})_v OC(O)R^{11}$, —$(CR^9R^{10})_v OC(O)NR^6R^6$, —$(CR^9R^{10})_v O(CR^9R^{10})_v OR^{11}$, —$(CR^9R^{10})_v O(CR^9R^{10})_w OH$, —$(CR^9R^{10})_v O(CR^9R^{10})_w NR^6R^7$, —$(CR^9R^{10})_w$OH, —$(CR^9R^{10})_w NR^6(CR^9R^{10})_w OR^{11}$, —$(CR^9R^{10})_v C(O)NR^6R^7$, —$(CR^9R^{10})_v C(O)NR^6(CR^9R^{10})_w OR^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$.

In some embodiments of a compound of Formula (I) or Formula (II), at least one Y is selected from the group consisting of optionally substituted alkyl, optionally substituted heterocycle, optionally substituted heteroaryl, —NR$^6$R$^7$—(CR$^9$R$^{10}$)$_w$NR$^6$R$^7$, —(CR$^9$R$^{10}$)$_w$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_v$C(O)NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heterocycle, optionally substituted heteroaryl, —NR$^6$R$^7$, —(CR$^9$R$^{10}$)$_w$NR$^6$R$^7$, —(CR$^9$R$^{10}$)$_v$OH, —(CR$^9$R$^{10}$)$_w$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_w$N(R$^6$)C(=NR$^8$)R$^{11}$, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heteroaryl, —NR$^6$R$^7$, —(CR$^9$R$^{10}$)$_w$NR$^6$R$^7$, —(CR$^9$R$^{10}$)$_w$OH, —(CR$^9$R$^{10}$)$_v$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II), at least one Y is selected from the group consisting of optionally substituted heterocycle, optionally substituted heteroaryl, —NR$^6$C(=NR$^8$)NR$^6$R$^6$, —N(R$^6$)C(=NR$^8$)R$^{11}$, —NR$^6$C(R$^9$R$^{10}$)$_w$NR$^6$R$^7$, —(CR$^9$R$^{10}$)$_w$NR$^6$R$^7$, —(CR$^9$R$^{10}$)$_v$O(CR$^9$R$^{10}$)$_w$NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, and —C(O)NR$^6$(CR$^9$R$^{10}$)$_w$NR$^6$R$^7$.

In some embodiments of a compound of Formula (I) or Formula (II), at least one Y is selected from the group consisting of fluoro, chloro, iodo, boronic acid, optionally substituted alkyl, optionally substituted alkynyl, optionally substituted heterocycle, optionally substituted heteroaryl, —OH, —OR$^{11}$, —O(CR$^9$R$^{10}$)$_w$NR$^6$R$^7$, —NR$^6$R$^7$, —NO$_2$, —(CR$^9$R$^{10}$)$_v$NR$^6$R$^7$, —(CR$^9$R$^{10}$)$_v$S(O)$_{0,1,2}$(CR$^9$R$^{10}$)$_v$NR$^6$R$^7$, —(CR$^9$R$^{10}$)$_v$Heterocyclyl-(NR$^6$R$^7$)$_2$, —C(O)NR$^6$O(CR$^9$R$^{10}$)$_w$NR$^6$R$^7$, —(CR$^9$R$^{10}$)$_v$C(O)NR$^6$R$^7$, —(CR$^9$R$^{10}$)$_v$C(O)NR$^6$NR$^6$R$^7$, —(CR$^9$R$^{10}$)$_v$OH, —(CR$^9$R$^{10}$)$_v$NR$^6$(CR$^9$R$^{10}$)$_v$OH, —(CR$^9$R$^{10}$)$_v$N(R$^6$)C(O)(CR$^9$R$^{10}$)$_v$NR$^6$R$^7$, —(CR$^9$R$^{10}$)$_v$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)C(O)(CR$^9$R$^{10}$)$_v$ONR$^6$R$^7$, —(CR$^9$R$^{10}$)$_v$N(R$^6$)S(O)$_{0,1,2}$R$^{11}$, —(CR$^9$R$^{10}$)$_v$O(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$Heterocyclyl, —(CR$^9$R$^{10}$)$_v$Heteroaryl-NR$^6$R$^7$, —(CR$^9$R$^{10}$)$_v$Heteroaryl(CR$^9$R$^{10}$)$_v$NR$^6$R$^7$, —CN, —C(O)OH, —C(O)OR$^{11}$, —C(O)NR$^6$R$^7$, —C(O)NR$^6$(CR$^9$R$^{10}$)$_w$NR$^6$R$^7$, —S(O)$_{0,1,2}$R$^{11}$, and —S(O)$_{0,1,2}$(CR$^9$R$^{10}$)$_w$NR$^6$R$^7$.

In some embodiments of a compound of Formula (I) or Formula (II), at least one Y is —CH$_2$—Y$^2$ and Y$^2$ is selected from the group consisting of —NR$^6$R$^7$, —O(CR$^9$R$^{10}$)$_w$NR$^6$R$^7$, —C(O)NR$^6$(CR$^9$R$^{10}$)$_w$NR$^6$R$^7$, —N(R$^6$)C(O)(CR$^9$R$^{10}$)$_v$NR$^6$R$^7$, —NR$^6$(CR$^9$R$^{10}$)$_w$NR$^6$R$^7$, —N(R$^6$)C(=NR$^8$)R$^{11}$, —C(=NR$^8$)NR$^6$R$^7$, —N(R$^6$)C(=NR$^8$)NR$^6$R$^7$, —C(=NR$^8$)NR$^6$C(=NR$^8$)NR$^6$R$^7$, heterocyclyl, and heteroaryl.

In some embodiments of a compound of Formula (I) or Formula (II), at least one Y is —(CR$^9$R$^{10}$)$_v$NR$^6$R$^7$.

In some embodiments of a compound of Formula (I) or Formula (II), at least one Y is —(CR$^9$R$^{10}$)$_v$N(R$^6$)C(=NR$^8$)NR$^6$R$^7$.

In some embodiments of a compound of Formula (I) or Formula (II), p is 0.

In some embodiments of a compound of Formula (I) or Formula (II), p is 1.

In some embodiments of a compound of Formula (I) or Formula (II), p is 2.

In some embodiments of a compound of Formula (I) or Formula (II), R$^6$ and R$^7$ are independently selected from the group consisting of hydrogen, —OH, optionally substituted C$_1$-C$_6$ alkyl, optionally substituted alkoxyalkyl, optionally substituted hydroxyalkyl, and optionally substituted heterocyclyl.

In some embodiments of a compound of Formula (I) or Formula (II), R$^6$ and R$^7$ are independently selected from the group consisting of hydrogen and optionally substituted C$_1$-C$_6$ alkyl.

In some embodiments of a compound of Formula (I) or Formula (II), R$^6$ and R$^7$ are hydrogen.

In some embodiments of a compound of Formula (I) or Formula (II), R$^8$ is hydrogen, —OH, —CN, —NO$_2$, —NR$^6$, or optionally substituted C$_1$-C$_6$ alkyl.

In some embodiments of a compound of Formula (I) or Formula (II), $R^8$ is hydrogen or —CN.

In some embodiments of a compound of Formula (I) or Formula (II), $R^9$ and $R^{10}$ are independently selected from the group consisting of hydrogen, —OH, fluoro, chloro, optionally substituted $C_1$-$C_6$ alkyl, —$(CR^aR^b)_v NR^6R^7$, and —$(CR^aR^b)_v C(O)NR^6R^7$.

In some embodiments of a compound of Formula (I) or Formula (II), $R^9$ and $R^{10}$ are hydrogen.

In some embodiments of a compound of Formula (I) or Formula (II), $R^{11}$ is optionally substituted $C_1$-$C_6$ alkyl.

In some embodiments of a compound of Formula (I) or Formula (II), v is 1 or 2.

In some embodiments of a compound of Formula (I) or Formula (II), w is 2 or 3.

In some embodiments of a compound of Formula (I) or Formula (II), v is 1 and w is 2.

In another aspect, provided herein is a compound selected from the group represented by the following structures:

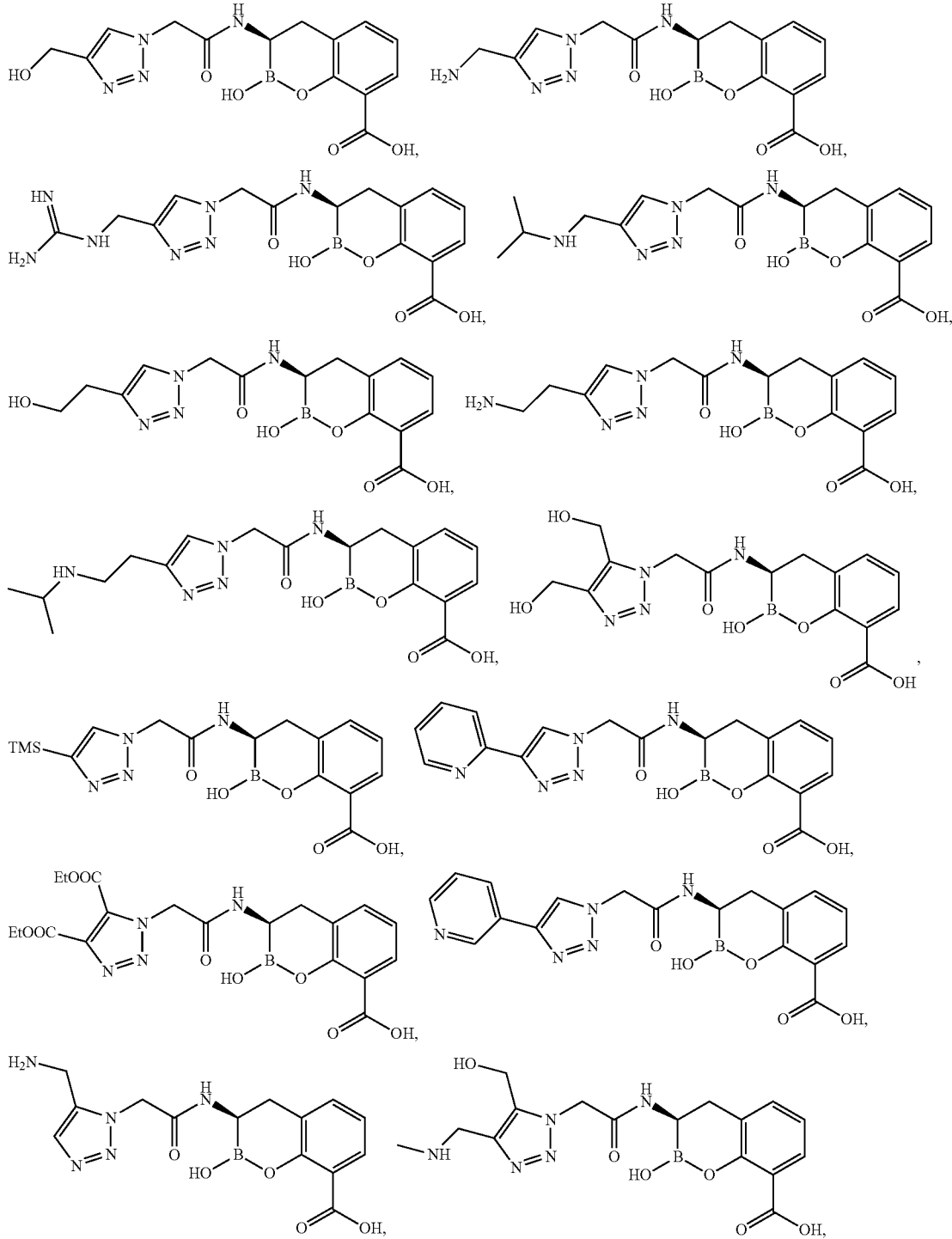

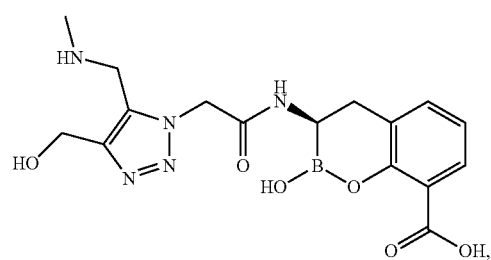
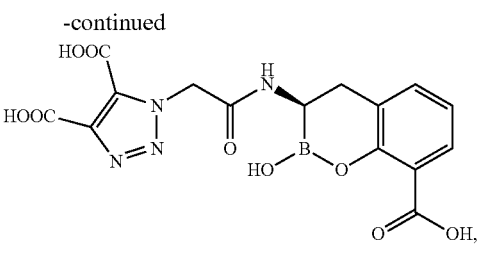
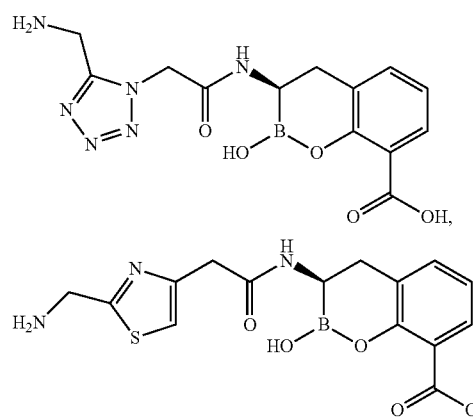
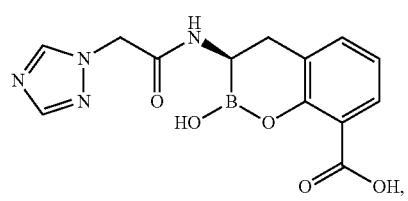
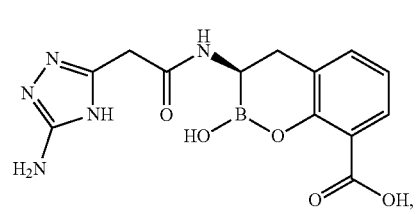
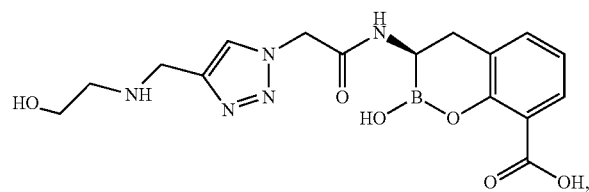
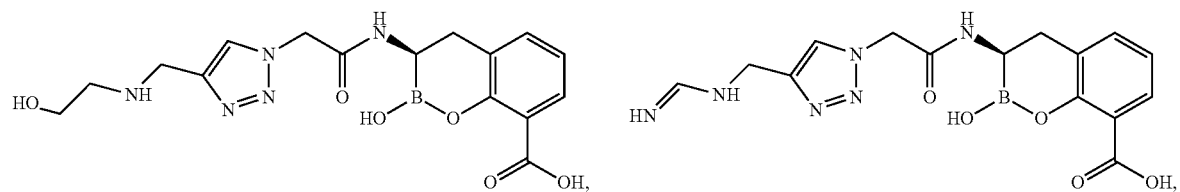
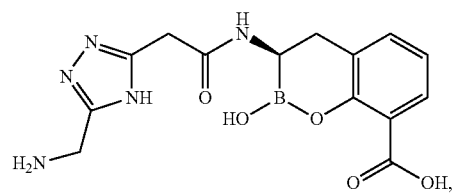
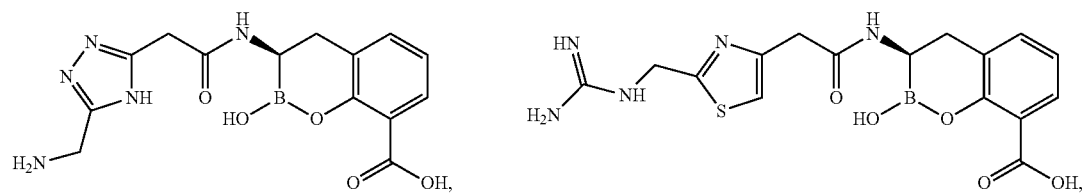
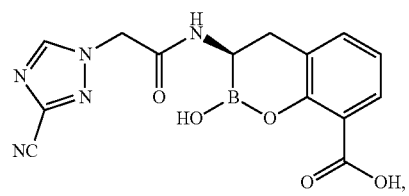
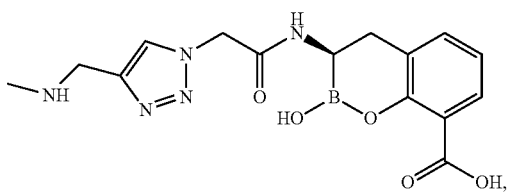
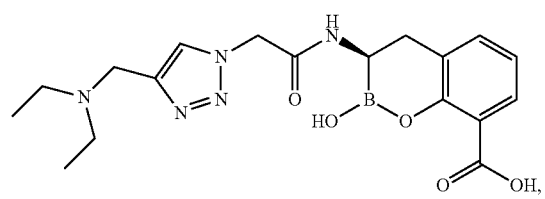
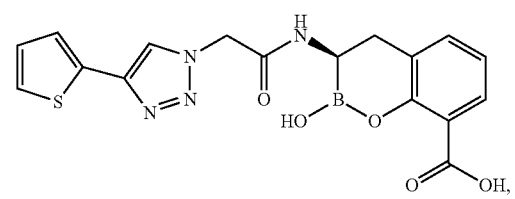
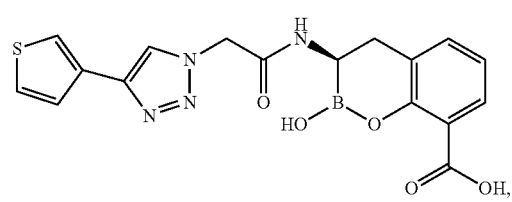
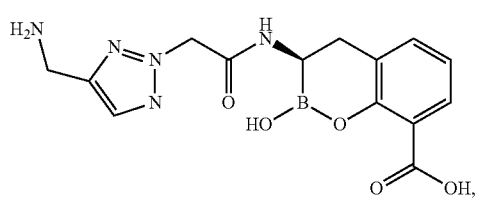

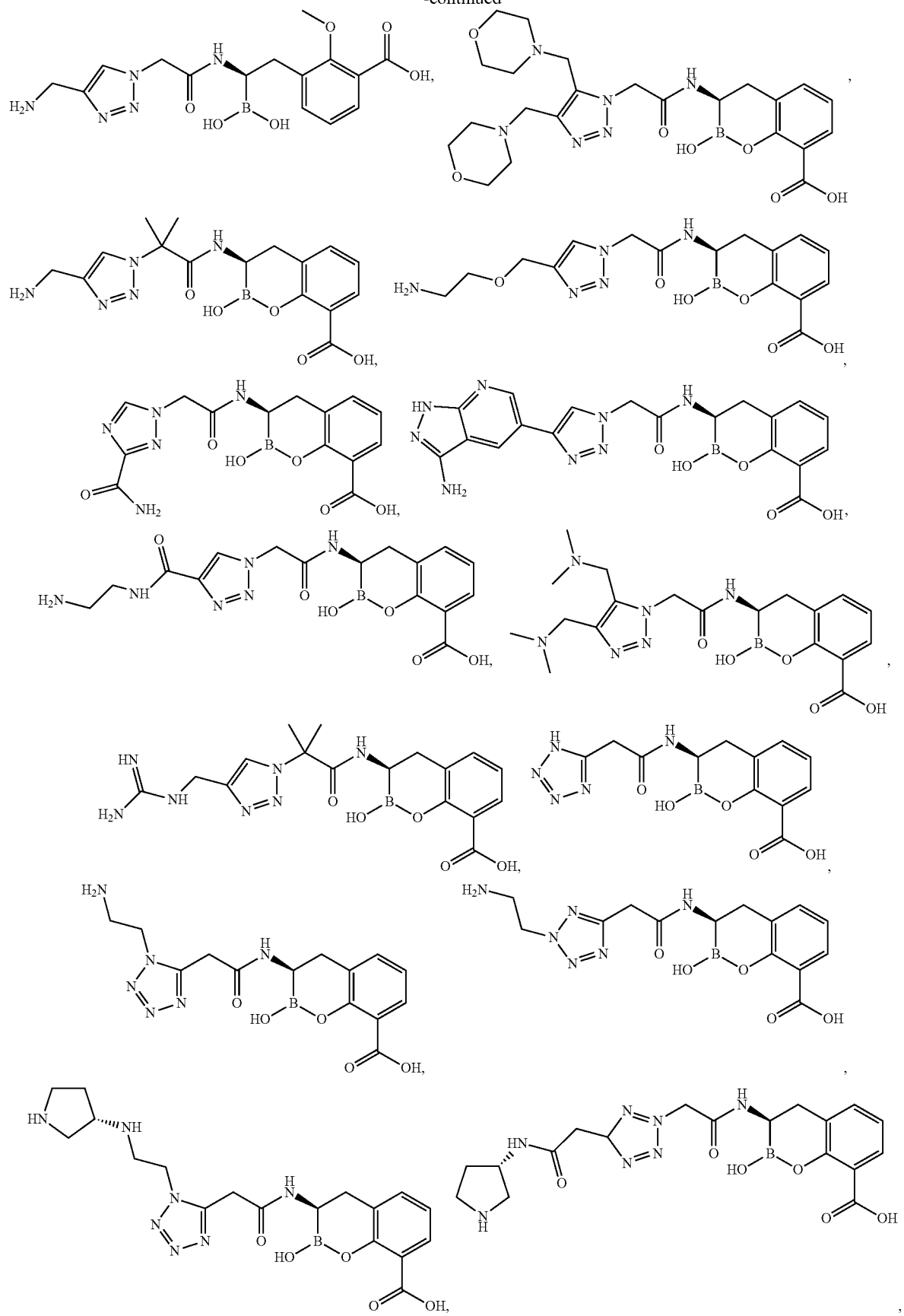

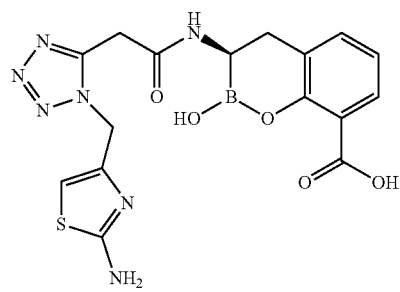
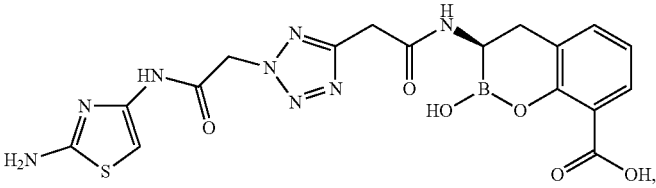
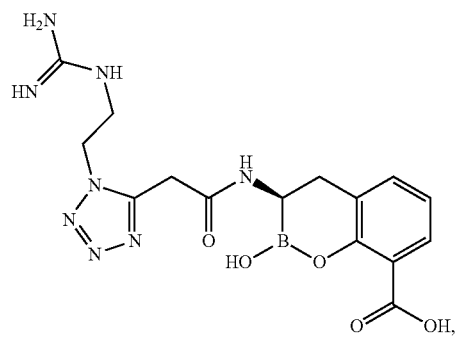
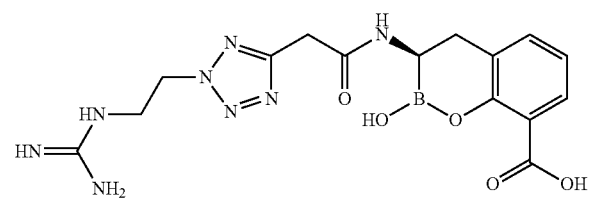
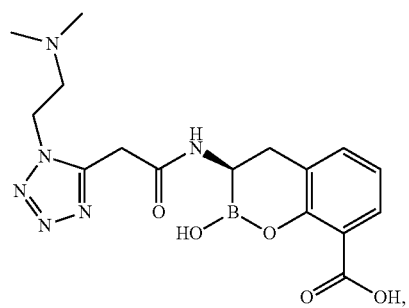
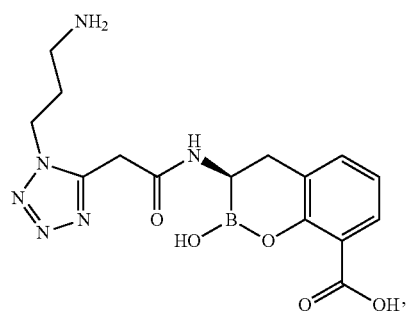
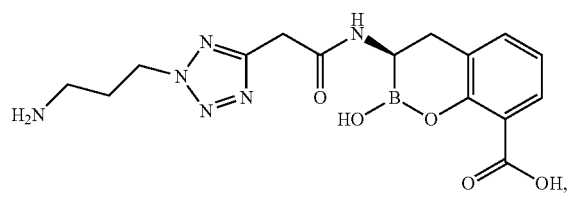
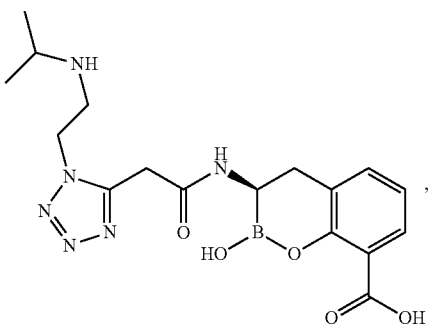
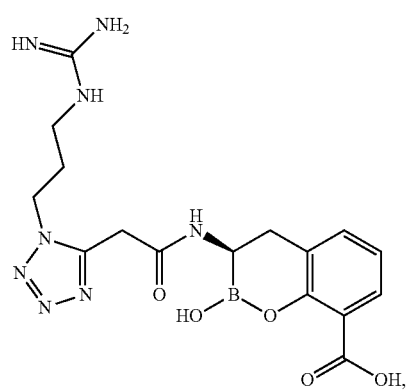
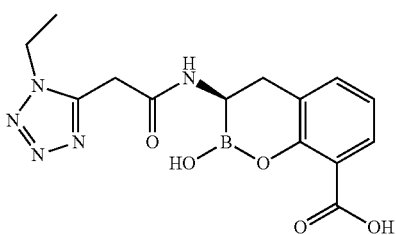

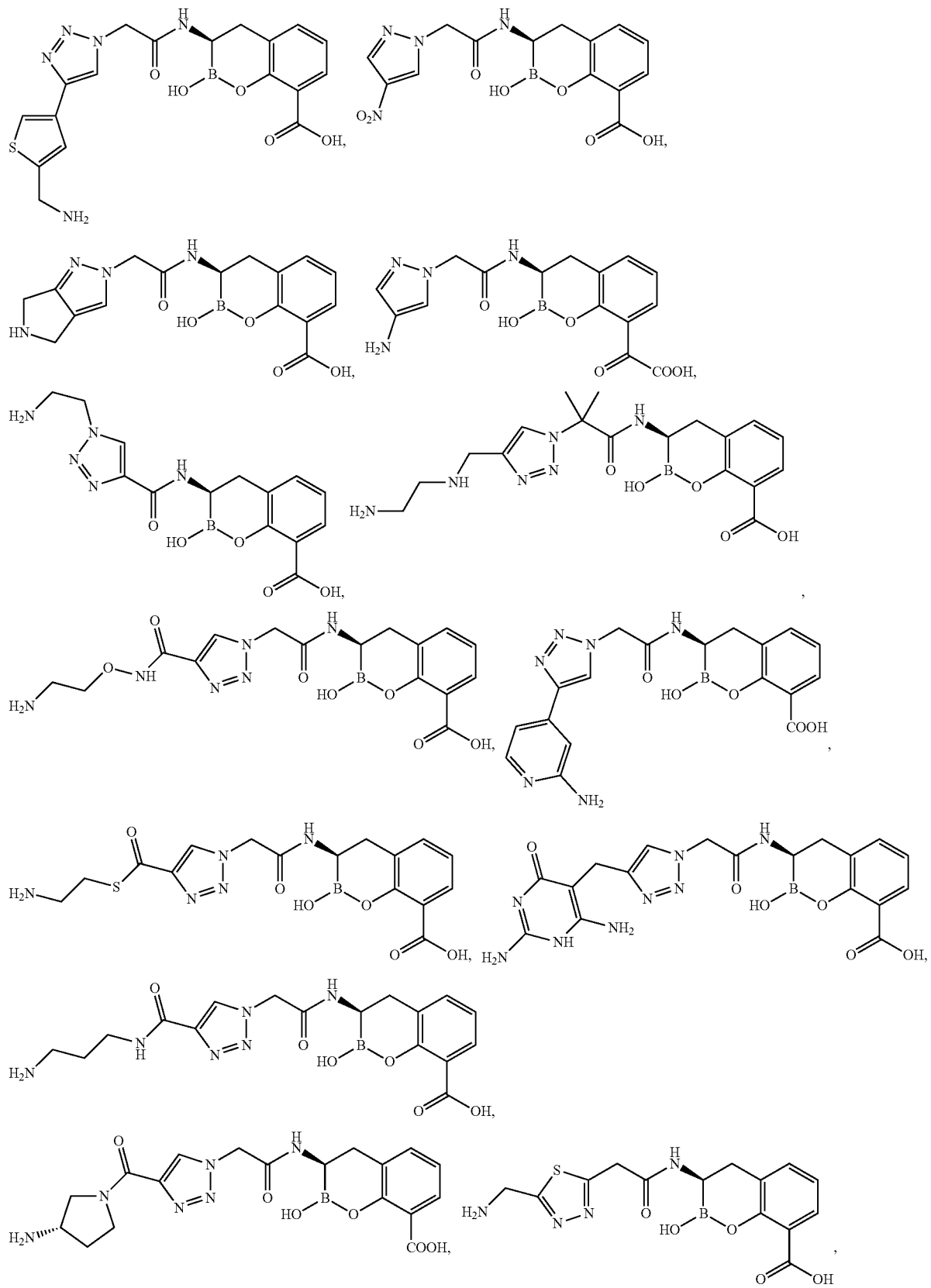

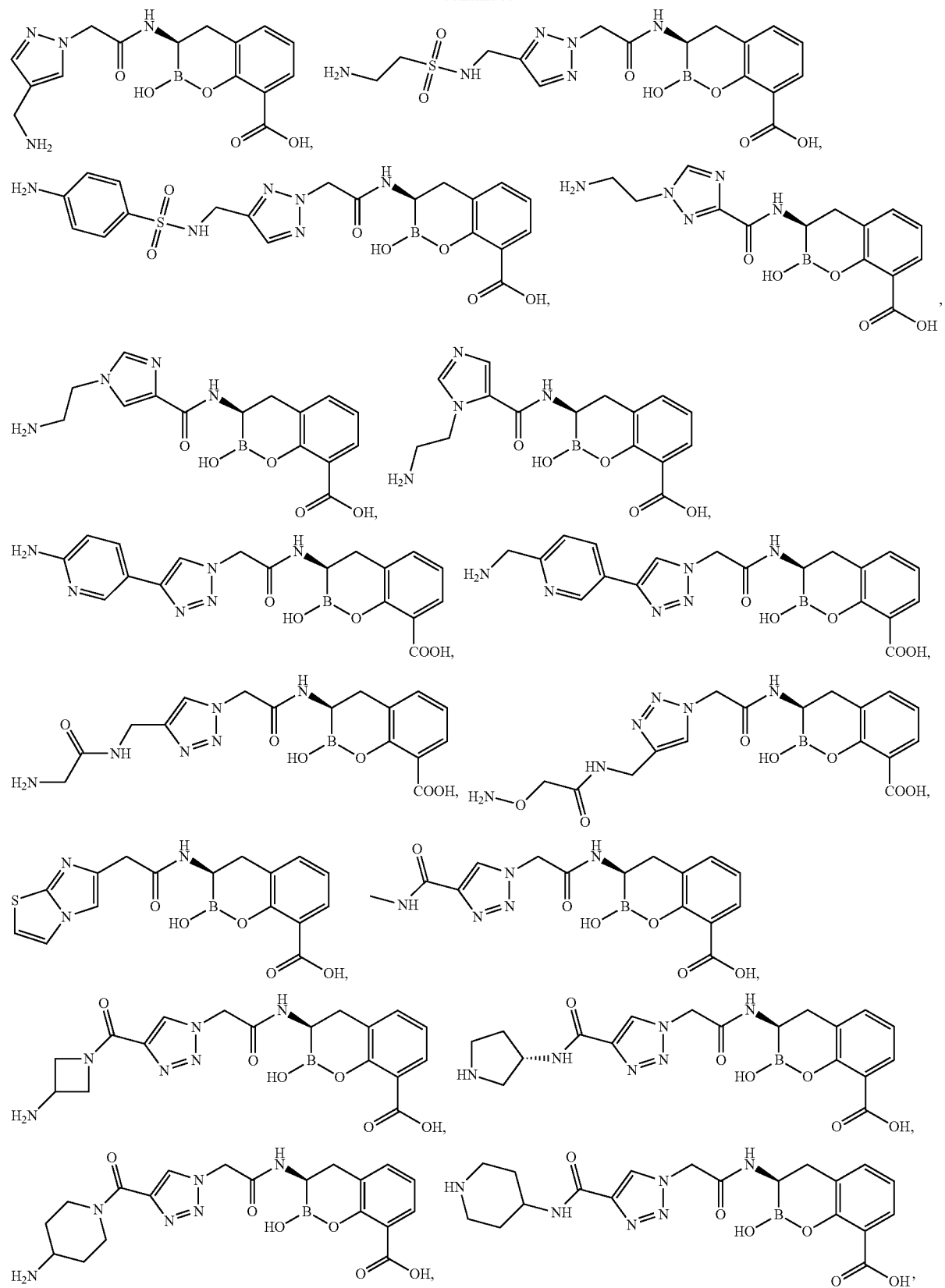

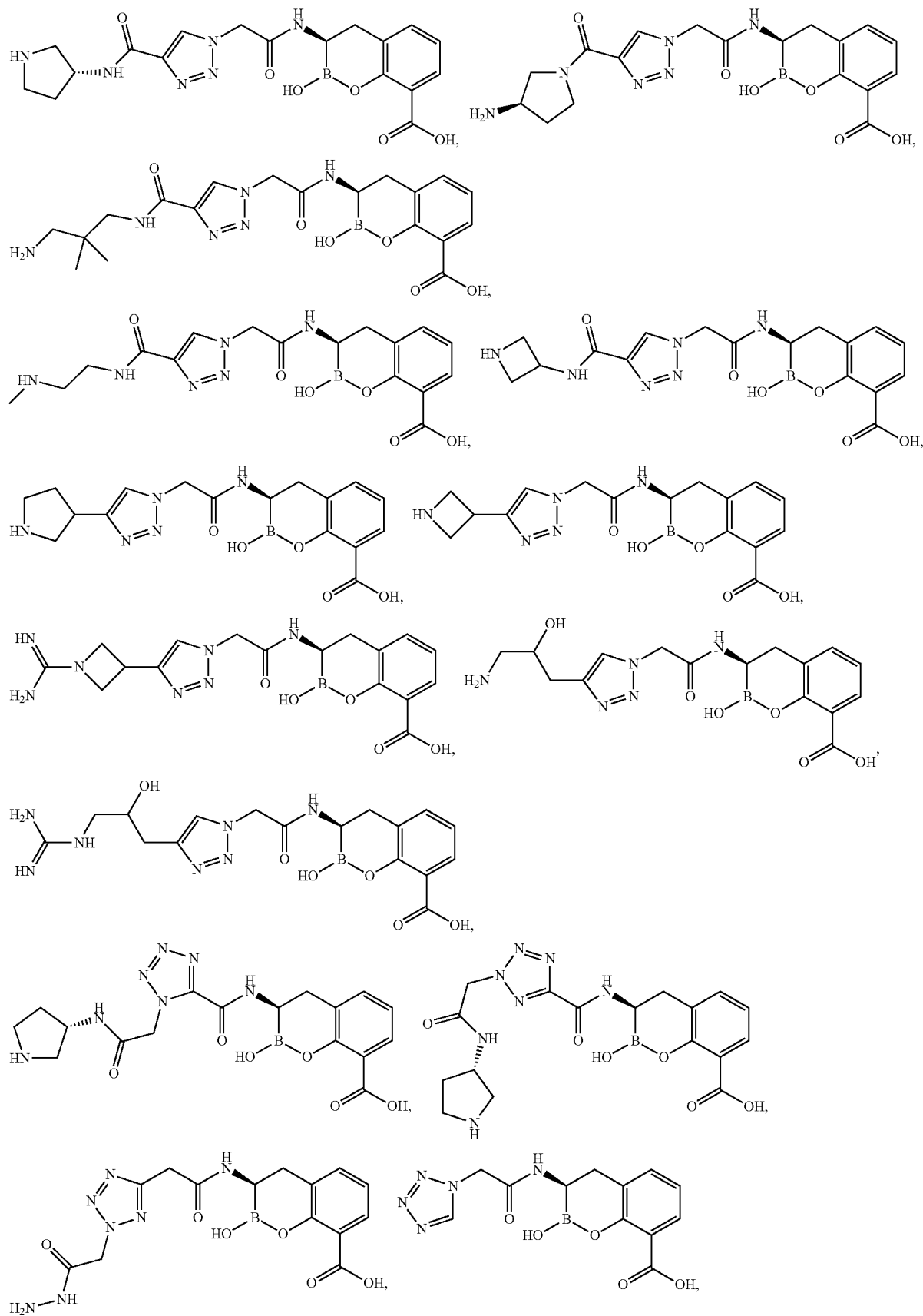

-continued
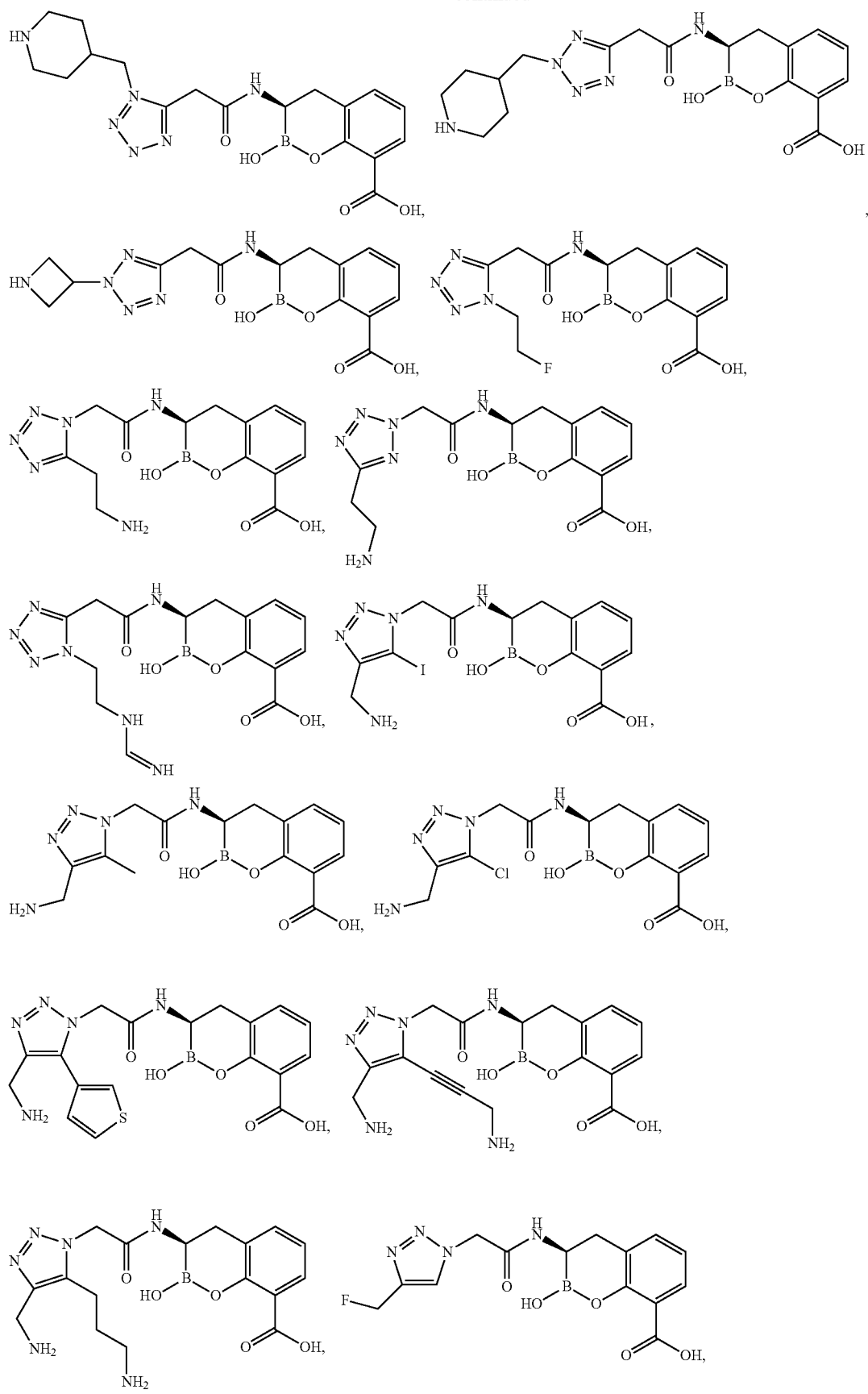

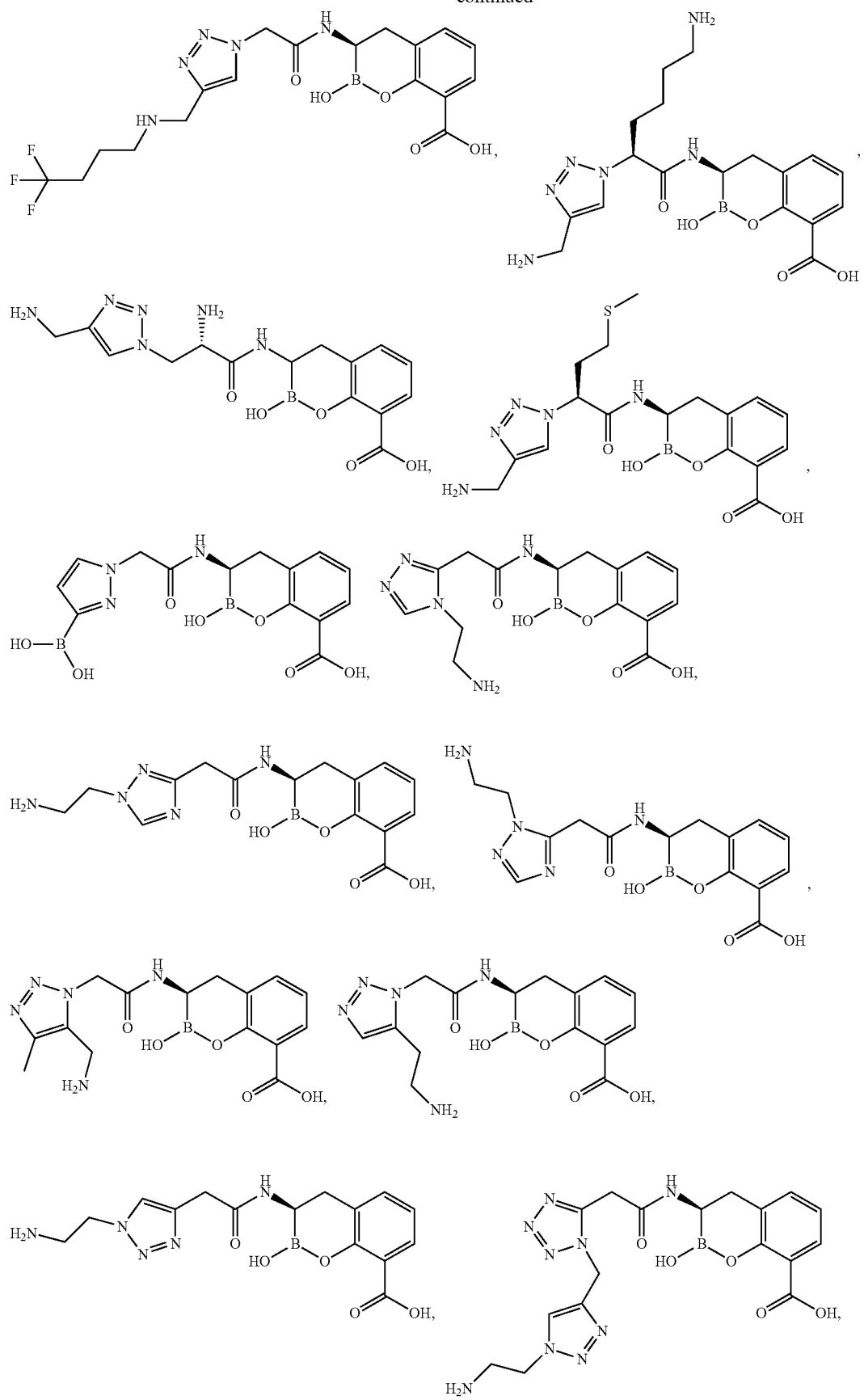

-continued
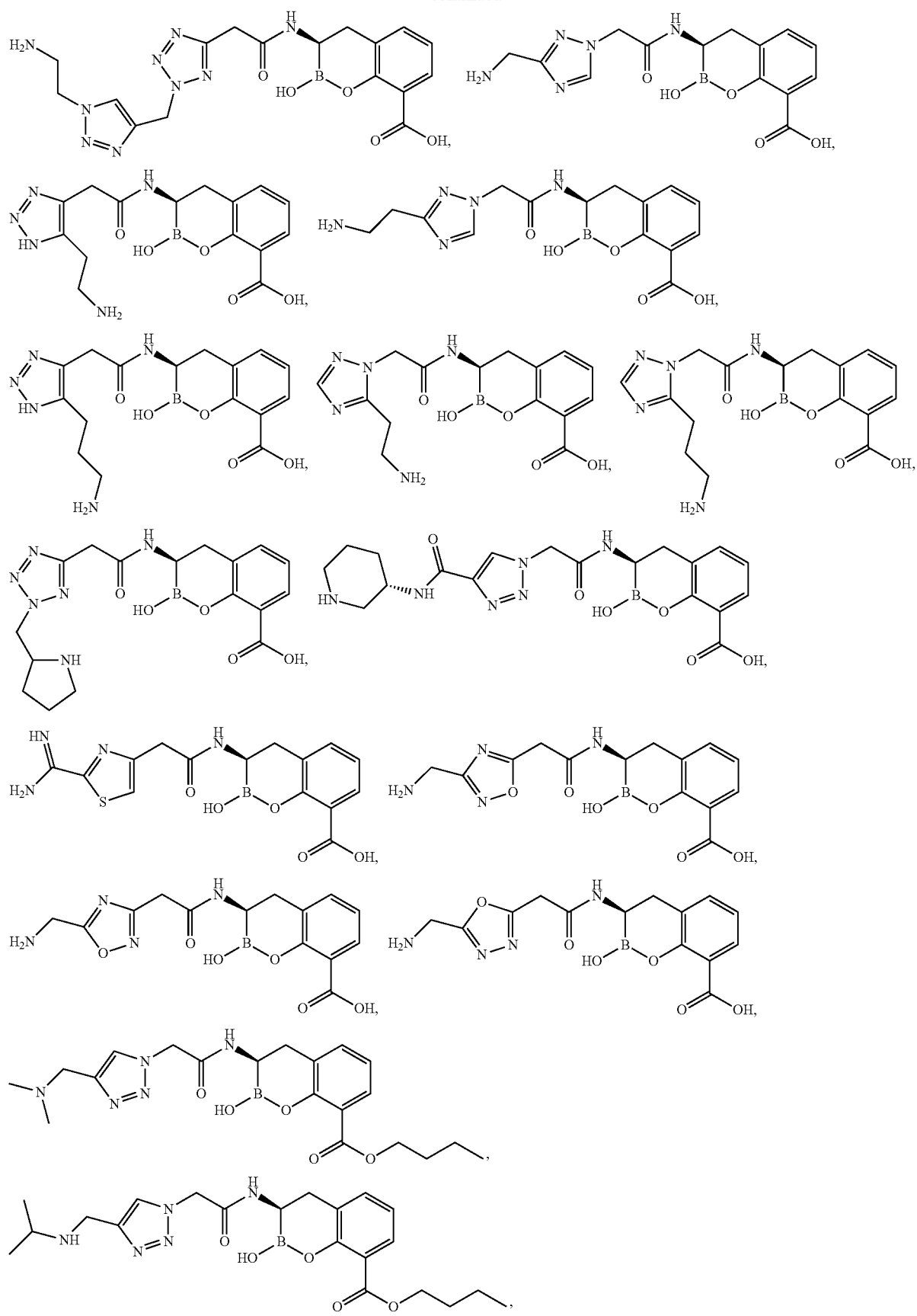

-continued
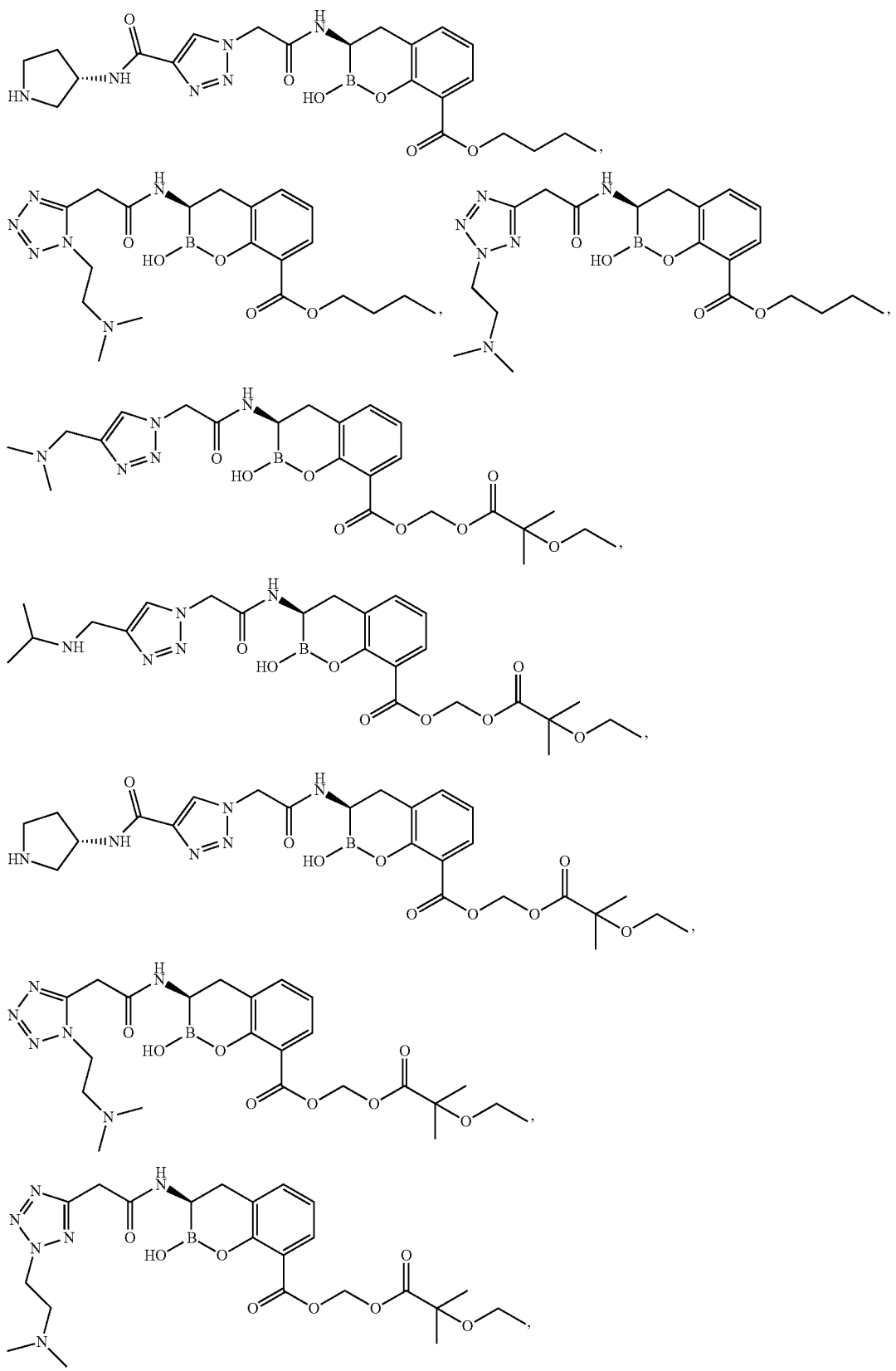

-continued
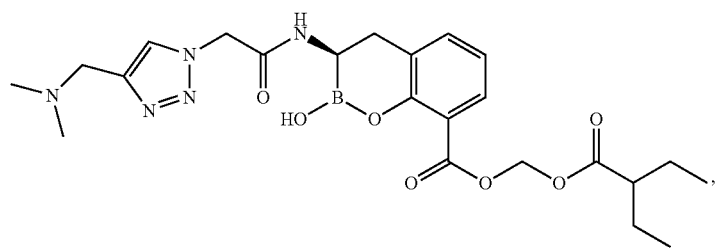
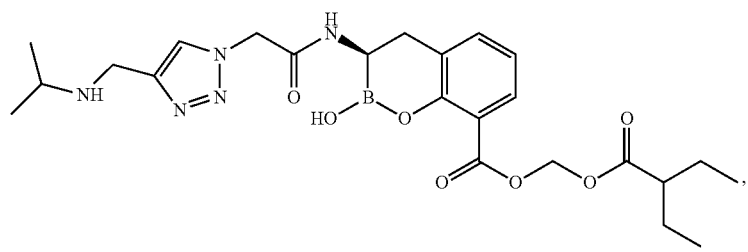
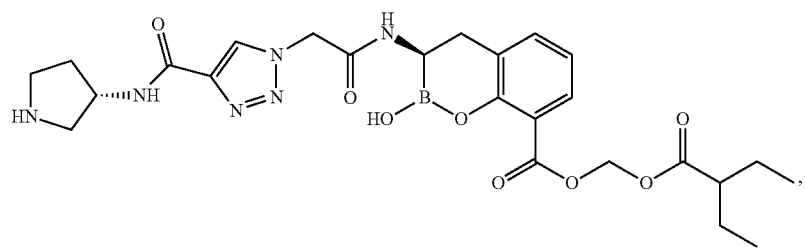
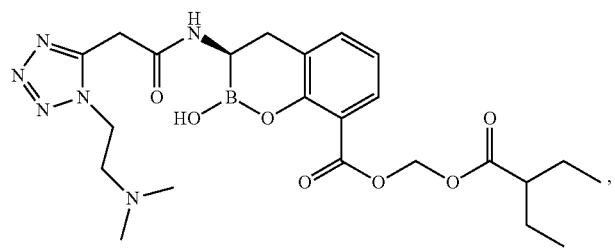
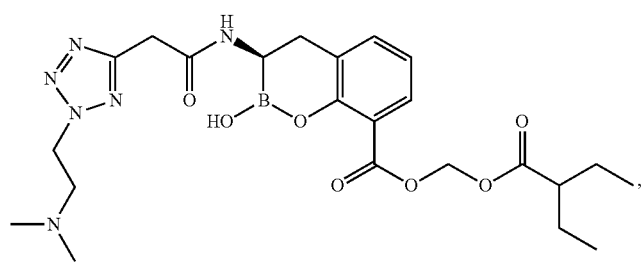
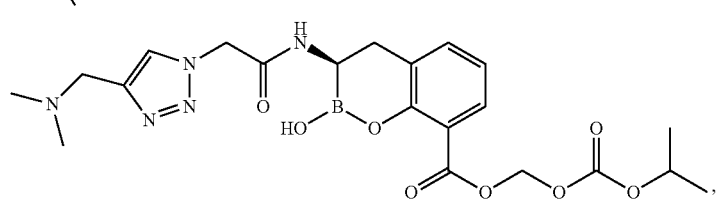
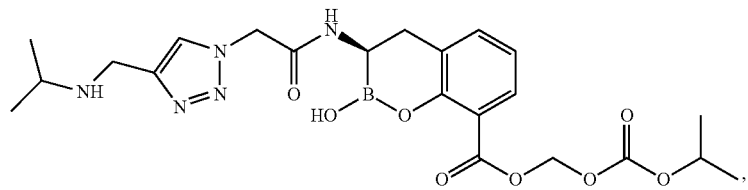

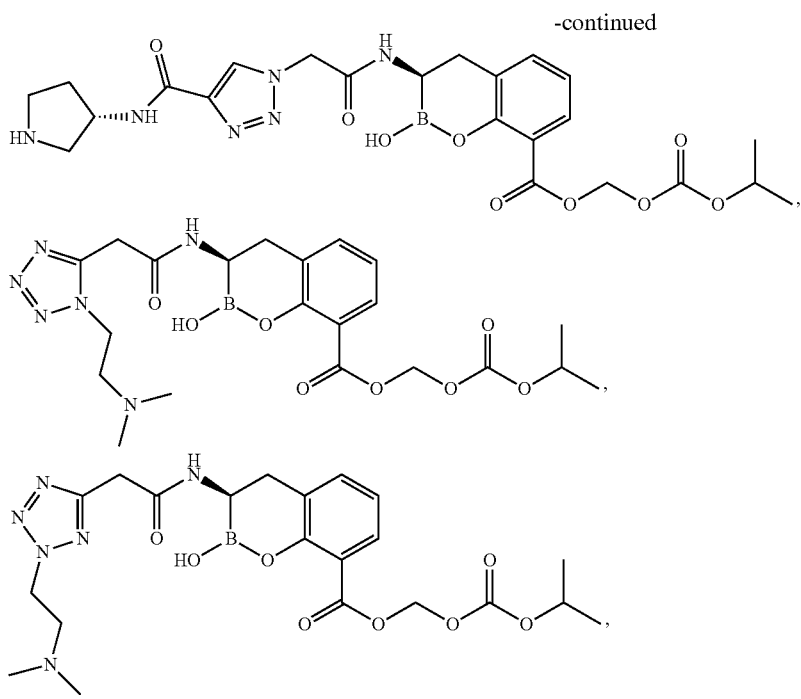

or a pharmaceutically acceptable salt, solvate, stereoisomer, tautomer, prodrug, metabolite, N-oxide, or isomer thereof, wherein the compound is present in a closed, cyclic form, an open, acyclic form, or mixtures thereof.

In another aspect, provided herein is a pharmaceutical composition comprising a compound of Formula (I) or Formula (II) or a pharmaceutically acceptable salt, solvate, stereoisomer, tautomer, prodrug, metabolite, N-oxide, or isomer thereof, and a pharmaceutically acceptable excipient. In some embodiments, the pharmaceutical composition further comprises a beta-lactam antibiotic.

In some embodiments, the beta-lactam antibiotic is a penicillin, cephalosporin, carbapenem, monobactam, bridged monobactam, or a combination thereof.

In another aspect, provided herein is a method of treating a bacterial infection in a subject, comprising administering to the subject a compound a Formula (I) or Formula (II), optionally in combination with a beta-lactam antibiotic.

In another aspect, provided herein is a method of treating a bacterial infection in a subject, comprising administering to the subject a pharmaceutical composition comprising a compound a Formula (I) or Formula (II), optionally in combination with a beta-lactam antibiotic.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These beta-lactamase inhibitors are poorly active against the diversity of beta-lactamase enzymes (both serine- and metallo-based) now emerging clinically. In addition, these enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases. To address this growing therapeutic vulnerability, a new generation of beta-lactamase inhibitors must be developed with broad spectrum functionality. The novel boronic acid based inhibitors described herein address this medical need.

Use of a boronic acid compound to inhibit a beta-lactamase enzyme has been limited. For example, U.S. Pat. No. 7,271,186 discloses beta-lactamase inhibitors that target AmpC (from class C). Ness et al. (Biochemistry (2000) 39:5312-21) discloses beta-lactamase inhibitors that target TEM-1 (a non-ESBL TEM variant from class A; one of approximately 140 known TEM-type beta-lactamase variants). Because there are four major molecular classes of serine-based beta-lactamases, and each of these classes contain significant numbers of beta-lactamase variants, inhibition of one or a small number of beta-lactamases is unlikely to be of therapeutic value. Therefore, there is an imperative need to develop novel beta-lactamase inhibitors with broad spectrum functionality. In particular, there is a need for compounds that are active against both serine- and metallo-based beta-lactamase enzymes.

The present invention is directed to certain boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a (β-lactam functionality Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The (β-lactamase can be an enzyme which catalyzes the hydrolysis of the β-lactam ring of a β-lactam antibiotic. Of particular interest herein are microbial β-lactamases. The β-lactamase may be, for example, a serine (β-lactamase or a metallo-β-lactamase. β-Lactamases of interest include those disclosed in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity Inhibiting β-lactamase activity means inhibiting the activity of a class A, B, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The terms below, as used herein, have the following meanings, unless indicated otherwise.

"Amino" refers to the —NH$_2$ radical.

"Boronic acid" refers to the —B(OH)$_2$ radical.

"Boronic ester" refers to —B(OR$_a$)$_2$ wherein each R$_a$ are independently hydrogen, optionally substituted alkyl, optionally substituted cycloalkyl, optionally substituted alkoxyalkyl, optionally substituted hydroxyalkyl, optionally substituted aminoalkyl, optionally substituted heterocycl, optionally substituted aryl, optionally substituted heteroaryl, optionally substituted cycloalkylalkyl, optionally substituted heterocyclealkyl, optionally substituted aralkyl, optionally substituted heteroaralkyl, (poly ethylene glycol) ethyl, or an optionally substituted saccharide provided that they are not both hydrogen. Two R$_a$ may be taken together with the atom to which they are attached to form an optionally substituted heterocycle or cyclic boronic ester. In some embodiments, the cyclic boronic ester is formed from pinanediol, pinacol, 1,2-ethanediol, 1,3-propanediol, 1,2-propanediol, 2,3-butanediol, 1,2-diisopropylethandiol, 5,6-decanediol, 1,2-dicyclohexylethanediol, diethanolamine, 1,2-diphenyl-1,2-ethanediol, 2,6,6-trimethylbicyclo[3.1.1]heptane-2,3-diol, or (1S,2S,3R,5S)-2,6,6-trimethylbicyclo[3.1.1]heptane-2,3-diol.

"Cyano" or "nitrile" refers to the —CN radical.

"Hydroxy" or "hydroxyl" refers to the —OH radical.

"Nitro" refers to the —NO$_2$ radical.

"Oxo" refers to the =O substituent.

"Oxime" refers to the =N—OH substituent.

"Thioxo" refers to the =S substituent.

"Alkyl" refers to an optionally substituted straight-chain, or optionally substituted branched-chain saturated hydrocarbon monoradical having from one to about ten carbon atoms, more preferably one to six carbon atoms, wherein an sp3-hybridized carbon of the alkyl residue is attached to the rest of the molecule by a a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. Unless stated otherwise specifically in the specification, an alkyl group may be optionally substituted as described below, for example, with oxo, amino, nitrile, nitro, hydroxyl, alkyl, alkylene, alkynyl, alkoxy, aryl, cycloalkyl, heterocyclyl, heteroaryl, and the like.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

"Alkylene" or "alkylene chain" refers to a straight or branched divalent hydrocarbon chain Unless stated otherwise specifically in the specification, an alkylene group may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cyclohexenyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —$OR_a$ where $R_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2H$, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—$N^+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarily, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

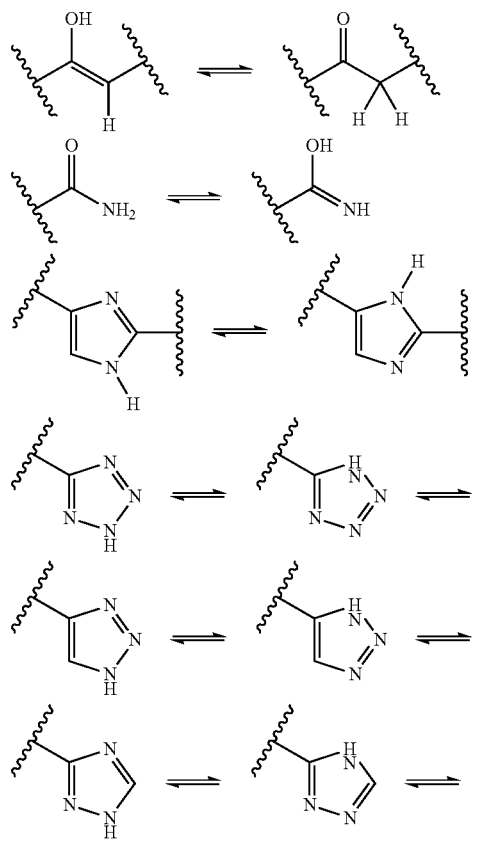
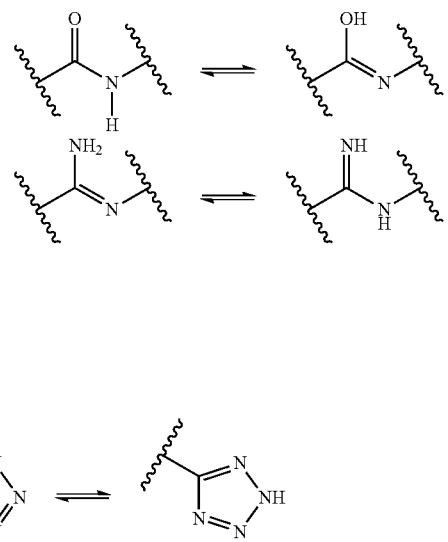

Compounds

Described herein are compounds that modulate the activity of beta-lactamase. In some embodiments, the compounds described herein inhibit beta-lactamase. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula (I) or Formula (II), or pharmaceutically acceptable salts, solvates, stereoisomers, tautomers, prodrugs, metabolites, N-oxides, or isomers thereof:

Formula (I)

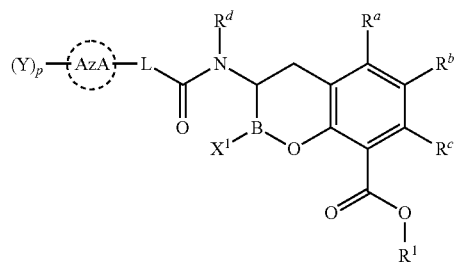

-continued

Formula (II)

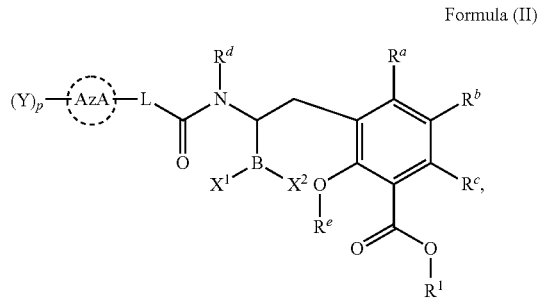

wherein:

L is $-(CR^2R^3)_n-$;

n is 0, 1, 2, 3, 4, 5, or 6;

p is 0, 1, 2 or 3;

$X^1$ and $X^2$ are independently selected from —OH, $-OR^X$, and F;

AzA is a five-membered heteroaromatic ring system bearing at least one heteroatom from the group consisting of N, O, and S;

each Y is selected from the group consisting of fluoro, chloro, bromo, iodo, boronic acid, optionally substituted boronic ester, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_v$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_v$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_v$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NO$_2$, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_w$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)CN, —(CR$^9$R$^{10}$)$_w$NR$^6$R$^7$, —(CR$^9$R$^{10}$)$_w$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$O(CR$^9$R$^{10}$)$_w$OR$^{11}$, —(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$S(O)$_{0,1,2}$(CR$^9$R$^{10}$)$_v$NR$^6$R$^7$, —(CR$^9$R$^{10}$)$_w$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heteroaryl(CR$^9$R$^{10}$)$_v$NR$^6$R$^7$, —(CR$^9$R$^{10}$)$_v$Heterocyclyl-NR$^6$R$^7$, —(CR$^9$R$^{10}$)$_v$Heterocyclyl(CR$^9$R$^{10}$)$_v$NR$^6$R$^7$, —(CR$^9$R$^{10}$)$_v$Heterocyclyl-(NR$^6$R$^7$)$_2$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$O(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-$—(CR$^9$R$^{10}$)$_v$(T)$^+$Q$^-$, and —O(CR$^9$R$^{10}$)$_w$NR$^6$R$^6$R$^{12+}$Q$^-$;

wherein:

T is pyridine-1-yl, pyrimidin-1-yl, or thiazol-3-yl;

Q is a pharmaceutically acceptable counterion; and v is 1-4;

w is 2-4;

or two Ys taken together with the atoms to which they are attached form an optionally substituted carbocycle, an optionally substituted heterocycle, or an optionally substituted heteroaryl;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

each R$^x$ are independently optionally substituted C$_1$-C$_6$ alkyl, optionally substituted C$_3$-C$_6$ cycloalkyl, optionally substituted alkoxyalkyl, optionally substituted hydroxyalkyl, optionally substituted aminoalkyl, optionally substituted heterocyclalkyl, optionally substituted aryl, optionally substituted heteroaryl, optionally substituted cycloalkylalkyl, optionally substituted heterocylealkyl, optionally substituted aralkyl, optionally substituted heteroaralkyl, (poly ethylene glycol) ethyl, or an optionally substituted saccharide;

or two R$^x$ taken together with the atom to which they are attached form an optionally substituted heterocycle;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted $C_3$-$C_6$ cycloalkyl, —OH, —$OR^{11}$, —$SR^{11}$, —$NR^6R^7$, —$(CR^9R^{10})C(O)NR^6R^7$, —$(CR^9R^{10})C(O)OH$, —$(CR^9R^{10})OH$, —$(CR^9R^{10})NR^6R^7$, and —$(CR^9R^{10})_wN(R^6)C(=NR^8)NR^6R^7$;

or $R^2$ and $R^3$ on the same carbon are taken together to form an oxo or optionally substituted oxime;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —CN, —OH, —$S(O)_2R^{11}$, —$S(O)_2NH_2$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, —OH, —$OR^{11}$, —CN, —$NO_2$, or optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_vNR^6R^7$, —$(CR^aR^b)_vC(O)NR^6R^7$, —$C(O)NR^6R^7$, —$C(O)OR^{11}$, —C(O)OH, —$NR^6SO_2R^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In one aspect, provided herein are compounds of Formula (I) or Formula (II), or pharmaceutically acceptable salts, solvates, stereoisomers, tautomers, prodrugs, metabolites, N-oxides, or isomers thereof:

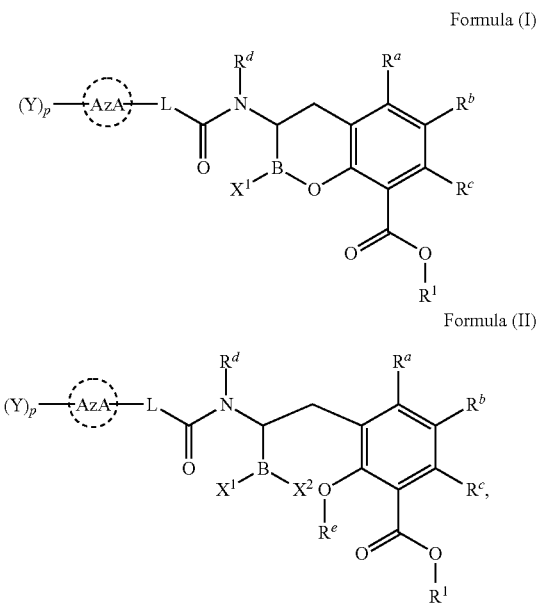

Formula (I)

Formula (II)

wherein:
L is —$(CR^2R^3)_n$—;
n is 0, 1, 2, 3, 4, 5, or 6;
p is 0, 1, 2 or 3;
$X^1$ and $X^2$ are independently selected from —OH, —$OR^x$, and F;
AzA is a five-membered heteroaromatic ring system bearing at least one heteroatom from the group consisting of N, O, and S;
each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_wOH$, —$O(CR^9R^{10})_wOR^{11}$, —$O(CR^9R^{10})_wNR^6R^7$, —$O(CR^9R^{10})_wNR^6C(O)R^{11}$, —$O(CR^9R^{10})_wNR^6C(O)OR^{11}$, —$O(CR^9R^{10})_wNR^6C(O)NR^6R^7$, —$O(CR^9R^{10})_wC(O)NR^6R^7$, —$O(CR^9R^{10})_wNR^6S(O)_{0,1,2}R^{11}$, —$O(CR^9R^{10})_wNR^6S(O)_{0,1,2}NR^6R^7$, —$O(CR^9R^{10})_wS(O)_{0,1,2}R^{11}$, —$O(CR^9R^{10})_wS(O)_{0,1,2}NR^6R^7$, —$O(CR^6R^7)_vC(=NR^8)NR^6R^7$, —$O(CR^9R^{10})_wN(R^6)C(=NR^8)R^{11}$, —$O(CR^9R^{10})_wC(=NR^8)NR^6C(=NR^8)NR^6R^7$, —$O(CR^9R^{10})_wN(R^6)C(=NR^8)NR^6R^7$, —$O(CR^9R^{10})_wS(O)_{0,1,2}R^{11}$, —$O(CR^9R^{10})_wS(O)_{0,1,2}NR^6R^7$, —$OC(O)R^{11}$, —$OC(O)(CR^9R^{10})_wNR^6R^7$, —$OC(O)NR^6R^7$, —$OC(O)OR^{11}$, —$OC(O)NR^6(CR^9R^{10})_wNR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_wNR^6$-Heteroaryl, —$O(CR^9R^{10})_wNR^6$-Heterocyclyl, —$O(CR^9R^{10})_wO$-Heterocyclyl, —$NO_2$, —$NR^6R^7$, —$NR^6(CR^9R^{10})_wNR^6R^7$, —$NR^6(CR^9R^{10})_wOH$, —$NR^6(CR^9R^{10})_wOR^{11}$, —$NR^6C(O)R^{11}$, —$NR^6C(O)OR^{11}$, —$N(R^6)C(O)(CR^9R^{10})_wNR^6R^7$, —$NR^6C(O)NR^6R^7$, —$NR^6C(O)NR^6(CR^9R^{10})_wNR^6R^7$, —$NR^6(CR^9R^{10})_wS(O)_{0,1,2}R^{11}$, —$NR^6(CR^9R^{10})_wS(O)_{0,1,2}NR^6R^7$, —$NR^6(CR^9R^{10})_wNR^6R^7S(O)_{0,1,2}R^{11}$, —$NR^6(CR^9R^{10})_wNR^6S(O)_{0,1,2}NR^6R^6$, —$NR^6C(=NR^8)NR^6R^6$, —$N(R^6)C(=NR^8)R^{11}$, —$NR^6(CR^9R^{10})_wN$ $(R^6)C(=NR^8)R^{11}$, $-NR^6(CR^9R^{10})_wC(=NR^8)NR^6R^7$, $-NR^6(CR^9R^{10})_wN(R^6)C(=NR^8)NR^6R^7$, $-NR^6(CR^9R^{10})_wNR^6C(=O)NR^6R^7$, $-NR^6(CR^9R^{10})_wNR^6C(=O)OR^{11}$, $-NR^6SO_2R^{11}$, $-NR^6(CR^9R^{10})_wCO_2H$, $-NR^6(CR^9R^{10})_wCO_2R^{11}$, $-NR^6(CR^9R^{10})_wC(O)NR^6R^7$, $-N(R^6)$-Heteroaryl-$NR^6R^7$, $-N(R^6)$-Heterocyclyl-$NR^6R^7$, $-NR^6(CR^9R^{10})_v$Heteroaryl, $-NR^6(CR^9R^{10})_v$Heterocyclyl, $-NR^6(CR^9R^{10})_wNR^6$-Heteroaryl, $-NR^6(CR^9R^{10})_wNR^6$-Heterocyclyl, $-CN$, $-(CR^9R^{10})CN$, $-(CR^9R^{10})_wNR^6R^7$, $-(CR^9R^{10})_vOH$, $-(CR^9R^{10})_wOR^{11}$, $-(CR^9R^{10})_vOC(O)R^{11}$, $-(CR^9R^{10})_vOC(O)NR^6R^6$, $-(CR^9R^{10})_vO(CR^9R^{10})_wOR^{11}$, $-(CR^9R^{10})_vO(CR^9R^{10})_wOH$, $-(CR^9R^{10})_vO(CR^9R^{10})_wNR^6R^7$, $-(CR^9R^{10})_wNR^6(CR^9R^{10})_wOH$, $-(CR^9R^{10})_wNR^6(CR^9R^{10})_wOR^{11}$, $-(CR^9R^{10})_wC(O)NR^6R^7$, $-(CR^9R^{10})_wC(O)NR^6NR^6R^7$, $-(CR^9R^{10})_wC(O)NR^6(CR^9R^{10})_wNR^6R^7$, $-(CR^9R^{10})_wC(O)NR^6(CR^9R^{10})_wOR^{11}$, $-(CR^9R^{10})_wN(R^6)C(O)R^{11}$, $-(CR^9R^{10})_wN(R^6)C(O)OR^{11}$, $-(CR^9R^{10})_wN(R^6)C(O)NR^6R^7$, $-(CR^9R^{10})_wN(R^6)C(O)(CR^9R^{10})_wNR^6R^7$, $-(CR^9R^{10})_wN(R^6)C(O)(CR^9R^{10})_vONR^6R^7$, $-(CR^9R^{10})_wN(R^6)S(O)_{0,1,2}R^{11}$, $-(CR^9R^{10})_wN(R^6)S(O)_{0,1,2}NR^6R^7$, $-(CR^9R^{10})_wS(O)_{0,1,2}NR^6R^7$, $-(CR^9R^{10})_vS(O)_{0,1,2}(CR^9R^{10})_wNR^6R^7$, $-(CR^9R^{10})_wNR^6(CR^9R^{10})_wNR^6R^7$, $-(CR^9R^{10})_wN(R^6)CH(=NR^8)$, $-(CR^9R^{10})_wN(R^6)C(=NR^8)R^{11}$, $-(CR^9R^{10})_wC(=NR^8)NR^6R^7$, $-(CR^9R^{10})_wN(R^6)C(=NR^8)NR^6R^7$, $-(CR^9R^{10})_wC(=NR^8)NR^6C(=NR^8)NR^6R^7$, $-(CR^9R^{10})_v$Heteroaryl-$NR^6R^7$, $-(CR^9R^{10})_v$Heterocyclyl-$NR^6R^7$, $-(CR^9R^{10})_v$Heterocyclyl-$(NR^6R^7)_2$, $-(CR^9R^{10})_v$Heteroaryl-$N(R^6)C(=NR^8)NR^6R^7$, $-(CR^9R^{10})_v$Heterocyclyl-$N(R^6)C(=NR^8)NR^6R^7$, $-(CR^9R^{10})_v$Heteroaryl, $-(CR^9R^{10})_v$Heterocyclyl, $-C(O)OH$, $-C(O)OR^{11}$, $-C(O)NR^6R^7$, $-C(O)NR^6(CR^9R^{10})_wNR^6R^7$, $-C(O)NR^6O(CR^9R^{10})_wNR^6R^7$, $-C(O)NR^6(CR^9R^{10})_wOH$, $-C(O)NR^6(CR^9R^{10})_wOR^{11}$, $-C(=NR^8)NR^6R^7$, $-C(=NR^8)NR^6C(O)R^{11}$, $-S(O)_{0,1,2}R^{11}$, $-S(O)_{0,1,2}(CR^9R^{10})_wNR^6R^7$, $-S(O)_{0,1,2}(CR^9R^{10})_wOH$, $-S(O)_{0,1,2}(CR^9R^{10})_wOR^{11}$, $-SO_2NR^6R^7$, $-S(O)_{0,1,2}NR^6(CR^9R^{10})_wNR^6R^7$, $-S(O)_{0,1,2}(CR^9R^{10})_wN(R^6)C(=NR^8)R^{11}$, $-S(O)_{0,1,2}(CR^9R^{10})_wC(=NR^8)NR^6R^7$, $-S(O)_{0,1,2}(CR^9R^{10})_wN(R^6)C(=NR^8)NR^6R^7$, $-S(O)_{0,1,2}(CR^9R^{10})_wC(=NR^8)NR^6C(=NR^8)NR^6R^7$, $-Si(R^{11})_3$, $-NR^6R^7R^{12+}Q^-$, $-(CR^9R^{10})_wNR^6R^7R^{12+}Q^-$, $-NR^6(CR^9R^{10})_wNR^6R^7R^{12+}Q^-$, $-NR^6R^{12+}(CR^9R^{10})_wNR^6R^7R^{12+}Q^-_2$, and $-O(CR^9R^{10})_wNR^6R^6R^{12+}Q^-$;

wherein:
T is pyridine-1-yl, pyrimidin-1-yl, or thiazol-3-yl;
Q is a pharmaceutically acceptable counterion; and
v is 1-4;
w is 2-4;
or two Ys taken together with the atoms to which they are attached form an optionally substituted carbocycle or an optionally substituted heterocycle;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, $-OH$, $-OR^{11}$, $-NR^6R^7$, and $-SR^{11}$;

$R^e$ is hydrogen, optionally substituted $C_1$-$C_6$ alkyl, or optionally substituted $C_3$-$C_6$ cycloalkyl;

$R^x$ is optionally substituted $C_1$-$C_6$ alkyl, optionally substituted $C_3$-$C_6$ cycloalkyl, or a pharmaceutically acceptable boronate ester group;

$R^1$ is hydrogen, $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;
each $R^{30}$ is independently $-CH_2-$, $-CH(CH_3)-$, $-C(CH_3)_2-$, or optionally substituted 1,1'-cyclopropylene;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two $R^{31}$ are taken together with the Nitrogen to which they are attached to form a $C_3$-$C_8$ heterocyclyl;

each $R^2$ and $R^3$ are independently selected from the group consisting of hydrogen, fluoro, chloro, bromo, optionally substituted $C_1$-$C_6$ alkyl, optionally substituted $C_3$-$C_6$ cycloalkyl, $-OH$, $-OR^{11}$, $-SR^{11}$, $-NR^6R^7$, $-(CR^9R^{10})_vC(O)NR^6R^7$, $-(CR^9R^{10})_vC(O)OH$, $-(CR^9R^{10})_vOH$, $-(CR^9R^{10})_vNR^6R^7$, and $-(CR^9R^{10})_vN(R^6)C(=NR^8)NR^6R^7$;

or $R^2$ and $R^3$ on the same carbon are taken together to form an oxo or optionally substituted oxime;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, $-OH$, $-CN$, $-S(O)_2R^{11}$, $-S(O)_2NH_2$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, $-OH$, $-OR^{11}$, $-CN$, $-NO_2$, $-NR_6$, optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, $-OH$, $-OR^{11}$, $-SR^{11}$, $-NR^6R^7$, $-NR^6C(O)R^{11}$, —(CR$^a$R$^b$)$_v$NR$^6$R$^7$, —(CR$^a$R$^b$)$_v$C(O)NR$^6$R$^7$, —C(O)NR$^6$R$^7$, —C(O)OR$^{11}$, —C(O)OH, —NR$^6$SO$_2$R$^{11}$, optionally substituted heterocyclyl, optionally substituted aryl, and optionally substituted heteroaryl;

or R$^9$ and R$^{10}$ taken together with the carbon atom to which they are attached form an optionally substituted oxime, an optionally substituted carbocycle, or an optionally substituted heterocycle;

R$^{11}$ is optionally substituted C$_1$-C$_6$ alkyl, optionally substituted C$_3$-C$_6$ cycloalkyl, optionally substituted heteroaryl, optionally substituted heterocyclyl, or optionally substituted aryl; and R$^{12}$ is optionally substituted C$_1$-C$_6$ alkyl or optionally substituted C$_3$-C$_6$ cycloalkyl.

In one aspect, provided herein are compounds of Formula (I) or Formula (II), or pharmaceutically acceptable salts, solvates, polymorphs, stereoisomers, tautomers, prodrugs, metabolites, N-oxides, or isomers thereof:

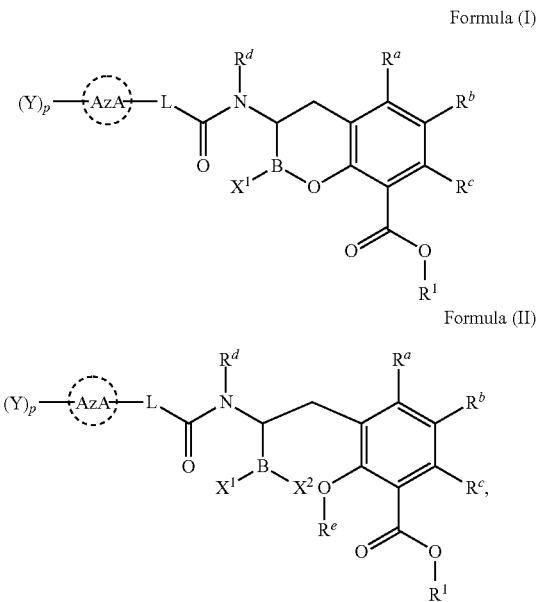

Formula (I)

Formula (II)

wherein:
L is —(CR$^2$R$^3$)$_n$—;
n is 0, 1, 2, 3, 4, 5, or 6;
p is 0, 1, 2 or 3;
X$^1$ and X$^2$ are independently selected from —OH, —OR$^X$, and F;
AzA is a five-membered heteroaromatic ring system bearing at least one heteroatom from the group consisting of N, O, and S;
each Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$), —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_w$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_w$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_v$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_v$OH, —(CR$^9$R$^{10}$)$_w$NR$^6$(CR$^9$R$^{10}$)$_w$OR$^{11}$, —(CR$^9$R$^{10}$)C(O)NR$^6$R$^7$, —(CR$^9$R$^{10}$)C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)OR$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_w$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$)—(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_v$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion; and
v is 1-4;
w is 2-4;

or two Ys taken together with the carbon atoms to which they are attached form an optionally substituted carbocycle or an optionally substituted heterocycle;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —OR$^{11}$, —NR$^6$R$^7$, and —SR$^{11}$;

$R^e$ is hydrogen, optionally substituted $C_1$-$C_6$ alkyl, or optionally substituted $C_3$-$C_6$ cycloalkyl;

$R^x$ is optionally substituted $C_1$-$C_6$ alkyl, optionally substituted $C_3$-$C_6$ cycloalkyl, or a pharmaceutically acceptable boronate ester group;

$R^1$ is hydrogen, $R^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each $R^{30}$ is independently —CH$_2$—, —CH(CH$_3$)—, —C(CH$_3$)$_2$—, or optionally substituted 1,1'-cyclopropylene;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two $R^{31}$ are taken together with the Nitrogen to which they are attached to form a $C_3$-$C_8$ heterocyclyl;

each $R^2$ and $R^3$ are independently selected from the group consisting of hydrogen, fluoro, chloro, bromo, optionally substituted $C_1$-$C_6$ alkyl, optionally substituted $C_3$-$C_6$ cycloalkyl, —OH, —OR$^{11}$, —SR$^{11}$, and NR$^6$R$^7$;

or $R^2$ and $R^3$ on the same carbon are taken together to form an oxo or optionally substituted oxime;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —S(O)$_2$R$^{11}$, —S(O)$_2$NH$_2$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, —OH, —OR$^{11}$, —CN, —NO$_2$, —NR$_6$, optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR$^{11}$, —SR$^{11}$, —NR$^6$R$^7$, —NR$^6$C(O)R$^{11}$, —(CR$^a$R$^b$)$_x$NR$^6$R$^7$, —(CR$^a$R$^b$)$_x$C(O)NR$^6$R$^7$, —C(O)NR$^6$R$^7$, —NR$^6$SO$_2$R$^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In one aspect of a compound of Formula (I) or Formula (II), n is 1, 2, 3, 4, 5, or 6 and AzA is a five-membered heteroaromatic ring system bearing at least three heteroatoms from the group consisting of N, O, and S.

In another aspect of a compound of Formula (I) or Formula (II), AzA is a five-membered heteroaromatic ring system bearing at least one N heteratom.

In another aspect of a compound of Formula (I) or Formula (II), n is 1, 2, 3, 4, 5, or 6; p is 1, 2, or 3; and AzA is a five-membered heteroaromatic ring system bearing at least two heteroatoms from the group consisting of N, O, and S; provided that AzA is not thiazolyl.

In another aspect of a compound of Formula (I) or Formula (II), n is 1, 2, 3, 4, 5, or 6; provided that when AzA is a five-membered heteroaromatic ring system bearing two heteroatoms from the group consisting of N, O, and S, then p is 1, 2, or 3; and provided that when AzA is thiazolyl at least one Y is not —NR$^6$R$^7$ or —NR$^6$C(O)R$^{11}$; and $R^2$ and $R^3$ on the same carbon cannot be taken together to form an optionally substituted oxime.

In another aspect of a compound of Formula (I) or Formula (II), n is 1, 2, 3, 4, 5, or 6; p is 1, 2, or 3; and Y is not —NR$^6$R$^7$, —NR$^6$C(O)R$^{11}$, or —N(R$^6$)C(O)(CR$^9$R$^{10}$)$_x$NR$^6$R$^7$.

In another aspect of a compound of Formula (I) or Formula (II), n is 2, 3, 4, 5, or 6 and p is 1, 2, or 3.

In another aspect of a compound of Formula (I) or Formula (II), n is 0, 1, 2, 3, 4, 5, or 6; p is 1, 2, or 3; and Y is not phenyl, methyl, —NH$_2$, —NHC(O)CH$_3$, —NHC(O)CH$_2$NH$_2$, or

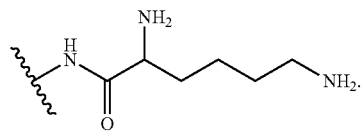 [SMILES: *NC(=O)C(N)CCCCN]

In another aspect of a compound of Formula (I) or Formula (II), AzA is a five-membered heteroaromatic ring system bearing at least three N heteroatoms.

In another aspect of a compound of Formula (I) or Formula (II), AzA is a five-membered heteroaromatic ring system bearing four N heteroatoms.

In another aspect of a compound of Formula (I) or Formula (II), AzA is a five-membered heteroaromatic ring system bearing at least three heteroatoms from the group consisting of N, O, and S, wherein at least two heteroatoms are N; provided that when p is 1, then Y is not —$NH_2$.

In another aspect of a compound of Formula (II), the compound is not (R)-3-(2-borono-2-(imidazo[2,1-b]thiazole-6-carboxamido)ethyl)-2-hydroxybenzoic acid.

In some embodiments of a compound of Formula (I) or Formula (II), n is 1, 2, or 3. In some embodiments of a compound of Formula (I) or Formula (II), n is 0. In some embodiments of a compound of Formula (I) or Formula (II), n is 1. In some embodiments of a compound of Formula (I) or Formula (II), n is 2. In some embodiments of a compound of Formula (I) or Formula (II), n is 3. In some embodiments of a compound of Formula (I) or Formula (II), n is 4. In some embodiments of a compound of Formula (I) or Formula (II), n is 5. In some embodiments of a compound of Formula (I) or Formula (II), n is 6. In some embodiments of a compound of Formula (I) or Formula (II), n is at least 2.

In some embodiments of a compound of Formula (I) or Formula (II), each $R^2$ and $R^3$ are independently selected from the group consisting of hydrogen, fluoro, chloro, bromo, optionally substituted $C_1$-$C_6$ alkyl, optionally substituted $C_3$-$C_6$ cycloalkyl, —OH, —$OR^{11}$, —$SR^{11}$, and —$NR^6R^7$.

In some embodiments of a compound of Formula (I) or Formula (II), each $R^2$ and $R^3$ are independently selected from the group consisting of hydrogen, fluoro, chloro, optionally substituted $C_1$-$C_6$alkyl, —OH, —$OR^{11}$, —$NR^6R^7$, and and —$SR^{11}$.

In some embodiments of a compound of Formula (I) or Formula (II), each $R^2$ and $R^3$ are independently selected from the group consisting of hydrogen and $C_1$-$C_6$ alkyl optionally substituted with $NR^6R^7$ or —$SR^{11}$.

In some embodiments of a compound of Formula (I) or Formula (II), $R^2$ and $R^3$ are as defined above and $R^6$ and $R^7$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In some embodiments, $R^6$ and $R^7$ are independently selected from the group consisting of hydrogen and optionally substituted $C_1$-$C_6$ alkyl. In some embodiments, $R^6$ and $R^7$ are hydrogen. In some embodiments, $R^6$ is hydrogen and $R^7$ is $C_1$-$C_6$ alkyl. In some embodiments, $R^6$ and $R^7$ are independently $C_1$-$C_6$ alkyl.

In some embodiments of a compound of Formula (I) or Formula (II), $R^2$ and $R^3$ are as defined above and $R^{11}$ is optionally substituted $C_1$-$C_6$ alkyl.

In some embodiments of a compound of Formula (I) or Formula (II), each $R^2$ and $R^3$ are independently selected from the group consisting of hydrogen, fluoro, chloro, bromo, $C_1$-$C_6$ alkyl, and —$CF_3$. In some embodiments, each $R^2$ and $R^3$ are hydrogen. In some embodiments, each $R^2$ and $R^3$ are independently hydrogen or $C_1$-$C_6$ alkyl. In some embodiments, each $R^2$ and $R^3$ are independently hydrogen or methyl. In some embodiments, each $R^2$ and $R^3$ are methyl. In some embodiments, when n is at least 2, two $R^2$ on adjacent carbons are taken together to form a double bond; or two $R^2$ and two $R^3$ on adjacent carbons are taken together to form a triple bond. In some embodiments, $R^2$ and $R^3$ on the same carbon are taken together to form an oxo or optionally substituted oxime. In some embodiments, $R^2$ and $R^3$ on the same carbon cannot be taken together to form an optionally substituted oxime. In some embodiments, $R^2$ and $R^3$ on the same carbon are taken together to form an optionally substituted spiro-carbocycle or optionally substituted spiro-heterocycle with the carbon to which they are attached. In some embodiments, when n is at least 2, two $R^2$ on different carbons are taken together form an optionally substituted carbocycle or optionally substituted heterocycle with the carbons to which they are attached.

In some embodiments of a compound of Formula (I) or Formula (II), n is 1, 2, or 3 and each $R^2$ and $R^3$ are independently selected from the group consisting of hydrogen, fluoro, chloro, bromo, $C_1$-$C_6$ alkyl, and —$CF_3$.

In some embodiments of a compound of Formula (I) or Formula (II), n is 1, 2, or 3 and each $R^2$ and $R^3$ are independently selected from the group consisting of hydrogen and $C_1$-$C_6$ alkyl.

In some embodiments of a compound of Formula (I) or Formula (II), n is 1, 2, or 3 and each $R^2$ and $R^3$ are hydrogen. In some embodiments of a compound of Formula (I) or Formula (II), n is 1 and each $R^2$ and $R^3$ are hydrogen. In some embodiments of a compound of Formula (I) or Formula (II), n is 2 and each $R^2$ and $R^3$ are hydrogen. In some embodiments of a compound of Formula (I) or Formula (II), n is 3 and each $R^2$ and $R^3$ are hydrogen.

In some embodiments of a compound of Formula (I) or Formula (II), AzA is pyrrolyl, thiophenyl, furanyl, imidazolyl, pyrazolyl, thiazolyl, oxazolyl, isoxazolyl, isothiazolyl, triazolyl, thiadiazolyl, oxadiazolyl, or tetrazolyl. In some embodiments, AzA is imidazolyl, pyrazolyl, thiazolyl, oxazolyl, triazolyl, thiadiazolyl, oxadiazolyl, or tetrazolyl. In some embodiments, AzA is triazolyl, thiadiazolyl, oxadiazolyl, or tetrazolyl. In some embodiments, AzA is triazolyl. In some embodiments, AzA is 1,2,3-triazolyl or 1,2,4-triazolyl. In some embodiments, AzA is N-linked 1,2,3-triazolyl or N-linked 1,2,4-triazolyl. In some embodiments, AzA is N-linked 1,2,3-triazolyl or N-linked 1,2,4-triazolyl and p is 0. In some embodiments, AzA is N-linked 1,2,3-triazolyl or N-linked 1,2,4-triazolyl and p is 1. In some embodiments, AzA is N-linked 1,2,3-triazolyl or N-linked 1,2,4-triazolyl and p is 2. In some embodiments, AzA is C-linked 1,2,3-triazolyl or C-linked 1,2,4-triazolyl. In some embodiments, AzA is C-linked 1,2,3-triazolyl or C-linked 1,2,4-triazolyl and p is 0. In some embodiments, AzA is C-linked 1,2,3-triazolyl or C-linked 1,2,4-triazolyl and p is 1. In some embodiments, AzA is C-linked 1,2,3-triazolyl or C-linked 1,2,4-triazolyl and p is 2. In some embodiments, AzA is tetrazoyl. In some embodiments, AzA is N-linked tetrazoyl. In some embodiments, AzA is N-linked tetrazoyl and p is 0. In some embodiments, AzA is N-linked tetrazoyl and p is 1. In some embodiments, AzA is C-linked tetrazoyl. In some embodiments, AzA is C-linked tetrazoyl and p is 0. In some embodiments, AzA is C-linked tetrazoyl and p is 1. In some embodiments, AzA is not thiazolyl. In some embodiments, AzA is not pyrazolyl. In some embodiments, AzA is not isoxazolyl.

In some embodiments of a compound of Formula (I) or Formula (II), $(Y)_p$-AzA is selected from:

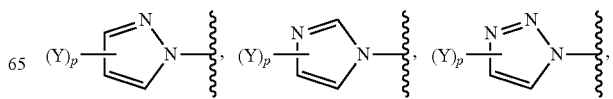

-continued
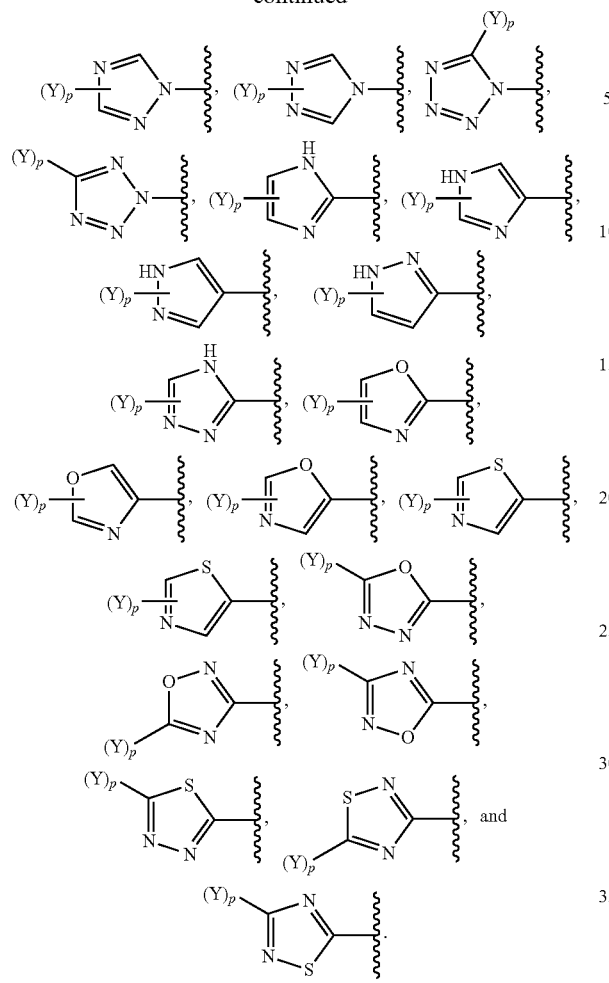
In some embodiments of a compound of Formula (I) or Formula (II), $(Y)_p$-AzA is selected from:
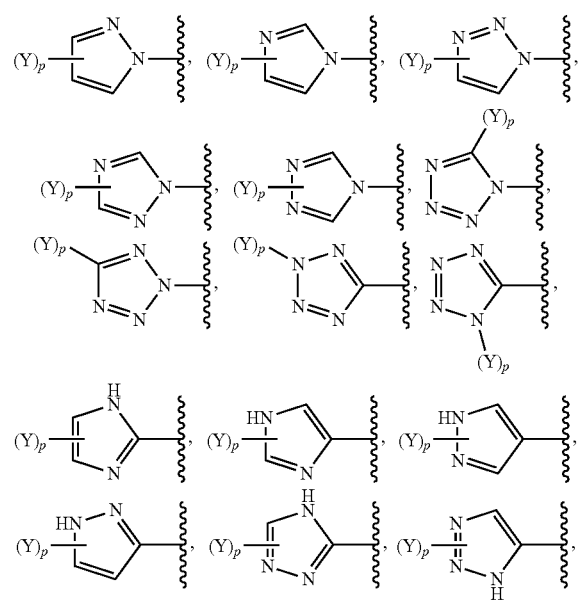
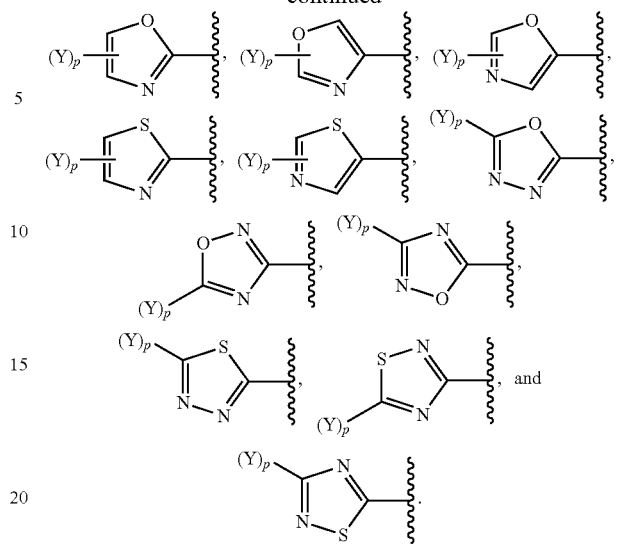
In some embodiments of a compound of Formula (I) or Formula (II), $(Y)_p$-AzA is selected from:
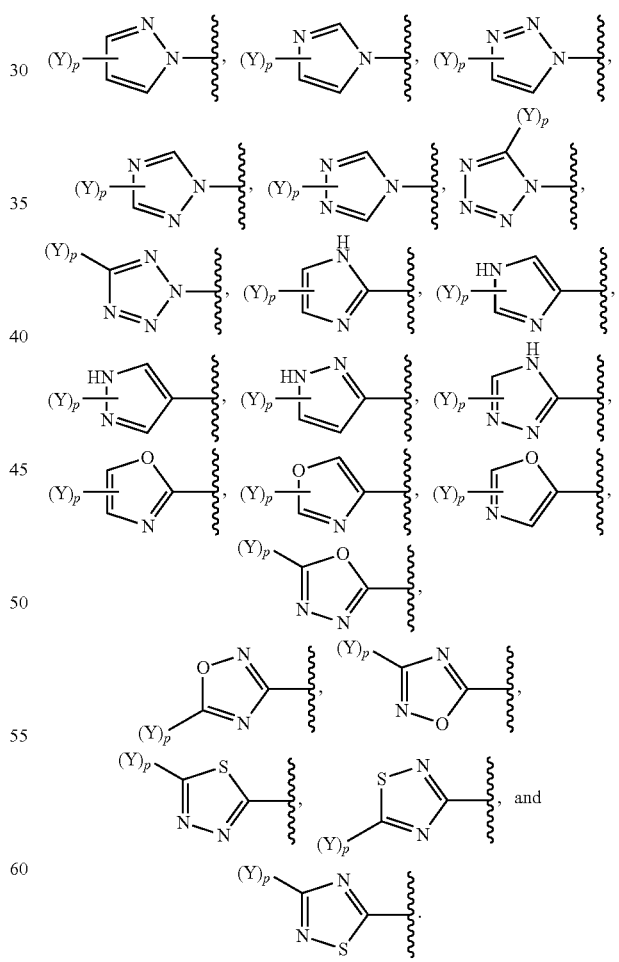
In some embodiments of a compound of Formula (I) or Formula (II), $(Y)_p$-AzA is selected from:

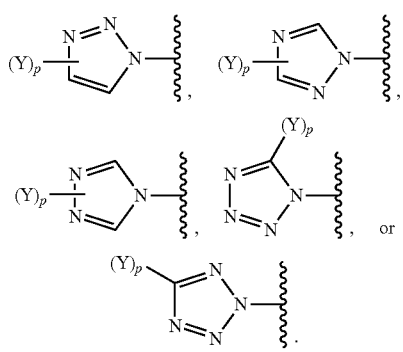

In some embodiments of a compound of Formula (I) or Formula (II), $(Y)_p$-AzA is selected from:

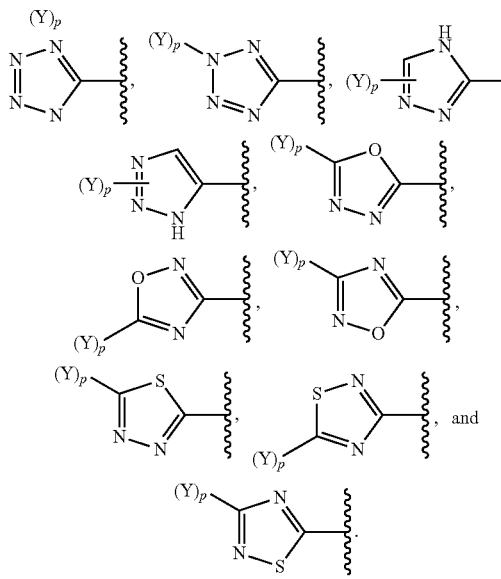

In some embodiments of a compound of Formula (I) or Formula (II), $(Y)_p$-AzA is selected from:

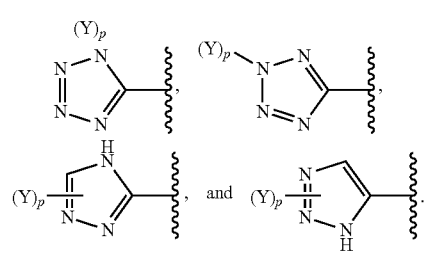

In some embodiments of a compound of Formula (I) or Formula (II), $(Y)_p$-AzA is selected from:

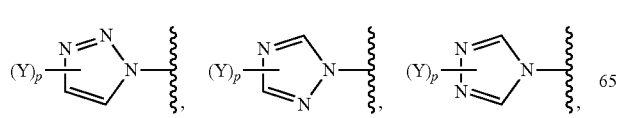

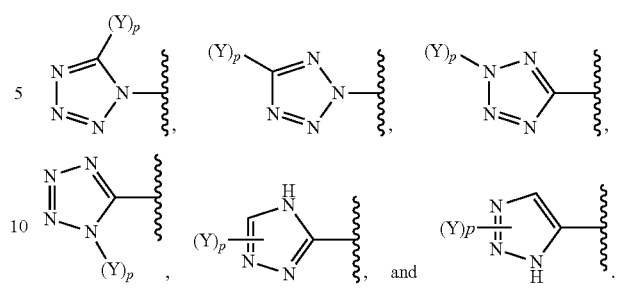

In some embodiments of a compound of Formula (I) or Formula (II), $(Y)_p$-AzA is selected from:

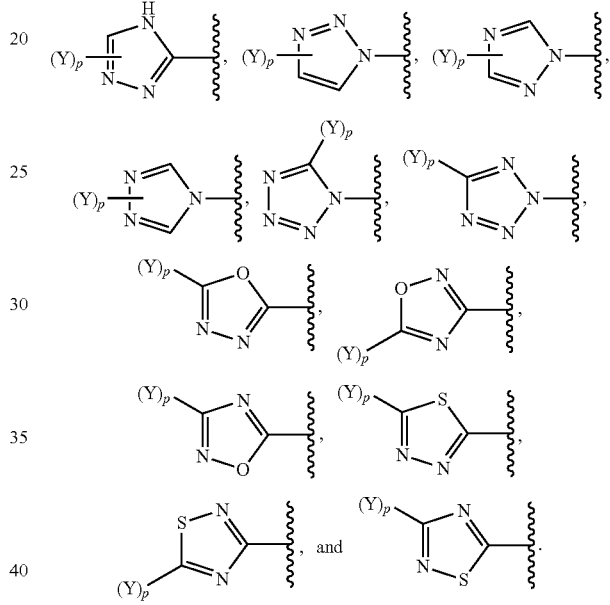

In some embodiments of a compound of Formula (I) or Formula (II), $(Y)_p$-AzA is selected from:

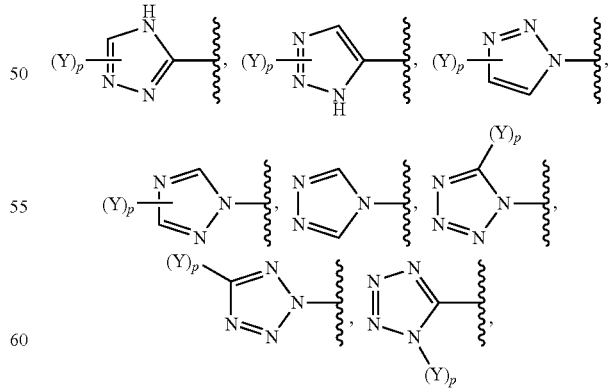

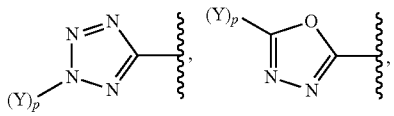

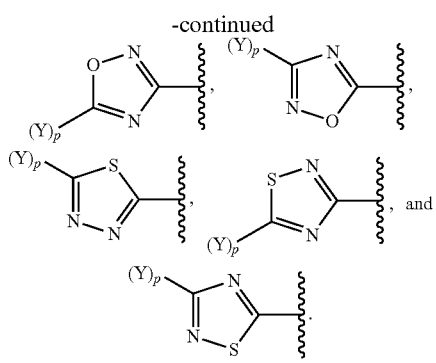, and

In some embodiments of a compound of Formula (I) or Formula (II), $(Y)_p$-AzA is selected from:

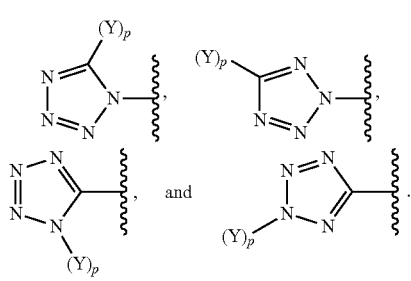

In some embodiments of a compound of Formula (I) or Formula (II), $(Y)_p$-AzA is selected from:

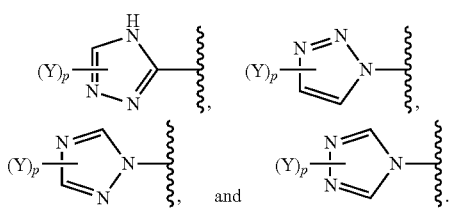

In some embodiments of a compound of Formula (I) or Formula (II), $(Y)_p$-AzA is selected from:

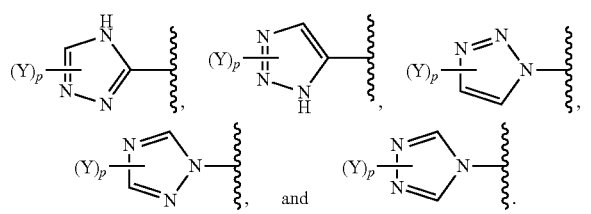

In some embodiments of a compound of Formula (I) or Formula (II), $(Y)_p$-AzA is selected from:

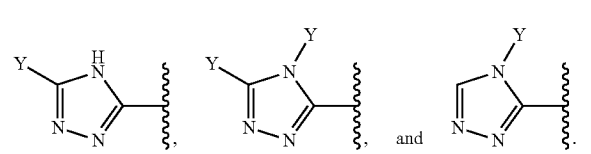

In some embodiments of a compound of Formula (I) or Formula (II), $(Y)_p$-AzA is selected from:

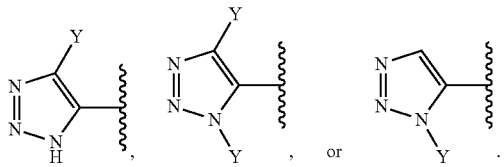

In some embodiments of a compound of Formula (I) or Formula (II), $(Y)_p$-AzA is selected from:

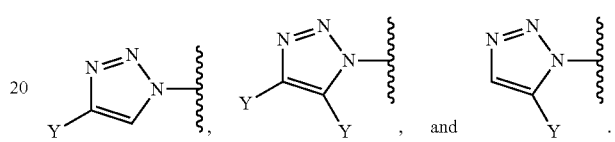

In some embodiments of a compound of Formula (I) or Formula (II), $(Y)_p$-AzA is selected from:

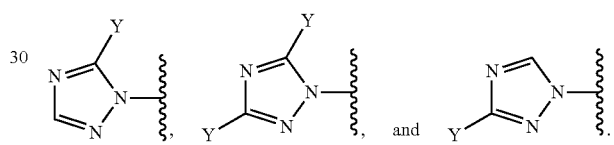

In some embodiments of a compound of Formula (I) or Formula (II), $(Y)_p$-AzA is selected from:

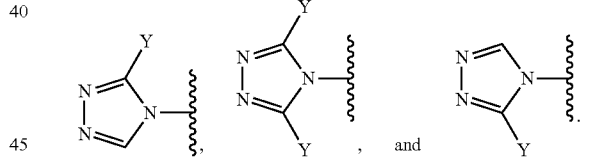

In some embodiments of a compound of Formula (I) or Formula (II), $(Y)_p$-AzA is selected from:

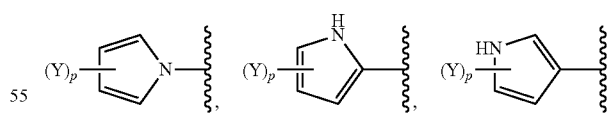

In some embodiments of a compound of Formula (I) or Formula (II), $(Y)_p$-AzA is selected from:

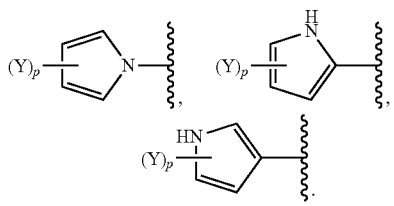

In some embodiments of a compound of Formula (I) or Formula (II), at least one Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_w$OH, —$O(CR^9R^{10})_w OR^{11}$, —$O(CR^9R^{10})_w NR^6R^7$, —$O(CR^9R^{10})_w NR^6C(O)R^{11}$, —$O(CR^9R^{10})_w NR^6C(O)OR^{11}$, —$O(CR^9R^{10})_w NR^6C(O)NR^6R^7$, —$O(CR^9R^{10})_w C(O)NR^6R^7$, —$O(CR^9R^{10})_w NR^6S(O)_{0,1,2}R^{11}$, —$O(CR^9R^{10})_w NR^6S(O)_{0,1,2}NR^6R^7$, —$O(CR^9R^{10})_w S(O)_{0,1,2}R^{11}$, —$O(CR^9R^{10})_w S(O)_{0,1,2}NR^6R^7$, —$O(CR^9R^7)_v C(=NR^8)NR^6R^7$, —$O(CR^9R^{10})_w N(R^6)C(=NR^8)R^{11}$, —$O(CR^9R^{10})_w C(=NR^8)NR^6C(=NR^8)NR^6R^7$, —$O(CR^9R^{10})_w N(R^6)C(=NR^8)NR^6R^7$, —$O(CR^9R^{10})_w S(O)_{0,1,2}R^{11}$, —$O(CR^9R^{10})_w S(O)_{0,1,2}NR^6R^7$, —$OC(O)R^{11}$, —$OC(O)(CR^9R^{10})_w NR^6R^7$, —$OC(O)NR^6R^7$, —$OC(O)OR^{11}$, —$OC(O)NR^6(CR^9R^{10})_w NR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_w NR^6$-Heteroaryl, —$O(CR^9R^{10})_w NR^6$-Heterocyclyl, —$O(CR^9R^{10})_w$O-Heterocyclyl, —$NR^6R^7$, —$NR^6(CR^9R^{10})_w NR^6R^7$, —$NR^6(CR^9R^{10})_w$OH, —$NR^6(CR^9R^{10})_w OR^{11}$, —$NR^6C(O)R^{11}$, —$NR^6C(O)OR^{11}$, —$N(R^6)C(O)(CR^9R^{10})_w NR^6R^7$, —$NR^6C(O)NR^6R^7$, —$NR^6C(O)NR^6(CR^9R^{10})_w NR^6R^7$, —$NR^6(CR^9R^{10})_w S(O)_{0,1,2}R^{11}$, —$NR^6(CR^9R^{10})_w S(O)_{0,1,2}NR^6R^7$, —$NR^6(CR^9R^{10})_w NR^6R^7 S(O)_{0,1,2}R^{11}$, —$NR^6(CR^9R^{10})_w NR^6S(O)_{0,1,2}NR^6R^6$, —$NR^6C(=NR^8)NR^6R^6$, —$N(R^6)C(=NR^8)R^{11}$, —$NR^6(CR^9R^{10})_w N(R^6)C(=NR^8)R^{11}$, —$NR^6(CR^9R^{10})_w C(=NR^8)NR^6R^7$, —$NR^6(CR^9R^{10})_w N(R^6)C(=NR^8)NR^6R^7$, —$NR^6(CR^9R^{10})_w NR^6C(=O)R^{11}$, —$NR^6(CR^9R^{10})_w NR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_w NR^6$-Heteroaryl, —$NR^6(CR^9R^{10})_w NR^6$-Heterocyclyl, —CN, —$(CR^9R^{10})_v$CN, —$(CR^9R^{10})_w NR^6R^7$, —$(CR^9R^{10})_w$OH, —$(CR^9R^{10})_v OR^{11}$, —$(CR^9R^{10})_v OC(O)R^{11}$, —$(CR^9R^{10})_v OC(O)NR^6R^6$, —$(CR^9R^{10})_v O(CR^9R^{10})_w OR^{11}$, —$(CR^9R^{10})_v O(CR^9R^{10})_w$OH, —$(CR^9R^{10})_v O(CR^9R^{10})_w NR^6R^7$, —$(CR^9R^{10})_v NR^6(CR^9R^{10})_w$OH, —$(CR^9R^{10})_w NR^6(CR^9R^{10})_w OR^{11}$, —$(CR^9R^{10})_v C(O)NR^6R^7$, —$(CR^9R^{10})_v C(O)NR^6(CR^9R^{10})_w NR^6R^7$, —$(CR^9R^{10})_w C(O)NR^6(CR^9R^{10})_w OR^{11}$, —$(CR^9R^{10})_w N(R^6)C(O)R^{11}$, —$(CR^9R^{10})_w N(R^6)C(O)OR^{11}$, —$(CR^9R^{10})_w N(R^6)C(O)NR^6R^7$, —$(CR^9R^{10})_w N(R^6)C(O)(CR^9R^{10})_w NR^6R^7$, —$(CR^9R^{10})_w N(R^6)S(O)_{0,1,2}R^{11}$, —$(CR^9R^{10})_w N(R^6)S(O)_{0,1,2}NR^6R^7$, —$(CR^9R^{10})_w S(O)_{0,1,2}NR^6R^7$, —$(CR^9R^{10})_w NR^6(CR^9R^{10})_w NR^6R^7$, —$(CR^9R^{10})_w N(R^6)$, —$(CR^9R^{10})_w N(R^6)CH(=NR^8)$, —$(CR^9R^{10})_w N(R^6)C(=NR^8)R^{11}$, —$(CR^9R^{10})_w C(=NR^8)NR^6R^7$, —$(CR^9R^{10})_v N(R^6)C(=NR^8)NR^6R^7$, —$(CR^9R^{10})_w C(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_v$Heteroaryl, —$(CR^9R^{10})_v$Heterocyclyl, —C(O)OH, —$C(O)OR^{11}$, —$C(O)NR^6R^7$, —$C(O)NR^6(CR^9R^{10})_w NR^6R^7$, —$C(O)NR^6(CR^9R^{10})_w$OH, —$C(O)NR^6(CR^9R^{10})_w OR^{11}$, —$C(=NR^8)NR^6R^7$, —$C(=NR^8)NR^6C(O)R^{11}$, —$S(O)_{0,1,2}R^{11}$, —$S(O)_{0,1,2}(CR^9R^{10})_w NR^6R^7$, —$S(O)_{0,1,2}(CR^9R^{10})_w$OH, —$S(O)_{0,1,2}(CR^9R^{10})_w OR^{11}$, —$SO_2NR^6R^7$, —$S(O)_{0,1,2}NR^6(CR^9R^{10})_w NR^6R^7$, —$S(O)_{0,1,2}(CR^9R^{10})_w N(R^6)C(=NR^8)R^{11}$, —$S(O)_{0,1,2}(CR^9R^{10})_w C(=NR^8)NR^6R^7$, —$S(O)_{0,1,2}(CR^9R^{10})_w N(R^6)C(=NR^8)NR^6R^7$, —$S(O)_{0,1,2}C(=NR^8)NR^6R^7$, —$Si(R^{11})_3$, —$NR^6R^7R^{12+}Q^-$, —$(CR^9R^{10})_w NR^6R^7R^{12+}Q^-$, —$NR^6(CR^9R^{10})_w NR^6R^7R^{12+}Q^-$, —$NR^6R^{12+}(CR^9R^{10})_v NR^6R^7R^{12+}Q^-_2$, —$(CR^9R^{10})_v(T)^+Q^-$, and —$O(CR^9R^{10})_w NR^6R^6R^{12+}Q^-$;

wherein:
T is pyridine-1-yl, pyrimidin-1-yl, or thiazol-3-yl;
Q is a pharmaceutically acceptable counterion; and
v is 1-4;
w is 2-4;

In some embodiments of a compound of Formula (I) or Formula (II), at least one Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_w$OH, —$O(CR^9R^{10})_w OR^{11}$, —$O(CR^9R^{10})_w NR^6R^7$, —$O(CR^9R^{10})_w NR^6C(O)R^{11}$, —$O(CR^9R^{10})_w NR^6C(O)OR^{11}$, —$O(CR^9R^{10})_w NR^6C(O)NR^6R^7$, —$O(CR^9R^{10})_w C(O)NR^6R^7$, —$O(CR^9R^{10})_w NR^6S(O)_{0,1,2}R^{11}$, —$O(CR^9R^{10})_w NR^6S(O)_{0,1,2}NR^6R^7$, —$O(CR^9R^{10})_w S(O)_{0,1,2}R^{11}$, —$O(CR^9R^{10})_w S(O)_{0,1,2}NR^6R^7$, —$O(CR^6R^7)_v C(=NR^8)NR^6R^7$, —$O(CR^9R^{10})_w(R^6)(=NR^8)R^{11}$, —$O(CR^9R^{10})_v C(=NR^8)NR^6C(=NR^8)NR^6R^7$, —$O(CR^9R^{10})_w$, —$(R^6)C(=NR^8)NR^6R^7$, —$O(CR^9R^{10})_w S(O)_{0,1,2}R^{11}$, —$O(CR^9R^{10})_w S(O)_{0,1,2}NR^6R^7$, —$OC(O)R^{11}$, —$OC(O)(CR^9R^{10})_w NR^6R^7$, —$OC(O)NR^6R^7$, —$OC(O)OR^{11}$, —$OC(O)NR^6(CR^9R^{10})_w NR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_w NR^6$-Heteroaryl, —$O(CR^9R^{10})_w NR^6$-Heterocyclyl, —$O(CR^9R^{10})_w$O-Heterocyclyl, —$NR^6R^7$, —$NR^6(CR^9R^{10})_w NR^6R^7$, —$NR^6(CR^9R^{10})_w$OH, —$NR^6(CR^9R^{10})_w OR^{11}$, —$NR^6C(O)R^{11}$, —$NR^6C(O)OR^{11}$, —$N(R^6)C(O)(CR^9R^{10})_w NR^6R^7$, —$NR^6C(O)NR^6R^7$, —$NR^6C(O)NR^6(CR^9R^{10})_w NR^6R^7$, —$NR^6(CR^9R^{10})_w S(O)_{0,1,2}R^{11}$, —$NR^6(CR^9R^{10})_w S(O)_{0,1,2}NR^6R^7$, —$NR^6(CR^9R^{10})_w NR^6R^7 S(O)_{0,1,2}R^{11}$, —$NR^6(CR^9R^{10})_w NR^6S(O)_{0,1,2}NR^6R^6$, —$NR^6C(=NR^8)NR^6R^6$, —$N(R^6)C(=NR^8)R^{11}$, —$NR^6(CR^9R^{10})_w N(R^6)C(=NR^8)R^{11}$, —$NR^6(CR^9R^{10})_w C(=NR^8)NR^6R^7$, —$NR^6(CR^9R^{10})_w N(R^6)C(=NR^8)NR^6R^7$, —$NR^6(CR^9R^{10})_w NR^6C(=O)NR^6R^7$, —$NR^6(CR^9R^{10})_w NR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_w NR^6$-Heteroaryl, —$NR^6(CR^9R^{10})_w NR^6$-Heterocyclyl, —CN, —$(CR^9R^{10})_v$CN, —$(CR^9R^{10})_w NR^6R^7$, —$(CR^9R^{10})_v$OH, —$(CR^9R^{10})_v OR^{11}$, —$(CR^9R^{10})_v OC(O)R^{11}$, —$(CR^9R^{10})_v OC(O)NR^6R^6$, —$(CR^9R^{10})_v O(CR^9R^{10})_w OR^{11}$, —$(CR^9R^{10})_v O(CR^9R^{10})_w$OH, —$(CR^9R^{10})_v O(CR^9R^{10})_w NR^6R^7$, —$(CR^9R^{10})_v NR^6(CR^9R^{10})_w$OH, —$(CR^9R^{10})_v NR^6(CR^9R^{10})_w OR^{11}$, —$(CR^9R^{10})_v C(O)NR^6R^7$, —$(CR^9R^{10})_v C(O)NR^6(CR^9R^{10})_w NR^6R^7$, —$(CR^9R^{10})_v C(O)NR^6(CR^9R^{10})_w OR^{11}$, —$(CR^9R^{10})_v N(R^6)C(O)R^{11}$, —$(CR^9R^{10})_v N(R^6)C(O)OR^{11}$, —$(CR^9R^{10})_v N(R^6)C(O)NR^6R^7$, —$(CR^9R^{10})_v N(R^6)C(O)$ $-(CR^9R^{10})_v NR^6R^7$, $-(CR^9R^{10})_v N(R^6)S(O)_{0L2}R^{11}$, $-(CR^9R^{10})_v N(R^6)S(O)_{0,1,2}NR^6R^7$, $-(CR^9R^{10})_v S(O)_{0,1,2}NR^6R^7$, $-(CR^9R^{10})_v NR^6(CR^9R^{10})_w NR^6R^7$, $-(CR^9R^{10})_v N(R^6)CH(=NR^8)$, $-(CR^9R^{10})_v N(R^6)C(=NR^8)R^{11}$, $-(CR^9R^{10})_v C(=NR^8)NR^6R^7$, $-(CR^9R^{10})_v N(R^6)C(=NR^8)NR^6R^7$, $-(CR^9R^{10})_v C(=NR^8)NR^6C(=NR^8)NR^6R^7$, $-(CR^9R^{10})_v$Heteroaryl-NR$^6$R$^7$, $4CR^9R^{10})_v$Heterocyclyl-NR$^6$R$^7$, $-(CR^9R^{10})_v$Heteroaryl-N(R$^6$)C(=NR$^8$)NR$^6$R$^7$, $-(CR^9R^{10})_v$Heterocyclyl-N(R$^6$)C(=NR$^8$)NR$^6$R$^7$, $-(CR^9R^{10})_v$Heteroaryl, $-(CR^9R^{10})_v$Heterocyclyl, $-C(O)OH$, $-C(O)OR^{11}$, $-C(O)NR^6R^7$, $-C(O)NR^6(CR^9R^{10})_w NR^6R^7$, $-C(O)NR^6(CR^9R^{10})_w OH$, $-C(O)NR^6(CR^9R^{10})_w OR^{11}$, $-C(=NR^8)NR^6R^7$, $-C(=NR^8)NR^6C(O)R^{11}$, $-S(O)_{0,1,2}R^{11}$, $-S(O)_{0,1,2}(CR^9R^{10})_w NR^6R^7$, $-S(O)_{0,1,2}(CR^9R^{10})_w OH$, $-S(O)_{0,1,2}(CR^9R^{10})_w OR^{11}$, $-SO_2 NR^6R^7$, $-S(O)_{0,1,2}NR^6(CR^9R^{10})_w NR^6R^7$, $-S(O)_{0,1,2}(CR^9R^{10})_w N(R^6)C(=NR^8)R^{11}$, $-S(O)_{0,1,2}(CR^9R^{10})_w C(=NR^8)NR^6R^7$, $-S(O)_{0,1,2}(CR^9R^{10})_v N(R^6)C(=NR^8)NR^6R^7$, $-S(O)_{0,1,2}(CR^9R^{10})_v C(=NR^8)NR^6C(=NR^8)NR^6R^7$.

In some embodiments of a compound of Formula (I) or Formula (II), at least one Y is selected from the group consisting of fluoro, chloro, bromo, iodo, boronic acid, optionally substituted boronic ester, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, $-OH$, $-OR^{11}$, $-O(CR^9R^{10})_w OH$, $-O(CR^9R^{10})_w OR^{11}$, $-O(CR^9R^{10})_w NR^6R^7$, $-O(CR^9R^{10})_w NR^6 C(O)R^{11}$, $-O(CR^9R^{10})_w NR^6 C(O)OR^{11}$, $-O(CR^9R^{10})_w NR^6 C(O)NR^6R^7$, $-O(CR^9R^{10})_w C(O)NR^6R^7$, $-O(CR^9R^{10})_w NR^6 S(O)_{0,1,2}R^{11}$, $-O(CR^9R^{10})_w NR^6 S(O)_{0,1,2}NR^6R^7$, $-O(CR^9R^{10})_w S(O)_{0,1,2}R^{11}$, $-O(CR^9R^{10})_w S(O)_{0,1,2}NR^6R^7$, $-O(CR^6R^7)_v C(=NR^8)NR^6R^7$, $-O(CR^9R^{10})_w N(R^6)C(=NR^8)R^{11}$, $-O(CR^9R^{10})C(=NR^8)NR^6C(=NR^8)NR^6R^7$, $-O(CR^9R^{10})_w N(R^6)C(=NR^8)NR^6R^7$, $-O(CR^9R^{10})_w S(O)_{0,1,2}R^{11}$, $-O(CR^9R^{10})_w S(O)_{0,1,2}NR^6R^7$, $-OC(O)R^{11}$, $-OC(O)(CR^9R^{10})_w NR^6R^7$, $-OC(O)NR^6R^7$, $-OC(O)OR^{11}$, $-OC(O)NR^6(CR^9R^{10})_w NR^6R^7$, $-O$-Heteroaryl, $-O$-Heterocyclyl, $-O(CR^9R^{10})_v$Heteroaryl, $-O(CR^9R^{10})_v$Heterocyclyl, $-O(CR^9R^{10})_w NR^6$-Heteroaryl, $-O(CR^9R^{10})_w NR^6$-Heterocyclyl, $-O(CR^9R^{10})_w O$-Heterocyclyl, $-NO_2$, $-NR^6R^7$, $-NR^6(CR^9R^{10})_w NR^6R^7$, $-NR^6(CR^9R^{10})_w OH$, $-NR^6(CR^9R^{10})_w OR^{11}$, $-NR^6C(O)R^{11}$, $-NR^6C(O)OR^{11}$, $-N(R^6)C(O)(CR^9R^{10})_v NR^6R^7$, $-NR^6C(O)NR^6R^7$, $-NR^6C(O)NR^6(CR^9R^{10})_w NR^6R^7$, $-NR^6(CR^9R^{10})_w S(O)_{0,1,2}R^{11}$, $-NR^6(CR^9R^{10})_w S(O)_{0,1,2}NR^6R^7$, $-NR^6(CR^9R^{10})_w NR^6R^7S(O)_{0L2}R^{11}$, $-NR^6(CR^9R^{10})_w NR^6S(O)_{0,1,2}NR^6R^6$, $-NR^6C(=NR^8)NR^6R^6$, $-N(R^6)C(=NR^8)R^{11}$, $-NR^6(CR^9R^{10})_w N(R^6)C(=NR^8)R^{11}$, $-NR^6(CR^9R^{10})_v C(=NR^8)NR^6R^7$, $-NR^6(CR^9R^{10})_w N(R^6)C(=NR^8)NR^6R^7$, $-NR^6(CR^9R^{10})_w NR^6C(=O)NR^6R^7$, $-NR^6(CR^9R^{10})_w NR^6C(=O)OR^{11}$, $-NR^6SO_2R^{11}$, $-NR^6(CR^9R^{10})CO_2H$, $-NR^6(CR^9R^{10})CO_2R^{11}$, $-NR^6(CR^9R^{10})C(O)NR^6R^7$, $-N(R^6)$-Heteroaryl-NR$^6$R$^7$, $-N(R^6)$-Heterocyclyl-NR$^6$R$^7$, $-NR^6(CR^9R^{10})_v$Heteroaryl, $-NR^6(CR^9R^{10})_v$Heterocyclyl, $-NR^6(CR^9R^{10})_w NR^6$-Heteroaryl, $-NR^6(CR^9R^{10})_w NR^6$-Heterocyclyl, $-CN$, $-(CR^9R^{10})_v CN$, $-(CR^9R^{10})_v NR^6R^7$, $-(CR^9R^{10})_v OH$, $-(CR^9R^{10})_v OR^{11}$, $-(CR^9R^{10})_v OC(O)R^{11}$, $-(CR^9R^{10})_v OC(O)NR^6R^6$, $-(CR^9R^{10})_v O(CR^9R^{10})_w OR^{11}$, $-(CR^9R^{10})_v O(CR^9R^{10})_w OH$, $-(CR^9R^{10})_v O(CR^9R^{10})_w NR^6R^7$, $-(CR^9R^{10})_v NR^6(CR^9R^{10})_w OH$, $-(CR^9R^{10})_v NR^6$ $-(CR^9R^{10})_w OR^{11}$, $-(CR^9R^{10})_v C(O)NR^6R^7$, $-(CR^9R^{10})_v C(O)NR^6(CR^9R^{10})_w NR^6R^7$, $-(CR^9R^{10})_v C(O)NR^6(CR^9R^{10})_w OR^{11}$, $-(CR^9R^{10})_v N(R^6)C(O)R^{11}$, $-(CR^9R^{10})_v N(R^6)C(O)OR^{11}$, $-(CR^9R^{10})_v N(R^6)C(O)NR^6R^7$, $-(CR^9R^{10})_v N(R^6)C(O)(CR^9R^{10})_v NR^6R^7$, $-(CR^9R^{10})_v N(R^6)S(O)_{0,1,2}R^{11}$, $-(CR^9R^{10})_v N(R^6)S(O)_{0,1,2}NR^6R^7$, $-(CR^9R^{10})_v S(O)_{0,1,2}NR^6R^7$, $-(CR^9R^{10})_v S(O)_{0,1,2}(CR^9R^{10})_w NR^6R^7$, $-(CR^9R^{10})_v NR^6(CR^9R^{10})_w NR^6R^7$, $-(CR^9R^{10})_v N(R^6)CH(=NR^8)$, $-(CR^9R^{10})_v N(R^6)C(=NR^8)R^{11}$, $-(CR^9R^{10})_v C(=NR^8)NR^6R^7$, $-(CR^9R^{10})_v N(R^6)C(=NR^8)NR^6R^7$, $-(CR^9R^{10})_v C(=NR^8)NR^6C(=NR^8)NR^6R^7$, $-(CR^9R^{10})_v$Heteroaryl-NR$^6$R$^7$, $-(CR^9R^{10})_v$Heteroaryl(CR$^9$R$^{10}$)$_w$NR$^6$R$^7$, $-(CR^9R^{10})_v$Heterocyclyl-NR$^6$R$^7$, $-(CR^9R^{10})_v$Heterocyclyl(CR$^9$R$^{10}$)$_w$NR$^6$R$^7$, $-(CR^9R^{10})_v$Heterocyclyl-(NR$^6$R$^7$)$_2$, $-(CR^9R^{10})_v$Heteroaryl-N(R$^6$)C(=NR$^8$)NR$^6$R$^7$, $-(CR^9R^{10})_v$Heterocyclyl-N(R$^6$)C(=NR$^8$)NR$^6$R$^7$, $-(CR^9R^{10})_v$Heteroaryl, $-(CR^9R^{10})_v$Heterocyclyl, $-C(O)OH$, $-C(O)OR^{11}$, $-C(O)NR^6R^7$, $-C(O)NR^6(CR^9R^{10})_w NR^6R^7$, $-C(O)NR^6O(CR^9R^{10})_w NR^6R^7$, $-C(O)NR^6(CR^9R^{10})_w OH$, $-C(O)NR^6(CR^9R^{10})_w OR^{11}$, $-C(=NR^8)NR^6R^7$, $-C(=NR^8)NR^6C(O)R^{11}$, $-S(O)_{0,1,2}R^{11}$, $-S(O)_{0,1,2}(CR^9R^{10})_w NR^6R^7$, $-S(O)_{0,1,2}(CR^9R^{10})_w OH$, $-S(O)_{0,1,2}(CR^9R^{10})_w OR^{11}$, $-SO_2NR^6R^7$, $-S(O)_{0,1,2}NR^6(CR^9R^{10})_w NR^6R^7$, $-S(O)_{0,1,2}(CR^9R^{10})_w N(R^6)C(=NR^8)R^{11}$, $-S(O)_{0,1,2}(CR^9R^{10})_w C(=NR^8)NR^6R^7$, $-S(O)_{0,1,2}(CR^9R^{10})_w N(R^6)C(=NR^8)NR^6R^7$, $-S(O)_{0,1,2}(CR^9R^{10})C(=NR^8)NR^6C(=NR^8)NR^6R^7$.

In some embodiments of a compound of Formula (I) or Formula (II), at least one Y is selected from the group consisting of optionally substituted alkyl, optionally substituted heterocycle, optionally substituted heteroaryl, $-NR^6R^7$, $-NR^6(CR^9R^{10})_w NR^6R^7$, $-NR^6C(O)R^{11}$, $-NR^6C(O)OR^{11}$, $-N(R^6)C(O)(CR^9R^{10})_v NR^6R^7$, $-NR^6C(O)NR^6R^7$, $-NR^6C(O)NR^6(CR^9R^{10})_w NR^6R^7$, $-NR^6(CR^9R^{10})_w S(O)_{0,1,2}R^{11}$, $-NR^6(CR^9R^{10})_w S(O)_{0,1,2}NR^6R^7$, $-NR^6(CR^9R^{10})_w NR^6R^7S(O)_{0,1,2}R^{11}$, $-NR^6(CR^9R^{10})_w NR^6S(O)_{0,1,2}NR^6R^6$, $-NR^6C(=NR^8)NR^6R^6$, $-N(R^6)C(=NR^8)R^{11}$, $-NR^6(CR^9R^{10})_w N(R^6)C(=NR^8)R^{11}$, $-NR^6(CR^9R^{10})_v C(=NR^8)NR^6R^7$, $-NR^6(CR^9R^{10})_w N(R^6)C(=NR^8)NR^6R^7$, $-NR^6(CR^9R^{10})_w NR^6C(=O)NR^6R^7$, $-NR^6(CR^9R^{10})_w NR^6C(=O)OR^{11}$, $-NR^6SO_2R^{11}$, $-NR^6(CR^9R^{10})CO_2H$, $-NR^6(CR^9R^{10})CO_2R^{11}$, $-NR^6(CR^9R^{10})C(O)NR^6R^7$, $-N(R^6)$-Heteroaryl-NR$^6$R$^7$, $-N(R^6)$-Heterocyclyl-NR$^6$R$^7$, $-NR^6(CR^9R^{10})_v$Heteroaryl, $-NR^6(CR^9R^{10})_v$Heterocyclyl, $-NR^6(CR^9R^{10})_w NR^6$-Heteroaryl, $-NR^6(CR^9R^{10})_w NR^6$-Heterocyclyl, $-CN$, $-(CR^9R^{10})_w NR^6R^7$, $-(CR^9R^{10})_w OH$, $-(CR^9R^{10})_v OR^{11}$, $-(CR^9R^{10})_v OC(O)R^{11}$, $-(CR^9R^{10})_v OC(O)NR^6R^6$, $-(CR^9R^{10})_v O(CR^9R^{10})_w OR^{11}$, $-(CR^9R^{10})_v O(CR^9R^{10})_w OH$, $-(CR^9R^{10})_v O(CR^9R^{10})_w NR^6R^7$, $-(CR^9R^{10})_v NR^6(CR^9R^{10})_w OH$, $-(CR^9R^{10})_v NR^6(CR^9R^{10})_w OR^{11}$, $-(CR^9R^{10})_v C(O)NR^6R^7$, $-(CR^9R^{10})_v C(O)NR^6(CR^9R^{10})_w NR^6R^7$, $-(CR^9R^{10})_v C(O)NR^6(CR^9R^{10})_w OR^{11}$, $-(CR^9R^{10})_v N(R^6)C(O)R^{11}$, $-(CR^9R^{10})_v N(R^6)C(O)OR^{11}$, $-(CR^9R^{10})_v N(R^6)C(O)NR^6R^7$, $-(CR^9R^{10})_v N(R^6)C(O)(CR^9R^{10})_v NR^6R^7$, $-(CR^9R^{10})_v N(R^6)S(O)_{0,1,2}R^{11}$, $-(CR^9R^{10})_v N(R^6)S(O)_{0,1,2}NR^6R^7$, $-(CR^9R^{10})_v S(O)_{0,1,2}NR^6R^7$, $-(CR^9R^{10})_v S(O)_{0,1,2}(CR^9R^{10})_w NR^6R^7$, $-(CR^9R^{10})_v N(R^6)CH(=NR^8)$, $-(CR^9R^{10})_v N(R^6)C(=NR^8)R^{11}$, $-(CR^9R^{10})_v C(=NR^8)NR^6R^7$, $-(CR^9R^{10})_v N(R^6)C(=NR^8)NR^6R^7$, $-(CR^9R^{10})_v C(=NR^8)NR^6C(=NR^8)NR^6R^7$, $-(CR^9R^{10})_v$Heteroaryl-NR$^6$R$^7$, $-(CR^9R^{10})_v$Heterocyclyl-NR$^6$R$^7$, $-(CR^9R^{10})_v$Heteroaryl-N(R$^6$)C(=NR$^8$)NR$^6$R$^7$, $-(CR^9R^{10})_v$Heterocyclyl-N(R$^6$)C(=NR$^8$)NR$^6$R$^7$, $-(CR^9R^{10})_v$Heteroaryl, $-(CR^9R^{10})_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$.

In some embodiments of a compound of Formula (I) or Formula (II), at least one Y is selected from the group consisting of chloro, iodo, boronic acid, optionally substituted alkyl, optionally substituted alkynyl, optionally substituted heterocycle, optionally substituted heteroaryl, —NR$^6$R$^7$, —NR$^6$(CR$^9$R$^{10}$)$_w$NR$^6$R$^7$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_w$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)$_w$CO$_2$R$^{11}$, —NR$^6$(CR$^9$R$^{10}$)C(O)NR$^6$R$^7$, —N(R$^6$)-Heteroaryl- NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$NR$^6$R$^7$, —(CR$^9$R$^{10}$)$_w$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_w$C(O)NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$, —(CR$^9$R$^{10}$)$_w$S(O)$_{0,1,2}$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heteroaryl(CR$^9$R$^{10}$)$_w$NR$^6$R$^7$, —(CR$^9$R$^{10}$)$_v$Heterocyclyl-NR$^6$R$^7$, —(CR$^9$R$^{10}$)$_v$Heterocyclyl(CR$^9$R$^{10}$)$_w$NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$.

In some embodiments of a compound of Formula (I) or Formula (II), at least one Y is selected from the group consisting of optionally substituted alkyl, optionally substituted heterocycle, optionally substituted heteroaryl, —NR$^6$R$^7$—(CR$^9$R$^{10}$)$_w$NR$^6$R$^7$, —(CR$^9$R$^{10}$)$_w$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_w$C(O)NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heterocycle, optionally substituted heteroaryl, —NR$^6$R$^7$, —(CR$^9$R$^{10}$)$_w$NR$^6$R$^7$, —(CR$^9$R$^{10}$)$_v$OH, —(CR$^9$R$^{10}$)$_w$NR$^6$(CR$^9$R$^{10}$)$_v$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_w$N(R$^6$)C(=NR$^8$)R$^{11}$, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heteroaryl, —NR$^6$R$^7$, —(CR$^9$R$^{10}$)$_w$NR$^6$R$^7$, —(CR$^9$R$^{10}$)$_w$OH, —(CR$^9$R$^{10}$)$_w$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II), at least one Y is selected from the group consisting of fluoro, alkyl, optionally substituted heterocycle, optionally substituted heteroaryl, —OH —OR$^{11}$, —O(CR$^9$R$^{10}$)$_w$NR$^6$R$^7$, —NR$^6$R$^7$, —NO$_2$, —(CR$^9$R$^{10}$)$_w$NR$^6$R$^7$, —(CR$^9$R$^{10}$)$_w$S(O)$_{0,1,2}$(CR$^9$R$^{10}$)$_w$NR$^6$R$^7$, —(CR$^9$R$^{10}$)$_v$Heterocyclyl-(NR$^6$R$^7$)$_2$, —C(O)NR$^6$O(CR$^9$R$^{10}$)$_w$NR$^6$R$^7$, —(CR$^9$R$^{10}$)$_w$C(O)NR$^6$R$^7$, —(CR$^9$R$^{10}$)$_w$C(O)NR$^6$NR$^6$R$^7$, —(CR$^9$R$^{10}$)$_w$OH, —(CR$^9$R$^{10}$)$_w$NR$^6$(CR$^9$R$^{10}$)$_w$OH, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_v$Heterocyclyl, —(CR$^9$R$^{10}$)$_v$Heteroaryl-NR$^6$R$^7$, —CN, —C(O)OH, —C(O)OR$^{11}$, —C(O)NR$^6$R$^7$, —C(O)NR$^6$(CR$^9$R$^{10}$)$_w$NR$^6$R$^7$, —S(O)$_{0,1,2}$R$^{11}$, and —S(O)$_{0,1,2}$(CR$^9$R$^{10}$)$_w$NR$^6$R$^7$.

In some embodiments of a compound of Formula (I) or Formula (II), at least one Y is selected from the group consisting of alkyl, optionally substituted heterocycle, optionally substituted heteroaryl, —NR$^6$R$^7$, —NO$_2$, —(CR$^9$R$^{10}$)$_w$NR$^6$R$^7$, —(CR$^9$R$^{10}$)$_v$S(O)$_{0,1,2}$(CR$^9$R$^{10}$)$_v$NR$^6$R$^7$, —(CR$^9$R$^{10}$)$_v$Heterocyclyl-(NR$^6$R$^7$)$_2$, —C(O)NR$^6$O(CR$^9$R$^{10}$)$_w$NR$^6$R$^7$, —(CR$^9$R$^{10}$)C(O)NR$^6$R$^7$, —(CR$^9$R$^{10}$)C(O)NR$^6$NR$^6$R$^7$, —(CR$^9$R$^{10}$)$_v$OH, —(CR$^9$R$^{10}$)$_w$NR$^6$(CR$^9$R$^{10}$)$_v$OH, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_v$Heterocyclyl, —(CR$^9$R$^{10}$)$_v$Heteroaryl-NR$^6$R$^7$, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II), at least one Y is selected from the group consisting of fluoro, chloro, iodo, boronic acid, optionally substituted alkyl, optionally substituted alkynyl, optionally substituted heterocycle, optionally substituted heteroaryl, —OH, —OR$^{11}$, —O(CR$^9$R$^{10}$)$_w$NR$^6$R$^7$, —NR$^6$R$^7$, —NO$_2$, —(CR$^9$R$^{10}$)$_w$NR$^6$R$^7$, —(CR$^9$R$^{10}$)$_w$S(O)$_{0,1,2}$(CR$^9$R$^{10}$)$_w$NR$^6$R$^7$, —(CR$^9$R$^{10}$)$_x$Heterocyclyl-(NR$^6$R$^7$)$_2$, —C(O)NR$^6$O(CR$^9$R$^{10}$)$_w$NR$^6$R$^7$, —(CR$^9$R$^{10}$)$_w$C(O)NR$^6$R$^7$, —(CR$^9$R$^{10}$)$_w$C(O)NR$^6$NR$^6$R$^7$, —(CR$^9$R$^{10}$)$_w$OH, —(CR$^9$R$^{10}$)$_w$NR$^6$(CR$^9$R$^{10}$)$_w$OH, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_x$Heterocyclyl, —(CR$^9$R$^{10}$)$_x$Heteroaryl-NR$^6$R$^7$, —(CR$^9$R$^{10}$)$_x$Heteroaryl(CR$^9$R$^{10}$)$_w$NR$^6$R$^7$, —CN, —C(O)OH, —C(O)OR$^{11}$, —C(O)NR$^6$R$^7$, —C(O)NR$^6$(CR$^9$R$^{10}$)$_w$NR$^6$R$^7$, —S(O)$_{0,1,2}$R$^{11}$, and —S(O)$_{0,1,2}$(CR$^9$R$^{10}$)$_w$NR$^6$R$^7$.

In some embodiments of a compound of Formula (I) or Formula (II), at least one Y is selected from the group consisting of chloro, iodo, boronic acid, optionally substituted alkyl, optionally substituted alkynyl, optionally substituted heterocycle, optionally substituted heteroaryl, —NR$^6$R$^7$, —NO$_2$, —(CR$^9$R$^{10}$)$_w$NR$^6$R$^7$, —(CR$^9$R$^{10}$)$_w$S(O)$_{0,1,2}$(CR$^9$R$^{10}$)$_w$NR$^6$R$^7$, —(CR$^9$R$^{10}$)$_x$Heterocyclyl-(NR$^6$R$^7$)$_2$, —C(O)NR$^6$O(CR$^9$R$^{10}$)$_w$NR$^6$R$^7$, —(CR$^9$R$^{10}$)$_w$C(O)NR$^6$R$^7$, —(CR$^9$R$^{10}$)$_w$C(O)NR$^6$NR$^6$R$^7$, —(CR$^9$R$^{10}$)$_w$OH, —(CR$^9$R$^{10}$)$_w$NR$^6$(CR$^9$R$^{10}$)$_w$OH, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_x$Heterocyclyl, —(CR$^9$R$^{10}$)$_x$Heteroaryl-NR$^6$R$^7$, —(CR$^9$R$^{10}$)$_x$Heteroaryl(CR$^9$R$^{10}$)$_w$NR$^6$R$^7$, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II), at least one Y is selected from the group consisting of optionally substituted heterocycle, optionally substituted heteroaryl, —NR$^6$C(=NR$^8$)NR$^6$R$^6$, —N(R$^6$)C(=NR$^8$)R$^{11}$, —NR$^6$(CR$^9$R$^{10}$)$_w$NR$^6$R$^7$, —(CR$^9$R$^{10}$)$_w$NR$^6$R$^7$, —(CR$^9$R$^{10}$)$_v$O(CR$^9$R$^{10}$)$_w$NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$(=NR$^8$)NR$^6$R$^7$, —(CR$^9$R$^{10}$)$_x$Heteroaryl-NR$^6$R$^7$, —(CR$^9$R$^{10}$)$_x$Heterocyclyl-NR$^6$R$^7$, —(CR$^9$R$^{10}$)$_x$Heteroaryl-N(R$^6$)C(=NR$^8$)NR$^6$R$^7$, —(CR$^9$R$^{10}$)$_x$Heterocyclyl-N(R$^6$)C(=NR$^8$)NR$^6$R$^7$, —(CR$^9$R$^{10}$)$_x$Heteroaryl, —(CR$^9$R$^{10}$)$_x$Heterocyclyl, and —C(O)NR$^6$(CR$^9$R$^{10}$)$_w$NR$^6$R$^7$.

In some embodiments of a compound of Formula (I) or Formula (II), at least one Y is CH$_2$—Y$^2$ and Y$^2$ is selected from the group consisting of —NR$^6$R$^7$, —O(CR$^9$R$^{10}$)$_w$NR$^6$R$^7$, —C(O)NR$^6$(CR$^9$R$^{10}$)$_w$NR$^6$R$^7$, —N(R$^6$)C(O)(CR$^9$R$^{10}$)$_w$NR$^6$R$^7$, —NR$^6$(CR$^9$R$^{10}$)$_w$NR$^6$R$^7$, —N(R$^6$)C(=NR$^8$)R$^{11}$, —C(=NR$^8$)NR$^6$R$^7$, —N(R$^6$)C(=NR$^8$)NR$^6$R$^7$, —C(=NR$^8$)NR$^6$C(=NR$^8$)NR$^6$R$^7$, heterocyclyl, and heteroaryl.

In some embodiments of a compound of Formula (I) or Formula (II), at least one Y is —(CR$^9$R$^{10}$)$_v$—Y$^2$ and Y$^2$ is selected from the group consisting of —NR$^6$R$^7$, —O(CR$^9$R$^{10}$)$_w$NR$^6$R$^7$, —C(O)NR$^6$(CR$^9$R$^{10}$)$_w$NR$^6$R$^7$, —N(R$^6$)C(O)(CR$^9$R$^{10}$)$_w$NR$^6$R$^7$, —NR$^6$(CR$^9$R$^{10}$)$_w$NR$^6$R$^7$, —N(R$^6$)C(=NR$^8$)R$^{11}$, —C(=NR$^8$)NR$^6$R$^7$, —N(R$^6$)C(=NR$^8$)NR$^6$R$^7$, —C(O)NR$^6$R$^7$, —C(O)NR$^6$NR$^6$R$^7$, —S(O)$_{0,1,2}$(CR$^9$R$^{10}$)$_w$NR$^6$R$^7$, —NR$^6$S(O)$_{0,1,2}$R$^{11}$, heterocyclyl, and heteroaryl.

In some embodiments of a compound of Formula (I) or Formula (II), at least one Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^9$R$^7$)$_v$C(=NR$^8$)NR$^6$R$^7$, —O(CR$^9$R$^{10}$)$_w$N(R$^6$)C(=NR$^8$)R$^{11}$, O(CR$^9$R$^{10}$)$_w$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_w$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_x$Heteroaryl, —O(CR$^9$R$^{10}$)$_x$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)OR$^{11}$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_w$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)$_w$CO$_2$H, —NR$^6$(CR$^9$R$^{10}$)$_w$CO$_2$R$^{11}$, —NR$^6$(CR$^9$R$^{10}$)$_w$C(O)NR$^6$R$^7$, —N(R$^6$)-Heteroaryl- NR$^6$R$^7$, —N(R$^6$)-Heterocyclyl-NR$^6$R$^7$, —NR$^6$(CR$^9$R$^{10}$)$_x$Heteroaryl, —NR$^6$(CR$^9$R$^{10}$)$_x$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$CN, —(CR$^9$R$^{10}$)$_w$NR$^6$R$^7$, —(CR$^9$R$^{10}$)$_v$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)C(O)NR$^6$R$^7$, —(CR$^9$R$^{10}$)C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$—(CR$^9$R$^{10}$)$_w$S(O)$_{0,1,2}$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_x$Heterocyclyl-NR$^6$R$^7$, —(CR$^9$R$^{10}$)$_x$Heteroaryl-N(R$^6$)C(=NR$^8$)NR$^6$R$^7$, —(CR$^9$R$^{10}$)$_x$Heterocyclyl-N(R$^6$)C(=NR$^8$)NR$^6$R$^7$, —(CR$^9$R$^{10}$)$_x$Heteroaryl, —(CR$^9$R$^{10}$)$_x$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_w$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$R$^7$, —NR$^6$R$^7$R$^{12+}$Q$^-$, —Si(R$^{11}$)$_3$, —(CR$^9$R$^{10}$)$_w$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-$$_2$, —(CR$^9$R$^{10}$)$_v$(T)$^+$Q$^-$, and —O(CR$^9$R$^{10}$)$_w$NR$^6$R$^6$R$^{12+}$Q$^-$.

In some embodiments of a compound of Formula (I) or Formula (II), at least one Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_v$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_v$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^9$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_w$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_w$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)OR$^{11}$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$CN, —(CR$^9$R$^{10}$)$_w$NR$^6$R$^7$, —(CR$^9$R$^{10}$)$_v$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)C(O)NR$^6$R$^7$, —(CR$^9$R$^{10}$)C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$, —(CR$^9$R$^{10}$)$_w$S(O)$_{0,1,2}$NR$^6$R$^7$, —(CR$^9$R$^{10}$)$_w$N(R$^6$)(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$.

In some embodiments of a compound of Formula (I) or Formula (II), at least one Y is selected from the group consisting of optionally substituted alkyl, optionally substituted heterocycle, optionally substituted heteroaryl, —NR$^6$(CR$^9$R$^{10}$)$_w$NR$^6$R$^7$, —NR$^6$C(O)OR$^{11}$, —N(R$^6$)C(O)(CR$^9$R$^{10}$)$_w$NR$^6$R$^7$, —NR$^6$C(O)NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$NR$^6$R$^7$, —(CR$^9$R$^{10}$)$_w$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_w$C(O)NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$.

In some embodiments of a compound of Formula (I) or Formula (II), at least one Y is selected from the group consisting of optionally substituted alkyl, optionally substituted heterocycle, optionally substituted heteroaryl —(CR$^9$R$^{10}$)$_w$NR$^6$R$^7$, —(CR$^9$R$^{10}$)$_v$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_w$C(O)NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$ (=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heterocycle, optionally substituted heteroaryl, —(CR$^9$R$^{10}$)$_w$NR$^6$R$^7$, —(CR$^9$R$^{10}$)$_w$OH, —(CR$^9$R$^{10}$)$_w$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)NR$^6$R$^7$, —(CR$^9$R$^{10}$)$_w$N(R$^6$)C(=NR$^8$)R$^{11}$, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_w$NR$^6$R$^7$.

In some embodiments of a compound of Formula (I) or Formula (II), at least one Y is selected from the group consisting of optionally substituted heteroaryl, —(CR$^9$R$^{10}$)$_v$NR$^6$R$^7$, —(CR$^9$R$^{10}$)$_v$OH, —(CR$^9$R$^{10}$)$_v$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II), at least one Y is —(CR$^9$R$^{10}$)$_v$NR$^6$R$^7$.

In some embodiments of a compound of Formula (I) or Formula (II), at least one Y is —(CR$^9$R$^{10}$)$_v$N(R$^6$)C(=NR$^8$)NR$^6$R$^7$.

In some embodiments of a compound of Formula (I) or Formula (II), at least one Y is selected from the group consisting of heterocycle or heteroaryl, both optionally substituted with one to three substituents selected from the group consisting of fluoro, chloro, bromo, —CN, C$_1$-C$_6$ alkyl, C$_1$-C$_6$ haloalkyl, C$_3$-C$_6$ cycloalkyl, heterocycle, aryl, heteroaryl, —OH, —OR$^{11}$, —SR$^{11}$, —NR$^6$R$^7$, —(CR$^9$R$^{10}$)$_v$NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, -Heteroaryl-NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, -Heteroaryl-NR$^6$R$^7$, -Heterocyclyl-NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl, and —(CR$^9$R$^{10}$)$_v$Heterocyclyl.

In some embodiments of a compound of Formula (I) or Formula (II), at least one Y is alkyl optionally substituted with one to three substituents selected from the group consisting of fluoro, chloro, bromo, —CN, C$_3$-C$_6$ cycloalkyl, heterocycle, aryl, heteroaryl, —OH, —OR$^{11}$, —SR$^{11}$, —NR$^6$R$^7$, —(CR$^9$R$^{10}$)$_v$NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, -Heteroaryl-NR$^6$R$^7$, -Heterocyclyl-NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl, and —(CR$^9$R$^{10}$)$_v$Heterocyclyl.

In some embodiments of a compound of Formula (I) or Formula (II), at least one Y is fluoroalkyl.

In some embodiments of a compound of Formula (I) or Formula (II), at least one Y is alkynyl optionally substituted with one to three substituents selected from the group consisting of fluoro, chloro, bromo, —CN, C$_3$-C$_6$ cycloalkyl, heterocycle, aryl, heteroaryl, —OH, —OR$^{11}$, —SR$^{11}$, —NR$^6$R$^7$, —(CR$^9$R$^{10}$)$_v$NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, -Heteroaryl-NR$^6$R$^7$, -Heterocyclyl-NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl, and —(CR$^9$R$^{10}$)$_v$Heterocyclyl.

In some embodiments of a compound of Formula (I) or Formula (II), at least one Y is alkynyl optionally substituted with —NR$^6$R$^7$.

In some embodiments of a compound of Formula (I) or Formula (II), two Y groups taken together with the carbon atoms to which they are attached form an optionally substituted carbocycle or an optionally substituted heterocycle. In some embodiments, the carbocycle or heterocycle are both optionally substituted with one to three substituents selected from the group consisting of fluoro, chloro, bromo, —CN, C$_1$-C$_6$ alkyl, C$_3$-C$_6$ cycloalkyl, heterocycle, aryl, heteroaryl, —OH, —OR$^{11}$, —SR$^{11}$, —NR$^6$R$^7$, —(CR$^9$R$^{10}$)$_v$NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, Heteroaryl NR$^6$R$^7$, Heterocyclyl NR$^6$R$^7$, —(CR$^9$R$^{10}$)$_v$Heteroaryl NR$^6$R$^7$, —(CR$^9$R$^{10}$)$_v$Heterocyclyl NR$^6$R$^7$, —(CR$^9$R$^{10}$)$_v$Heteroaryl, and —(CR$^9$R$^{10}$)$_v$Heterocyclyl.

In some embodiments of a compound of Formula (I) or Formula (II), two Ys taken together with the atoms to which they are attached form an optionally substituted carbocycle, an optionally substituted heterocycle, or an optionally substituted heteroaryl. In some embodiments of a compound of Formula (I) or Formula (II), two Ys taken together with the atoms to which they are attached form an optionally substituted 5-membered heteroaryl. In some embodiments of a compound of Formula (I) or Formula (II), two Ys taken together with the atoms to which they are attached form an optionally substituted 5-membered heterocycle. In some embodiments of a compound of Formula (I) or Formula (II), the carbocycle, heterocycle, or heteroaryl are optionally substituted with one to three substituents selected from the group consisting of fluoro, chloro, bromo, —CN, C$_1$-C$_6$ alkyl, C$_3$-C$_6$ cycloalkyl, heterocycle, aryl, heteroaryl, —OH, —OR$^{11}$, —SR$^{11}$, —NR$^6$R$^7$, —(CR$^9$R$^{10}$)$_v$NR$^6$R$^7$, —(CR$^9$R$^{10}$)$_v$SR$^{11}$, —(CR$^9$R$^{10}$)$_v$S(CR$^9$R$^{10}$)$_v$NR$^6$R$^7$, —NR$^6$(CR$^9$R$^{10}$)$_w$NR$^6$R$^7$, —O(CR$^9$R$^{10}$)$_w$NR$^6$R$^7$, —NR$^6$C(=NR$^8$)NR$^6$R$^7$, —C(=NR$^8$)NR$^6$R$^7$, Heteroaryl NR$^6$R$^7$, Heterocyclyl NR$^6$R$^7$, —(CR$^9$R$^{10}$)$_v$Heteroaryl NR$^6$R$^7$, —(CR$^9$R$^{10}$)$_v$Heteroaryl(CR$^9$R$^{10}$)$_v$NR$^6$R$^7$, —(CR$^9$R$^{10}$)$_v$Heterocyclyl NR$^6$R$^7$, —(CR$^9$R$^{10}$)$_v$Heterocyclyl(CR$^9$R$^{10}$)$_v$NR$^6$R$^7$, —(CR$^9$R$^{10}$)$_v$Heteroaryl, and —(CR$^9$R$^{10}$)$_v$Heterocyclyl.

In some embodiments of a compound of Formula (I) or Formula (II), Y is defined as in any of the embodiments above or below and R$^6$ and R$^7$ are independently selected from the group consisting of hydrogen, —OH, optionally substituted C$_1$-C$_6$ alkyl, optionally substituted alkoxyalkyl, optionally substituted hydroxyalkyl, and optionally substituted heterocyclyl. In some embodiments, R$^6$ and R$^7$ are independently selected from the group consisting of hydrogen and optionally substituted C$_1$-C$_6$ alkyl. In some embodiments, R$^6$ and R$^7$ are hydrogen. In some embodiments, R$^6$ is hydrogen and R$^7$ is C$_1$-C$_6$ alkyl. In some embodiments, R$^6$ and R$^7$ are independently C$_1$-C$_6$ alkyl.

In some embodiments of a compound of Formula (I) or Formula (II), Y is defined as in any of the embodiments above and R$^8$ is hydrogen, —OH, —CN, —NO$_2$, —NR$^6$, or optionally substituted C$_1$-C$_6$ alkyl. In some embodiments of a compound of Formula (I) or Formula (II), Y is defined as in any of the embodiments above and R$^8$ is hydrogen, —OH, —CN, —NO$_2$, or optionally substituted C$_1$-C$_6$ alkyl. In some embodiments, R$^8$ is hydrogen or —CN. In some embodiments, R$^8$ is hydrogen.

In some embodiments of a compound of Formula (I) or Formula (II), Y is defined as in any of the embodiments above or below and $R^9$ and $R^{10}$ are independently selected from the group consisting of hydrogen, —OH, fluoro, chloro, optionally substituted $C_1$-$C_6$ alkyl, —$(CR^aR^b)_v NR^6R^7$, and —$(CR^aR^b)_v C(O)NR^6R^7$. In some embodiments, $R^9$ and $R^{10}$ are independently selected from the group consisting of hydrogen, $C_1$-$C_6$ alkyl, —$(CR^aR^b)_v NR^6R^7$, and —$(CR^aR^b)_v C(O)NR^6R^7$; and IV and $R^b$ are hydrogen. In some embodiments, $R^9$ and $R^{10}$ are hydrogen.

In some embodiments of a compound of Formula (I) or Formula (II), Y is defined as in any of the embodiments above or below and $R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_v NR^6R^7$, —$(CR^aR^b)_v C(O)NR^6R^7$, —$C(O)NR^6R^7$, —$C(O)OR^{11}$, —$C(O)OH$, —$NR^6SO_2R^{11}$, optionally substituted heterocyclyl, optionally substituted aryl, and optionally substituted heteroaryl.

In some embodiments of a compound of Formula (I) or Formula (II), Y is defined as in any of the embodiments above or below and $R^{11}$ is optionally substituted $C_1$-$C_6$ alkyl.

In some embodiments of a compound of Formula (I) or Formula (II), Y is defined as in any of the embodiments above or below and v is 1 or 2. In some embodiments of a compound of Formula (I) or Formula (II), Y is defined as in any of the embodiments above and w is 2 or 3. In some embodiments of a compound of Formula (I) or Formula (II), Y is defined as in any of the embodiments above and v is 1 and w is 2.

In some embodiments of a compound of Formula (I) or Formula (II), Y is defined as in any of the embodiments above or below and $R^6$ and $R^7$ are independently selected from the group consisting of hydrogen and $C_1$-$C_6$ alkyl; $R^8$ is hydrogen or —CN; each $R^9$ and $R^{10}$ are independently selected from the group consisting of hydrogen, $C_1$-$C_6$ alkyl, —$(CR^aR^b)_v NR^6R^7$, and —$(CR^aR^b)_v C(O)NR^6R^7$; $R^{11}$ is $C_1$-$C_6$ alkyl; v is 1 or 2; and w is 2 or 3.

In some embodiments of a compound of Formula (I) or Formula (II), Y is defined as in any of the embodiments above or below and $R^6$ and $R^7$ are independently selected from the group consisting of hydrogen and $C_1$-$C_6$ alkyl; each $R^9$ and $R^{10}$ are independently selected from the group consisting of hydrogen, $C_1$-$C_6$ alkyl, —$(CR^aR^b)_v NR^6R^7$, and —$(CR^aR^b)_v C(O)NR^6R^7$; v is 1 or 2; and w is 2 or 3.

In some embodiments of a compound of Formula (I) or Formula (II), Y is defined as in any of the embodiments above or below and $R^6$ and $R^7$ are independently selected from the group consisting of hydrogen and $C_1$-$C_6$ alkyl; each $R^9$ and $R^{10}$ are independently selected from the group consisting of hydrogen, $C_1$-$C_6$ alkyl, —$(CR^aR^b)_v NR^6R^7$, and —$(CR^aR^b)_v C(O)NR^6R^7$; and v is 1 or 2.

In some embodiments of a compound of Formula (I) or Formula (II), Y is defined as in any of the embodiments above or below and $R^6$ and $R^7$ are independently selected from the group consisting of hydrogen and $C_1$-$C_6$ alkyl; $R^8$ is hydrogen or —CN; each $R^9$ and $R^{10}$ are independently selected from the group consisting of hydrogen, $C_1$-$C_6$ alkyl, —$(CR^aR^b)_v NR^6R^7$, and —$(CR^aR^b)_v C(O)NR^6R^7$; and v is 1 or 2.

In some embodiments of a compound of Formula (I) or Formula (II) two Ys taken together with the atoms to which they are attached form an optionally substituted carbocycle or an optionally substituted heterocycle. In some embodiments of a compound of Formula (I) or Formula (II) two Ys taken together with the carbon atoms to which they are attached form an optionally substituted carbocycle or an optionally substituted heterocycle. In some embodiments of a compound of Formula (I) or Formula (II), each Y is defined by the inclusion of non-hydrogen atoms. In some embodiments, each Y comprises at least 1, 2, 3, 4, 5, 6, 7, 8, 9, 10, 12, 14, 16, 18, 20, 24, 28, 32, 36, 40, 50, or 60 non-hydrogen atoms. In some embodiments, each Y comprises fewer than 50, 40, 36, 32, 28, 24, 20, 18, 16, 14, 12, 10, 9, 8, 7, 6, 5, 4, 3 or 2 non-hydrogen atoms. In some embodiments, each Y is independently a group comprising 1-50 non-hydrogen atoms. In some embodiments, non-hydrogen atoms are atoms generally found in organic molecules. In some embodiments, non-hydrogen atoms are atoms selected from the group consisting of C, N, O, S and P. In some embodiments, each Y is independently a group comprising 1-50 non-hydrogen atoms selected from the group consisting of C, N, O, S, and P. In some embodiments, each Y is independently a group comprising 1-50 non-hydrogen atoms selected from the group consisting of halogen, C, N, O, S, and P.

In some embodiments of a compound of Formula (I) or Formula (II), each Y is defined by its molecular formula. For example, in some embodiments, each Y has the formula $C_w H_x N_y O_z$; wherein each w is independently 0-30; each x is independently 1-69; each y is independently 1-8; and each z is independently 0-10. In some embodiments, each Y has the formula $C_w H_x N_y O_z$; wherein each w is independently 0-10; each x is independently 1-25; each y is independently 1-4; and each z is independently 0-3. In some embodiments, each y is 2.

In some embodiments of a compound of Formula (I) or Formula (II), each Y is defined by its molecular weight. For example, in some embodiments, each Y has a molecular weight of less than 500, 450, 400, 350, 300, 250, 200, 190, 180, 170, 160, 150, 140, 130, 120, 110, 100, 90, 80, 75, 70 or 50 daltons. In some embodiments, each Y has a molecular weight of less than 200 daltons. In some embodiments, each Y has a molecular weight of less than 150 daltons. In some embodiments, each Y has a molecular weight between 30 and 280 daltons.

In some embodiments of a compound of Formula (I) or Formula (II), each Y is defined by the number of basic nitrogen atoms it comprises. For example, in some embodiments, each Y can comprise 10, 9, 8, 7, 6, 5, 4, 3, 2, 1, or 0 basic nitrogen atoms. In some embodiments, each Y comprises 1-6 basic nitrogen atoms. In some embodiments, each Y comprises 1, 2, or 3 basic nitrogen atoms. In some embodiments, each Y comprises 2 basic nitrogen atoms. In some embodiments, at least one Y comprises 1-6 basic nitrogen atoms. In some embodiments, at least one Y comprises 1, 2, or 3 basic nitrogen atoms. In some embodiments, at least one Y comprises 2 basic nitrogen atoms. A basic nitrogen atom is a nitrogen atom that can be at least partially protonated in a substantially neutral aqueous buffer. For example, a basic nitrogen atom can be a nitrogen atom of an amine group or a nitrogen atom in a functional group such as an alkyl amine, a cycloalkyl amine, a heterocycloalkyl group, a heteroaryl group comprising a nitrogen, an amidine, or a guanidine. In some embodiments, each Y comprises 1-6 nitrogen atoms. In some embodiments, each Y comprises 1, 2, or 3 nitrogen atoms. In some embodiments, each Y comprises 2 nitrogen atoms. In some embodiments, at least one Y comprises 1-6 nitrogen atoms. In some embodiments, at least one Y comprises 1, 2, or 3 nitrogen atoms. In some embodiments, at least one Y comprises 2 nitrogen atoms.

In some embodiments of a compound of Formula (I) or Formula (II), p is 0. In some embodiments of a compound of Formula (I) or Formula (II), p is not 0. In some embodiments, p is 1. In some embodiments, p is 2. In some embodiments, p is 3. In some embodiments, p is at least 2.

In some embodiments of a compound of Formula (I) or Formula (II), $R^a$, $R^b$, and $R^c$ are independently selected from the group consisting of hydrogen, fluoro, chloro, optionally substituted $C_1$-$C_6$ alkyl, —OH, —$OR^{11}$, —$NR^6R^7$, and —$SR^{11}$.

In some embodiments of a compound of Formula (I) or Formula (II), $R^a$ and $R^b$ are hydrogen and $R^c$ is selected from the group consisting of hydrogen, fluoro, chloro, optionally substituted $C_1$-$C_6$ alkyl, —OH, —$OR^{11}$, —$NR^6R^7$, and —$SR^{11}$. In some embodiments of a compound of Formula (I) or Formula (II), $R^a$ and $R^b$ are hydrogen and is selected fluoro or chloro.

In some embodiments of a compound of Formula (I) or Formula (II), $R^b$ and $R^c$ are hydrogen and $R^a$ is selected from the group consisting of hydrogen, fluoro, chloro, optionally substituted $C_1$-$C_6$ alkyl, —OH, —$OR^{11}$, —$NR^6R^7$, and —$SR^{11}$. In some embodiments of a compound of Formula (I) or Formula (II), $R^b$ and $R^c$ are hydrogen and IV is selected fluoro or chloro.

In some embodiments of a compound of Formula (I) or Formula (II), $R^a$ and $R^c$ are hydrogen and $R^b$ is selected from the group consisting of hydrogen, fluoro, chloro, optionally substituted $C_1$-$C_6$ alkyl, —OH, —$OR^{11}$, —$NR^6R^7$, and —$SR^{11}$. In some embodiments of a compound of Formula (I) or Formula (II), $R^a$ and $R^c$ are hydrogen and $R^b$ is selected fluoro or chloro.

In some embodiments of a compound of Formula (I) or Formula (II), $R^a$, $R^b$, and $R^c$ are as defined above and $R^6$ and $R^7$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In some embodiments, $R^6$ and $R^7$ are independently selected from the group consisting of hydrogen and optionally substituted $C_1$-$C_6$ alkyl. In some embodiments, $R^6$ and $R^7$ are hydrogen. In some embodiments, $R^6$ is hydrogen and $R^7$ is $C_1$-$C_6$ alkyl. In some embodiments, $R^6$ and $R^7$ are independently $C_1$-$C_6$ alkyl.

In some embodiments of a compound of Formula (I) or Formula (II), $R^a$, $R^b$, and $R^c$ are as defined above and $R^{11}$ is optionally substituted $C_1$-$C_6$ alkyl.

In some embodiments, $R^a$, $R^b$, and $R^c$ are independently selected from the group consisting of hydrogen, fluoro, chloro, —OH, and —$OCH_3$. In some embodiments, $R^a$, $R^b$, and $R^c$ are hydrogen. In some embodiments, $R^a$, $R^b$, $R^c$, and $R^e$ are hydrogen.

In some embodiments of a compound of Formula (I) or Formula (II), $X^1$ is —OH and $X^2$ is —OH when present. In some embodiments of a compound of Formula (I) or Formula (II), $X^1$ is —$OR^x$ and $X^2$ is —OH when present. In some embodiments of a compound of Formula (I) or Formula (II), $X^1$ is —$OR^x$ and $X^2$ is —$OR^x$ when present. In some embodiments of a compound of Formula (I) or Formula (II), $X^1$ is —$OR^x$ and $X^2$ is —$OR^x$ when present and two $R^x$ are taken together with the atom to which they are attached to form an optionally substituted heterocycle.

In some embodiments of a compound of Formula (I) or Formula (II), $R^d$ is hydrogen or $C_1$-$C_6$ alkyl. In some embodiments, $R^d$ is hydrogen. In some embodiments, $R^d$ is methyl.

In some embodiments of a compound of Formula (I) or Formula (II), $R^e$ is hydrogen.

In some embodiments of a compound of Formula (I) or Formula (II), $R^1$ is hydrogen, $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one.

In some embodiments of a compound of Formula (I) or Formula (II), $R^1$ is hydrogen. In some embodiments, $R^1$ is $R^{31}$ and $R^{31}$ is optionally substituted $C_1$-$C_{12}$ alkyl. In some embodiments, $R^1$ is methyl, ethyl, propyl, butyl, or isopropyl.

In some embodiments of a compound of Formula (I) or Formula (II), $R^1$ is —$(R^{30})_qOR^{31}$ or —$(R^{30})_qO(R^{30})_qOR^{31}$; $R^{30}$ is —$CH_2$—, —$CH(CH_3)$—, —$C(CH_3)_2$—; q is 2; and $R^{31}$ is optionally substituted $C_1$-$C_{12}$ alkyl.

In some embodiments of a compound of Formula (I) or Formula (II), $R^1$ is —$R^{30}OC(O)R^{31}$ or —$R^{30}OC(O)OR^{31}$; $R^{30}$ is —$CH_2$—, —$CH(CH_3)$—, —$C(CH_3)_2$—; and $R^{31}$ is optionally substituted $C_1$-$C_{12}$ alkyl.

In some embodiments of a compound of Formula (I) or Formula (II), $R^{30}OC(O)R^{31}$ or —$R^{30}OC(O)OR^{31}$; $R^{30}$ is —$CH_2$—, —$CH(CH_3)$—, —$C(CH_3)_2$—; and $R^{31}$ is $C_1$-$C_{12}$ alkyl optionally substituted with —$OR^{11}$.

In some embodiments of a compound of Formula (I) or Formula (II):

L is —$(CR^2R^3)_n$—;

n is 0, 1, 2, 3, 4, 5, or 6;

p is 0 or 1;

$X^1$ and $X^2$ are independently selected from —OH, —$OR^x$, and F;

AzA is tetrazole;

each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_wOH$, —$O(CR^9R^{10})_wOR^{11}$, —$O(CR^9R^{10})_wNR^6R^7$, —$O(CR^9R^{10})_wNR^6C(O)R^{11}$, —$O(CR^9R^{10})_wNR^6C(O)OR^{11}$, —$O(CR^9R^{10})_wNR^6C(O)NR^6R^7$, —$O(CR^9R^{10})_wC(O)NR^6R^7$, —$O(CR^9R^{10})_wNR^6S(O)_{0,1,2}R^{11}$, —$O(CR^9R^{10})_wNR^6S(O)_{0,1,2}NR^6R^7$, —$O(CR^9R^{10})_wS(O)_{0,1,2}R^{11}$, —$O(CR^9R^{10})_wS(O)_{0,1,2}NR^6R^7$, —$O(CR^9R^7)_wC(=NR^8)NR^6R^7$, —$O(CR^9R^{10})_wN(R^6)C(=NR^8)R^{11}$, —$O(CR^9R^{10})_wC(=NR^8)NR^6C(=NR^8)NR^6R^7$, —$O(CR^9R^{10})_wN(R^6)C(=NR^8)NR^6R^7$, —$O(CR^9R^{10})_wS(O)_{0,1,2}R^{11}$, —$O(CR^9R^{10})_wS(O)_{0,1,2}NR^6R^7$, —$OC(O)R^{11}$, —$OC(O)(CR^9R^{10})_wNR^6R^7$, —$OC(O)NR^6R^7$, —$OC(O)OR^{11}$, —$OC(O)NR^6(CR^9R^{10})_wNR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_wNR^6$-Heteroaryl, —$O(CR^9R^{10})_wNR^6$-Heterocyclyl, —$O(CR^9R^{10})_w$O-Heterocyclyl, —$NO_2$, —$NR^6R^7$, —$NR^6(CR^9R^{10})_wNR^6R^7$, —$NR^6(CR^9R^{10})_wOH$, —$NR^6(CR^9R^{10})_wOR^{11}$, —$NR^6C(O)R^{11}$, —$NR^6C(O)OR^{11}$, —$N(R^6)C(O)(CR^9R^{10})_wNR^6R^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_w$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)C(O)(CR$^9$R$^{10}$)$_v$ONR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$S(O)$_{0,1,2}$(CR$^9$R$^{10}$)$_v$NR$^6$R$^7$, —(CR$^9$R$^{10}$)$_w$NR$^6$(CR$^9$R$^{10}$)$_v$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heterocyclyl-(NR$^6$R$^7$)$_2$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$O(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-$$_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion;
v is 1-4;
w is 2-4;
or two Ys taken together with the atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;
each R$^{30}$ is independently —CH$_2$—, —CH(CH$_3$)—, —C(CH$_3$)$_2$—, or optionally substituted 1,1'-cyclopropylene;
each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or
two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, —NR$^6$R$^7$, —(CR$^9$R$^{10}$)$_v$C(O)NR$^6$R$^7$, —(CR$^9$R$^{10}$)$_v$C(O)OH, —(CR$^9$R$^{10}$)$_v$OH, —(CR$^9$R$^{10}$)$_v$NR$^6$R$^7$, and —(CR$^9$R$^{10}$)$_v$N(R$^6$)C(=NR$^8$)NR$^6$R$^7$;

or R$^2$ and R$^3$ on the same carbon are taken together to form an oxo or optionally substituted oxime;
or R$^2$ and R$^3$ on the same carbon are taken together to form an optionally substituted spiro-carbocycle or optionally substituted spiro-heterocycle with the carbon to which they are attached;
or when n is at least 2, two R$^2$ on different carbons are taken together form an optionally substituted carbocycle or optionally substituted heterocycle with the carbons to which they are attached;
or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

$R^8$ is Hydrogen, —OH, —$OR^{11}$, —CN, —$NO_2$, —$NR_6$, optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_wNR^6R^7$, —$(CR^aR^b)_vC(O)NR^6R^7$, —C(O)$NR^6R^7$, —C(O)$OR^{11}$, —C(O)OH, —$NR^6SO_2R^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II):

L is —$(CR^2R^3)_n$—;

n is 0, 1, 2, or 3;

p is 0 or 1;

$X^1$ is —OH and $X^2$ is —OH when present;

AzA is tetrazole;

each Y is selected from the group consisting of optionally substituted alkyl, optionally substituted heterocycle, optionally substituted heteroaryl, —$NR^6R^7$, —$NR^6(CR^9R^{10})_wNR^6R^7$, —$NR^6C(O)R^{11}$, —$NR^6C(O)OR^{11}$, —$N(R^6)C(O)(CR^9R^{10})_wNR^6R^7$, —$NR^6C(O)NR^6R^7$, —$NR^6C(O)NR^6(CR^9R^{10})_wNR^6R^7$, —$NR^6(CR^9R^{10})_wS(O)_{0,1,2}R^{11}$, —$NR^6(CR^9R^{10})_wS(O)_{0,1,2}NR^6R^7$, —$NR^6(CR^9R^{10})_wNR^6R^7S(O)_{0,1,2}R^{11}$, —$NR^6(CR^9R^{10})_wNR^6S(O)_{0,1,2}NR^6R^6$, —$NR^6C(=NR^8)NR^6R^6$, —$N(R^6)C(=NR^8)R^{11}$, —$NR^6(CR^9R^{10})_wN(R^6)C(=NR^8)R^{11}$, —$NR^6(CR^9R^{10})_wC(=NR^8)NR^6R^7$, —$NR^6(CR^9R^{10})_wN(R^6)C(=NR^8)NR^6R^7$, —$NR^6(CR^9R^{10})_wNR^6C(=O)NR^6R^7$, —$NR^6(CR^9R^{10})_wNR^6C(=O)OR^{11}$, —$NR^6SO_2R^{11}$, —$NR^6(CR^9R^{10})_wCO_2H$, —$NR^6(CR^9R^{10})_wCO_2R^{11}$, —$NR^6(CR^9R^{10})_wC(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_wNR^6$-Heteroaryl, —$NR^6(CR^9R^{10})_wNR^6$-Heterocyclyl, —CN, —$(CR^9R^{10})_wNR^6R^7$, —$(CR^9R^{10})_wOH$, —$(CR^9R^{10})_wOR^{11}$, —$(CR^9R^{10})_vOC(O)R^{11}$, —$(CR^9R^{10})_vOC(O)NR^6R^6$, —$(CR^9R^{10})_vO(CR^9R^{10})_wOR^{11}$, —$(CR^9R^{10})_vO(CR^9R^{10})_wOH$, —$(CR^9R^{10})_vO(CR^9R^{10})_wNR^6R^7$, —$(CR^9R^{10})_wNR^6(CR^9R^{10})_wOH$, —$(CR^9R^{10})_wNR^6(CR^9R^{10})_wOR^{11}$, —$(CR^9R^{10})_wC(O)NR^6R^7$, —$(CR^9R^{10})_wC(O)NR^6(CR^9R^{10})_wNR^6R^7$, —$(CR^9R^{10})_wC(O)NR^6(CR^9R^{10})_wOR^{11}$, —$(CR^9R^{10})_wN(R^6)C(O)R^{11}$, —$(CR^9R^{10})_wN(R^6)C(O)OR^{11}$, —$(CR^9R^{10})_wN(R^6)C(O)NR^6R^7$, —$(CR^9R^{10})_wN(R^6)C(O)(CR^9R^{10})_wNR^6R^7$, —$(CR^9R^{10})_wN(R^6)S(O)_{0,1,2}R^{11}$, —$(CR^9R^{10})_wN(R^6)S(O)_{0,1,2}NR^6R^7$, —$(CR^9R^{10})_wS(O)_{0,1,2}NR^6R^7$, —$(CR^9R^{10})_wNR^6(CR^9R^{10})_wNR^6R^7$, —$(CR^9R^{10})_wN(R^6)CH(=NR^8)$, —$(CR^9R^{10})_wN(R^6)C(=NR^8)R^{11}$, —$(CR^9R^{10})_wC(=NR^8)NR^6R^7$, —$(CR^9R^{10})_wC(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_vC(O)$Heteroaryl, —$(CR^9R^{10})_v$Heterocyclyl, —CN, —C(O)OH, —$C(O)OR^{11}$, —$C(O)NR^6R^7$, —$C(O)NR^6(CR^9R^{10})_wNR^6R^7$, —$C(O)NR^6(CR^9R^{10})_wOH$, —$C(O)NR^6(CR^9R^{10})_wOR^{11}$, —$C(=NR^8)NR^6R^7$, and —$C(=NR^8)NR^6C(O)R^{11}$;

$R^a$, $R^b$, and $R^c$ are independently selected from the group consisting of hydrogen, fluoro, chloro, and $C_1$-$C_6$ alkyl;

$R^e$ is hydrogen, optionally substituted $C_1$-$C_6$ alkyl, or optionally substituted $C_3$-$C_6$ cycloalkyl;

$R^1$ is hydrogen, $R^{31}$, —$R^{30}OC(O)R^{31}$, or —$R^{30}OC(O)OR^{31}$;

each $R^{30}$ is independently —$CH_2$— or —$CH(CH_3)$—;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and $C_1$-$C_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —$S(O)_2R^{11}$, —$S(O)_2NH_2$, and $C_1$-$C_6$ alkyl;

$R^8$ is hydrogen or —CN;

$R^9$ and $R^{10}$ are independently selected from the group consisting of hydrogen, fluoro, chloro, and $C_1$-$C_6$ alkyl;

$R^{11}$ is $C_1$-$C_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, —$NR^6R^7$, —$(CR^9R^{10})_vNR^6R^7$, —$(CR^9R^{10})_vOH$, —$(CR^9R^{10})_vNR^6(CR^9R^{10})_wOH$, —$(CR^9R^{10})_vO(CR^9R^{10})_wNR^6R^7$, —$(CR^9R^{10})_vN(R^6)CH(=NR^8)$, —$(CR^9R^{10})_vN(R^6)C(=NR^8)NR^6R^7$, —$(CR^9R^{10})_vN(R^6)C(=NR^8)R^{11}$, —$(CR^9R^{10})_v$Heterocyclyl, —CN, —C(O)OH, —$C(O)OR^{11}$, —$C(O)NR^6R^7$, —$C(O)NR^6(CR^9R^{10})_wNR^6R^7$, —$NR^6C(=NR^8)NR^6R^6$, —$N(R^6)C(=NR^8)R^{11}$, —$NR^6C(O)NR^6R^7$, and —$N(R^6)C(O)(CR^9R^{10})_vNR^6R^7$.

In some embodiments of a compound of Formula (I) or Formula (II), at least one Y is selected from the group consisting of optionally substituted heteroaryl, —$NR^6R^7$, —$(CR^9R^{10})_vNR^6R^7$, —$(CR^9R^{10})_vOH$, —$(CR^9R^{10})_wNR^6(CR^9R^{10})_wOH$, —$(CR^9R^{10})_vO(CR^9R^{10})_wNR^6R^7$, —$(CR^9R^{10})_wN(R^6)CH(=NR^8)$, —$(CR^9R^{10})_wN(R^6)C(=NR^8)NR^6R^7$, —$(CR^9R^{10})_v$Heterocyclyl, —CN, —C(O)OH, —$C(O)OR^{11}$, —$C(O)NR^6R^7$, and —$C(O)NR^6(CR^9R^{10})_wNR^6R^7$.

In some embodiments of a compound of Formula (I) or Formula (II), the compound has the Formula (Ia) or Formula (IIa):

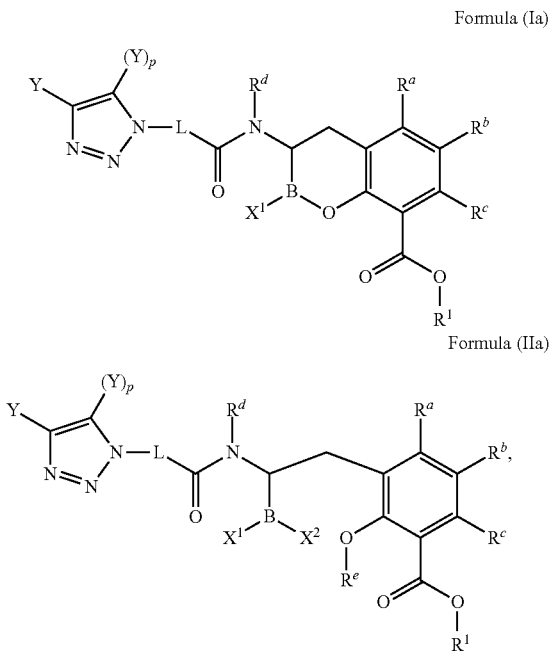

Formula (Ia)

Formula (IIa)

wherein
L is —(CR$^2$R$^3$)$_n$—;
n is 0, 1, 2, 3, 4, 5, or 6;
p is 0 or 1;
X$^1$ and X$^2$ are independently selected from —OH, —OR$^X$, and F;
each Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_v$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_w$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_w$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NO$_2$, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$ NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)$_v$CO$_2$H, —NR$^6$(CR$^9$R$^{10}$)$_v$CO$_2$R$^{11}$, —NR$^6$(CR$^9$R$^{10}$)$_v$C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$NR$^6$R$^7$, —(CR$^9$R$^{10}$)C(O)NR$^6$(CR$^9$R$^{10}$)$_w$NR$^6$R$^7$, —(CR$^9$R$^{10}$)C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)C(O)(CR$^9$R$^{10}$)$_v$ONR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$S(O)$_{0,1,2}$(CR$^9$R$^{10}$)$_v$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heterocyclyl-(NR$^6$R$^7$)$_2$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$O(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$NR$^6$C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-$$_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion;
v is 1-4;
w is 2-4;
or two Ys taken together with the atoms to which they are attached form an optionally substituted carbocycle or an optionally substituted heterocycle;
R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;
R$^e$ is hydrogen, optionally substituted C$_1$-C$_6$ alkyl, or optionally substituted C$_3$-C$_6$ cycloalkyl;

$R^x$ is optionally substituted $C_1$-$C_6$ alkyl, optionally substituted $C_3$-$C_6$ cycloalkyl, or a pharmaceutically acceptable boronate ester group;

$R^1$ is hydrogen, $R^{31}$, —$(R^{30})_q OR^{31}$, —$(R^{30})_q O(R^{30})_q OR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each $R^{30}$ is independently —$CH_2$—, —$CH(CH_3)$—, —$C(CH_3)_2$—, or optionally substituted 1,1'-cyclopropylene;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two $R^{31}$ are taken together with the Nitrogen to which they are attached to form a $C_3$-$C_8$ heterocyclyl;

each $R^2$ and $R^3$ are independently selected from the group consisting of hydrogen, fluoro, chloro, bromo, optionally substituted $C_1$-$C_6$ alkyl, optionally substituted $C_3$-$C_6$ cycloalkyl, —OH, —$OR^{11}$, —$SR^{11}$, —$NR^6R^7$, —$(CR^9R^{10})_vC(O)NR^6R^7$, —$(CR^9R^{10})_vC(O)OH$, —$(CR^9R^{10})_vOH$, —$(CR^9R^{10})_vNR^6R^7$, and —$(CR^9R^{10})_vN(R^6)C(=NR^8)NR^6R^7$;

or $R^2$ and $R^3$ on the same carbon are taken together to form an oxo or optionally substituted oxime;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —$S(O)_2R^{11}$, —$S(O)_2NH_2$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, —OH, —$OR^{11}$, —CN, —$NO_2$, —$NR_6$, optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_wNR^6R^7$, —$(CR^aR^b)_vC(O)NR^6R^7$, —$C(O)NR^6R^7$, —$C(O)OR^{11}$, —C(O)OH, —$NR^6SO_2R^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II), the compound has the Formula (Ia) or Formula (IIa):

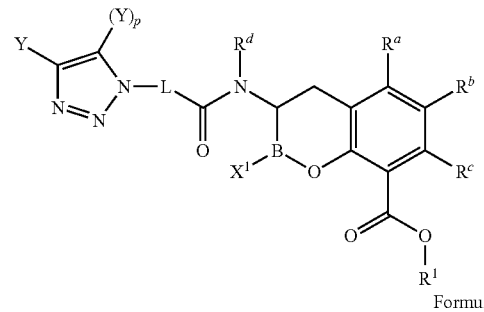

Formula (Ia)

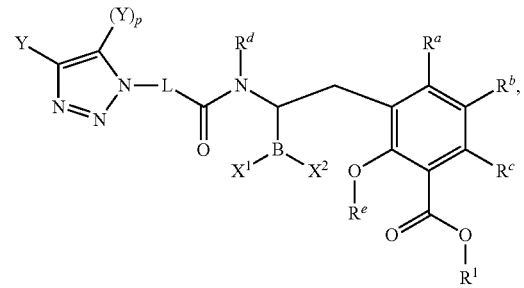

Formula (IIa)

wherein:

L is —$(CR^2R^3)_n$—;

n is 0, 1, 2, or 3;

p is 0 or 1;

$X^1$ is —OH and $X^2$ is —OH when present;

each Y is selected from the group consisting of optionally substituted alkyl, optionally substituted heterocycle, optionally substituted heteroaryl, —$NR^6R^7$, —$NR^6(CR^9R^{10})_wNR^6R^7$, —$NR^6C(O)R^{11}$, —$NR^6C(O)OR^{11}$, —$N(R^6)C(O)(CR^9R^{10})_wNR^6R^7$, —$NR^6C(O)NR^6R^7$, —$NR^6C(O)NR^6(CR^9R^{10})_wNR^6R^7$, —$NR^6(CR^9R^{10})_wS(O)_{0,1,2}R^{11}$, —$NR^6(CR^9R^{10})_wS(O)_{0,1,2}NR^6R^7$, —$NR^6(CR^9R^{10})_wNR^6R^7S(O)_{0,1,2}R^{11}$, —$NR^6(CR^9R^{10})_wNR^6S(O)_{0,1,2}NR^6R^6$, —$NR^6C(=NR^8)NR^6R^6$, —$N(R^6)C(=NR^8)R^{11}$, —$NR^6(CR^9R^{10})_wN(R^6)C(=NR^8)R^{11}$, —$NR^6(CR^9R^{10})_wC(=NR^8)NR^6R^7$, —$NR^6(CR^9R^{10})_wN(R^6)C(=NR^8)NR^6R^7$, —$NR^6(CR^9R^{10})_wNR^6C(=O)NR^6R^7$, —$NR^6(CR^9R^{10})_wNR^6C(=O)OR^{11}$, —$NR^6SO_2R^{11}$, —$NR^6(CR^9R^{10})$ CO₂H, —NR⁶(CR⁹R¹⁰)CO₂R¹¹, —NR⁶(CR⁹R¹⁰)C(O)NR⁶R⁷, —N(R⁶)-Heteroaryl-NR⁶R⁷, —N(R⁶)-Heterocyclyl-NR⁶R⁷, —NR⁶(CR⁹R¹⁰)ᵥHeteroaryl, —NR⁶(CR⁹R¹⁰)ᵥHeterocyclyl, —NR⁶(CR⁹R¹⁰)ᵥNR⁶-Heteroaryl, —NR⁶(CR⁹R¹⁰)ᵥNR⁶-Heterocyclyl, —CN, —(CR⁹R¹⁰)ᵥNR⁶R⁷, —(CR⁹R¹⁰)ᵥOH, —(CR⁹R¹⁰)ᵥOR¹¹, —(CR⁹R¹⁰)ᵥOC(O)R¹¹, —(CR⁹R¹⁰)ᵥOC(O)NR⁶R⁶, —(CR⁹R¹⁰)ᵥO(CR⁹R¹⁰)ᵥOR¹¹, —(CR⁹R¹⁰)ᵥO(CR⁹R¹⁰)ᵥOH, —(CR⁹R¹⁰)ᵥO(CR⁹R¹⁰)ᵥNR⁶R⁷, —(CR⁹R¹⁰)ᵥNR⁶(CR⁹R¹⁰)ᵥOH, —(CR⁹R¹⁰)ᵥNR⁶(CR⁹R¹⁰)ᵥOR¹¹, —(CR⁹R¹⁰)ᵥC(O)NR⁶R⁷, —(CR⁹R¹⁰)C(O)NR⁶(CR⁹R¹⁰)ᵥNR⁶R⁷, —(CR⁹R¹⁰)ᵥC(O)NR⁶(CR⁹R¹⁰)ᵥOR¹¹, —(CR⁹R¹⁰)ᵥN(R⁶)C(O)R¹¹, —(CR⁹R¹⁰)ᵥN(R⁶)C(O)OR¹¹, —(CR⁹R¹⁰)ᵥN(R⁶)C(O)NR⁶R⁷, —(CR⁹R¹⁰)ᵥN(R⁶)C(O)(CR⁹R¹⁰)ᵥNR⁶R⁷, —(CR⁹R¹⁰)ᵥN(R⁶)S(O)₀,₁,₂R¹¹, —(CR⁹R¹⁰)ᵥN(R⁶)S(O)₀,₁,₂NR⁶R⁷, —(CR⁹R¹⁰)ᵥS(O)₀,₁,₂NR⁶R⁷, —(CR⁹R¹⁰)ᵥNR⁶(CR⁹R¹⁰)ᵥNR⁶R⁷, —(CR⁹R¹⁰)ᵥN(R⁶)CH(=NR⁸), —(CR⁹R¹⁰)ᵥN(R⁶)C(=NR⁸)R¹¹, —(CR⁹R¹⁰)ᵥC(=NR⁸)NR⁶R⁷, —(CR⁹R¹⁰)ᵥN(R⁶)C(=NR⁸)NR⁶R⁷, —(CR⁹R¹⁰)ᵥC(=NR⁸)NR⁶C(=NR⁸)NR⁶R⁷, —(CR⁹R¹⁰)ᵥHeteroaryl-NR⁶R⁷, —(CR⁹R¹⁰)ᵥHeterocyclyl-NR⁶R⁷, —(CR⁹R¹⁰)ᵥHeteroaryl-N(R⁶)C(=NR⁸)NR⁶R⁷, —(CR⁹R¹⁰)ᵥHeterocyclyl-N(R⁶)C(=NR⁸)NR⁶R⁷, —(CR⁹R¹⁰)ᵥHeteroaryl, —(CR⁹R¹⁰)ᵥHeterocyclyl, —CN, —C(O)OH, —C(O)OR¹¹, —C(O)NR⁶R⁷, —C(O)NR⁶(CR⁹R¹⁰)ᵥNR⁶R⁷, —C(O)NR⁶(CR⁹R¹⁰)ᵥOH, —C(O)NR⁶(CR⁹R¹⁰)ᵥOR¹¹, —C(=NR⁸)NR⁶R⁷, and —C(=NR⁸)NR⁶C(O)R¹¹;

Rᵃ, Rᵇ, and Rᶜ are independently selected from the group consisting of hydrogen, fluoro, chloro, and C₁-C₆ alkyl;

Rᵉ is hydrogen, optionally substituted C₁-C₆ alkyl, or optionally substituted C₃-C₆ cycloalkyl;

R¹ is hydrogen, R³¹, —R³⁰OC(O)R³¹, or —R³⁰OC(O)OR³¹;

each R³⁰ is independently —CH₂— or —CH(CH₃)—;
each R³¹ is optionally substituted C₁-C₁₂ alkyl, optionally substituted C₁-C₁₂ alkenyl, optionally substituted C₁-C₁₂ alkynyl, C₃-C₈ cycloalkyl, C₃-C₈ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each R² and R³ are independently selected from the group consisting of hydrogen, fluoro, chloro, and C₁-C₆ alkyl;

or R² and R³ on the same carbon are taken together to form an oxo;

or R² and R³ on the same carbon are taken together to form an optionally substituted spiro-carbocycle or optionally substituted spiro-heterocycle with the carbon to which they are attached;

or when n is at least 2, two R² on different carbons are taken together form an optionally substituted carbocycle or optionally substituted heterocycle with the carbons to which they are attached;

or when n is at least 2, two R² on adjacent carbons are taken together to form a double bond; or two R² and two R³ on adjacent carbons are taken together to form a triple bond;

Rᵈ, R⁶ and R⁷ are independently selected from the group consisting of hydrogen, —OH, —CN, —S(O)₂R¹¹, —S(O)₂NH₂, and C₁-C₆ alkyl;

R⁸ is hydrogen or —CN;

R⁹ and R¹⁰ are independently selected from the group consisting of hydrogen, fluoro, chloro, and C₁-C₆ alkyl;

R¹¹ is C₁-C₆ alkyl;

v is 1-4; and w is 2-4.

In some embodiments of a compound of Formula (Ia) or Formula (IIa), Y is selected from the group consisting of optionally substituted heterocycle, optionally substituted heteroaryl, —NR⁶R⁷, —(CR⁹R¹⁰)ᵥNR⁶R⁷, —(CR⁹R¹⁰)ᵥOH, —(CR⁹R¹⁰)ᵥNR⁶(CR⁹R¹⁰)ᵥOH, —(CR⁹R¹⁰)ᵥO(CR⁹R¹⁰)ᵥNR⁶R⁷, —(CR⁹R¹⁰)ᵥN(R⁶)CH(=NR⁸), —(CR⁹R¹⁰)ᵥN(R⁶)C(=NR⁸)NR⁶R⁷, —(CR⁹R¹⁰)ᵥN(R⁶)C(=NR⁸)R¹¹, —(CR⁹R¹⁰)ᵥHeterocyclyl, —CN, —C(O)OH, —C(O)OR¹¹, —C(O)NR⁶R⁷, —C(O)NR⁶(CR⁹R¹⁰)ᵥNR⁶R⁷, —NR⁶C(=NR⁸)NR⁶R⁶, —N(R⁶)C(=NR⁸)R¹¹, —NR⁶C(O)NR⁶R⁷, and —N(R⁶)C(O)(CR⁹R¹⁰)ᵥNR⁶R⁷.

In some embodiments of a compound of Formula (Ia) or Formula (IIa), Y is selected from the group consisting of optionally substituted heteroaryl, —NR⁶R⁷, —(CR⁹R¹⁰)ᵥNR⁶R⁷, —(CR⁹R¹⁰)ᵥOH, —(CR⁹R¹⁰)ᵥNR⁶(CR⁹R¹⁰)ᵥOH, —(CR⁹R¹⁰)ᵥO(CR⁹R¹⁰)ᵥNR⁶R⁷, —(CR⁹R¹⁰)ᵥN(R⁶)CH(=NR⁸), —(CR⁹R¹⁰)ᵥN(R⁶)C(=NR⁸)NR⁶R⁷, —(CR⁹R¹⁰)ᵥHeterocyclyl, —CN, —C(O)OH, —C(O)OR¹¹, —C(O)NR⁶R⁷, and —C(O)NR⁶(CR⁹R¹⁰)ᵥNR⁶R⁷.

In some embodiments of a compound of Formula (I) or Formula (II):

L is —(CR²R³)ₙ—;
n is 0, 1, 2, 3, 4, 5, or 6;
p is 0, 1 or 2;
X¹ and X² are independently selected from —OH, —ORˣ, and F;
AzA is a five-membered heteroaromatic ring system bearing at least three N heteroatoms;
each Y is selected from the group consisting of fluoro, chloro, bromo, optionally substituted C₁-C₆ alkyl, optionally substituted C₃-C₆ cycloalkyl, optionally substituted heterocycle, optionally substituted aryl, optionally substituted heteroaryl, Heteroaryl-NR⁶R⁷, -Heterocyclyl-NR⁶R⁷, -Heteroaryl-N(R⁶)C(=NR⁸)NR⁶R⁷, -Heterocyclyl-N(R⁶)C(=NR⁸)NR⁶R⁷, —OH, —OR¹¹, —O(CR⁹R¹⁰)ᵥOH, —O(CR⁹R¹⁰)ᵥOR¹¹, —O(CR⁹R¹⁰)ᵥNR⁶R⁷, —O(CR⁹R¹⁰)ᵥNR⁶C(O)R¹¹, —O(CR⁹R¹⁰)ᵥNR⁶C(O)OR¹¹, —O(CR⁹R¹⁰)ᵥNR⁶C(O)NR⁶R⁷, —O(CR⁹R¹⁰)ᵥC(O)NR⁶R⁷, —O(CR⁹R¹⁰)ᵥNR⁶S(O)₀,₁,₂R¹¹, —O(CR⁹R¹⁰)ᵥNR⁶S(O)₀,₁,₂NR⁶R⁷, —O(CR⁹R¹⁰)ᵥS(O)₀,₁,₂R¹¹, —O(CR⁹R¹⁰)ᵥS(O)₀,₁,₂NR⁶R⁷, —O(CR⁹R⁷)ᵥC(=NR⁸)NR⁶R⁷, —O(CR⁹R¹⁰)ᵥN(R⁶)C(=NR⁸)R¹¹, —O(CR⁹R¹⁰)ᵥC(=NR⁸)NR⁶C(=NR⁸)NR⁶R⁷, —O(CR⁹R¹⁰)ᵥN(R⁶)C(=NR⁸)NR⁶R⁷, —O(CR⁹R¹⁰)ᵥS(O)₀,₁,₂R¹¹, —O(CR⁹R¹⁰)ᵥS(O)₀,₁,₂NR⁶R⁷, —OC(O)R¹¹, —OC(O)(CR⁹R¹⁰)ᵥNR⁶R⁷, —OC(O)NR⁶R⁷, —OC(O)OR¹¹, —OC(O)NR⁶(CR⁹R¹⁰)ᵥNR⁶R⁷, —O-Heteroaryl, —O-Heterocyclyl, —O(CR⁹R¹⁰)ᵥHeteroaryl, —O(CR⁹R¹⁰)ᵥHeterocyclyl, —O(CR⁹R¹⁰)ᵥNR⁶-Heteroaryl, —O(CR⁹R¹⁰)ᵥNR⁶-Heterocyclyl, —O(CR⁹R¹⁰)ᵥO-Heterocyclyl, —NO₂, —NR⁶R⁷, —NR⁶(CR⁹R¹⁰)ᵥNR⁶R⁷, —NR⁶(CR⁹R¹⁰)ᵥOH, —NR⁶(CR⁹R¹⁰)ᵥOR¹¹, —NR⁶C(O)R¹¹, —NR⁶C(O)OR¹¹, —N(R⁶)C(O)(CR⁹R¹⁰)ᵥNR⁶R⁷, —NR⁶C(O)NR⁶R⁷, —NR⁶C(O)NR⁶(CR⁹R¹⁰)ᵥNR⁶R⁷, —NR⁶(CR⁹R¹⁰)ᵥS(O)₀,₁,₂R¹¹, —NR⁶(CR⁹R¹⁰)ᵥS(O)₀,₁,₂NR⁶R⁷, —NR⁶(CR⁹R¹⁰)ᵥNR⁶R⁷S(O)₀,₁,₂R¹¹, —NR⁶(CR⁹R¹⁰)ᵥNR⁶S(O)₀,₁,₂NR⁶R⁶, —NR⁶C(=NR⁸)NR⁶R⁷, —NR⁶C(=NR⁸)R¹¹, —NR⁶(CR⁹R¹⁰)ᵥN(R⁶)C(=NR⁸)R¹¹, —NR⁶(CR⁹R¹⁰)ᵥC(=NR⁸)NR⁶R⁷, —NR⁶(CR⁹R¹⁰)ᵥN(R⁶)C(=NR⁸)NR⁶R⁷, —NR⁶(CR⁹R¹⁰)ᵥNR⁶C(=O)NR⁶R⁷, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$CN, —(CR$^9$R$^{10}$)$_w$NR$^6$R$^7$, —(CR$^9$R$^{10}$)$_w$OH, —(CR$^9$R$^{10}$)$_w$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_w$C(O)NR$^6$R$^7$, —(CR$^9$R$^{10}$)$_w$C(O)NR$^6$NR$^6$R$^7$, —(CR$^9$R$^{10}$)$_w$C(O)NR$^6$(CR$^9$R$^{10}$)$_w$NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)C(O)(CR$^9$R$^{10}$)$_v$ONR$^6$R$^7$, —(CR$^9$R$^{10}$)$_w$N(R$^6$)S(O)$_{0,1,2}$R$^{11}$, —(CR$^9$R$^{10}$)$_w$N(R$^6$)S(O)$_{0,1,2}$NR$^6$R$^7$, —(CR$^9$R$^{10}$)$_w$S(O)$_{0,1,2}$NR$^6$R$^7$, —(CR$^9$R$^{10}$)$_w$S(O)$_{0,1,2}$(CR$^9$R$^{10}$)$_w$NR$^6$R$^7$, —(CR$^9$R$^{10}$)$_w$NR$^6$(CR$^9$R$^{10}$)$_w$NR$^6$R$^7$, —(CR$^9$R$^{10}$)$_w$N(R$^6$)CH(=NR$^8$), —(CR$^9$R$^{10}$)$_w$N(R$^6$)C(=NR$^8$)R$^{11}$, —(CR$^9$R$^{10}$)$_w$C(=NR$^8$)NR$^6$R$^7$, —(CR$^9$R$^{10}$)$_w$N(R$^6$)C(=NR$^8$)NR$^6$R$^7$, —(CR$^9$R$^{10}$)$_w$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heterocyclyl-(NR$^6$R$^7$)$_2$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$O(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_w$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_w$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$$_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion;
v is 1-4;
w is 2-4;
or two Ys taken together with the atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;
each R$^{30}$ is independently —CH$_2$—, —CH(CH$_3$)—, —C(CH$_3$)$_2$—, or optionally substituted 1,1'-cyclopropylene;
each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, —NR$^6$R$^7$, —(CR$^9$R$^{10}$)$_v$C(O)NR$^6$R$^7$, —(CR$^9$R$^{10}$)$_v$C(O)OH, —(CR$^9$R$^{10}$)$_v$OH, —(CR$^9$R$^{10}$)$_v$NR$^6$R$^7$, and —(CR$^9$R$^{10}$)$_v$N(R$^6$)C(=NR$^8$)NR$^6$R$^7$;

or R$^2$ and R$^3$ on the same carbon are taken together to form an oxo or optionally substituted oxime;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_v$NR$^6$R$^7$, —(CR$^a$R$^b$)$_v$C(O)NR$^6$R$^7$, —C(O)NR$^6$R$^7$, —C(O)OR$^{11}$, —C(O)OH, —NR$^6$SO$_2$R$^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II):

L is —$(CR^2R^3)_n$—;
n is 0, 1, 2, or 3;
p is 0, 1 or 2;
$X^1$ is —OH and $X^2$ is —OH when present;
AzA is a five-membered heteroaromatic ring system bearing at least three N heteroatoms;

each Y is selected from the group consisting of optionally substituted alkyl, optionally substituted heterocycle, optionally substituted heteroaryl, —$NR^6R^7$, —$NR^6(CR^9R^{10})_wNR^6R^7$, —$NR^6C(O)R^{11}$, —$NR^6C(O)OR^{11}$, —$N(R^6)C(O)(CR^9R^{10})_vNR^6R^7$, —$NR^6C(O)NR^6R^7$, —$NR^6C(O)NR^6(CR^9R^{10})_wNR^6R^7$, —$NR^6(CR^9R^{10})_wS(O)_{0,1,2}R^{11}$, —$NR^6(CR^9R^{10})_wS(O)_{0,1,2}NR^6R^7$, —$NR^6(CR^9R^{10})_wNR^6R^7S(O)_{0,1,2}R^{11}$, —$NR^6(CR^9R^{10})_wNR^6S(O)_{0,1,2}NR^6R^6$, —$NR^6C(=NR^8)NR^6R^6$, —$N(R^6)C(=NR^8)R^{11}$, —$NR^6(CR^9R^{10})_wN(R^6)C(=NR^8)R^{11}$, —$NR^6(CR^9R^{10})_vC(=NR^8)NR^6R^7$, —$NR^6(CR^9R^{10})_wN(R^6)C(=NR^8)NR^6R^7$, —$NR^6(CR^9R^{10})_wNR^6C(=O)NR^6R^7$, —$NR^6(CR^9R^{10})_wNR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_wNR^6$-Heteroaryl, —$NR^6R^7$, —$NR^6(CR^9R^{10})_wNR^6$-Heterocyclyl, —CN, —$(CR^9R^{10})_wNR^6R^7$, —$(CR^9R^{10})_wOH$, —$(CR^9R^{10})_wOR^{11}$, —$(CR^9R^{10})_vOC(O)R^{11}$, —$(CR^9R^{10})_vOC(O)NR^6R^6$, —$(CR^9R^{10})_vO(CR^9R^{10})_wOR^{11}$, —$(CR^9R^{10})_vO(CR^9R^{10})_wOH$, —$(CR^9R^{10})_vO(CR^9R^{10})_wNR^6R^7$, —$(CR^9R^{10})_vNR^6(CR^9R^{10})_wOH$, —$(CR^9R^{10})_wOH$, —$(CR^9R^{10})_wNR^6(CR^9R^{10})_wOR^{11}$, —$(CR^9R^{10})_wC(O)NR^6R^7$, —$(CR^9R^{10})_wC(O)NR^6(CR^9R^{10})_wNR^6R^7$, —$(CR^9R^{10})_wC(O)NR^6(CR^9R^{10})_wOR^{11}$, —$(CR^9R^{10})_wN(R^6)C(O)R^{11}$, —$(CR^9R^{10})_wN(R^6)C(O)OR^{11}$, —$(CR^9R^{10})_wN(R^6)C(O)NR^6R^7$, —$(CR^9R^{10})_wN(R^6)C(O)(CR^9R^{10})_wNR^6R^7$, —$(CR^9R^{10})_wN(R^6)S(O)_{0,1,2}R^{11}$, —$(CR^9R^{10})_wN(R^6)S(O)_{0,1,2}NR^6R^7$, —$(CR^9R^{10})_wS(O)_{0,1,2}NR^6R^7$, —$(CR^9R^{10})_wNR^6(CR^9R^{10})_wNR^6R^7$, —$(CR^9R^{10})_wN(R^6)CH(=NR^8)$, —$(CR^9R^{10})_wN(R^6)C(=NR^8)R^{11}$, —$(CR^9R^{10})_wC(=NR^8)NR^6R^7$, —$(CR^9R^{10})_wN(R^6)C(=NR^8)NR^6R^7$, —$(CR^9R^{10})_wC(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_v$Heteroaryl, —$(CR^9R^{10})_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O))NR$^6$(CR$^9$R$^{10}$)$_w$OR$^{11}$, —C(=NR$^8$)NR$^6$R$^7$, and —C(=NR$^8$)NR$^6$C(O)R$^{11}$;

$R^a$, $R^b$, and $R^c$ are independently selected from the group consisting of hydrogen, fluoro, chloro, and $C_1$-$C_6$ alkyl;

$R^e$ is hydrogen, optionally substituted $C_1$-$C_6$ alkyl, or optionally substituted $C_3$-$C_6$ cycloalkyl;

$R^1$ is hydrogen, $R^{31}$, —$R^{30}OC(O)R^{31}$, or —$R^{30}OC(O)OR^{31}$;

each $R^{30}$ is independently —$CH_2$— or —$CH(CH_3)$—;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and $C_1$-$C_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —$S(O)_2R^{11}$, —$S(O)_2NH_2$, and $C_1$-$C_6$ alkyl;

$R^8$ is hydrogen or —CN;

$R^9$ and $R^{10}$ are independently selected from the group consisting of hydrogen, fluoro, chloro, and $C_1$-$C_6$ alkyl;

$R^{11}$ is $C_1$-$C_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, —$NR^6R^7$, —$(CR^9R^{10})_vNR^6R^7$, —$(CR^9R^{10})_vOH$, —$(CR^9R^{10})_vNR^6(CR^9R^{10})_wOH$, —$(CR^9R^{10})_vO(CR^9R^{10})_wNR^6R^7$, —$(CR^9R^{10})_vN(R^6)CH(=NR^8)$, —$(CR^9R^{10})_vN(R^6)C(=NR^8)NR^6R^7$, —$(CR^9R^{10})_vN(R^6)C(=NR^8)R^{11}$, —$(CR^9R^{10})_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_v$NR$^6$R$^7$.

In some embodiments of a compound of Formula (I) or Formula (II), at least one Y is selected from the group consisting of optionally substituted heteroaryl, —$NR^6R^7$, —$(CR^9R^{10})_vNR^6R^7$, —$(CR^9R^{10})_vOH$, —$(CR^9R^{10})_vNR^6(CR^9R^{10})_wOH$, —$(CR^9R^{10})_vO(CR^9R^{10})_wNR^6R^7$, —$(CR^9R^{10})_vN(R^6)CH(=NR^8)$, —$(CR^9R^{10})_vN(R^6)C(=NR^8)NR^6R^7$, —$(CR^9R^{10})_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II):

L is —$(CR^2R^3)_n$—;
n is 1, 2, 3, 4, 5, or 6;
p is 0, 1 or 2;
$X^1$ and $X^2$ are independently selected from —OH, —$OR^x$, and F;

AzA is a five-membered heteroaromatic ring system bearing at least three heteroatoms from the group consisting of N, O, and S;

each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, —OH, —$OR^{11}$, —$O(CR^9R^{10})_w$OH, —$O(CR^9R^{10})_w OR^{11}$, —$O(CR^9R^{10})_w NR^6R^7$, —$O(CR^9R^{10})_w NR^6C(O)R^{11}$, —$O(CR^9R^{10})_w NR^6C(O)OR^{11}$, —$O(CR^9R^{10})_w NR^6C(O)NR^6R^7$, —$O(CR^9R^{10})_w C(O)NR^6R^7$, —$O(CR^9R^{10})_w NR^6S(O)_{0,1,2}R^{11}$, —$O(CR^9R^{10})_w NR^6S(O)_{0,1,2}NR^6R^7$, —$O(CR^9R^{10})_w S(O)_{0,1,2}R^{11}$, —$O(CR^9R^{10})_w S(O)_{0,1,2}NR^6R^7$, —$O(CR^6R^7)_v C(=NR^8)NR^6R^7$, —$O(CR^9R^{10})_w N(R^6)C(=NR^8)R^{11}$, —$O(CR^9R^{10})_v C(=NR^8)NR^6C(=NR^8)NR^6R^7$, —$O(CR^9R^{10})_v N(R^6)C(=NR^8)NR^6R^7$, —$O(CR^9R^{10})_w S(O)_{0,1,2}R^{11}$, —$O(CR^9R^{10})_w S(O)_{0,1,2}NR^6R^7$, —$OC(O)R^{11}$, —$OC(O)(CR^9R^{10})_v NR^6R^7$, —$OC(O)NR^6R^7$, —$OC(O)OR^{11}$, —$OC(O)NR^6(CR^9R^{10})_w NR^6R^7$, —O-Heteroaryl, —O-Heterocyclyl, —$O(CR^9R^{10})_v$Heteroaryl, —$O(CR^9R^{10})_v$Heterocyclyl, —$O(CR^9R^{10})_w NR^6$-Heteroaryl, —$O(CR^9R^{10})_w NR^6$-Heterocyclyl, —$O(CR^9R^{10})_w O$-Heteroaryl, —$NO_2$, —$NR^6R^7$, —$NR^6(CR^9R^{10})_w NR^6R^7$, —$NR^6(CR^9R^{10})_w$OH, —$NR^6(CR^9R^{10})_w OR^{11}$, —$NR^6C(O)R^{11}$, —$NR^6C(O)OR^{11}$, —$N(R^6)C(O)(CR^9R^{10})_v NR^6R^7$, —$NR^6C(O)NR^6R^7$, —$NR^6C(O)NR^6(CR^9R^{10})_w NR^6R^7$, —$NR^6(CR^9R^{10})_w S(O)_{0,1,2}R^{11}$, —$NR^6(CR^9R^{10})_w S(O)_{0,1,2}NR^6R^7$, —$NR^6(CR^9R^{10})_w NR^6R^7 S(O)_{0,1,2}R^{11}$, —$NR^6(CR^9R^{10})_w NR^6S(O)_{0,1,2}NR^6R^6$, —$NR^6C(=NR^8)NR^6R^6$, —$N(R^6)C(=NR^8)R^{11}$, —$NR^6(CR^9R^{10})_w N(R^6)C(=NR^8)R^{11}$, —$NR^6(CR^9R^{10})_v C(=NR^8)NR^6R^7$, —$NR^6(CR^9R^{10})_w N(R^6)C(=NR^8)NR^6R^7$, —$NR^6(CR^9R^{10})_w NR^6C(=O)NR^6R^7$, —$NR^6(CR^9R^{10})_w NR^6C(=O)OR^{11}$, —$NR^6SO_2R^{11}$, —$NR^6(CR^9R^{10})CO_2H$, —$NR^6(CR^9R^{10})CO_2R^{11}$, —$NR^6(CR^9R^{10})C(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_w NR^6$-Heteroaryl, —$NR^6(CR^9R^{10})_w NR^6$-Heterocyclyl, —CN, —$(CR^9R^{10})_v$CN, —$(CR^9R^{10})_v NR^6R^7$, —$(CR^9R^{10})_v$OH, —$(CR^9R^{10})_v OR^{11}$, —$(CR^9R^{10})_v OC(O)R^{11}$, —$(CR^9R^{10})_v OC(O)NR^6R^6$, —$(CR^9R^{10})_v O(CR^9R^{10})_w OR^{11}$, —$(CR^9R^{10})_v O(CR^9R^{10})_w$OH, —$(CR^9R^{10})_v O(CR^9R^{10})_w NR^6R^7$, —$(CR^9R^{10})_v NR^6(CR^9R^{10})_w$OH, —$(CR^9R^{10})_v NR^6(CR^9R^{10})_w OR^{11}$, —$(CR^9R^{10})_v C(O)NR^6R^7$, —$(CR^9R^{10})_v C(O)NR^6 NR^6R^7$, —$(CR^9R^{10})C(O)NR^6(CR^9R^{10})_w NR^6R^7$, —$(CR^9R^{10})C(O)NR^6(CR^9R^{10})_w OR^{11}$, —$(CR^9R^{10})_v N(R^6)C(O)R^{11}$, —$(CR^9R^{10})_v N(R^6)C(O)OR^{11}$, —$(CR^9R^{10})_v N(R^6)C(O)NR^6R^7$, —$(CR^9R^{10})_v N(R^6)C(O)(CR^9R^{10})_v NR^6R^7$, —)) $(CR^9R^{10})_v N(R^6)C(O)(CR^9R^{10})_v ONR^6R^7$, —$(CR^9R^{10})_v N(R^6)S(O)_{0,1,2}R^{11}$, —$(CR^9R^{10})_v N(R^6)S(O)_{0,1,2}NR^6R^7$, —$(CR^9R^{10})_v S(O)_{0,1,2}NR^6R^7$, —$(CR^9R^{10})_v S(C)_{0,1,2}(CR^9R^{10})_v NR^6R^7$, —$(CR^9R^{10})_v NR^6(CR^9R^{10})_w NR^6R^7$, —$(CR^9R^{10})_v N(R^6)CH(=NR^8)$, —$(CR^9R^{10})_v N(R^6)C(=NR^8)R^{11}$, —$(CR^9R^{10})_v C(=NR^8)NR^6R^7$, —$(CR^9R^{10})_v N(R^6)C(=NR^8)NR^6R^7$, —$(CR^9R^{10})_v C(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heterocyclyl-$(NR^6R^7)_2$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_v$Heteroaryl, —$(CR^9R^{10})_v$Heterocyclyl, —C(O)OH, —$C(O)OR^{11}$, —$C(O)NR^6R^7$, —$C(O)NR^6(CR^9R^{10})_w NR^6R^7$, —$C(O)NR^6O(CR^9R^{10})_w NR^6R^7$, —$C(O)NR^6(CR^9R^{10})_w$OH, —$NR^6(CR^9R^{10})_w OR^{11}$, —$C(=NR^8)NR^6R^7$, —$C(=NR^8)NR^6C(O)R^{11}$, —$S(O)_{0,1,2}R^{11}$, —$S(O)_{0,1,2}(CR^9R^{10})_w NR^6R^7$, —$S(O)_{0,1,2}(CR^9R^{10})_w$OH, —$S(O)_{0,1,2}(CR^9R^{10})_w OR^{11}$, —$SO_2NR^6R^7$, —$S(O)_{0,1,2}NR^6(CR^9R^{10})_w NR^6R^7$, —$S(O)_{0,1,2}(CR^9R^{10})_v N(R^6)C(=NR^8)R^{11}$, —$S(O)_{0,1,2}(CR^9R^{10})_v C(=NR^8)NR^6R^7$, —$S(O)_{0,1,2}(CR^9R^{10})_w N(R^6)C(=NR^8)NR^6R^7$, —$S(O)_{0,1,2}(CR^9R^{10})_v C(=NR^8)NR^6C(=NR^8)NR^6R^7$, —$Si(R^{11})_3$, —$NR^6R^7 R^{12+}Q^-$, —$(CR^9R^{10})_v NR^6R^7 R^{12+}Q^-$, —$NR^6(CR^9R^{10})_w NR^6R^7 R^{12+}Q^-$, —$NR^6R^{12+}(CR^9R^{10})_w NR^6R^7 R^{12+}Q^-_2$, —$(CR^9R^{10})_v(T)^+Q^-$, and —$O(CR^9R^{10})_w NR^6R^6R^{12+}Q^-$;

wherein:
T is pyridine-1-yl, pyrimidin-1-yl, or thiazol-3-yl;
Q is a pharmaceutically acceptable counterion; and
v is 1-4;
w is 2-4;
or two Ys taken together with the atoms to which they are attached form an optionally substituted carbocycle or an optionally substituted heterocycle;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{11}$, —$NR^6R^7$, and —$SR^{11}$;

$R^e$ is hydrogen, optionally substituted $C_1$-$C_6$ alkyl, or optionally substituted $C_3$-$C_6$ cycloalkyl;

$R^x$ is optionally substituted $C_1$-$C_6$ alkyl, optionally substituted $C_3$-$C_6$ cycloalkyl, or a pharmaceutically acceptable boronate ester group;

$R^1$ is hydrogen, $R^{31}$, —$(R^{30})_q OR^{31}$, —$(R^{30})_q O(R^{30})_q OR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each $R^{30}$ is independently —$CH_2$—, —$CH(CH_3)$—, —$C(CH_3)_2$—, or optionally substituted 1,1'-cyclopropylene;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two $R^{31}$ are taken together with the Nitrogen to which they are attached to form a $C_3$-$C_8$ heterocyclyl;

each $R^2$ and $R^3$ are independently selected from the group consisting of hydrogen, fluoro, chloro, bromo, optionally substituted $C_1$-$C_6$ alkyl, optionally substituted $C_3$-$C_6$ cycloalkyl, —OH, —$OR^{11}$, —$SR^{11}$, —$NR^6R^7$, —$(CR^9R^{10})_v C(O)NR^6R^7$, —$(CR^9R^{10})_w C(O)OH$, —$(CR^9R^{10})_v$OH, —$(CR^9R^{10})_v NR^6R^7$, and —$(CR^9R^{10})_v N(R^6)C(=NR^8)NR^6R^7$;

or $R^2$ and $R^3$ on the same carbon are taken together to form an oxo or optionally substituted oxime;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —CN, —OH, —S(O)$_2$R$^{11}$, —S(O)$_2$NH$_2$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, —OH, —OR$^{11}$, —CN, —NO$_2$, —NR$_6$, optionally substituted $C_1$-$C_6$ alkyl;

$R^9$ and $R^{10}$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR$^{11}$, —SR$^{11}$, —NR$^6$R$^7$, —NR$^6$C(O)R$^{11}$, —(CR$^a$R$^b$)$_v$NR$^6$R$^7$, —(CR$^a$R$^b$)$_v$C(O)NR$^6$R$^7$, —C(O)NR$^6$R$^7$, —C(O)OR$^{11}$, —C(O)OH, —NR$^6$SO$_2$R$^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II):

L is —(CR$^2$R$^3$)$_n$—;

n is 1, 2, or 3;

p is 0, 1 or 2;

$X^1$ is —OH and $X^2$ is —OH when present;

AzA is a five-membered heteroaromatic ring system bearing at least three heteroatoms from the group consisting of N, O, and S;

each Y is selected from the group consisting of optionally substituted alkyl, optionally substituted heterocycle, optionally substituted heteroaryl, —NR$^6$R$^7$, —NR$^6$(CR$^9$R$^{10}$)$_w$NR$^6$R$^7$, —NR$^6$C(O)R$^{11}$, —NR$^6$C(O)OR$^{11}$, —N(R$^6$)C(O)(CR$^9$R$^{10}$)$_w$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_w$NR$^6$R$^7$, —(CR$^9$R$^{10}$)$_w$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_v$OH, —(CR$^9$R$^{10}$)$_v$O(CR$^9$R$^{10}$)NR$^6$R$^7$, —(CR$^9$R$^{10}$)$_w$NR$^6$(CR$^9$R$^{10}$)$_v$OH, —(CR$^9$R$^{10}$)$_w$NR$^6$(CR$^9$R$^{10}$)$_v$OR$^{11}$, —(CR$^9$R$^{10}$)C(O)NR$^6$R$^7$, —(CR$^9$R$^{10}$)C(O)NR$^6$(CR$^9$R$^{10}$)$_w$NR$^6$R$^7$, —(CR$^9$R$^{10}$)$_v$C(O)NR$^6$(CR$^9$R$^{10}$)$_v$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$;

$R^a$, $R^b$, and $R^c$ are independently selected from the group consisting of hydrogen, fluoro, chloro, and $C_1$-$C_6$ alkyl;

$R^e$ is hydrogen, optionally substituted $C_1$-$C_6$ alkyl, or optionally substituted $C_3$-$C_6$ cycloalkyl;

$R^1$ is hydrogen, $R^{31}$, —R$^{30}$OC(O)R$^{31}$, or —R$^{30}$OC(O)OR$^{31}$;

each $R^{30}$ is independently —CH$_2$— or —CH(CH$_3$)—;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and $C_1$-$C_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —S(O)$_2R^{11}$, —S(O)$_2$NH$_2$, and C$_1$-C$_6$ alkyl;

$R^8$ is hydrogen or —CN;

$R^9$ and $R^{10}$ are independently selected from the group consisting of hydrogen, fluoro, chloro, and C$_1$-C$_6$ alkyl;

$R^{11}$ is C$_1$-C$_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, —NR$^6$R$^7$, —(CR$^9$R$^{10}$)$_v$NR$^6$R$^7$, —(CR$^9$R$^{10}$)$_v$OH, —(CR$^9$R$^{10}$)$_v$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$N(R$^6$)C(=NR$^8$)R$^{11}$, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_v$NR$^6$R$^7$.

In some embodiments of a compound of Formula (I) or Formula (II), at least one Y is selected from the group consisting of optionally substituted heteroaryl, —NR$^6$R$^7$, —(CR$^9$R$^{10}$)$_v$NR$^6$R$^7$, —(CR$^9$R$^{10}$)$_v$OH, —(CR$^9$R$^{10}$)$_v$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II):

L is —(CR$^2$R$^3$)$_n$—;

n is 1, 2, 3, 4, 5, or 6;

p is 1, 2 or 3;

$X^1$ and $X^2$ are independently selected from —OH, —OR$^X$, and F;

AzA is a five-membered heteroaromatic ring system bearing at least two heteroatoms from the group consisting of N, O, and S, provided that AzA is not thiazolyl;

each Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, eteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=N R$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_v$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_v$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)$_w$CO$_2$H, —NR$^6$(CR$^9$R$^{10}$)$_w$CO$_2$R$^{11}$, —NR$^6$(CR$^9$R$^{10}$)$_v$C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_v$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$—(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH$^{11}$, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_w$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:

T is pyridine-1-yl, pyrimidin-1-yl, or thiazol-3-yl;

Q is a pharmaceutically acceptable counterion; and v is 1-4;

w is 2-4;

or two Ys taken together with the atoms to which they are attached form an optionally substituted carbocycle or an optionally substituted heterocycle;

$R^a$, $R^b$, and $R^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, and NR$^6$R$^7$;

or R$^2$ and R$^3$ on the same carbon are taken together to form an oxo or optionally substituted oxime;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_w$NR$^6$R$^7$, —(CR$^a$R$^b$)$_w$C(O)NR$^6$R$^7$, —C(O)NR$^6$R$^7$, —NR$^6$SO$_2$R$^{11}$, optionally substituted heterocyclyl, optionally substituted aryl, and optionally substituted heteroaryl;

or R$^9$ and R$^{10}$ taken together with the carbon atom to which they are attached form an optionally substituted oxime, an optionally substituted carbocycle, or an optionally substituted heterocycle;

R$^{11}$ is optionally substituted C$_1$-C$_6$ alkyl, optionally substituted C$_3$-C$_6$ cycloalkyl, optionally substituted heteroaryl, optionally substituted heterocyclyl, or optionally substituted aryl; and R$^{12}$ is optionally substituted C$_1$-C$_6$ alkyl or optionally substituted C$_3$-C$_6$ cycloalkyl.

In some embodiments of a compound of Formula (I) or Formula (II):

L is —(CR$^2$R$^3$)$_n$—;

n is 1, 2, or 3;

p is 1, 2 or 3;

X$^1$ is —OH and X$^2$ is —OH when present;

AzA is a five-membered heteroaromatic ring system bearing at least two heteroatoms from the group consisting of N, O, and S, provided that AzA is not thiazolyl;

each Y is selected from the group consisting of optionally substituted alkyl, optionally substituted heterocycle, optionally substituted heteroaryl, —NR$^6$R$^7$, —NR$^6$(CR$^9$R$^{10}$)$_w$NR$^6$R$^7$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_w$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$;

R$^a$, R$^b$, and R$^c$ are independently selected from the group consisting of hydrogen, fluoro, chloro, and C$_1$-C$_6$ alkyl;

R$^e$ is hydrogen, optionally substituted C$_1$-C$_6$ alkyl, or optionally substituted C$_3$-C$_6$ cycloalkyl;

R$^1$ is hydrogen, R$^{31}$, —R$^{30}$OC(O)R$^{31}$, or —R$^{30}$OC(O)OR$^{31}$;

each R$^{30}$ is independently —CH$_2$— or —CH(CH$_3$)—;

each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each R$^2$ and R$^3$ are independently selected from the group consisting of hydrogen, fluoro, chloro, and C$_1$-C$_6$ alkyl;

or R$^2$ and R$^3$ on the same carbon are taken together to form an oxo;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, and C$_1$-C$_6$ alkyl;

R$^8$ is hydrogen or —CN;

R$^9$ and R$^{10}$ are independently selected from the group consisting of hydrogen, fluoro, chloro, or C$_1$-C$_6$ alkyl;

R$^{11}$ is C$_1$-C$_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, —NR$^6$R$^7$, —(CR$^9$R$^{10}$)$_v$NR$^6$R$^7$, —(CR$^9$R$^{10}$)$_v$OH, —(CR$^9$R$^{10}$)$_w$NR$^6$(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)NR$^6$R$^7$, —(CR$^9$R$^{10}$)$_v$N(R$^6$)C(=NR$^8$)R$^{11}$, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —NR$^6$C(=NR$^8$)NR$^6$R$^6$, —N(R$^6$)C(=NR$^8$)R$^{11}$, —NR$^6$C(O)NR$^6$R$^7$, and —N(R$^6$)C(O)(CR$^9$R$^{10}$)$_v$NR$^6$R$^7$.

In some embodiments of a compound of Formula (I) or Formula (II), at least one Y is selected from the group consisting of optionally substituted heteroaryl, —NR$^6$R$^7$, —(CR$^9$R$^{10}$)$_v$NR$^6$R$^7$, —(CR$^9$R$^{10}$)$_v$OH, —(CR$^9$R$^{10}$)$_v$N(R$^6$)C(=NR$^8$)NR$^6$R$^7$, —(CR$^9$R$^{10}$)$_v$Heterocyclyl, —CN, —C(O)OH, —C(O)OR$^{11}$, —C(O)NR$^6$R$^7$, and —C(O)NR$^6$(CR$^9$R$^{10}$)$_w$NR$^6$R$^7$.

In some embodiments of a compound of Formula (I) or Formula (II):

L is —(CR$^2$R$^3$)$_n$—;

n is 1, 2, 3, 4, 5, or 6;

p is 0, 1, 2 or 3;

X$^1$ and X$^2$ are independently selected from —OH, —OR$^x$, and F;

AzA is a five-membered heteroaromatic ring system bearing at least two heteroatoms from the group consisting of N, O, and S, provided that when AzA is a five-membered heteroaromatic ring system bearing two heteroatoms then p is 1, 2, or 3;

each Y is selected from the group consisting of fluoro, chloro, bromo, optionally substituted C$_1$-C$_6$ alkyl, optionally substituted C$_3$-C$_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_v$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)R$^{11}$, —NR$^6$SO$_2$R$^{11}$, —NR$^6$(CR$^9$R$^{10}$)$_w$CO$_2$H, —NR$^6$(CR$^9$R$^{10}$)$_w$CO$_2$R$^{11}$, —NR$^6$(CR$^9$R$^{10}$)$_w$C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_v$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_w$OH, —(CR$^9$R$^{10}$)$_w$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O))NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_v$N(R$^6$)S(O)$_{0,1,2}$NR$^6$R$^7$—(CR$^9$R$^{10}$)$_v$S(O)$_{0,1,2}$NR$^6$R$^7$, —(CR$^9$R$^{10}$)$_w$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_w$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH$^{11}$, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
T is pyridine-1-yl, pyrimidin-1-yl, or thiazol-3-yl;
Q is a pharmaceutically acceptable counterion; and
v is 1-4;
w is 2-4;
or two Ys taken together with the atoms to which they are attached form an optionally substituted carbocycle or an optionally substituted heterocycle, provided that when AzA is thiazolyl, at least one Y is not —NR$^6$R$^7$ or —NR$^6$C(O)R$^{11}$;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;
each R$^{30}$ is independently —CH$_2$—, —CH(CH$_3$)—, —C(CH$_3$)$_2$—, or optionally substituted 1,1'-cyclopropylene;
each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or
two R$^{31}$ are taken together with the Nitrogen to which they are attached to form a C$_3$-C$_8$ heterocyclyl;
each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, and NR$^6$R$^7$;
or R$^2$ and R$^3$ on the same carbon are taken together to form an oxo;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_w$NR$^6$R$^7$, —(CR$^a$R$^b$)$_v$C(O)NR$^6$R$^7$, —C(O)NR$^6$R$^7$, —NR$^6$SO$_2$R$^{11}$, optionally substituted heterocyclyl, optionally substituted aryl, and optionally substituted heteroaryl;

or R$^9$ and R$^{10}$ taken together with the carbon atom to which they are attached form an optionally substituted oxime, an optionally substituted carbocycle, or an optionally substituted heterocycle;

R$^{11}$ is optionally substituted C$_1$-C$_6$ alkyl, optionally substituted C$_3$-C$_6$ cycloalkyl, optionally substituted heteroaryl, optionally substituted heterocyclyl, or optionally substituted aryl; and R$^{12}$ is optionally substituted C$_1$-C$_6$ alkyl or optionally substituted C$_3$-C$_6$ cycloalkyl.

In some embodiments of a compound of Formula (I) or Formula (II):
L is —(CR$^2$R$^3$)$_n$—;
n is 1, 2, or 3;
p is 0, 1, 2 or 3;
X$^1$ is —OH and X$^2$ is —OH when present;
AzA is a five-membered heteroaromatic ring system bearing at least two heteroatoms from the group consisting of N, O, and S, provided that when AzA is a five-membered heteroaromatic ring system bearing two heteroatoms then p is 1, 2, or 3;
each Y is selected from the group consisting of optionally substituted alkyl, optionally substituted heterocycle, optionally substituted heteroaryl, —NR$^6$R$^7$, —NR$^6$(CR$^9$R$^{10}$)$_w$NR$^6$R$^7$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$ $(CR^9R^{10})_wNR^6R^7S(O)_{0,1,2}R^{11}$, $-NR^6(CR^9R^{10})_wNR^6S(O)_{0,1,2}NR^6R^6$, $-NR^6C(=NR^8)NR^6R^6$, $-N(R^6)C(=NR^8)R^{11}$, $-NR^6(CR^9R^{10})_wN(R^6)C(=NR^8)R^{11}$, $-NR^6(CR^9R^{10})_vC(=NR^8)NR^6R^7$, $-NR^6(CR^9R^{10})_wN(R^6)C(=NR^8)NR^6R^7$, $-NR^6(CR^9R^{10})_wNR^6C(=O)NR^6R^7$, $-NR^6(CR^9R^{10})_wNR^6C(=O)OR^{11}$, $-NR^6SO_2R^{11}$, $-NR^6(CR^9R^{10})CO_2H$, $-NR^6(CR^9R^{10})CO_2R^{11}$, $-NR^6(CR^9R^{10})C(O)NR^6R^7$, $-N(R^6)$-Heteroaryl-$NR^6R^7$, $-N(R^6)$-Heterocyclyl-$NR^6R^7$, $-NR^6(CR^9R^{10})_v$Heteroaryl, $-NR^6(CR^9R^{10})_v$Heterocyclyl, $-NR^6(CR^9R^{10})_wNR^6$-Heteroaryl, $-NR^6(CR^9R^{10})_wNR^6$-Heterocyclyl, $-CN$, $-(CR^9R^{10})_vNR^6R^7$, $-(CR^9R^{10})_vOH$, $-(CR^9R^{10})_vOR^{11}$, $-(CR^9R^{10})_vOC(O)R^{11}$, $-(CR^9R^{10})_vOC(O)NR^6R^6$, $-(CR^9R^{10})_vO(CR^9R^{10})_wOR^{11}$, $-(CR^9R^{10})_vO(CR^9R^{10})_wOH$, $-(CR^9R^{10})_vO(CR^9R^{10})_wNR^6R^7$, $-(CR^9R^{10})_vNR^6(CR^9R^{10})_wOH$, $-(CR^9R^{10})_vNR^6(CR^9R^{10})_wOR^{11}$, $-(CR^9R^{10})_vC(O)NR^6R^7$, $-(CR^9R^{10})_vC(O)NR^6(CR^9R^{10})_wNR^6R^7$, $-(CR^9R^{10})_vC(O)NR^6(CR^9R^{10})_wOR^{11}$, $-(CR^9R^{10})_vN(R^6)C(O)R^{11}$, $-(CR^9R^{10})_vN(R^6)C(O)OR^{11}$, $-(CR^9R^{10})_vN(R^6)C(O)NR^6R^7$, $-(CR^9R^{10})_vN(R^6)S(O)_{0,1,2}R^{11}$, $-(CR^9R^{10})_vN(R^6)S(O)_{0,1,2}NR^6R^7$, $-(CR^9R^{10})_vS(O)_{0,1,2}NR^6R^7$, $-(CR^9R^{10})_vNR^6(CR^9R^{10})_wNR^6R^7$, $-(CR^9R^{10})_vN(R^6)CH(=NR^8)$, $-(CR^9R^{10})_vN(R^6)C(=NR^8)R^{11}$, $-(CR^9R^{10})_vC(=NR^8)NR^6R^7$, $-(CR^9R^{10})_vN(R^6)C(=NR^8)NR^6R^7$, $-(CR^9R^{10})_vC(=NR^8)NR^6C(=NR^8)NR^6R^7$, $-(CR^9R^{10})_v$Heteroaryl-$NR^6R^7$, $-(CR^9R^{10})_v$Heterocyclyl-$NR^6R^7$, $-(CR^9R^{10})_v$Heteroaryl-$N(R^6)C(=NR^8)NR^6R^7$, $-(CR^9R^{10})_v$Heterocyclyl-$N(R^6)C(=NR^8)NR^6R^7$, $-(CR^9R^{10})_v$Heteroaryl, $-(CR^9R^{10})_v$Heterocyclyl, $-CN$, $-C(O)OH$, $-C(O)OR^{11}$, $-C(O)NR^6R^7$, $-C(O)NR^6(CR^9R^{10})_wNR^6R^7$, $-C(O)NR^6(CR^9R^{10})_wOH$, $-C(O)NR^6(CR^9R^{10})_wOR^{11}$, $-C(=NR^8)NR^6R^7$, and $-C(=NR^8)NR^6C(O)R^{11}$, provided that when AzA is thiazolyl, at least one Y is not $-NR^6R^7$ or $-NR^6C(O)R^{11}$;

$R^a$, $R^b$, and $R^c$ are independently selected from the group consisting of hydrogen, fluoro, chloro, and $C_1$-$C_6$ alkyl;

$R^e$ is hydrogen, optionally substituted $C_1$-$C_6$ alkyl, or optionally substituted $C_3$-$C_6$ cycloalkyl;

$R^1$ is hydrogen, $R^{31}$, $-R^{30}OC(O)R^{31}$, or $-R^{30}OC(O)OR^{31}$;

each $R^{30}$ is independently $-CH_2-$ or $-CH(CH_3)-$;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and $C_1$-$C_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, $-OH$, $-CN$, $-S(O)_2R^{11}$, $-S(O)_2NH_2$, and $C_1$-$C_6$ alkyl;

$R^8$ is hydrogen or $-CN$;

$R^9$ and $R^{10}$ are independently selected from the group consisting of hydrogen, fluoro, chloro, or $C_1$-$C_6$ alkyl;

$R^{11}$ is $C_1$-$C_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, $-NR^6R^7$, $-(CR^9R^{10})_vNR^6R^7$, $-(CR^9R^{10})_vOH$, $-(CR^9R^{10})_vNR^6(CR^9R^{10})_wOH$, $-(CR^9R^{10})_vO(CR^9R^{10})_wNR^6R^7$, $-(CR^9R^{10})_vN(R^6)CH(=NR^8)$, $-(CR^9R^{10})_vN(R^6)C(=NR^8)NR^6R^7$, $-(CR^9R^{10})_vN(R^6)C(=NR^8)R^{11}$, $-(CR^9R^{10})_v$Heterocyclyl, $-CN$, $-C(O)OH$, $-C(O)OR^{11}$, $-C(O)NR^6R^7$, $-C(O)NR^6(CR^9R^{10})_wNR^6R^7$, $-NR^6C(=NR^8)NR^6R^6$, $-N(R^6)C(=NR^8)R^{11}$, $-NR^6C(O)NR^6R^7$, and $-N(R^6)C(O)(CR^9R^{10})_vNR^6R^7$.

In some embodiments of a compound of Formula (I) or Formula (II), at least one Y is selected from the group consisting of optionally substituted heteroaryl, $-NR^6R^7$, $-(CR^9R^{10})_vNR^6R^7$, $-(CR^9R^{10})_vOH$, $-(CR^9R^{10})_vNR^6(CR^9R^{10})_wOH$, $-(CR^9R^{10})_vO(CR^9R^{10})_wNR^6R^7$, $-(CR^9R^{10})_vN(R^6)CH(=NR^8)$, $-(CR^9R^{10})_vN(R^6)C(=NR^8)NR^6R^7$, $-(CR^9R^{10})_v$Heterocyclyl, $-CN$, $-C(O)OH$, $-C(O)OR^{11}$, $-C(O)NR^6R^7$, and $-C(O)NR^6(CR^9R^{10})_wNR^6R^7$.

In some embodiments of a compound of Formula (I) or Formula (II):

L is $-(CR^2R^3)_n-$;

n is 1, 2, 3, 4, 5, or 6;

p is 1, 2 or 3;

$X^1$ and $X^2$ are independently selected from $-OH$, $-OR^x$, and F;

AzA is a five-membered heteroaromatic ring system bearing at least two heteroatom from the group consisting of N, O, and S;

each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, $-OH$, $-OR^{11}$, $-O(CR^9R^{10})_wOH$, $-O(CR^9R^{10})_wOR^{11}$, $-O(CR^9R^{10})_wNR^6R^7$, $-O(CR^9R^{10})_wNR^6C(O)R^{11}$, $-O(CR^9R^{10})_wNR^6C(O)OR^{11}$, $-O(CR^9R^{10})_wNR^6C(O)NR^6R^7$, $-O(CR^9R^{10})_wC(O)NR^6R^7$, $-O(CR^9R^{10})_wNR^6S(O)_{0,1,2}R^{11}$, $-O(CR^9R^{10})_wNR^6S(O)_{0,1,2}NR^6R^7$, $-O(CR^9R^{10})_wS(O)_{0,1,2}R^{11}$, $-O(CR^9R^{10})_wS(O)_{0,1,2}NR^6R^7$, $-O(CR^6R^7)_vC(=NR^8)NR^6R^7$, $-O(CR^9R^{10})_wN(R^6)C(=NR^8)R^{11}$, $-O(CR^9R^{10})_vC(=NR^8)NR^6C(=NR^8)NR^6R^7$, $-O(CR^9R^{10})_wN(R^6)C(=NR^8)NR^6R^7$, $-O(CR^9R^{10})_wS(O)_{0,1,2}R^{11}$, $-O(CR^9R^{10})_wS(O)_{0,1,2}NR^6R^7$, $-OC(O)R^{11}$, $-OC(O)(CR^9R^{10})_wNR^6R^7$, $-OC(O)NR^6R^7$, $-OC(O)OR^{11}$, $-OC(O)NR^6(CR^9R^{10})_wNR^6R^7$, $-O$-Heteroaryl, $-O$-Heterocyclyl, $-O(CR^9R^{10})_v$Heteroaryl, $-O(CR^9R^{10})_v$Heterocyclyl, $-O(CR^9R^{10})_wNR^6$-Heteroaryl, $-O(CR^9R^{10})_wNR^6$-Heterocyclyl, —O(CR$^9$R$^{10}$)$_w$O-Heterocyclyl, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)OR$^{11}$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$C(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)$_v$CO$_2$H, —NR$^6$(CR$^9$R$^{10}$)$_v$CO$_2$R$^{11}$, —NR$^6$(CR$^9$R$^{10}$)$_v$C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_v$NR$^6$R$^7$, —(CR$^9$R$^{10}$)$_v$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_w$OH, —(CR$^9$R$^{10}$)$_v$O(CR$^9$R$^{10}$)$_w$NR$^6$R$^7$, —(CR$^9$R$^{10}$)$_v$NR$^6$(CR$^9$R$^{10}$)$_w$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_w$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_v$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_w$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
  T is pyridine-1-yl, pyrimidin-1-yl, or thiazol-3-yl;
  Q is a pharmaceutically acceptable counterion; and
  v is 1-4;
  w is 2-4;
  or two Ys taken together with the atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted C$_1$-C$_6$ alkyl, or optionally substituted C$_3$-C$_6$ cycloalkyl;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;
each R$^{30}$ is independently —CH$_2$—, —CH(CH$_3$)—, —C(CH$_3$)$_2$—, or optionally substituted 1,1'-cyclopropylene;
each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or
two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, and —NR$^6$R$^7$;
or R$^2$ and R$^3$ on the same carbon are taken together to form an oxo or optionally substituted oxime;
or R$^2$ and R$^3$ on the same carbon are taken together to form an optionally substituted spiro-carbocycle or optionally substituted spiro-heterocycle with the carbon to which they are attached;
or when n is at least 2, two R$^2$ on different carbons are taken together form an optionally substituted carbocycle or optionally substituted heterocycle with the carbons to which they are attached;
or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted $C_3$-$C_6$ cycloalkyl, —OH, —$OR^{11}$, —$SR^{11}$, —$NR^6R^7$, —$NR^6C(O)R^{11}$, —$(CR^aR^b)_vNR^6R^7$, —$(CR^aR^b)_vC(O)NR^6R^7$, —$C(O)NR^6R^7$, —$NR^6SO_2R^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted $C_1$-$C_6$ alkyl, optionally substituted $C_3$-$C_6$ cycloalkyl, optionally substituted heteroaryl, optionally substituted heterocyclyl, or optionally substituted aryl; and $R^{12}$ is optionally substituted $C_1$-$C_6$ alkyl or optionally substituted $C_3$-$C_6$ cycloalkyl.

In some embodiments of a compound of Formula (I) or Formula (II):

L is —$(CR^2R^3)_n$—;

n is 1, 2, or 3;

p is 1, 2 or 3;

$X^1$ is —OH and $X^2$ is —OH when present;

AzA is a five-membered heteroaromatic ring system bearing at least two heteroatom from the group consisting of N, O, and S;

each Y is selected from the group consisting of optionally substituted alkyl, optionally substituted heterocycle, optionally substituted heteroaryl, —$NR^6(CR^9R^{10})_w$ $NR^6R^7$, —$NR^6C(O)OR^{11}$, —$NR^6C(O)NR^6R^7$, —$NR^6C(O)NR^6(CR^9R^{10})_wNR^6R^7$, —$NR^6(CR^9R^{10})_wS(O)_{0,1,2}R^{11}$, —$NR^6(CR^9R^{10})_wS(O)_{0,1,2}NR^6R^7$, —$NR^6(CR^9R^{10})_wNR^6R^7S(O)_{0,1,2}R^{11}$, —$NR^6(CR^9R^{10})_wNR^6S(O)_{0,1,2}NR^6R^6$, —$NR^6C(=NR^8)NR^6R^6$, —$N(R^6)C(=NR^8)R^{11}$, —$NR^6(CR^9R^{10})_wN(R^6)C(=NR^8)R^{11}$, —$NR^6(CR^9R^{10})_wC(=NR^8)NR^6R^7$, —$NR^6(CR^9R^{10})_wN(R^6)C(=NR^8)NR^6R^7$, —$NR^6(CR^9R^{10})_wNR^6C(=O)NR^6R^7$, —$NR^6(CR^9R^{10})_wNR^6C(=O)OR^{11}$, —$NR^6SO_2R^{11}$, —$NR^6(CR^9R^{10})_vCO_2H$, —$NR^6(CR^9R^{10})_vCO_2R^{11}$, —$NR^6(CR^9R^{10})_vC(O)NR^6R^7$, —$N(R^6)$-Heteroaryl-$NR^6R^7$, —$N(R^6)$-Heterocyclyl-$NR^6R^7$, —$NR^6(CR^9R^{10})_v$Heteroaryl, —$NR^6(CR^9R^{10})_v$Heterocyclyl, —$NR^6(CR^9R^{10})_wNR^6$-Heteroaryl, —$NR^6(CR^9R^{10})_wNR^6$-Heterocyclyl, —CN, —$(CR^9R^{10})_wNR^6R^7$, —$(CR^9R^{10})_wOH$, —$(CR^9R^{10})_wOR^{11}$, —$(CR^9R^{10})_vOC(O)R^{11}$, —$(CR^9R^{10})_vOC(O)NR^6R^6$, —$(CR^9R^{10})_vO(CR^9R^{10})_wOR^{11}$, —$(CR^9R^{10})_vO(CR^9R^{10})_wOH$, —$(CR^9R^{10})_vO(CR^9R^{10})_wNR^6R^7$, —$(CR^9R^{10})_wNR^6(CR^9R^{10})_wOH$, —$(CR^9R^{10})_wNR^6(CR^9R^{10})_wOR^{11}$, —$(CR^9R^{10})_vC(O)NR^6R^7$, —$(CR^9R^{10})_wC(O)NR^6(CR^9R^{10})_wNR^6R^7$, —$(CR^9R^{10})_wC(O)NR^6(CR^9R^{10})_wOR^{11}$, —$(CR^9R^{10})_wN(R^6)C(O)R^{11}$, —$(CR^9R^{10})_wN(R^6)C(O)OR^{11}$, —$(CR^9R^{10})_vN(R^6)C(O)NR^6R^7$, —$(CR^9R^{10})_wN(R^6)C(O)(CR^9R^{10})_wNR^6R^7$, —$(CR^9R^{10})_wN(R^6)S(O)_{0,1,2}R^{11}$, —$(CR^9R^{10})_vN(R^6)S(O)_{0,1,2}NR^6R^7$, —$(CR^9R^{10})_wS(O)_{0,1,2}NR^6R^7$, —$(CR^9R^{10})_wNR^6(CR^9R^{10})_wNR^6R^7$, —$(CR^9R^{10})_wN(R^6)CH(=NR^8)$, —$(CR^9R^{10})_wN(R^6)C(=NR^8)R^{11}$, —$(CR^9R^{10})_wC(=NR^8)NR^6R^7$, —$(CR^9R^{10})_wN(R^6)C(=NR^8)NR^6R^7$, —$(CR^9R^{10})_wC(=NR^8)NR^6C(=NR^8)NR^6R^7$, —$(CR^9R^{10})_v$Heteroaryl-$NR^6R^7$, —$(CR^9R^{10})_v$Heterocyclyl-$NR^6R^7$, —$(CR^9R^{10})_v$Heteroaryl-$N(R^6)C(=NR^8)NR^6R^7$, —$(CR^9R^{10})_v$Heterocyclyl-$N(R^6)C(=NR^8)NR^6R^7$, —$(CR^9R^{10})_v$Heteroaryl, —$(CR^9R^{10})_v$Heterocyclyl, —CN, —C(O)OH, —$C(O)OR^{11}$, —$C(O)NR^6R^7$, —$C(O)NR^6(CR^9R^{10})_wNR^6R^7$, —$C(O)NR^6(CR^9R^{10})_wOH$, —$C(O))NR^6(CR^9R^{10})_wOR^{11}$, —$C(=NR^8)NR^6R^7$, and —$C(=NR^8)NR^6C(O)R^{11}$;

$R^a$, $R^b$, and $R^c$ are independently selected from the group consisting of hydrogen, fluoro, chloro, and $C_1$-$C_6$ alkyl;

$R^e$ is hydrogen, optionally substituted $C_1$-$C_6$ alkyl, or optionally substituted $C_3$-$C_6$ cycloalkyl;

$R^1$ is hydrogen, $R^{31}$, —$R^{30}OC(O)R^{31}$, or —$R^{30}OC(O)OR^{31}$;

each $R^{30}$ is independently —$CH_2$—, —$CH(CH_3)$—;

each $R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and $C_1$-$C_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —$S(O)_2R^{11}$, —$S(O)_2NH_2$, and $C_1$-$C_6$ alkyl;

$R^8$ is hydrogen or —CN;

$R^9$ and $R^{10}$ are independently selected from the group consisting of hydrogen, fluoro, chloro, or $C_1$-$C_6$ alkyl;

$R^{11}$ is $C_1$-$C_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, —$(CR^9R^{10})_vNR^6R^7$, —$(CR^9R^{10})_vOH$, —$(CR^9R^{10})_vNR^6(CR^9R^{10})_wOH$, —$(CR^9R^{10})_vO(CR^9R^{10})_wNR^6R^7$, —$(CR^9R^{10})_vN(R^6)CH(=NR^8)$, —$(CR^9R^{10})_vN(R^6)C(=NR^8)NR^6R^7$, —$(CR^9R^{10})_vN(R^6)C(=NR^8)R^{11}$, —$(CR^9R^{10})_v$Heterocyclyl, —CN, —C(O)OH, —$C(O)OR^{11}$, —$C(O)NR^6R^7$, —$C(O)NR^6(CR^9R^{10})_wNR^6R^7$, —$NR^6C(=NR^8)NR^6R^6$, —$N(R^6)C(=NR^8)R^{11}$, —$NR^6C(O)NR^6R^7$, and —$N(R^6)C(O)(CR^9R^{10})_vNR^6R^7$.

In some embodiments of a compound of Formula (I) or Formula (II), at least one Y is selected from the group consisting of optionally substituted heteroaryl, —$(CR^9R^{10})_vNR^6R^7$, —$(CR^9R^{10})_vOH$, —$(CR^9R^{10})NR^6(CR^9R^{10})OH$, —$(CR^9R^{10})O(CR^9R^{10})NR^6R^7$, —$(CR^9R^{10})N(R^6)CH(=NR^8)$, —$(CR^9R^{10})N(R^6)C(=NR^8)NR^6R^7$, —$(CR^9R^{10})$Heterocyclyl, —CN, —C(O)OH, —$C(O)OR^{11}$, —$C(O)NR^6R^7$, and —$C(O)NR^6(CR^9R^{10})_wNR^6R^7$.

In some embodiments of a compound of Formula (I) or Formula (II):

L is —$(CR^2R^3)_n$—;

n is 2, 3, 4, 5, or 6;

p is 1, 2 or 3;

$X^1$ and $X^2$ are independently selected from —OH, —OR$^X$, and F;

AzA is a five-membered heteroaromatic ring system bearing at least one heteroatom from the group consisting of N, O, and S;

each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-NR$^6$R$^7$, -Heterocyclyl-NR$^6$R$^7$, -Heteroaryl-N(R$^6$)C(=NR$^8$)NR$^6$R$^7$, -Heterocyclyl-N(R$^6$)C(=NR$^8$)NR$^6$R$^7$, —OH, —OR$^{11}$, —O(CR$^9$R$^{10}$)$_w$OH, —O(CR$^9$R$^{10}$)$_w$OR$^{11}$, —O(CR$^9$R$^{10}$)$_w$NR$^6$R$^7$, —O(CR$^9$R$^{10}$)$_w$NR$^6$C(O)R$^{11}$, —O(CR$^9$R$^{10}$)$_w$NR$^6$C(O)OR$^{11}$, —O(CR$^9$R$^{10}$)$_w$NR$^6$C(O)NR$^6$R$^7$, —O(CR$^9$R$^{10}$)$_w$C(O)NR$^6$R$^7$, —O(CR$^9$R$^{10}$)$_w$NR$^6$S(O)$_{0,1,2}$R$^{11}$, —O(CR$^9$R$^{10}$)$_w$NR$^6$S(O)$_{0,1,2}$NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —O(CR$^6$R$^7$)$_v$C(=NR$^8$)NR$^6$R$^7$, —O(CR$^9$R$^{10}$)$_w$N(R$^6$)C(=NR$^8$)R$^{11}$, —O(CR$^9$R$^{10}$)$_v$C(=NR$^8$)NR$^6$C(=NR$^8$)NR$^6$R$^7$, —O(CR$^9$R$^{10}$)$_w$N(R$^6$)C(=NR$^8$)NR$^6$R$^7$, —O(CR$^9$R$^{10}$)$_w$S(O)$_{0,1,2}$R$^{11}$, —O(CR$^9$R$^{10}$)$_w$S(O)$_{0,1,2}$NR$^6$R$^7$, —OC(O)R$^{11}$, —OC(O)(CR$^9$R$^{10}$)$_w$NR$^6$R$^7$, —OC(O)NR$^6$R$^7$, —OC(O)OR$^{11}$, —OC(O)NR$^6$(CR$^9$R$^{10}$)$_w$NR$^6$R$^7$, —O-Heteroaryl, —O-Heterocyclyl, —O(CR$^9$R$^{10}$)$_v$Heteroaryl, —O(CR$^9$R$^{10}$)$_v$Heterocyclyl, —O(CR$^9$R$^{10}$)$_w$NR$^6$-Heteroaryl, —O(CR$^9$R$^{10}$)$_w$NR$^6$-Heterocyclyl, —O(CR$^9$R$^{10}$)$_w$O-Heterocyclyl, —NR$^6$R$^7$, —NR$^6$(CR$^9$R$^{10}$)$_w$NR$^6$R$^7$, —NR$^6$(CR$^9$R$^{10}$)$_w$OH, —NR$^6$(CR$^9$R$^{10}$)$_w$OR$^{11}$, —NR$^6$C(O)R$^{11}$, —NR$^6$C(O)OR$^{11}$, —N(R$^6$)C(O)(CR$^9$R$^{10}$)$_v$NR$^6$R$^7$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_w$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_v$Heteroaryl, —NR$^6$(CR$^9$R$^{10}$)$_v$Heterocyclyl, —NR$^6$(CR$^9$R$^{10}$)$_w$NR$^6$-Heteroaryl, —NR$^6$(CR$^9$R$^{10}$)$_w$NR$^6$-Heterocyclyl, —CN, —(CR$^9$R$^{10}$)$_v$CN, —(CR$^9$R$^{10}$)$_w$NR$^6$R$^7$, —(CR$^9$R$^{10}$)$_w$OH, —(CR$^9$R$^{10}$)$_v$OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)$_v$O(CR$^9$R$^{10}$)$_v$OH, —(CR$^9$R$^{10}$)$_v$O(CR$^9$R$^{10}$)$_w$NR$^6$R$^7$, —(CR$^9$R$^{10}$)$_w$NR$^6$(CR$^9$R$^{10}$)$_v$OH, —(CR$^9$R$^{10}$)$_v$NR$^6$(CR$^9$R$^{10}$)$_w$OR$^{11}$, —(CR$^9$R$^{10}$)$_v$C(O)NR$^6$R$^7$, —(CR$^9$R$^{10}$)$_v$C(O)NR$^6$(CR$^9$R$^{10}$)$_w$NR$^6$R$^7$, —(CR$^9$R$^{10}$)$_v$C(O)NR$^6$(CR$^9$R$^{10}$)$_w$OR$^{11}$, —(CR$^9$R$^{10}$)$_v$N(R$^6$)C(O)R$^{11}$, —(CR$^9$R$^{10}$)$_v$N(R$^6$)C(O)OR$^{11}$, —(CR$^9$R$^{10}$)$_v$N(R$^6$)C(O)NR$^6$R$^7$, —(CR$^9$R$^{10}$)$_v$N(R$^6$)C(O)(CR$^9$R$^{10}$)$_v$NR$^6$R$^7$, —(CR$^9$R$^{10}$)$_v$N(R$^6$)S(O)$_{0,1,2}$R$^{11}$, —(CR$^9$R$^{10}$)$_v$N(R$^6$)S(O)$_{0,1,2}$NR$^6$R$^7$—(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, —C(=NR$^8$)NR$^6$C(O)R$^{11}$, —S(O)$_{0,1,2}$R$^{11}$, —S(O)$_{0,1,2}$(CR$^9$R$^{10}$)$_w$NR$^6$R$^7$, —S(O)$_{0,1,2}$(CR$^9$R$^{10}$)$_w$OH, —S(O)$_{0,1,2}$(CR$^9$R$^{10}$)$_w$OR$^{11}$, —SO$_2$NR$^6$R$^7$, —S(O)$_{0,1,2}$NR$^6$(CR$^9$R$^{10}$)$_w$NR$^6$R$^7$, —S(O)$_{0,1,2}$(CR$^9$R$^{10}$)$_w$N(R$^6$)C(=NR$^8$)R$^{11}$, —S(O)$_{0,1,2}$(CR$^9$R$^{10}$)$_v$C(=NR$^8$)NR$^6$R$^7$, —S(O)$_{0,1,2}$(CR$^9$R$^{10}$)$_w$N(R$^6$)C(=NR$^8$)NR$^6$R$^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-$$_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:

T is pyridine-1-yl, pyrimidin-1-yl, or thiazol-3-yl;

Q is a pharmaceutically acceptable counterion; and v is 1-4;

w is 2-4;

or two Ys taken together with the atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen, optionally substituted $C_1$-$C_6$ alkyl, or optionally substituted $C_3$-$C_6$ cycloalkyl;

R$^x$ is optionally substituted $C_1$-$C_6$ alkyl, optionally substituted $C_3$-$C_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a $C_3$-$C_8$ heterocyclyl;

each R$^2$ and R$^3$ are independently selected from the group consisting of hydrogen, fluoro, chloro, bromo, optionally substituted $C_1$-$C_6$ alkyl, optionally substituted $C_3$-$C_6$ cycloalkyl, —OH, —OR$^{11}$, —SR$^{11}$, and NR$^6$R$^7$;

or R$^2$ and R$^3$ on the same carbon are taken together to form an oxo or optionally substituted oxime;

or R$^2$ and R$^3$ on the same carbon are taken together to form an optionally substituted spiro-carbocycle or optionally substituted spiro-heterocycle with the carbon to which they are attached;

or two $R^2$ on different carbons are taken together form an optionally substituted carbocycle or optionally substituted heterocycle with the carbons to which they are attached;

or two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^6$ and $R^7$ taken together form an optionally substituted heterocycle with the nitrogen to which they are attached;

$R^8$ is Hydrogen, —OH, —OR$^{11}$, —CN, —NO$_2$, —NR$_6$, optionally substituted C$_1$-C$_6$ alkyl;

$R^9$ and $R^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_v$NR$^6$R$^7$, —(CR$^a$R$^b$)$_v$C(O)NR$^6$R$^7$, —C(O)NR$^6$R$^7$, —NR$^6$SO$_2$R$^{11}$, optionally substituted heterocyclyl, optionally substituted aryl, and optionally substituted heteroaryl;

or $R^9$ and $R^{10}$ taken together with the carbon atom to which they are attached form an optionally substituted oxime, an optionally substituted carbocycle, or an optionally substituted heterocycle;

$R^{11}$ is optionally substituted C$_1$-C$_6$ alkyl, optionally substituted C$_3$-C$_6$ cycloalkyl, optionally substituted heteroaryl, optionally substituted heterocyclyl, or optionally substituted aryl; and $R^{12}$ is optionally substituted C$_1$-C$_6$ alkyl or optionally substituted C$_3$-C$_6$ cycloalkyl.

In some embodiments of a compound of Formula (I) or Formula (II):

L is —(CR$^2$R$^3$)$_n$—;

n is 2 or 3;

p is 1, 2 or 3;

$X^1$ is —OH and $X^2$ is —OH when present;

AzA is a five-membered heteroaromatic ring system bearing at least one heteroatoms from the group consisting of N, O, and S;

each Y is selected from the group consisting of optionally substituted alkyl, optionally substituted heterocycle, optionally substituted heteroaryl, —NR$^6$(CR$^9$R$^{10}$)$_w$NR$^6$R$^7$, —NR$^6$C(O)OR$^{11}$, —NR$^6$C(O)NR$^6$R$^7$, —NR$^6$C(O)NR$^6$(CR$^9$R$^{10}$)$_w$NR$^6$R$^7$, —NR$^6$(CR$^9$R$^{10}$)$_w$S(O)$_{0,1,2}$R$^{11}$, —NR$^6$(CR$^9$R$^{10}$)$_w$S(O)$_{0,1,2}$NR$^6$R$^7$, —NR$^6$(CR$^9$R$^{10}$)$_w$NR$^6$R$^7$S(O)$_{0,1,2}$R$^{11}$, —NR$^6$(CR$^9$R$^{10}$)$_w$NR$^6$S(O)$_{0,1,2}$NR$^6$R$^6$, —NR$^6$C(=NR$^8$)NR$^6$R$^6$, —N(R$^6$)C(=NR$^8$)R$^{11}$, —NR$^6$(CR$^9$R$^{10}$)$_v$N(R$^6$)C(=NR$^8$)R$^{11}$, —NR$^6$(CR$^9$R$^{10}$)$_v$C(=NR$^8$)NR$^6$R$^7$, —NR$^6$(CR$^9$R$^{10}$)$_w$N(R$^6$)C(=NR$^8$)NR$^6$R$^7$, —NR$^6$(CR$^9$R$^{10}$)$_w$NR$^6$C(=O)NR$^6$R$^7$, —NR$^6$(CR$^9$R$^{10}$)$_w$NR$^6$C(=O)OR$^{11}$, —NR$^6$SO$_2$R$^{11}$, —NR$^6$(CR$^9$R$^{10}$)CO$_2$H, —NR$^6$(CR$^9$R$^{10}$)CO$_2$R$^{11}$, —NR$^6$(CR$^9$R$^{10}$)C(O)NR$^6$R$^7$, —N(R$^6$)-Heteroaryl-NR$^6$R$^7$, —N(R$^6$)-Heterocyclyl-NR$^6$R$^7$, —NR$^6$(CR$^9$R$^{10}$)$_w$Heteroaryl, —NR$^6$(CR$^9$R$^{10}$)$_w$Heterocyclyl, —NR$^6$(CR$^9$R$^{10}$)$_w$NR$^6$-Heteroaryl, —NR$^6$(CR$^9$R$^{10}$)NR$^6$-Heterocyclyl, —CN, —(CR$^9$R$^{10}$)NR$^6$R$^7$, —(CR$^9$R$^{10}$)OH, —(CR$^9$R$^{10}$)OR$^{11}$, —(CR$^9$R$^{10}$)$_v$OC(O)R$^{11}$, —(CR$^9$R$^{10}$)$_v$OC(O)NR$^6$R$^6$, —(CR$^9$R$^{10}$)$_v$O(CR$^9$R$^{10}$)$_w$OR$^{11}$, —(CR$^9$R$^{10}$)O(CR$^9$R$^{10}$)OH, —(CR$^9$R$^{10}$)O(CR$^9$R$^{10}$)NR$^6$R$^7$, —(CR$^9$R$^{10}$)NR$^6$(CR$^9$R$^{10}$)OH, —(CR$^9$R$^{10}$)NR$^6$(CR$^9$R$^{10}$)OR$^{11}$, —(CR$^9$R$^{10}$)C(O)NR$^6$R$^7$, —(CR$^9$R$^{10}$)C(O)NR$^6$(CR$^9$R$^{10}$)NR$^6$R$^7$, —(CR$^9$R$^{10}$)$_w$C(O)NR$^6$(CR$^9$R$^{10}$)$_w$OR$^{11}$, —(CR$^9$R$^{10}$)$_w$N(R$^6$)C(O)R$^{11}$, —(CR$^9$R$^{10}$)$_w$N(R$^6$)C(O)OR$^{11}$, —(CR$^9$R$^{10}$)$_w$N(R$^6$)C(O)NR$^6$R$^7$, —(CR$^9$R$^{10}$)$_w$N(R$^6$)C(O)(CR$^9$R$^{10}$)$_w$NR$^6$R$^7$, —(CR$^9$R$^{10}$)$_w$N(R$^6$)S(O)$_{0,1,2}$R$^{11}$, —(CR$^9$R$^{10}$)$_v$N(R$^6$)S(O)$_{0,1,2}$NR$^6$R$^7$, —(CR$^9$R$^{10}$)$_v$S(O)$_{0,1,2}$NR$^6$R$^7$, —(CR$^9$R$^{10}$)$_v$NR$^6$(CR$^9$R$^{10}$)$_w$NR$^6$R$^7$, —(CR$^9$R$^{10}$)$_v$N(R$^6$)CH(=NR$^8$), —(CR$^9$R$^{10}$)$_v$N(R$^6$)C(=NR$^8$)R$^{11}$, —(CR$^9$R$^{10}$)$_v$C(=NR$^8$)NR$^6$R$^7$, —(CR$^9$R$^{10}$)$_v$N(R$^6$)C(=NR$^8$)NR$^6$R$^7$, —(CR$^9$R$^{10}$)$_v$C(=NR$^8$)NR$^6$C(=NR$^8$)NR$^6$R$^7$, —(CR$^9$R$^{10}$)$_v$Heteroaryl-NR$^6$R$^7$, —(CR$^9$R$^{10}$)$_v$Heterocyclyl-NR$^6$R$^7$, —(CR$^9$R$^{10}$)$_v$Heteroaryl-N(R$^6$)C(=NR$^8$)NR$^6$R$^7$, —(CR$^9$R$^{10}$)$_v$Heterocyclyl-N(R$^6$)C(=NR$^8$)NR$^6$R$^7$, —(CR$^9$R$^{10}$)$_v$Heteroaryl, —(CR$^9$R$^{10}$)$_v$Heterocyclyl, —CN, —C(O)OH, —C(O)OR$^{11}$, —C(O)NR$^6$R$^7$, —C(O)NR$^6$(CR$^9$R$^{10}$)$_w$NR$^6$R$^7$, —C(O)NR$^6$(CR$^9$R$^{10}$)$_w$OH, —C(O)NR$^6$(CR$^9$R$^{10}$)$_w$OR$^{11}$, —C(=NR$^8$)NR$^6$R$^7$, and —C(=NR$^8$)NR$^6$C(O)R$^{11}$;

$R^a$, $R^b$, and $R^c$ are independently selected from the group consisting of hydrogen, fluoro, chloro, and C$_1$-C$_6$ alkyl;

$R^e$ is hydrogen, optionally substituted C$_1$-C$_6$ alkyl, or optionally substituted C$_3$-C$_6$ cycloalkyl;

$R^x$ is C$_1$-C$_6$ alkyl or a pharmaceutically acceptable boronate ester group;

$R^1$ is hydrogen, $R^{31}$, —R$^{30}$OC(O)R$^{31}$, —R$^{30}$OC(O)OR$^{31}$;

each $R^{30}$ is independently —CH$_2$— or —CH(CH$_3$)—;

each $R^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or each $R^2$ and $R^3$ are independently selected from the group consisting of hydrogen, fluoro, chloro, and C$_1$-C$_6$ alkyl;

or $R^2$ and $R^3$ on the same carbon are taken together to form an oxo;

or $R^2$ and $R^3$ on the same carbon are taken together to form an optionally substituted spiro-carbocycle or optionally substituted spiro-heterocycle with the carbon to which they are attached;

or when n is at least 2, two $R^2$ on different carbons are taken together form an optionally substituted carbocycle or optionally substituted heterocycle with the carbons to which they are attached;

or when n is at least 2, two $R^2$ on adjacent carbons are taken together to form a double bond; or two $R^2$ and two $R^3$ on adjacent carbons are taken together to form a triple bond;

$R^d$, $R^6$ and $R^7$ are independently selected from the group consisting of hydrogen, —OH, —CN, —S(O)$_2$R$^{11}$, —S(O)$_2$NH$_2$, and C$_1$-C$_6$ alkyl;

$R^8$ is hydrogen or —CN;

$R^9$ and $R^{10}$ are independently selected from the group consisting of hydrogen, fluoro, chloro, or C$_1$-C$_6$ alkyl;

$R^{11}$ is C$_1$-C$_6$ alkyl;

v is 1-4; and w is 2-4.

In some embodiments of a compound of Formula (I) or Formula (II), at least one Y is selected from the group consisting of optionally substituted heterocycle, optionally substituted heteroaryl, $-NR^6R^7$, $-(CR^9R^{10})_vNR^6R^7$, $-(CR^9R^{10})_vOH$, $-(CR^9R^{10})_vNR^6(CR^9R^{10})_wOH$, $-(CR^9R^{10})_vO(CR^9R^{10})_wNR^6R^7$, $-(CR^9R^{10})_vN(R^6)CH(=NR^8)$, $-(CR^9R^{10})_vN(R^6)C(=NR^8)NR^6R^7$, $-(CR^9R^{10})_vN(R^6)C(=NR^8)R^{11}$, $-(CR^9R^{10})_v$Heterocyclyl, $-CN$, $-C(O)OH$, $-C(O)OR^{11}$, $-C(O)NR^6R^7$, $-C(O)NR^6(CR^9R^{10})_wNR^6R^7$, $-NR^6C(=NR^8)NR^6R^6$, $-N(R^6)C(=NR^8)R^{11}$, $-NR^6C(O)NR^6R^7$, and $-N(R^6)C(O)(CR^9R^{10})_vNR^6R^7$.

In some embodiments of a compound of Formula (I) or Formula (II), at least one Y is selected from the group consisting of optionally substituted heteroaryl, $-NR^6R^7$, $-(CR^9R^{10})_wNR^6R^7$, $-(CR^9R^{10})_wOH$, $-(CR^9R^{10})_vNR^6(CR^9R^{10})_wOH$, $-(CR^9R^{10})_vO(CR^9R^{10})_wNR^6R^7$, $-(CR^9R^{10})_vN(R^6)CH(=NR^8)$, $-(CR^9R^{10})_vN(R^6)C(=NR^8)NR^6R^7$, $-(CR^9R^{10})_v$Heterocyclyl, $-CN$, $-C(O)OH$, $-C(O)OR^{11}$, $-C(O)NR^6R^7$, and $-C(O)NR^6(CR^9R^{10})_wNR^6R^7$.

In another aspect, provided herein are compounds of Formula (I) or Formula (II), or pharmaceutically acceptable salts, solvates, stereoisomers, tautomers, prodrugs, metabolites, N-oxides, or isomers thereof:

Formula (I)

Formula (II)

wherein:

L is $-(CR^2R^3)_n-$;

n is 0, 1, 2, 3, 4, 5, or 6;

p is 0, 1, 2 or 3;

$X^1$ is selected from $-OH$, $-OR^X$, and F;

$X^2$ is OH;

AzA is a five-membered heteroaromatic ring system bearing at least one heteroatom from the group consisting of N, O, and S;

each Y is selected from the group consisting of fluoro, chloro, bromo, optionally substituted $C_1$-$C_6$ alkyl, optionally substituted $C_3$-$C_6$ cycloalkyl, optionally substituted heterocycle, optionally substituted aryl, optionally substituted heteroaryl, Heteroaryl-$NR^6R^7$, -Heterocyclyl-$NR^6R^7$, -Heteroaryl-$N(R^6)C(=NR^8)NR^6R^7$, -Heterocyclyl-$N(R^6)C(=NR^8)NR^6R^7$, $-OH$, $-OR^{11}$, $-O(CR^9R^{10})_wOH$, $-O(CR^9R^{10})_wOR^{11}$, $-O(CR^9R^{10})_wNR^6R^7$, $-O(CR^9R^{10})_wNR^6C(O)R^{11}$, $-O(CR^9R^{10})_wNR^6C(O)OR^{11}$, $-O(CR^9R^{10})_wNR^6C(O)NR^6R^7$, $-O(CR^9R^{10})_wC(O)NR^6R^7$, $-O(CR^9R^{10})_wNR^6S(O)_{0,1,2}R^{11}$, $-O(CR^9R^{10})_wNR^6S(O)_{0,1,2}NR^6R^7$, $-O(CR^9R^{10})_wS(O)_{0,1,2}R^{11}$, $-O(CR^9R^{10})_wS(O)_{0,1,2}NR^6R^7$, $-O(CR^6R^7)_vC(=NR^8)NR^6R^7$, $-O(CR^9R^{10})_vN(R^6)C(=NR^8)R^{11}$, $-O(CR^9R^{10})_wC(=NR^8)NR^6C(=NR^8)NR^6R^7$, $-O(CR^9R^{10})_wN(R^6)C(=NR^8)NR^6R^7$, $-O(CR^9R^{10})_wS(O)_{0,1,2}R^{11}$, $-O(CR^9R^{10})_wS(O)_{0,1,2}NR^6R^7$, $-OC(O)R^{11}$, $-OC(O)(CR^9R^{10})_wNR^6R^7$, $-OC(O)NR^6R^7$, $-OC(O)OR^{11}$, $-OC(O)NR^6(CR^9R^{10})_wNR^6R^7$, $-O$-Heteroaryl, $-O$-Heterocyclyl, $-O(CR^9R^{10})_v$Heteroaryl, $-O(CR^9R^{10})_v$Heterocyclyl, $-O(CR^9R^{10})_wNR^6$-Heteroaryl, $-O(CR^9R^{10})_wNR^6$-Heterocyclyl, $-O(CR^9R^{10})_wO$-Heterocyclyl, $-NR^6R^7$, $-NR^6(CR^9R^{10})_wNR^6R^7$, $-NR^6(CR^9R^{10})_wOH$, $-NR^6(CR^9R^{10})_wOR^{11}$, $-NR^6C(O)R^{11}$, $-NR^6C(O)OR^{11}$, $-N(R^6)C(O)(CR^9R^{10})_wNR^6R^7$, $-NR^6C(O)NR^6R^7$, $-NR^6C(O)NR^6(CR^9R^{10})_wNR^6R^7$, $-NR^6(CR^9R^{10})_wS(O)_{0,1,2}R^{11}$, $-NR^6(CR^9R^{10})_wS(O)_{0,1,2}NR^6R^7$, $-NR^6(CR^9R^{10})_wNR^6R^7S(O)_{0,1,2}R^{11}$, $-NR^6(CR^9R^{10})_wNR^6S(O)_{0,1,2}NR^6R^6$, $-NR^6C(=NR^8)NR^6R^6$, $-N(R^6)C(=NR^8)R^{11}$, $-NR^6(CR^9R^{10})_wN(R^6)C(=NR^8)R^{11}$, $-NR^6(CR^9R^{10})_wC(=NR^8)NR^6R^7$, $-NR^6(CR^9R^{10})_wN(R^6)C(=NR^8)NR^6R^7$, $-NR^6(CR^9R^{10})_wNR^6C(=O)NR^6R^7$, $-NR^6(CR^9R^{10})_wNR^6C(=O)OR^{11}$, $-NR^6SO_2R^{11}$, $-NR^6(CR^9R^{10})CO_2H$, $-NR^6(CR^9R^{10})CO_2R^{11}$, $-NR^6(CR^9R^{10})C(O)NR^6R^7$, $-N(R^6)$-Heteroaryl-$NR^6R^7$, $-N(R^6)$-Heterocyclyl-$NR^6R^7$, $-NR^6(CR^9R^{10})_v$Heteroaryl, $-NR^6(CR^9R^{10})_v$Heterocyclyl, $-NR^6(CR^9R^{10})_wNR^6$-Heteroaryl, $-NR^6(CR^9R^{10})_wNR^6$-Heterocyclyl, $-CN$, $-(CR^9R^{10})_wCN$, $-(CR^9R^{10})_wNR^6R^7$, $-(CR^9R^{10})_wOH$, $-(CR^9R^{10})_wOR^{11}$, $-(CR^9R^{10})_vOC(O)R^{11}$, $-(CR^9R^{10})_vOC(O)NR^6R^6$, $-(CR^9R^{10})_vO(CR^9R^{10})_wOR^{11}$, $-(CR^9R^{10})_vO(CR^9R^{10})_wOH$, $-(CR^9R^{10})_vO(CR^9R^{10})_wNR^6R^7$, $-(CR^9R^{10})_wNR^6(CR^9R^{10})_wOH$, $-(CR^9R^{10})_wNR^6(CR^9R^{10})_wOR^{11}$, $-(CR^9R^{10})_wC(O)NR^6R^7$, $-(CR^9R^{10})_wC(O)NR^6(CR^9R^{10})_wNR^6R^7$, $-(CR^9R^{10})_wC(O)NR^6(CR^9R^{10})_wOR^{11}$, $-(CR^9R^{10})_wN(R^6)C(O)R^{11}$, $-(CR^9R^{10})_wN(R^6)C(O)OR^{11}$, $-(CR^9R^{10})_wN(R^6)C(O)NR^6R^7$, $-(CR^9R^{10})_wN(R^6)C(O)(CR^9R^{10})_wNR^6R^7$, $-(CR^9R^{10})_wN(R^6)S(O)_{0,1,2}R^{11}$, $-(CR^9R^{10})_wN(R^6)S(O)_{0,1,2}NR^6R^7$, $-(CR^9R^{10})_wS(O)_{0,1,2}NR^6R^7$, $-(CR^9R^{10})_wNR^6(CR^9R^{10})_wNR^6R^7$, $-(CR^9R^{10})_wN(R^6)CH(=NR^8)$, $-(CR^9R^{10})_wN(R^6)C(=NR^8)R^{11}$, $-(CR^9R^{10})_wC(=NR^8)NR^6R^7$, $-(CR^9R^{10})_wN(R^6)C(=NR^8)NR^6R^7$, $-(CR^9R^{10})_wC(=NR^8)NR^6C(=NR^8)NR^6R^7$, $-(CR^9R^{10})_v$Heteroaryl-$NR^6R^7$, $-(CR^9R^{10})_v$Heterocyclyl-$NR^6R^7$, $-(CR^9R^{10})_v$Heteroaryl-$N(R^6)C(=NR^8)NR^6R^7$, $-(CR^9R^{10})_v$Heterocyclyl-$N(R^6)C(=NR^8)NR^6R^7$, $-(CR^9R^{10})_v$Heteroaryl, $-(CR^9R^{10})_v$Heterocyclyl, $-C(O)OH$, $-C(O)OR^{11}$, $-C(O)NR^6R^7$, $-C(O)NR^6(CR^9R^{10})_wNR^6R^7$, $-C(O)NR^6(CR^9R^{10})_wOH$, $-C(O)NR^6(CR^9R^{10})_wOR^{11}$, $-C(=NR^8)NR^6R^7$, $-C(=NR^8)NR^6C(O)R^{11}$, $-S(O)_{0,1,2}R^{11}$, $-S(O)_{0,1,2}(CR^9R^{10})_wNR^6R^7$, $-S(O)_{0,1,2}(CR^9R^{10})_wOH^{11}$, $-S(O)_{0,1,2}(CR^9R^{10})_wOR^{11}$, $-SO_2NR^6R^7$, $-S(O)_{0,1,2}NR^6(CR^9R^{10})_wNR^6R^7$, $-S(O)_{0,1,2}(CR^9R^{10})_wN(R^6)C(=NR^8)R^{11}$, $-S(O)_{0,1,2}(CR^9R^{10})_vC(=NR^8)NR^6R^7$, $-S(O)_{0,1,2}(CR^9R^{10})_wN(R^6)C(=NR^8)NR^6R^7$, —S(O)$_{0,1,2}$(CR$^9$R$^{10}$)$_v$C(=NR$^8$)NR$^6$C(=NR$^8$)NR$^6$R$^7$, —Si(R$^{11}$)$_3$, —NR$^6$R$^7$R$^{12+}$Q$^-$, —(CR$^9$R$^{10}$)$_v$NR$^6$R$^7$R$^{12+}$Q$^-$, —NR$^6$(CR$^9$R$^{10}$)$_w$NR$^6$R$^7$R$^{12+}$Q$^-$, —NR$^6$R$^{12+}$(CR$^9$R$^{10}$)$_w$NR$^6$R$^7$R$^{12+}$Q$^-_2$, —(CR$^9$R$^{10}$)$_v$(T)$^+$Q$^-$, and —O(CR$^9$R$^{10}$)$_w$NR$^6$R$^6$R$^{12+}$Q$^-$;

wherein:
  T is pyridine-1-yl, pyrimidin-1-yl, or thiazol-3-yl;
  Q is a pharmaceutically acceptable counterion; and
  v is 1-4;
  w is 2-4;
  or two Ys taken together with the atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;

R$^e$ is hydrogen;

R$^x$ is optionally substituted C$_1$-C$_6$ alkyl, optionally substituted C$_3$-C$_6$ cycloalkyl, or a pharmaceutically acceptable boronate ester group;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or two R$^{31}$ are taken together with the Nitrogen to which they are attached to form a C$_3$-C$_8$ heterocyclyl;

each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, and —NR$^6$R$^7$;

or R$^2$ and R$^3$ on the same carbon are taken together to form an oxo or optionally substituted oxime;

or R$^2$ and R$^3$ on the same carbon are taken together to form an optionally substituted spiro-carbocycle or optionally substituted spiro-heterocycle with the carbon to which they are attached;

or when n is at least 2, two R$^2$ on different carbons are taken together form an optionally substituted carbocycle or optionally substituted heterocycle with the carbons to which they are attached;

or when n is at least 2, two R$^2$ on adjacent carbons are taken together to form a double bond; or two R$^2$ and two R$^3$ on adjacent carbons are taken together to form a triple bond;

R$^d$, R$^6$ and R$^7$ are independently selected from the group consisting of hydrogen, —CN, —OH, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^6$ and R$^7$ taken together form an optionally substituted heterocycle with the nitrogen to which they are attached;

R$^8$ is Hydrogen, —OH, —OR$^{11}$, —CN, —NO$_2$, —NR$_6$, optionally substituted C$_1$-C$_6$ alkyl;

R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_v$NR$^6$R$^7$, —(CR$^a$R$^b$)$_v$C(O)NR$^6$R$^7$, —C(O)NR$^6$R$^7$, —NR$^6$SO$_2$R$^{11}$, optionally substituted heterocyclyl, optionally substituted aryl, and optionally substituted heteroaryl;

or R$^9$ and R$^{10}$ taken together with the carbon atom to which they are attached form an optionally substituted oxime, an optionally substituted carbocycle, or an optionally substituted heterocycle;

R$^{11}$ is optionally substituted C$_1$-C$_6$ alkyl, optionally substituted C$_3$-C$_6$ cycloalkyl, optionally substituted heteroaryl, optionally substituted heterocyclyl, or optionally substituted aryl; and R$^{12}$ is optionally substituted C$_1$-C$_6$ alkyl or optionally substituted C$_3$-C$_6$ cycloalkyl.

Preparation of Compounds

Described herein are compounds of Formula (I) or Formula (II) that inhibit the activity of beta-lactamases, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula (I) or Formula (II) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may exist in an equilibrium between the "closed" cyclic form shown in Formula (I) or Formula (Ia) and the "open" acyclic form shown in Figure (II) or Formula (IIa). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of Formula (I) or Formula (II) include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of Formula (I) or Formula (II), or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of Formula (I) or Formula (II) and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} \text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In some embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

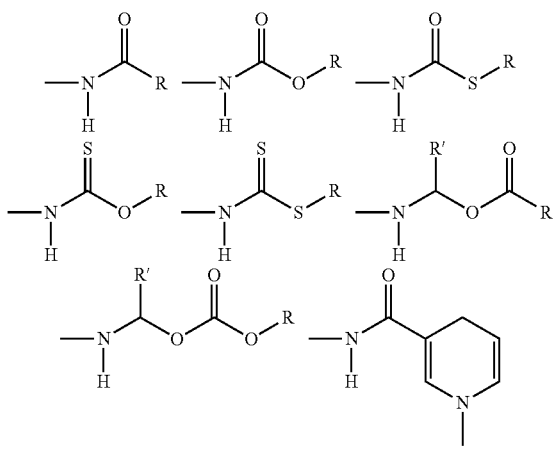

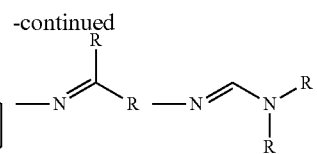

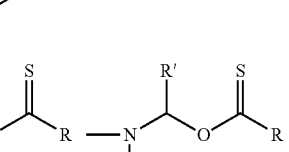

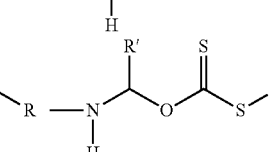

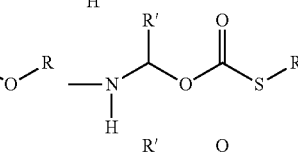

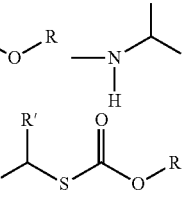

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

In some embodiments, compounds of Formula (I) or Formula (II) are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula (I) or Formula (II) described herein are metabolized upon administration to an organism in need to produce a metabolite that is then used to produce a desired effect, including a desired therapeutic effect.

Pharmaceutical Compositions/Formulations

In another aspect, provided herein are pharmaceutical composition comprising a compound of Formula (I) or Formula (II) as described herein, or a pharmaceutically acceptable salt, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds of Formula (I) or Formula (II) are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

Provided herein are pharmaceutical compositions that include a compound of Formula (I) or Formula (II) and at least one pharmaceutically acceptable inactive ingredient. In some embodiments, the compounds of Formula (I) or Formula (II) are administered as pharmaceutical compositions in which a compound of Formula (I) or Formula (II) is mixed with other active ingredients, as in combination therapy. In some embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I) or Formula (II) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds of Formula (I) or Formula (II) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I) or Formula (II) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/ butyl acrylate copolymer, sodium alginate and dextran.

Combination Treatment

The compounds of Formula (I) or Formula (II) may be used in combination with one or more antibiotics in the treatment of bacterial infections. Such antibiotics may be administered, by a route and in an amount commonly used therefore, contemporaneously or sequentially with a compound of Formula (I) or Formula (II). When a compound of Formula (I) or Formula (II) is used contemporaneously with one or more antibiotic, a pharmaceutical composition in unit dosage form containing such other drugs and the compound of the present invention is preferred. However, the combination therapy may also include therapies in which the compound of Formula (I) or Formula (II) and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound of Formula (I) or Formula (II). In some embodiments, a pharmaceutical composition comprising a compound of Formula (I) or Formula (II) further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula (I) or Formula (II) not only with one antibiotic, but also with two or more antibiotics. Likewise, compounds of Formula (I) or Formula (II), either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula (I) or Formula (II). When a compound of Formula (I) or Formula (II) is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula (I) or Formula (II). The weight ratio of the compound of Formula (I) or Formula (II) to the second active ingredient may be varied and will depend upon the effective dose of each ingredient. Generally, an effective dose of each will be used.

In some embodiments, the compounds of Formula (I) or Formula (II) are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephalosprins/ Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, cefornanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula (I) or Formula (II) and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g., Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of the invention are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula (I) or Formula (II) is administered to an experimental cell culture in vitro to prevent the growth of beta-lactam resistant bacteria. In certain some embodiments, a compound of Formula (I) or Formula (II) is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula (I) or Formula (II), or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia akalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter cob, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgates, Bacteroides ovalus, Bacteroides thetaiotaomicron, Bacteroides uniformis, Bacteroides eggerthii*, or *Bacteroides splanchnicus*.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tent-butyloxycarbonyl
BOP benzotriazol-1-yl-oxytris (dimethylamino) phosphonium
n-Bu n-butyl
t-Bu tert-butyl
Cbz benzyloxycarbonyl
Cy Cyclohexyl
DBU 1,8-Diazabicyclo[5.4.0]undec-7-ene
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI or EDC 1-ethyl-3-(3-dimethylaminopropyl) carbodiimide HCl
eq equivalent(s)
Et ethyl
Et$_2$O diethyl ether
EtOH ethanol
EtOAc ethyl acetate
HATU 1-[Bis(dimethylamino)methylene]-1H-1,2,3-triazolo[4,5-b]pyridinium 3-oxid hexafluorophosphate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium hexafluorophosphate
SOCl$_2$ thionyl chloride
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
RT room temperature
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
Tf$_2$O triflate anhydride
TMG 1,1,3,3-Tetramethylguanidine
THF tetrahydrofuran
THP tetrahydropyran
TLC thin layer chromatography
XPHOS 2-dicyclohexylphosphino-2',4',6'-triisopropylbiphenyl General Examples for the Preparation of Compounds of Formula (I) or Formula (II)

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines. The use of protective groups may be as described in methodology compendia such as *Greene's Protective Groups in Organic Synthesis*, Fourth Edition. John Wiley & Sons, Inc. 2006.

Certain compounds of Formula (I) or Formula (II) (I) (SCHEME 1) are prepared from the corresponding functional-group-protected boronic acid esters (II) by treatment with a Lewis acid such as BCl$_3$, in a solvent such as dichloromethane, at a temperature between −78° C. and 0° C. followed by an aqueous quench.

SCHEME 1

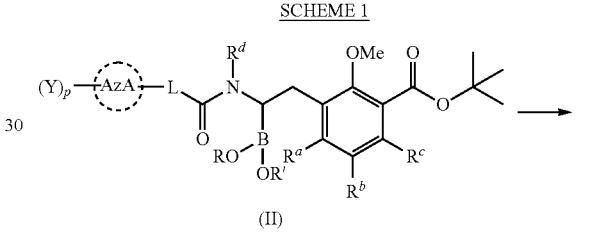

(II)

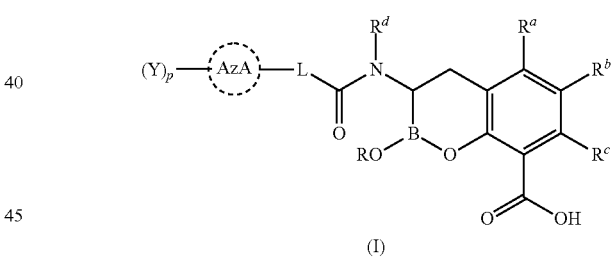

(I)

Alternatively, (I) is obtained from (II) by treatment of (II) with aqueous hydrochloric acid (around 3-5 Molar) in dioxane at a temperature between room temperature and 100° C.

The requisite boronic acid esters (II) are obtained (SCHEME 2) by coupling of amine (III) with carboxylic acid (IV). This transformation is effected by first activating the acid functionality as an acid chloride, anhydride or reactive ester (Va, Vb or Vc), followed by treatment of the activated substrate with (III) in a solvent such as DMF, DMA, NMP, THF or dichloromethane (or a mixture thereof) at about room temperature, usually in the presence of a non-nucleophilic base such as 4-methyl-morpholine, triethylamine or diisopropylethylamine.

SCHEME 2

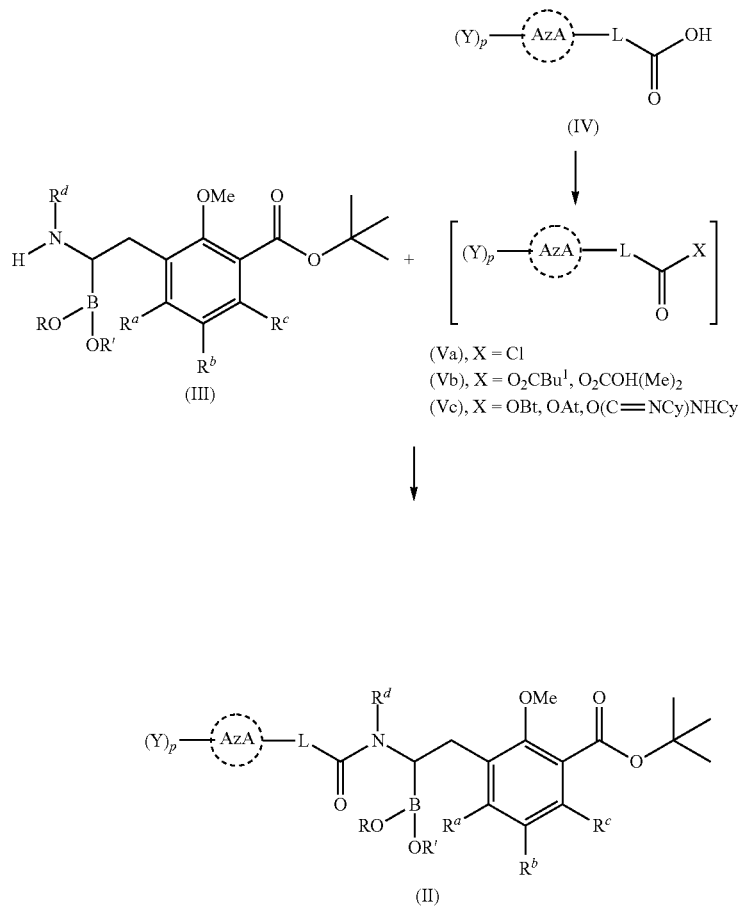

Carboxylic acids (IV) or acid chlorides (Va) may be obtained from commercial sources, prepared according to known methods in the literature, or prepared by a number of different reaction sequences. While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

Formation of the acid chloride (Va) involves treatment of (IV) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (Vb) involves treatment of (IV) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (Vc) involves treatment of (IV) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

The requisite amines (III) may be prepared according to literature methods (WO2010/130708).

SCHEME 3

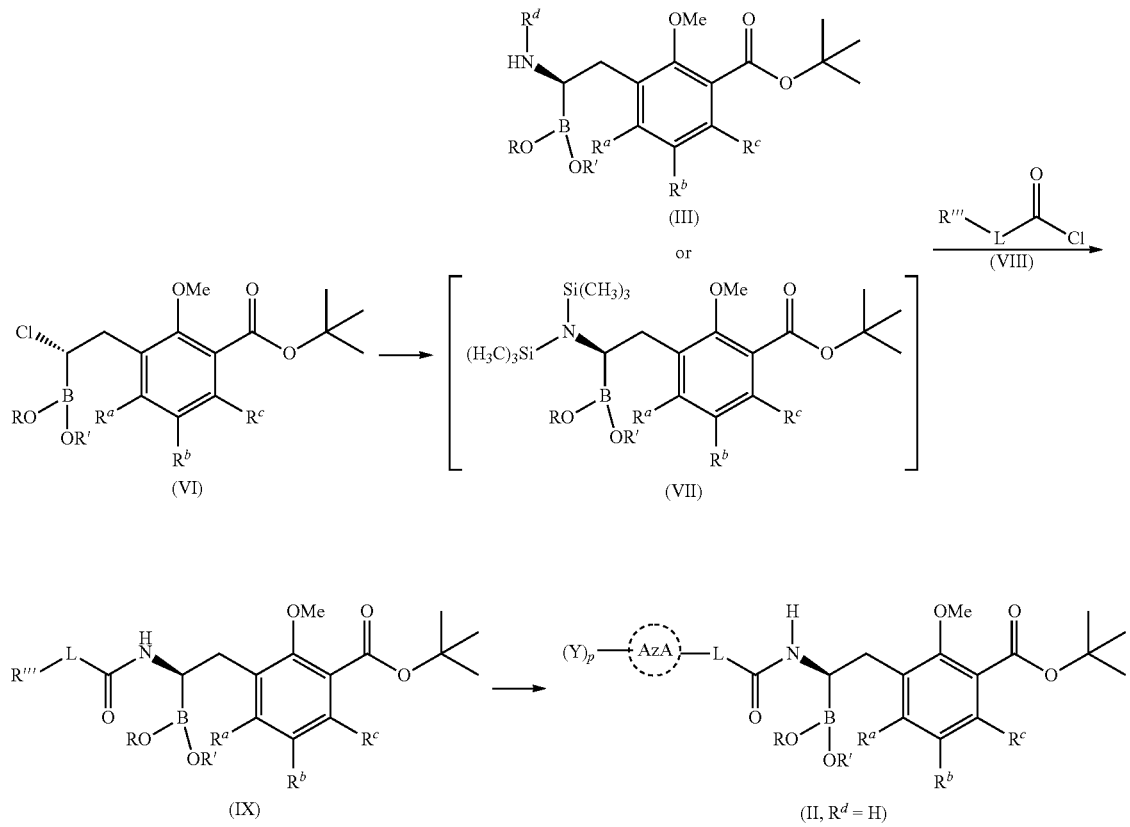

Alternatively, intermediate (VII) derived from the preparation of amines (III), may be acylated, for example with an acid chloride (VIII), to provide amides (IX) bearing functional groups useful for preparing substituted five-membered heteroaromatic ring systems AzA (SCHEME 3). For example, R''' may represent a halide (X), which can be substituted with a variety of nitrogen-containing five-membered ring heteroaromatic compounds, to provide amides (XII) bearing N-linked heteroaromatic substituents (SCHEME 4). Halides also may be converted into alkyl azides (XIII), by nucleophilic substitution with azide salts (such as sodium azide). Compounds (XV) with 1,2,3-triazoles as AzA are prepared by condensation of an appropriately substituted alkyne (XIV) with the resulting alkyl azide (XIII) in the presence of a copper catalyst (*Chemical Society Reviews* (2010), 39(4), 1302-1315) such as copper sulphate/sodium ascorbate, in a solvent such as DMF/water. Two regioisomeric products (XVa) or (XVb) may be formed, depending on the chemical nature of $R^f$ and $R^g$.

SCHEME 4

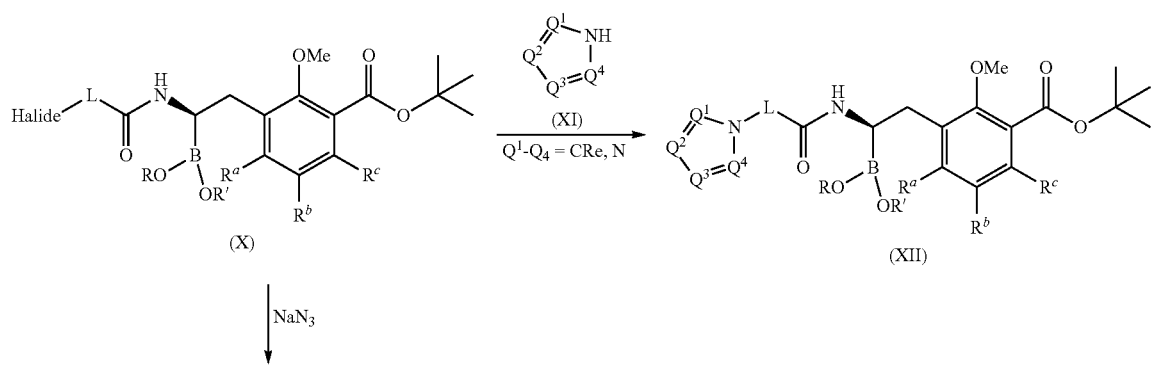

-continued

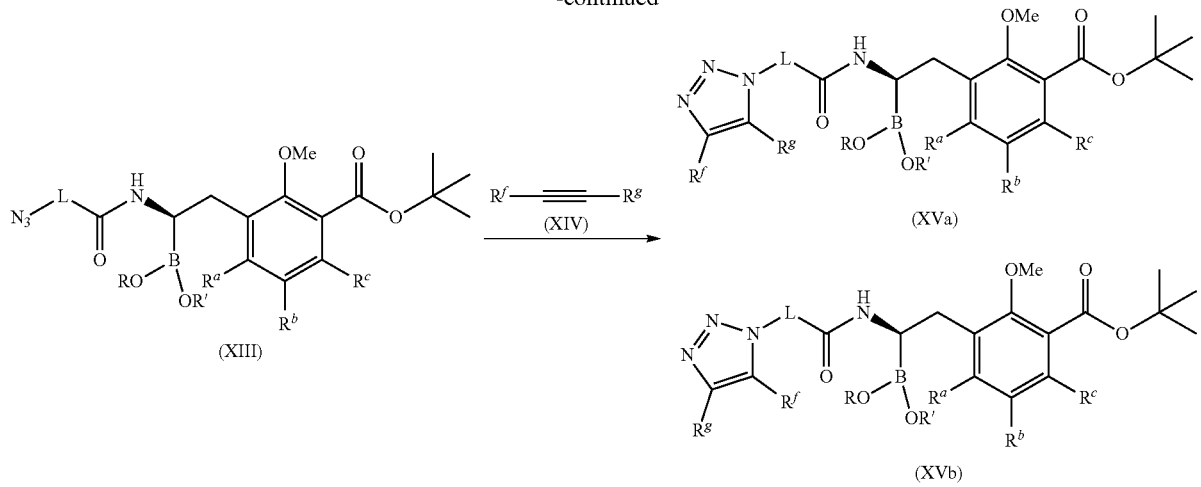

Amides (XVI) bearing an alkyne may also be converted into AzA groups, for example into isoxazoles (XVIII) by reaction with an appropriately substituted chloro-oxime (XVII) (SCHEME 5). Additionally, amides (XIX) containing a nitrile group may be condensed with an azide salt, or an alkyl- or silyl-azide with metal-ion catalysis to form tetrazoles (XX). Two regioisomeric substituted tetrazoles (XXa) and (XXb) may be formed in cases wherein $R^j$ is alkyl.

It is recognized that there exists extensive art for the preparation of five-membered heteroaromatic compounds, utilizing compounds (IX) wherein the R'" groups may be carboxylic acids, carboxylic esters, carboxamide, acylhydrazides, or nitriles. Examples of such methodologies are described in *Modern Heterocyclic Chemistry*, Vol. 2 and Vol. 3 (eds J. Alvarez-Builla, J. J. Vaquero and J. Barluenga), Wiley-VCH Verlag GmbH & Co. KGaA, Weinheim, Germany.

SCHEME 5

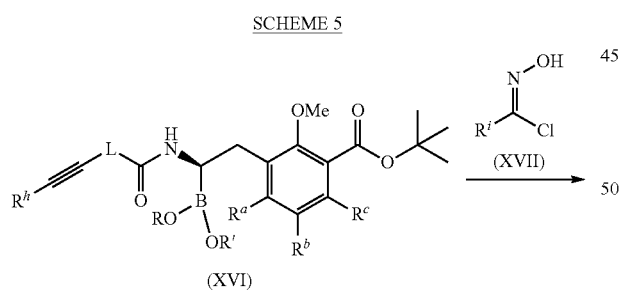

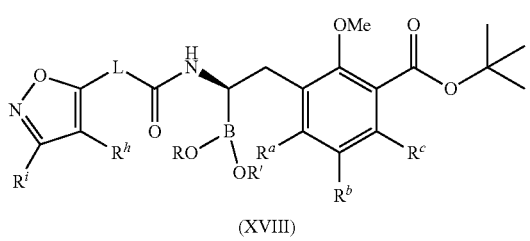

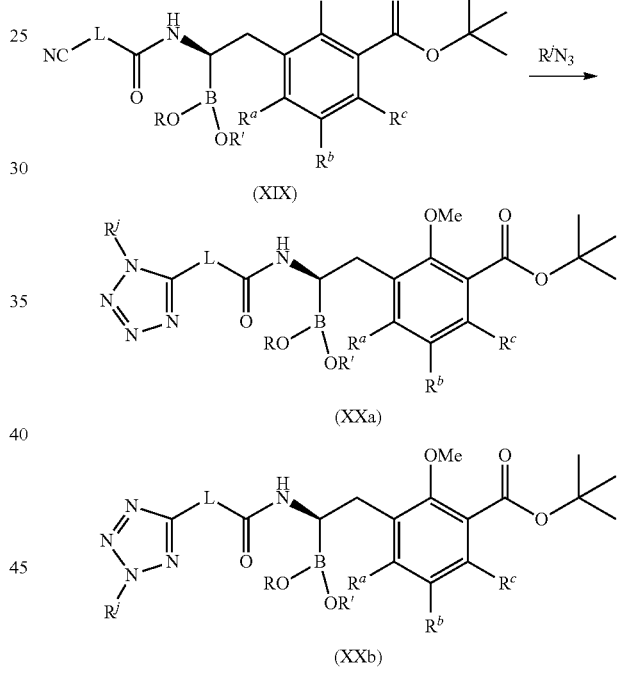

A broad range of suitable carboxylic acids (IV) may be prepared according to known methods, for example as described in *Modern Heterocyclic Chemistry*, Vol. 2 and Vol. 3 (eds J. Alvarez-Builla, J. J. Vaquero and J. Barluenga), Wiley-VCH Verlag GmbH & Co. KGaA, Weinheim, Germany. Representative schemes for the preparation of heteroaromatic-containing carboxylic esters are outlined in (SCHEME 6) for the case of L=CH$_2$. 1,2,4-oxadiazole acetates (XXIII) may be prepared from ethyl cyanoacetate (XXI) and N-hydroxyimidamidines (XXII) under zinc-catalysis. The regioisomeric 1,2,4-oxadiazole acetates (XXV) may be prepared by treatment of cyanoacetate (XXIV) with hydroxylamine hydrochloride, followed by condensation with the appropriate acid anhydride. 1,2,4-triazole acetates (XXVII) are available by the condensation of imidate (XXVI) with a suitable hydrazide. 1,2,4-Thiadiazoles (XXIX) may be prepared by reaction of amidines with trichloromethylsulfenyl chloride, with subsequent nucleophilic reaction of the resulting chlorothiadiazole (XXX) with ethyl acetate under strongly basic conditions. 5-Substituted amino-1,2,4-thiadiazoles (XXXIII) are prepared from sulfonyloxyimine chlorides (XXXII) in a two-step process. Chlorides (XXXII) are available in a three-step process from the appropriate aldehydes (XXXI). The corresponding acids (V) may be obtained by appropriate hydrolysis of the esters (SCHEME 6), for example by treatment with lithium, sodium, or potassium hydroxide in aqueous alcohol solvents. The t-butyl esters may be converted to the corresponding carboxylic acids by treatment with trifluoroacetic acid.

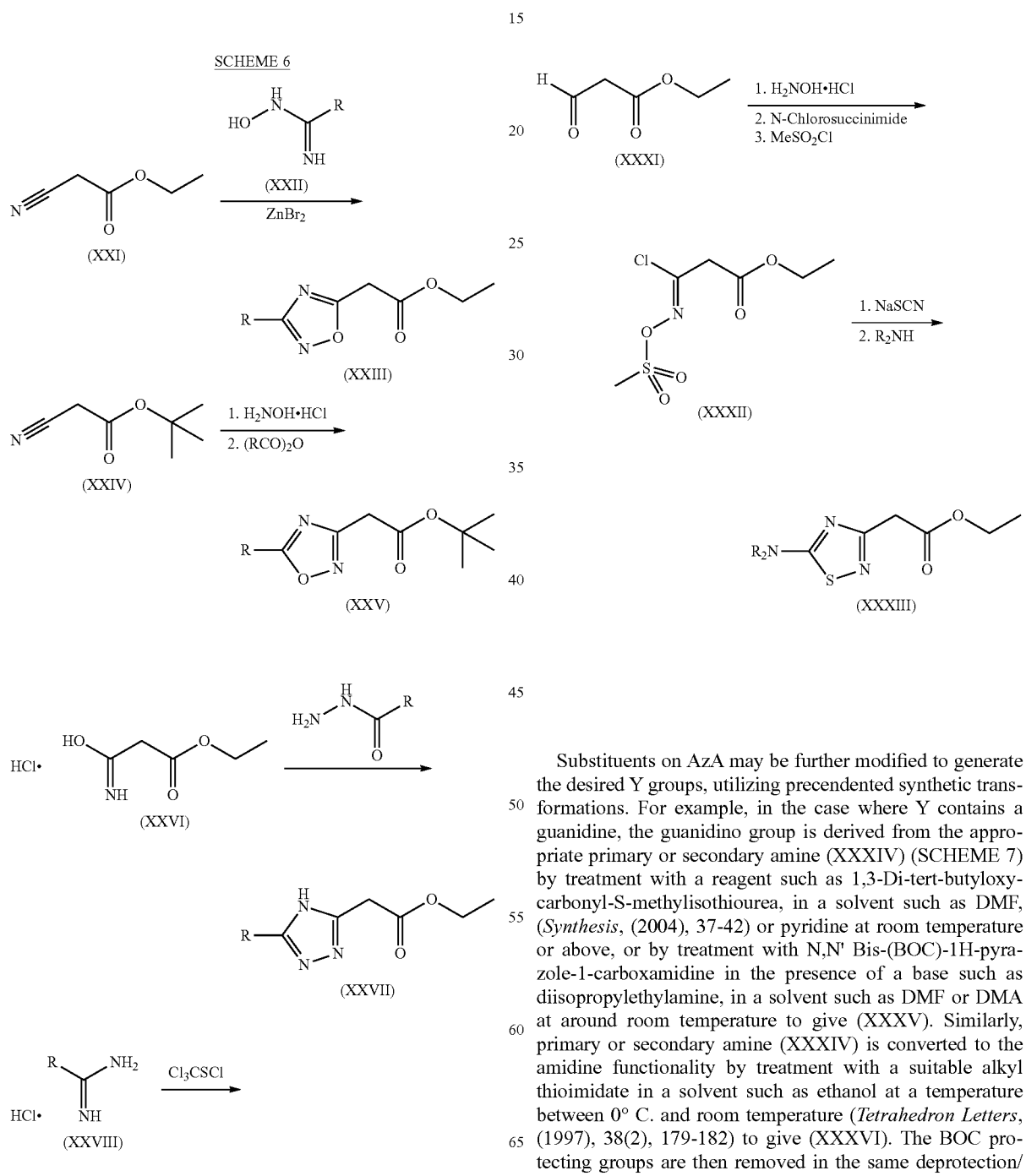

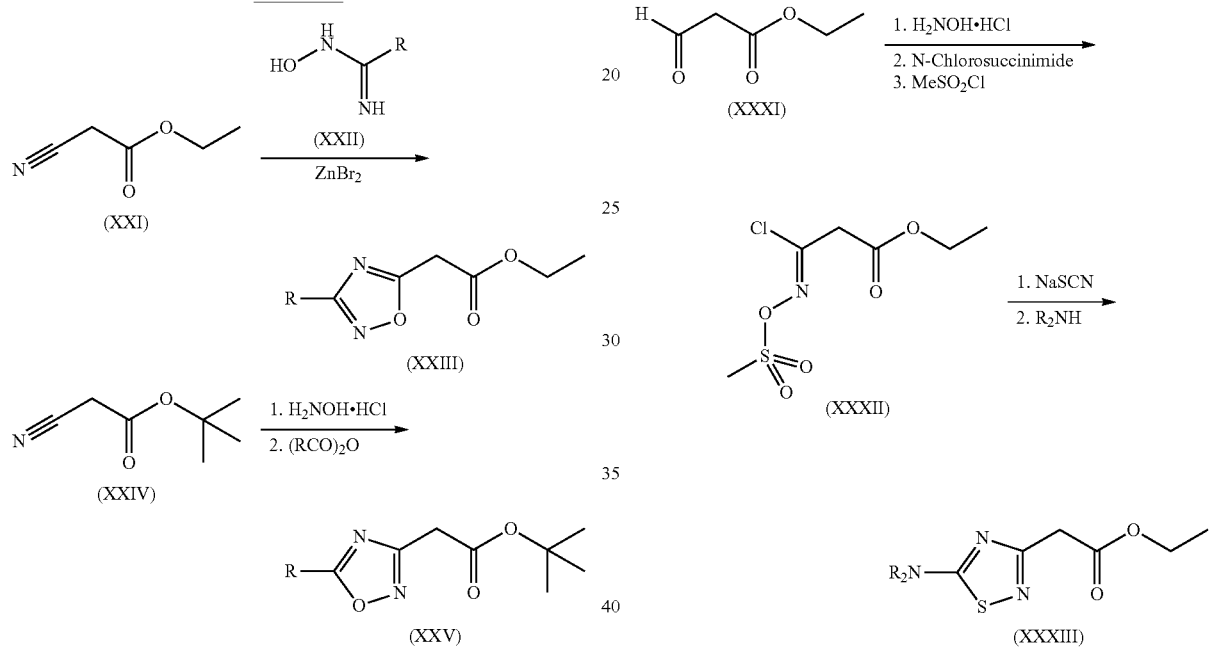

Substituents on AzA may be further modified to generate the desired Y groups, utilizing precendented synthetic transformations. For example, in the case where Y contains a guanidine, the guanidino group is derived from the appropriate primary or secondary amine (XXXIV) (SCHEME 7) by treatment with a reagent such as 1,3-Di-tert-butyloxycarbonyl-S-methylisothiourea, in a solvent such as DMF, (*Synthesis*, (2004), 37-42) or pyridine at room temperature or above, or by treatment with N,N' Bis-(BOC)-1H-pyrazole-1-carboxamidine in the presence of a base such as diisopropylethylamine, in a solvent such as DMF or DMA at around room temperature to give (XXXV). Similarly, primary or secondary amine (XXXIV) is converted to the amidine functionality by treatment with a suitable alkyl thioimidate in a solvent such as ethanol at a temperature between 0° C. and room temperature (*Tetrahedron Letters*, (1997), 38(2), 179-182) to give (XXXVI). The BOC protecting groups are then removed in the same deprotection/cyclization step as described in (SCHEME 1).

SCHEME 7

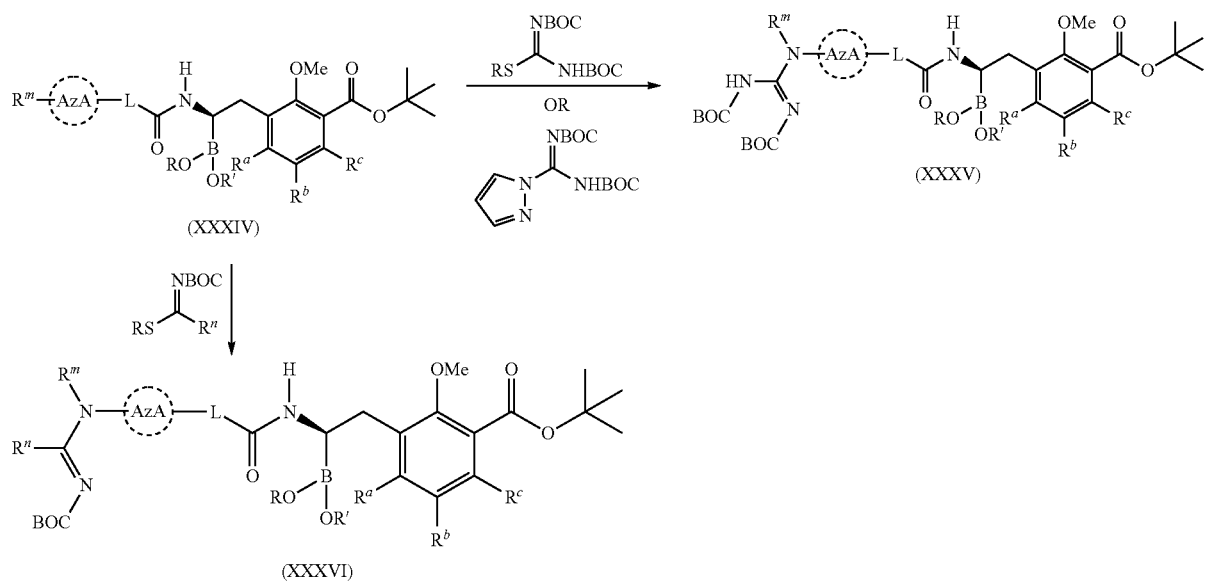

SYNTHETIC EXAMPLES

The following preparations of compounds of Formula (I) or Formula (II) and intermediates are given to enable those of skill in the art to more clearly understand and to practice the present invention. They should not be considered as limiting the scope of the invention, but merely as illustrative and representative thereof.

Example 1: (R)-2-hydroxy-3-(2-(4-(hydroxymethyl)-1H-1,2,3-triazol-1-yl)acetamido)-3,4-dihydro-2H-benzo[e][1,2]oxaborinine-8-carboxylic Acid

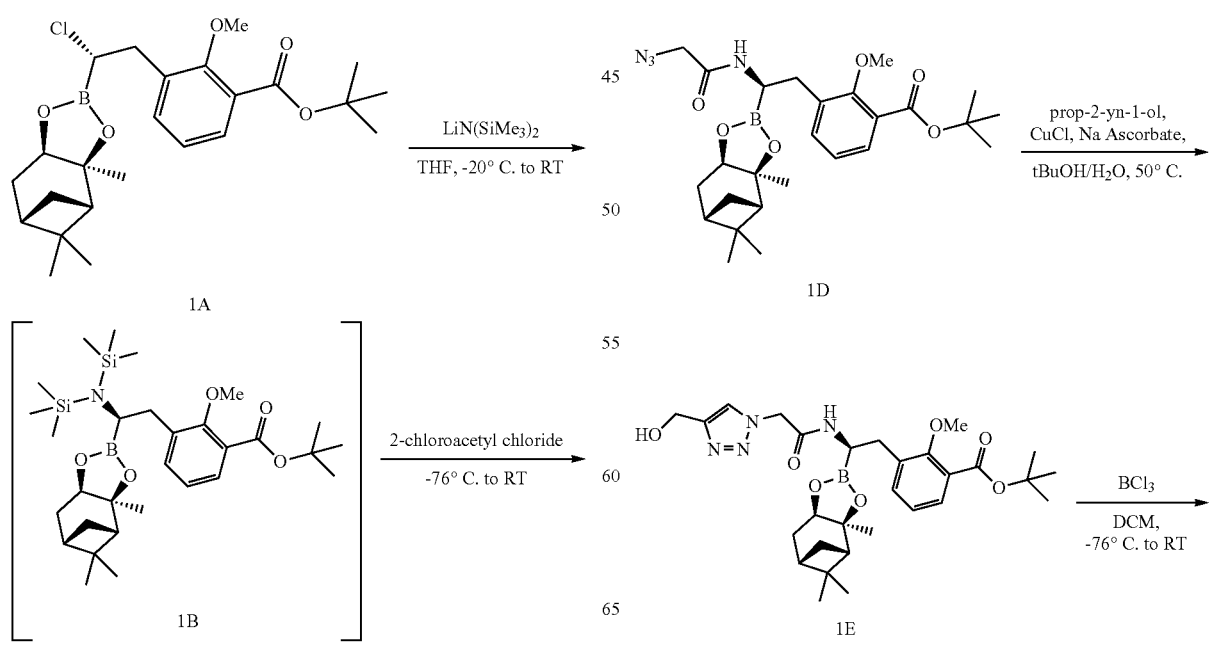

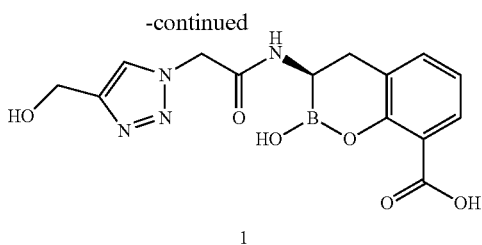

1

Step 1A: Synthesis of tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2-methoxybenzoate (1A)

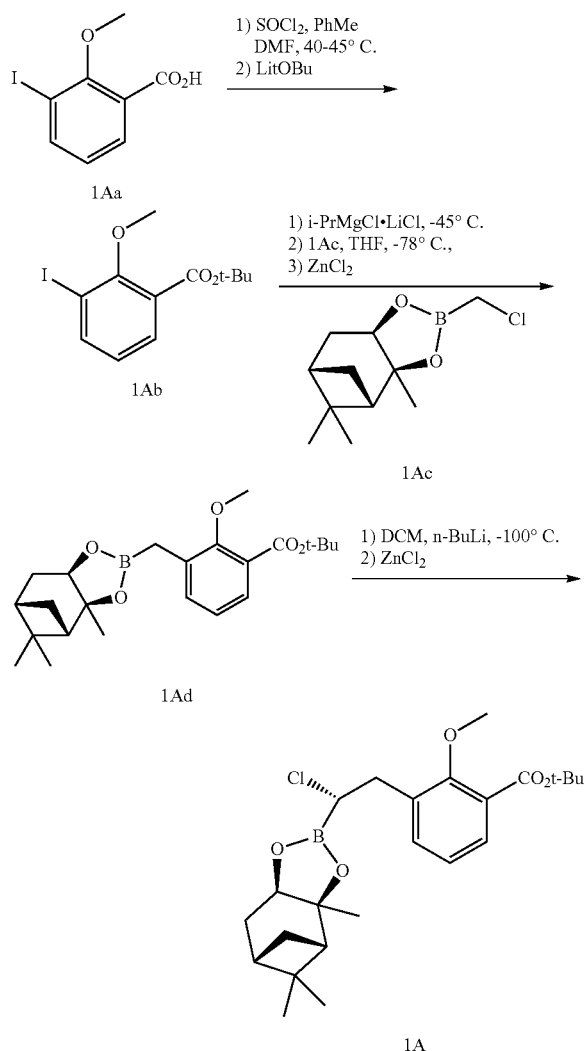

Step 1A-1: Synthesis of 3-iodo-2-methoxy-benzoic Acid Tert-Butyl Ester (1Ab)

To a suspension of 3-iodo-2-methoxy-benzoic acid (100.1 g, 360 mmol) in toluene (257 mL) and DMF (0.84 mL) at 45° C. was added $SOCl_2$ over 15 min. After the addition was completed, the resulted yellow solution as stirred at 50° C. for 2.5 hr, cooled to ambient temperature, and concentrated under reduced pressure to dryness. The mixture was dissolved in anhydrous toluene (30 ml) and concentrated under reduced pressure to give acid chloride intermediate as a brown oil (110.1 g).

To a solution of t-butanol (39.3 mL, 410 mmol) in THF (640 mL) in an ice water bath was added n-butyllithium (158 mL, 396 mmol, 2.5 M in hexanes) over 15 min. After the addition was completed, the mixture was stirred for 30 min, then a solution of the acid chloride (110.1 g) in THF (64 mL) was added over 10 min. The cold bath was removed, stirring continued for 1 hr, and then HCl (0.2 M, 720 mL) was added. The mixture was extracted with ether (1.6 L and additional 0.6 L). The ether extracts were combined, washed with brine, dried over $Na_2SO_4$, concentrated, and flash chromatographed on a silica gel column (500 g), eluted with hexanes/EtOAc (0-1.5%) to give the title compound as a yellow oil (113.5 g, 94.3% yield). ESI-MS m/z $(MH)^+$ 335 and $(MNa)^+$ 357.

Step 1A-2: Synthesis of 4-chloromethyl-2,9,9-trimethyl-3,5-dioxa-4-bora-tricyclo[6.1.1.02,6]-decane (1Ac)

To a solution of chloroiodomethane (27.0 mL, 367 mmol) in THF (367 mL) at −78° C. was added triisopropyl borate (78.5 mL, 340 mmol) followed by slowly addition of n-BuLi solution (147 mL, 367 mmol, 2.5 M in hexanes), down the side of the flask over 50 min, and stirring was continued for additional 40 min. To the resulted milky mixture was added chlorotrimethylsilane (46.6 mL, 367 mmol) over 5 min. The cold bath was removed, and stirring continued for 18 hr. To the resulted mixture was added a solution of (1S, 2S, 3R, 5S)-(+)-2,3-pinanediol (57.87 g, 340 mmol) in THF (170 mL) over 5 min, and stirring continued for 4 hr. The resulted yellow solution was diluted with ether (1.5 L) and washed $H_2O$ (400 mL). The organic layer was separated and washed with brine, dried over $Na_2SO_4$, concentrated, and flash chromatographed on a silica gel (1040 g) column, eluted with hexanes/EtOAc (0-4%) to give an oil (69.5 g). The compound was immediately used in next step of reaction.

Step 1A-3: Synthesis of 2-methoxy-3-(2,9,9-trimethyl-3,5-dioxa-4-bora-tricyclo[6.1.1.02,6]dec-4-ylmethyl)-benzoic Acid Tert-Butyl Ester (1Ad)

To a cooled (−45° C., acetone/dry ice) solution of 3-iodo-2-methoxy-benzoic acid tert-butyl ester (60.15 g, 180 mmol) in THF (450 mL) was added dropwise isopropyl magnesium chloride lithium chloride complex solution (138 mL, 180 mmol, 1.3 M in THF) over 30 min. After the addition was completed, the resulted solution was continued to stirred for 30 min, cooled to −78° C., then a solution of 4-chloromethyl-2,9,9-trimethyl-3,5-dioxa-4-bora-tricyclo[6.1.1.02,6] decane (41.13 g, 180 mmol) in THF (48 mL) was added dropwise, down the side of the flask over 20 min, and stirred for additional 5 min after the addition was completed. The cold bath was removed, the mixture was stirred for 18 hr, then diluted with ether (900 mL), washed with 0.1 M HCl (750 mL) and brine, dried over $Na_2SO_4$, concentrated, and flash chromatographed on a silica gel (500 g) column, eluted with hexanes/EtOAc (0-5%) and dried in vacuo to give the title compound as a white solid (66.7 g, 92.6% yield). ESI-MS m/z 423 $(MNa)^+$.

Step 1A-4: Synthesis of 3-[2-chloro-2-(2,9,9-trimethyl-3,5-dioxa-4-bora-tricyclo[6.1.1.02,6]dec-4-yl)-ethyl]-2-methoxy-benzoic Acid Tert-Butyl Ester (1A)

To a cooled (−100° C., liquid $N_2$/MeOH) solution of DCM (19.4 mL, 303 mmol) in THF (276 mL) was added dropwise, down the side of the flask n-butyllithium (77.4 mL, 193 mmol, 2.5 M in hexanes) over a period of 40 min. After the addition was completed, the resulted white milky mixture was stirred for 30 min, then a solution of 2-methoxy-3-(2,9,9-trimethyl-3,5-dioxa-4-bora-tricyclo[6.1.1.02,6]dec-4-ylmethyl)-benzoic acid tert-butyl ester (55.3 g, 138 mmol) in THF (100 mL) was added dropwise, down the side of the flask over 30 min. After the addition was completed, the mixture was stirred for 45 min, then a solution of $ZnCl_2$ (182 mL, 182 mmol, 1.0 M in ether) was added slowly, down the side of the flask over 30 min period, and stirring continued for additional 5 min. The cold bath was replaced with a dry ice/acetone bath (−10° C.), and stirring was continued for 80 min. The resulted yellow solution was diluted with ether (1000 mL), washed with HCl (0.05 M, 800 mL). The organic layer was separated, washed with brine, dried over $Na_2SO_4$, concentrated, and flash chromatographed on silica gel (500 g) column, eluted with hexanes/EtOAc (2-5%) to give the title compound as a colorless oil (56.5 g, 91.2% yield). ESI-MS m/z 471 (MNa)$^+$.

Step 1: Synthesis of tert-butyl 3-((R)-2-(2-chloroacetamido)-2-((3aS,4S,6S,7aR)-3a,5,5-trimethylhexahydro-4,6-methanobenzo[d][1,3,2]dioxaborol-2-yl)ethyl)-2-methoxybenzoate (1C)

To a solution of compound 1A (4.0 g, 8.9 mmol) in anhydrous THF (40 mL) at −76° C. was added LiHMDS (10 mL, 1 M in THF) dropwise. The reaction mixture was stirred and allowed to warm up to RT overnight to afford intermediate 1B. A portion of the above reaction mixture (4.9 mmol) was cooled down to −76° C. and to this solution was added 2-chloroacetyl chloride (0.6 mL, 7.5 mmol) dropwise at the same temperature. The reaction mixture was stirred −76° C. for 30 min before the cooling bath was removed and the reaction mixture was allowed to warm up to RT. Water was then added to quench the reaction. The mixture was extracted with EtOAc. The organic phase was washed with $NaHCO_3$ and brine, dried over $Na_2SO_4$, filtered concentrated in vacuo to afford the crude 1C, which was carried on to the next step without further purification.

Step 2: Synthesis of tert-butyl 3-((R)-2-(2-azidoacetamido)-2-((3aS,4S,6S,7aR)-3a,5,5-trimethylhexahydro-4,6-methanobenzo[d][1,3,2]dioxaborol-2-yl)ethyl)-2-methoxybenzoate (1D)

To a solution of compound 1C from step 1 (4.9 mmol) in DMSO (20 mL) was added $NaN_3$ solid (1.0 g, 15.3 mmol). The resulting reaction mixture was stirred at RT overnight. Water was added and the mixture was extracted with EtOAc. The organic phase was washed with brine, dried over $Na_2SO_4$, and concentrated. The crude product was purified by flash chromatography (EtOAc/Hexane, 10% to 80%) to afford the product as pale yellow oil. ESI-MS m/z 535 (MNa)$^+$.

Step 3: Synthesis of tert-butyl 3-((R)-2-(2-(4-(hydroxymethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (1E)

To a mixture of compound 1D (0.45 g, 0.88 mmol) and prop-2-yn-1-ol (0.11 g, 2 mmol) in tBuOH (9 mL) and $H_2O$ (1 mL) was added CuCl (0.020 g, 0.2 mmol) and sodium ascorbate (0.080 g, 0.4 mmol). The resulting reaction mixture was stirred at 50° C. for 3 hr. EtOAc was then added and the organic phase washed with water and brine, dried over $Na_2SO_4$, filtered and concentrated in vacuo to afford the crude product, which was purified by flash chromatography (EtOAc/Hexane 10% to 80%) to afford the title compound (0.24 g, 49%) as white foamy solid. ESI-MS m/z 591 (MNa)$^+$.

Step 4: Synthesis of (R)-2-hydroxy-3-(2-(4-(hydroxymethyl)-1H-1,2,3-triazol-1-yl)acetamido)-3,4-dihydro-2H-benzo[e][1,2]oxaborinine-8-carboxylic acid (1)

To a solution of compound 1E (0.24 g, 0.44 mmol) in DCM (8 mL) at −76° C. was added $BCl_3$ (3 mL, 1 M in DCM) dropwise. The reaction mixture was stirred at same temperature for 20 min and was allowed to warm up to 0° C. Water (3 mL) was added slowly to the reaction mixture. Aqueous residue was purified by reverse phase chromatography (acetonitrile/$H_2O$, 0.1% TFA) and dried using lyophilization to afford the title compound as while solid. ESI-MS m/z 347 (MH)$^+$.

Example 2: (R)-3-(2-(4-(aminomethyl)-1H-1,2,3-triazol-1-yl)acetamido)-2-hydroxy-3,4-dihydro-2H-benzo[e][1,2]oxaborinine-8-carboxylic Acid

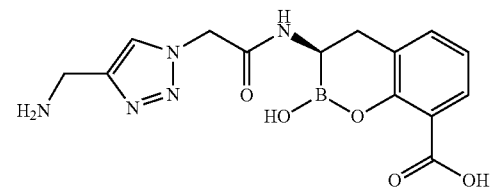 [SMILES: NCc1cn(CC(=O)N[C@H]2Cc3cccc(C(=O)O)c3OB2O)nn1]

Step 1: Synthesis of tert-butyl 3-((R)-2-(2-(4-(((tert-butoxycarbonyl)amino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate The title compound was prepared from 1D in Example 1 following the procedure described in Step 3, Example 1 using tert-butyl prop-2-yn-1-ylcarbamate.

Step 2: Synthesis of (R)-3-(2-(4-(aminomethyl)-1H-1,2,3-triazol-1-yl)acetamido)-2-hydroxy-3,4-dihydro-2H-benzo[e][1,2]oxaborinine-8-carboxylic acid The title compound was prepared from tert-butyl 3-((R)-2-(2-(4-(((tert-butoxycarbonyl)amino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate and $BCl_3$ following the procedure described in Step 4 of Example 1. The crude product was purified by reverse phase chromatography and dried using lyophilization. ESI-MS m/z 346 (MH)$^+$.

Example 3: (R)-3-(2-(4-(guanidinomethyl)-1H-1,2,3-triazol-1-yl)acetamido)-2-hydroxy-3,4-dihydro-2H-benzo[e][1,2]oxaborinine-8-carboxylic Acid

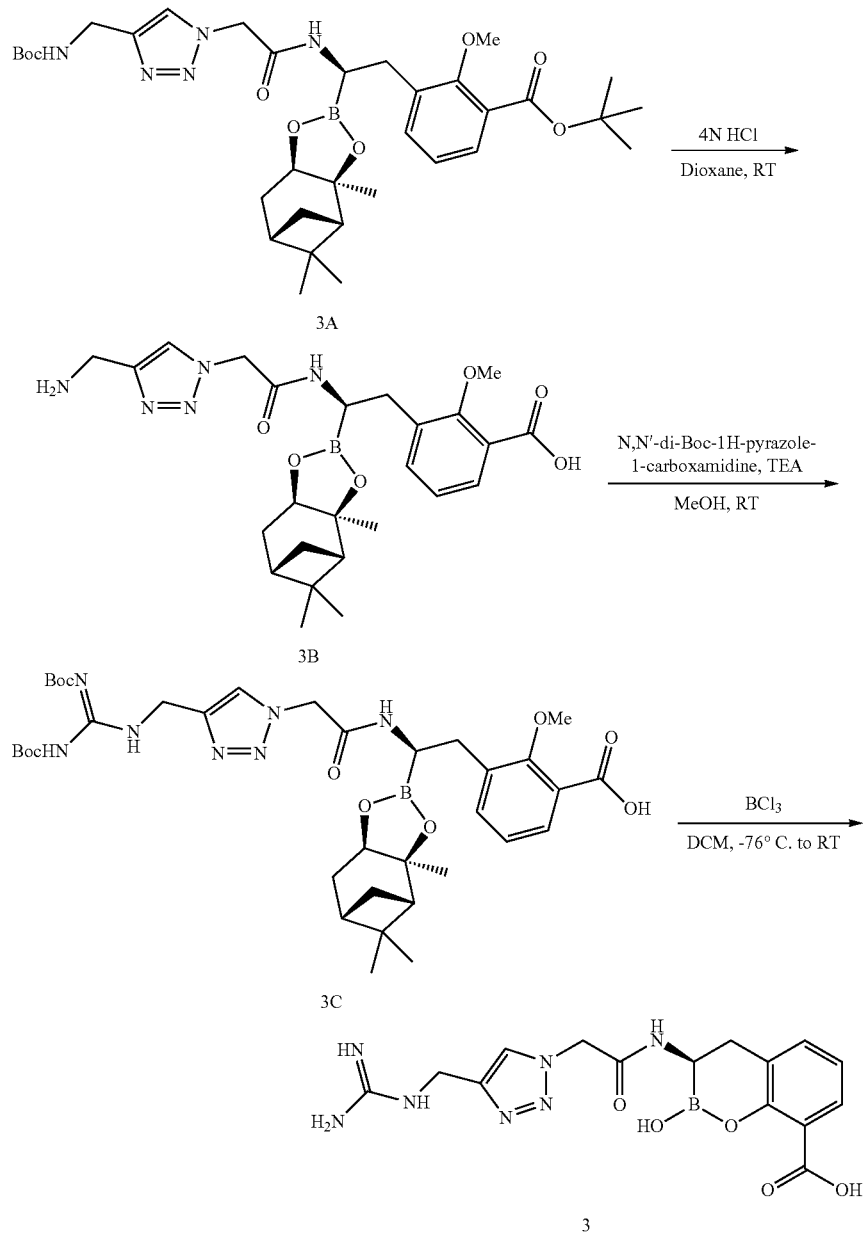

Step 1: Synthesis of 3-((R)-2-(2-(4-(aminomethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoic Acid (3B)

To compound 3A (from Step 1, Example 2, 0.30 g, 0.45 mmol) was added HCl (4 mL, 4N in dioxane) at RT. The reaction mixture was stirred for 1 hr. Diethyl ether was added and the precipitate was collected to afford the title compound as while solid (0.16 g) which was used directly to the next step without further purification.

Step 2: Synthesis of 3-((R)-2-(2-(4-(((E)-2,3-bis(tert-butoxycarbonyl)guanidino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoic Acid (3C)

To compound 3B (0.16 g, 0.3 mmol) in MeOH (5 mL) was added TEA (0.14 mL, 1 mmol), followed by N,N'-bis(tert-butoxycarbonyl)-1H-pyrazole-1-carboxamidine (0.31 g, 1 mmol). The resulting reaction mixture was stirred at RT overnight. Solvent was then removed in vacuo, the residue was redissolved in EtOAc, washed with 1 N HCl and brine, dried over Na$_2$SO$_4$, filtered and concentrated in vacuo to afford the crude product, which was used directly in the next step without further purification.

Step 3: Synthesis of (R)-3-(2-(4-(guanidinomethyl)-1H-1,2,3-triazol-1-yl)acetamido)-2-hydroxy-3,4-dihydro-2H-benzo[e][1,2]oxaborinine-8-carboxylic Acid (3)

Compound 3 was prepared from compound 3C and BCl₃ following the procedure described in Step 4 of Example 1. The crude product was purified by reverse phase chromatography and dried using lyophilization. ESI-MS m/z 388 (MH)⁺.

Example 4: (R)-2-hydroxy-3-(2-(4-((isopropylamino)methyl)-1H-1,2,3-triazol-1-yl)acetamido)-3,4-dihydro-2H-benzo[e][1,2]oxaborinine-8-carboxylic Acid

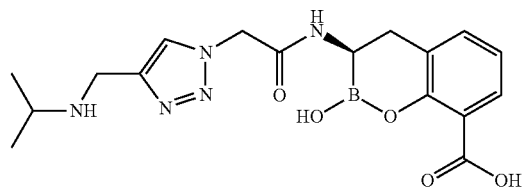 [SMILES: CC(C)NCc1cn(CC(=O)N[C@H]2Cc3cccc(C(=O)O)c3OB2O)nn1]

To (R)-3-(2-(4-(aminomethyl)-1H-1,2,3-triazol-1-yl)acetamido)-2-hydroxy-3,4-dihydro-2H-benzo[e][1,2]oxaborinine-8-carboxylic acid (0.030 g, from Example 2) in MeOH (2 mL) was added acetone (0.05 mL), followed by NaBH(OAc)₃ (1 mmol). The resulting reaction mixture was stirred at RT for 4 hr. After removal of the solvent, the residue was purified by reverse phase chromatography and dried using lyophilization to afford the title compound as white solid. ESI-MS m/z 388 (MH)⁺.

Example 5: (R)-2-hydroxy-3-(2-(4-(2-hydroxyethyl)-1H-1,2,3-triazol-1-yl)acetamido)-3,4-dihydro-2H-benzo[e][1,2]oxaborinine-8-carboxylic Acid

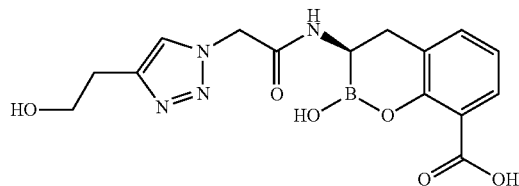 [SMILES: O=C(Cn1cc(CCO)nn1)N[C@H]1Cc2cccc(C(=O)O)c2OB1O]

Compound 5 was prepared following a similar procedure as described in Example 1 (Steps 3 and 4) replacing prop-2-yn-1-ol in step 3 with but-3-yn-1-ol. The crude product was purified by reverse phase chromatography and dried using lyophilization to afford the title compound as white solid. ESI-MS m/z 361 (MH)⁺.

Example 6: (R)-3-(2-(4-(2-aminoethyl)-1H-1,2,3-triazol-1-yl)acetamido)-2-hydroxy-3,4-dihydro-2H-benzo[e][1,2]oxaborinine-8-carboxylic Acid

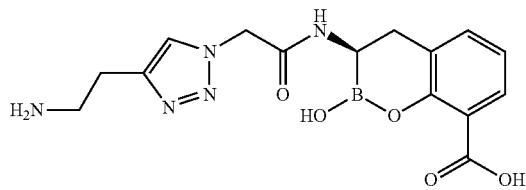 [SMILES: NCCc1cn(CC(=O)N[C@H]2Cc3cccc(C(=O)O)c3OB2O)nn1]

Compound 6 was prepared following a similar procedure as described in Example 2 (Steps 1 and 2) replacing tert-butyl prop-2-yn-1-ylcarbamate in step 1 with tert-butyl but-3-yn-1-ylcarbamate. The crude product was purified by reverse phase chromatography and dried using lyophilization to afford the title compound as white solid. ESI-MS m/z 360 (MH)⁺.

Example 7: (R)-2-hydroxy-3-(2-(4-(2-(isopropylamino)ethyl)-1H-1,2,3-triazol-1-yl)acetamido)-3,4-dihydro-2H-benzo[e][1,2]oxaborinine-8-carboxylic Acid

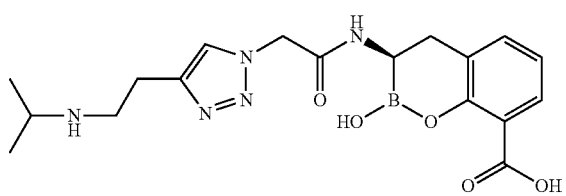 [SMILES: CC(C)NCCc1cn(CC(=O)N[C@H]2Cc3cccc(C(=O)O)c3OB2O)nn1]

Compound 7 was prepared from compound 6 following a similar procedure as described in Example 4. The crude product was purified by reverse phase chromatography and dried using lyophilization to afford the title compound as white solid. ESI-MS m/z 402 (MH)⁺.

Example 8: (R)-3-(2-(4,5-bis(hydroxymethyl)-1H-1,2,3-triazol-1-yl)acetamido)-2-hydroxy-3,4-dihydro-2H-benzo[e][1,2]oxaborinine-8-carboxylic Acid

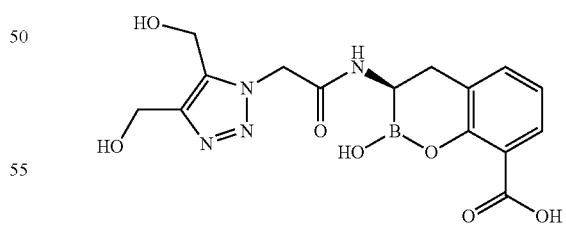

Step 1: Synthesis of tert-butyl 3-((R)-2-(2-(4,5-bis(hydroxymethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate A solution of tert-butyl 3-((R)-2-(2-azidoacetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.51 g, 1 mmol) and but-2-yne-1,4-diol (0.20 g, 2.3 mmol) in dioxane (5 mL) was heated under reflux overnight. After removal of the solvent, the residue was purified by flash chromatography to afford the title compound (0.20 g).

Step 2: Synthesis of (R)-3-(2-(4,5-bis(hydroxymethyl)-1H-1,2,3-triazol-1-yl)acetamido)-2-hydroxy-3,4-dihydro-2H-benzo[e][1,2]oxaborinine-8-carboxylic acid (8)

Compound 8 was prepared following the procedure described in Step 4 of Example 1. The crude product was purified by reverse phase chromatography and dried using lyophilization. ESI-MS m/z 377(MH)⁺.

Example 9: (R)-2-hydroxy-3-(2-(4-(trimethylsilyl)-1H-1,2,3-triazol-1-yl)acetamido)-3,4-dihydro-2H-benzo[e][1,2]oxaborinine-8-carboxylic Acid

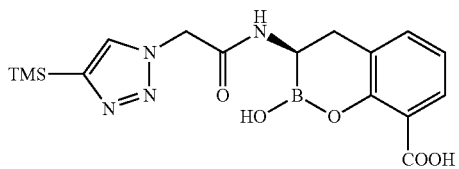 [SMILES: C[Si](C)(C)c1cn(CC(=O)N[C@H]2Cc3cccc(C(=O)O)c3OB2O)nn1]

Step 1: Synthesis of tert-butyl 2-methoxy-3-((R)-2-((3aS,4S,6S,7aR)-3a,5,5-trimethylhexahydro-4,6-methanobenzo[d][1,3,2]dioxaborol-2-yl)-2-(2-(4-(trimethylsilyl)-1H-1,2,3-triazol-1-yl)acetamido)ethyl)benzoate The title compound was prepared from 1D and ethynyltrimethylsilane following the procedure described in Step 3 of Example 1.

Step 2: Synthesis of (R)-2-hydroxy-3-(2-(4-(trimethylsilyl)-1H-1,2,3-triazol-1-yl)acetamido)-3,4-dihydro-2H-benzo[e][1,2]oxaborinine-8-carboxylic Acid (9)

The title compound was prepared from tert-butyl 2-methoxy-3-((R)-2-((3aS,4S,6S,7aR)-3a,5,5-trimethylhexahydro-4,6-methanobenzo[d][1,3,2]dioxaborol-2-yl)-2-(2-(4-(trimethylsilyl)-1H-1,2,3-triazol-1-yl)acetamido)ethyl)benzoate and BCl₃ following the procedure described in step 4 of Example 1. The crude product was purified by reverse phase chromatography and dried using lyophilization. ESI-MS m/z 389 (MH)⁺.

Example 10: (R)-2-hydroxy-3-(2-(4-(pyridin-2-yl)-1H-1,2,3-triazol-1-yl)acetamido)-3,4-dihydro-2H-benzo[e][1,2]oxaborinine-8-carboxylic Acid

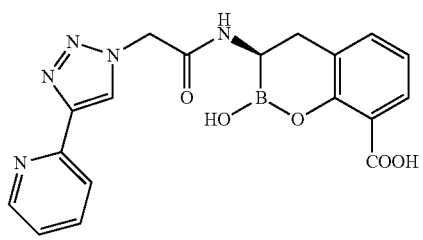 [SMILES: O=C(Cn1cc(-c2ccccn2)nn1)N[C@H]1Cc2cccc(C(=O)O)c2OB1O]

Step 1: Synthesis of tert-butyl 2-methoxy-3-((R)-2-(2-(4-(pyridin-2-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate The title compound was prepared from 1D and 2-ethynylpyridine following the procedure described in Step 3 of Example 1.

Step 2: Synthesis of (R)-2-hydroxy-3-(2-(4-(pyridin-2-yl)-1H-1,2,3-triazol-1-yl)acetamido)-3,4-dihydro-2H-benzo[e][1,2]oxaborinine-8-carboxylic Acid (10)

The title compound was prepared from tert-butyl 2-methoxy-3-((R)-2-(2-(4-(pyridin-2-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate and BCl₃ following the procedure described in Step 4 of Example 1. The crude product was purified by reverse phase chromatography and dried using lyophilization. ESI-MS m/z 394 (MH)⁺.

Example 11: (R)-3-(2-(4,5-bis(ethoxycarbonyl)-1H-1,2,3-triazol-1-yl)acetamido)-2-hydroxy-3,4-dihydro-2H-benzo[e][1,2]oxaborinine-8-carboxylic Acid

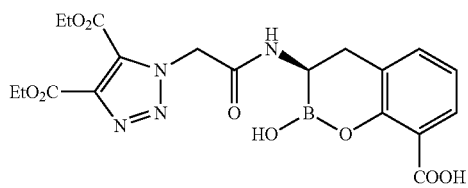

Step 1: Synthesis of diethyl 1-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-2-oxoethyl)-1H-1,2,3-triazole-4,5-dicarboxylate The title compound was prepared from 1D and diethyl but-2-ynedioate following the procedure described in Step 3 of Example 1.

Step 2: Synthesis of (R)-3-(2-(4,5-bis(ethoxycarbonyl)-1H-1,2,3-triazol-1-yl)acetamido)-2-hydroxy-3,4-dihydro-2H-benzo[e][1,2]oxaborinine-8-carboxylic Acid (11)

Prepared from diethyl 1-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-2-oxoethyl)-1H-1,2,3-triazole-4,5-dicarboxylate and BCl₃ following the procedure described in Step 4 of Example 1. The crude product was purified by reverse phase chromatography and dried using lyophilization. ESI-MS m/z 461 (MH)⁺.

Example 12: (R)-2-hydroxy-3-(2-(4-(pyridin-3-yl)-1H-1,2,3-triazol-1-yl)acetamido)-3,4-dihydro-2H-benzo[e][1,2]oxaborinine-8-carboxylic Acid

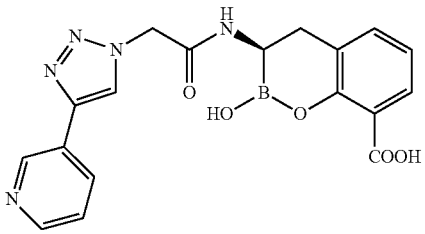 [SMILES: O=C(Cn1cc(-c2cccnc2)nn1)N[C@H]1Cc2cccc(C(=O)O)c2OB1O]

Step 1: Synthesis of tert-butyl 2-methoxy-3-((R)-2-(2-(4-(pyridin-3-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate The title compound was prepared from 1D in Example 1 following the procedure described in Step 3 in Example 1 using 3-ethynylpyridine.

Step 2: Synthesis of (R)-2-hydroxy-3-(2-(4-(pyridin-3-yl)-1H-1,2,3-triazol-1-yl)acetamido)-3,4-dihydro-2H-benzo[e][1,2]oxaborinine-8-carboxylic Acid (12)

The title compound was prepared from tert-butyl 2-methoxy-3-((R)-2-(2-(4-(pyridin-3-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate and BCl$_3$ following the procedure described in step 4 of Example 1. The crude product was purified by reverse phase chromatography and dried using lyophilization. ESI-MS m/z 394 (MH)$^+$.

Example 13: (R)-3-(2-(5-(aminomethyl)-1H-1,2,3-triazol-1-yl)acetamido)-2-hydroxy-3,4-dihydro-2H-benzo[e][1,2]oxaborinine-8-carboxylic Acid

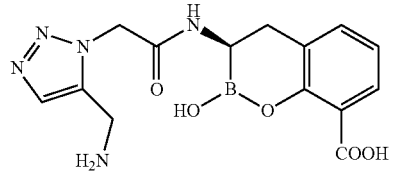 [SMILES: NCc1cnnn1CC(=O)N[C@H]1Cc2cccc(C(=O)O)c2OB1O]

Step 1: Synthesis of tert-butyl 3-((R)-2-(2-(5-(((tert-butoxycarbonyl)amino)methyl)-1H-1,2,3-triazol-1-yl)acetamido)-2-((3aS,4S,6S,7aR)-3a,5,5-trimethyl-hexahydro-4,6-methanobenzo[d][1,3,2]dioxaborol-2-yl)ethyl)-2-methoxybenzoate A mixture of 1D (0.1 g, 0.2 mmol), tert-butyl prop-2-yn-1-ylcarbamate (60 mg, 0.4 mmol) and pentamethylcyclopentadienylbis(triphenylphosphine)ruthenium(II) chloride [Cp*RuCl(PPh$_3$)$_2$, 30 mg, 0.04 mmol] in 2 mL of toluene was flushed with argon, then, heated at 60° C. for 24 hr. After cooling to RT, the solvent was removed under vacuum, and the residue was purified by flash chromatography (EtOAc/Hexane, 10% to 80%) to afford the title compound as brown oil. ESI-MS m/z 668 (MH)$^+$.

Step 2: Synthesis of (R)-3-(2-(5-(aminomethyl)-1H-1,2,3-triazol-1-yl)acetamido)-2-hydroxy-3,4-dihydro-2H-benzo[e][1,2]oxaborinine-8-carboxylic Acid (13)

The title compound was prepared from tert-butyl 3-((R)-2-(2-(5-(((tert-butoxycarbonyl)amino)methyl)-1H-1,2,3-triazol-1-yl)acetamido)-2-((3aS,4S,6S,7aR)-3a,5,5-trimethyl-hexahydro-4,6-methanobenzo[d][1,3,2]dioxaborol-2-yl)ethyl)-2-methoxybenzoate and BCl$_3$ following the procedure described in step 4 of Example 1. The crude product was purified by reverse phase chromatography and dried using lyophilization. ESI-MS m/z 346 (MH)$^+$.

Example 14 and 15: (R)-2-hydroxy-3-(2-(5-(hydroxymethyl)-4-((methylamino)methyl)-1H-1,2,3-triazol-1-yl)acetamido)-3,4-dihydro-2H-benzo[e][1,2]oxaborinine-8-carboxylic Acid (14) and (R)-2-hydroxy-3-(2-(4-(hydroxymethyl)-5-((methylamino)methyl)-1H-1,2,3-triazol-1-yl)acetamido)-3,4-dihydro-2H-benzo[e][1,2]oxaborinine-8-carboxylic Acid (15)

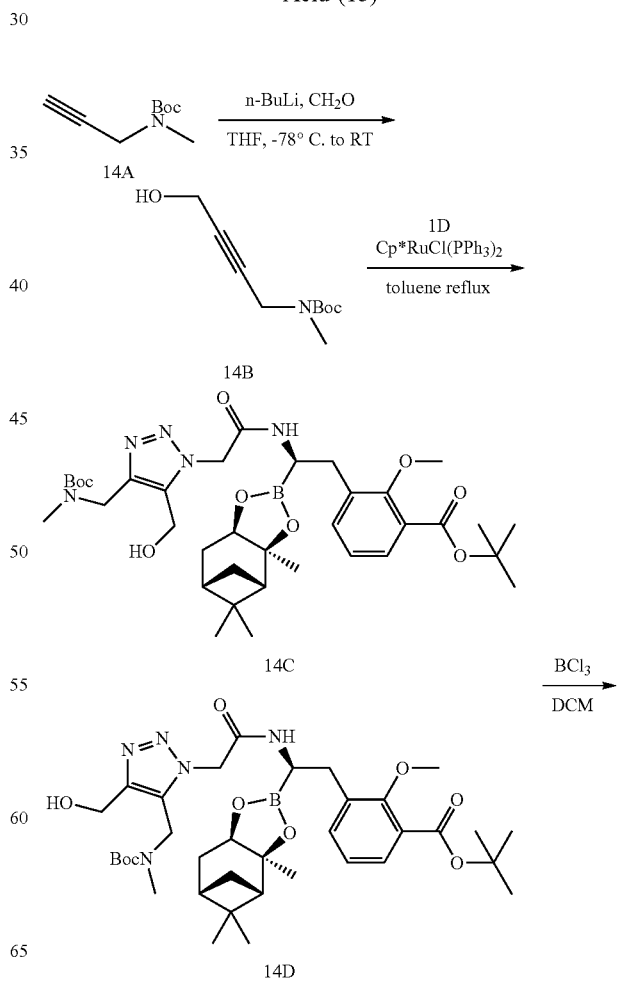

-continued

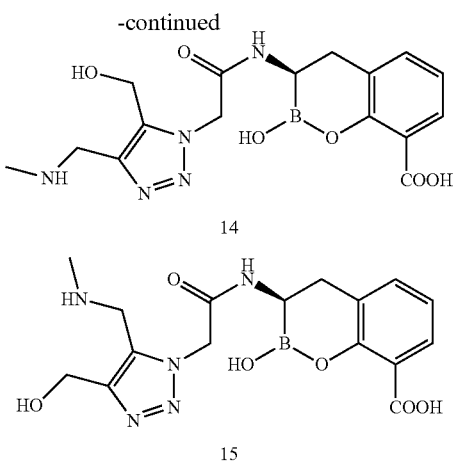

14

15

Step 1: Synthesis of tert-butyl (4-hydroxybut-2-yn-1-yl)(methyl)carbamate (14B)

n-BuLi (1.6 N in Hexanes, 2 mL) was added to a solution of 14A (0.5 g in 6 mL of THF) at −78° C. under argon, and the resulting mixture was stirred for 20 min. Formaldehyde (140 mg) was added and the mixture was stirred at −78° C. for 1 hr. The reaction mixture was warmed to RT, quenched with saturated ammonium chloride solution and extracted with ethyl acetate. The solvent was removed under vacuum, and purified by flash chromatograph (EtOAc/hexane, 1:3) to give 14B as yellow oil (0.4 g). $^1$H NMR (CDCl$_3$, 300 MHz) δ 4.25 (s, 2H), 4.05 (s, 2H), 2.95 (s, 3H), 1.43 (s, 9H).

Step 2: Synthesis of tert-butyl 3-((R)-2-(2-(4-(((tert-butoxycarbonyl)(methyl)amino)methyl)-5-(hydroxymethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (14C) and tert-butyl 3-((R)-2-(2-(5-(((tert-butoxycarbonyl)(methyl)amino)methyl)-4-(hydroxymethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (14D)

The title compounds (14C and 14D) were prepared as a mixture from 1D and 14B following the procedure described in Step 1 of Example 13.

Step 3: Synthesis of (R)-2-hydroxy-3-(2-(5-(hydroxymethyl)-4-((methylamino)methyl)-1H-1,2,3-triazol-1-yl)acetamido)-3,4-dihydro-2H-benzo[e][1,2]oxaborinine-8-carboxylic Acid (14) and (R)-2-hydroxy-3-(2-(4-(hydroxymethyl)-5-((methylamino)methyl)-1H-1,2,3-triazol-1-yl)acetamido)-3,4-dihydro-2H-benzo[e][1,2]oxaborinine-8-carboxylic Acid (15)

The title compound was prepared from 14C and 14D and BCl$_3$ following the procedure described in Step 4 of Example 1. The crude product was purified by reverse phase chromatography and dried using lyophilization to give the two isomers 14 and 15 (retention time: 2.754 min. and 2.752 min.). ESI-MS m/z 390 (MH)$^+$.

Example 16: (R)-1-(2-((8-carboxy-2-hydroxy-3,4-dihydro-2H-benzo[e][1,2]oxaborinin-3-yl)amino)-2-oxoethyl)-1H-1,2,3-triazole-4,5-dicarboxylic Acid

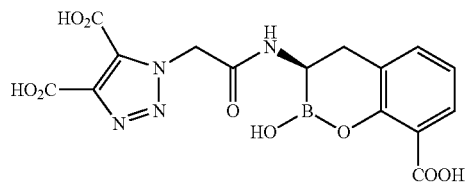 [SMILES: O=C(Cn1nnc(C(=O)O)c1C(=O)O)N[C@H]1Cc2cccc(C(=O)O)c2OB1O]

Step 1: Synthesis of di-tert-butyl 1-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-2-oxoethyl)-1H-1,2,3-triazole-4,5-dicarboxylate The title compound was prepared from 1D and di-tert-butyl acetylenedicarboxylate following the procedure described in Step 1 of Example 8.

Step 2: Synthesis of (R)-1-(2-((8-carboxy-2-hydroxy-3,4-dihydro-2H-benzo[e][1,2]oxaborinin-3-yl)amino)-2-oxoethyl)-1H-1,2,3-triazole-4,5-dicarboxylic Acid (16)

The title compound was prepared from tert-butyl 3-((R)-2-(2-(5-(((tert-butoxycarbonyl)amino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate and BCl$_3$ following the procedure described in step 4 of Example 1. The crude product was purified by reverse phase chromatography and dried using lyophilization. ESI-MS m/z 346 (MH)$^+$.

Example 17: (R)-3-(2-(5-(aminomethyl)-1H-tetrazol-1-yl)acetamido)-2-hydroxy-3,4-dihydro-2H-benzo[e][1,2]oxaborinine-8-carboxylic Acid

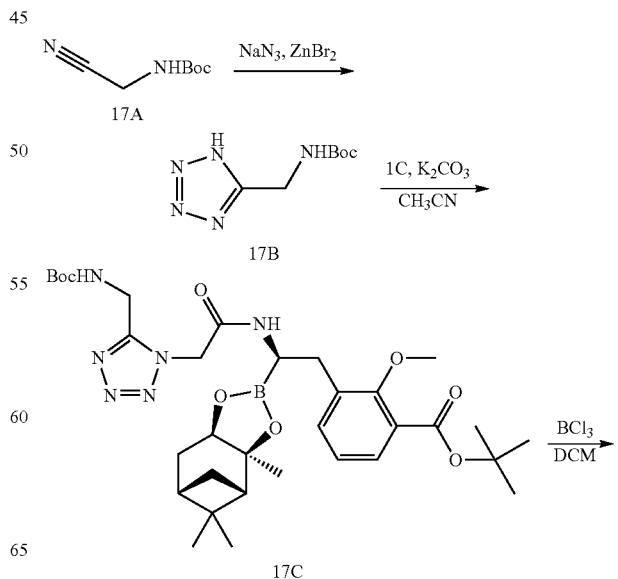

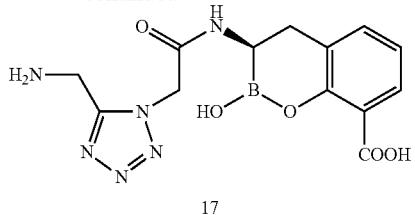

17

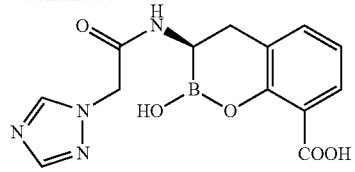

18

Step 1: Synthesis of tert-butyl ((1H-tetrazol-5-yl)methyl)carbamate (17B)

Compound 17B was prepared following the literature procedure (Sureshbabu, Vommina V. et al., *Synthetic Communications*, 39(3), 395-406; 2009).

Step 2: Synthesis of tert-butyl 3-((R)-2-(2-(5-(((tert-butoxycarbonyl)amino)methyl)-1H-tetrazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (17C)

A mixture of 1C (0.1 g, 0.2 mmol), 17B (0.2 g, 0.5 mmol), 15-crown-5 (20 mg, 0.09 mmol) and K₂CO₃ (50 mg, 0.36 mmol) in 2 mL of CH₃CN was stirred at RT for 3 days. The reaction was quenched with water (2 mL), extracted with DCM (10 mL), and purified by column (EtOAc/Hexanes 1:2) to give 17C as yellow oil. ESI-MS m/z 691 (MH)⁺.

Step 3: Synthesis of (R)-3-(2-(5-(aminomethyl)-1H-tetrazol-1-yl)acetamido)-2-hydroxy-3,4-dihydro-2H-benzo[e][1,2]oxaborinine-8-carboxylic acid (17)

The title compound was prepared from 17C and BCl₃ following the procedure described in Step 4 of Example 1. The crude product was purified by reverse phase chromatography and dried using lyophilization. ESI-MS m/z 347 (MH)⁺.

Example 18: (R)-3-(2-(1H-1,2,4-triazol-1-yl)acetamido)-2-hydroxy-3,4-dihydro-2H-benzo[e][1,2]oxaborinine-8-carboxylic Acid

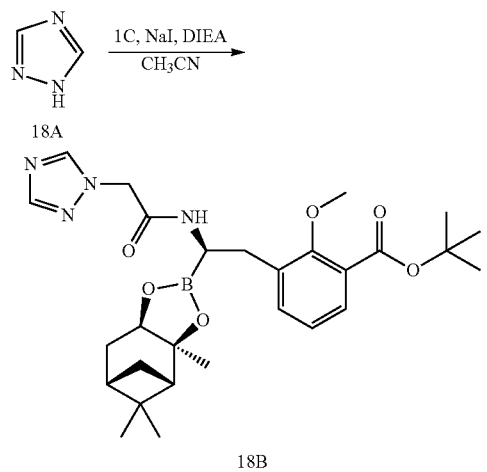

Step 1: Synthesis of tert-butyl 3-((R)-2-(2-(1H-1,2,4-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (18B)

A mixture of 1C (0.1 g, 0.2 mmol), 18A (0.03 g, 0.4 mmol), DIPEA (0.04 g, 0.3 mmol), K₂CO₃ (0.05 g) and NaI (20 mg, 0.1 mmol) in 0.5 mL of CH₃CN was stirred at 50° C. for 24 hr and 65° C. for 24 hr. The mixture was cooled to RT, and purified by flash chromatography (EtOAc/Hexane 10% to 80%) to give 18B (50 mg, 45%). ESI-MS m/z 539 (MH)⁺.

Step 2: Synthesis of (R)-3-(2-(1H-1,2,4-triazol-1-yl)acetamido)-2-hydroxy-3,4-dihydro-2H-benzo[e][1,2]oxaborinine-8-carboxylic Acid (18)

The title compound was prepared from 18B and BCl₃ following the procedure described in Step 4 of Example 1. The crude product was purified by reverse phase chromatography and dried using lyophilization. ESI-MS m/z 317 (MH)⁺.

Example 19: (R)-3-(2-(2-(aminomethyl)thiazol-4-yl)acetamido)-2-hydroxy-3,4-dihydro-2H-benzo[e][1,2]oxaborinine-8-carboxylic Acid

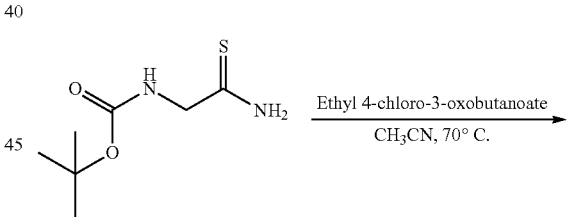

19A

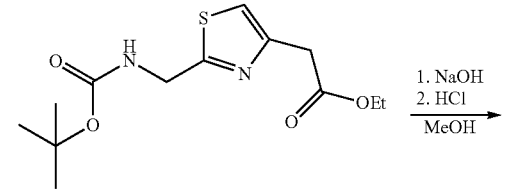

19B

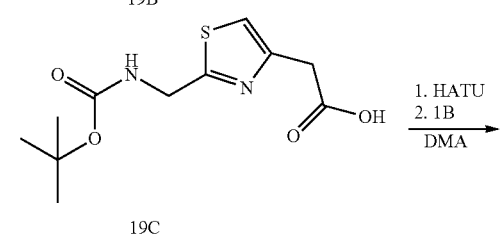

19C

-continued

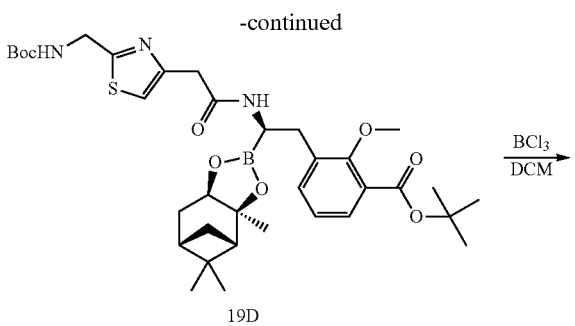

Step 1: Synthesis of ethyl 2-(2-(((tert-butoxycarbonyl)amino)methyl)thiazol-4-yl)acetate (19B)

A mixture of 19A (0.45 g, 2.4 mmol) and ethyl-4-chloro-3-oxabutanoate (0.4 g, 2.4 mmol) in 5 mL of $CH_3CN$ was heated at 70° C. for 24 hr. After cooled to RT, diluted with EtOAc (50 mL), and with saturated $NaHCO_3$ (15 mL). The organic layer was washed with brine, concentrated in vacuo, and purified by flash chromatography (EtOAc/Hexanes 10% to 80%) to give 19C as a yellow oil (0.2 g, 29%). ESI-MS m/z 301 $(MH)^+$.

Step 2: Synthesis of 2-(2-(((tert-butoxycarbonyl)amino)methyl)thiazol-4-yl)acetic Acid (19C)

NaOH (2N in water, 1 mL) was added to a solution of 19B (0.2 g) in MeOH (4 mL) at 0° C. After 4 hr at 0° C., the mixture was warmed to RT for 20 hr. The reaction mixture was concentrated under vacuum at RT to remove most of the MeOH. The residue was cooled with ice-water, acidified with HCl (0.5 N) to pH 2, extracted with EtOAc, and concentrated to give crude 19C as yellow solid (0.15 g). ESI-MS m/z 273 $(MH)^+$.

Step 3: Synthesis of tert-butyl 3-((R)-2-(2-(2-(((tert-butoxycarbonyl)amino)methyl)thiazol-4-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (19D)

Preparation of solution 1B: LiHMDS (1.2 mL, 1.0 M in THF) was added to a solution of 1A (0.5 g, 1.1 mmol) in 2 mL of THF at 78° C. After 30 min, the reaction mixture was warmed to RT for 1.5 h. In a separate vial, DIEPA (0.13 g, 1 mmol) was added to a mixture of 19C (0.25 g, 0.92 mmol) and HATU (0.42 g, 1.1 mmol) in 4 mL of DMA at RT. The mixture was stirred at RT for 2 hr, then, the solution A (from above) was added and the mixture was stirred at RT for 3 hr. The reaction mixture was diluted with $Et_2O$ (20 mL), and washed with HCl (0.5 N, 4 mL)/water (6 mL)/brine (10 mL). The solvent was removed under vacuum and the residue was purified by flash chromatography (EtOAc/Hexanes 10% to 100%) to give 19D as yellow solid (0.15 g, 24%). ESI-MS m/z 684 $(MH)^+$.

Step 4: Synthesis of (R)-3-(2-(2-(aminomethyl)thiazol-4-yl)acetamido)-2-hydroxy-3,4-dihydro-2H-benzo[e][1,2]oxaborinine-8-carboxylic Acid (19)

Prepared from 19D and $BCl_3$ following the procedure described in Step 4 of Example 1. The crude product was purified by reverse phase chromatography and dried using lyophilization. ESI-MS m/z 362 $(MH)^+$.

Example 20: (R)-3-(2-(5-amino-4H-1,2,4-triazol-3-yl)acetamido)-2-hydroxy-3,4-dihydro-2H-benzo[e][1,2]oxaborinine-8-carboxylic Acid

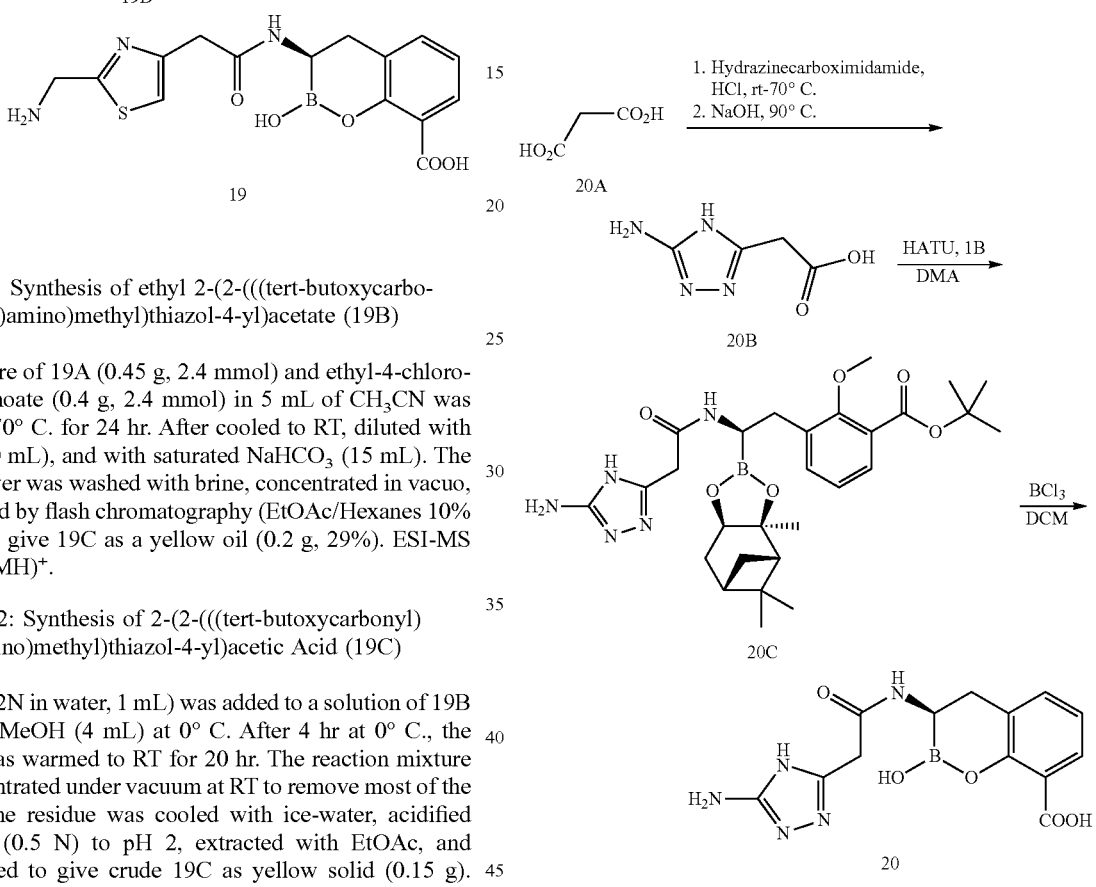

Step 1: Synthesis of 2-(5-amino-4H-1,2,4-triazol-3-yl)acetic Acid (20B)

Compound 20B was prepared following the procedure of Chernyshev, V. M. et al., *Russian Journal of Applied Chemistry*, 82(2), 276-281; 2009.

Step 2: Synthesis of tert-butyl 3-((R)-2-(2-(5-amino-4H-1,2,4-triazol-3-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (20C)

The title compound was prepared from 20B following the procedure described in Step 3 of Example 19.

Step 3: Synthesis of (R)-3-(2-(5-amino-4H-1,2,4-triazol-3-yl)acetamido)-2-hydroxy-3,4-dihydro-2H-benzo[e][1,2]oxaborinine-8-carboxylic Acid (20)

The title compound was prepared from 20C and $BCl_3$ following the procedure described in Step 4 of Example 1.

The crude product was purified by reverse phase chromatography and dried using lyophilization. ESI-MS m/z 332 (MH)+.

Example 21: (R)-2-hydroxy-3-(2-(4-(((2-hydroxyethyl)amino)methyl)-1H-1,2,3-triazol-1-yl)acetamido)-3,4-dihydro-2H-benzo[e][1,2]oxaborinine-8-carboxylic Acid

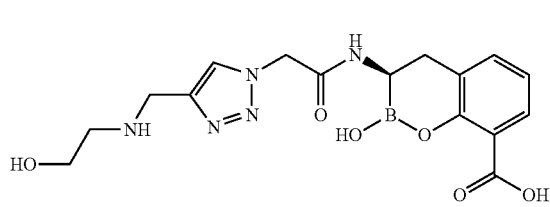 [SMILES: O=C(Cn1cc(CNCCO)nn1)N[C@H]1Cc2cccc(C(=O)O)c2OB1O]

Step 1: Synthesis of (R)-3-(2-(4-(((2-((tert-butyldimethylsilyl)oxy)ethyl)amino)methyl)-1H-1,2,3-triazol-1-yl)acetamido)-2-hydroxy-3,4-dihydro-2H-benzo[e][1,2]oxaborinine-8-carboxylic Acid To a solution of (R)-3-(2-(4-(aminomethyl)-1H-1,2,3-triazol-1-yl)acetamido)-2-hydroxy-3,4-dihydro-2H-benzo[e][1,2]oxaborinine-8-carboxylic acid (Example 2, 0.040 g, 0.12 mmol) and 2-((tert-butyldimethylsilyl)oxy)acetaldehyde (0.040, 0.24 mmol) in MeOH (5 mL) was added Pd on Carbon (50 mg) and the resulting reaction mixture was stirred at RT under hydrogen atmosphere (balloon) overnight. The catalyst was filtered and the solvent removed under reduced pressure to afford the title compound, which was used in the next step without further purification.

Step 2: Synthesis of (R)-2-hydroxy-3-(2-(4-(((2-hydroxyethyl)amino)methyl)-1H-1,2,3-triazol-1-yl)acetamido)-3,4-dihydro-2H-benzo[e][1,2]oxaborinine-8-carboxylic Acid (21)

The title compound was prepared following the procedure described in Step 4 of Example 1. The crude product was purified by reverse phase chromatography and dried using lyophilization. ESI-MS m/z 390(MH)+.

Example 22: (R)-3-(2-(4-(formimidamidomethyl)-1H-1,2,3-triazol-1-yl)acetamido)-2-hydroxy-3,4-dihydro-2H-benzo[e][1,2]oxaborinine-8-carboxylic Acid

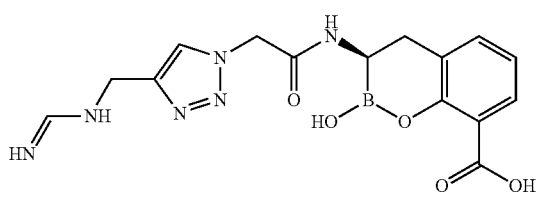 [SMILES: N=CNCc1cn(CC(=O)N[C@H]2Cc3cccc(C(=O)O)c3OB2O)nn1]

To (R)-3-(2-(4-(aminomethyl)-1H-1,2,3-triazol-1-yl)acetamido)-2-hydroxy-3,4-dihydro-2H-benzo[e][1,2]oxaborinine-8-carboxylic acid (Example 2, 0.030 g, 0.1 mmol)) in MeOH (5 mL) was added TEA (5 eq), followed by isopropyl formimidate hydrochloride (1.2 eq). The reaction mixture was stirred at room temperature for overnight. The mixture was then concentrated in vacuo and the crude product was purified using reverse phase HPLC to afford the title compound. ESI-MS m/z 373 (MH)+.

Example 23: (R)-3-(2-(5-(aminomethyl)-4H-1,2,4-triazol-3-yl)acetamido)-2-hydroxy-3,4-dihydro-2H-benzo[e][1,2]oxaborinine-8-carboxylic Acid

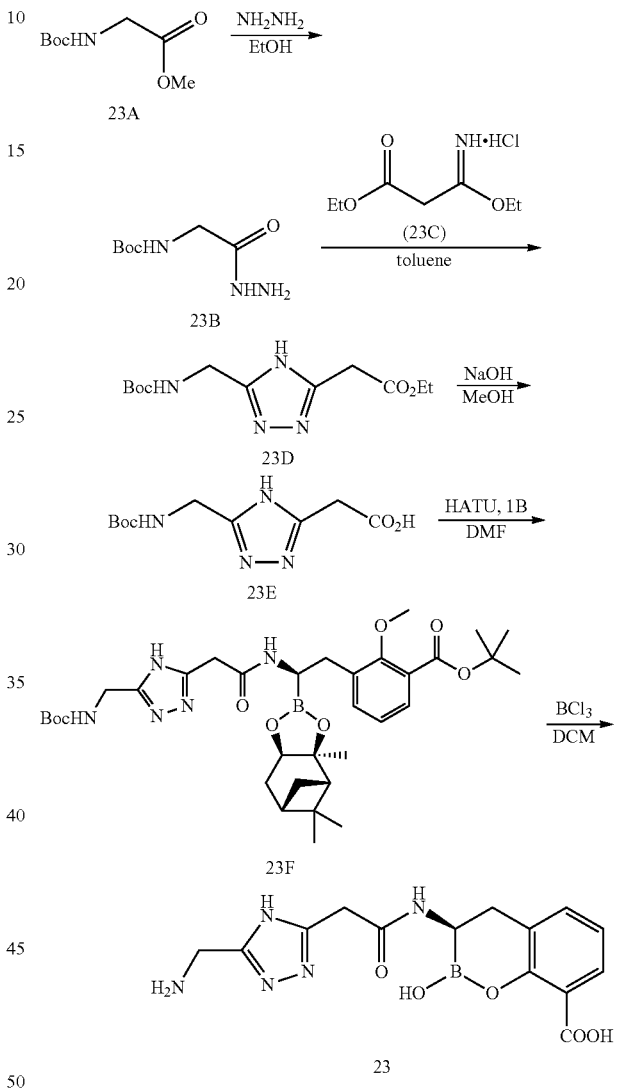

Step 1: Synthesis of tert-Butyl (2-hydrazinyl-2-oxoethyl)carbamate (23B)

Hydrazine hydrate (5 g, 100 mmol) was added to a solution of 23A (4 g, 21 mmol in 50 mL EtOH) at RT. After 30 min, the reaction was heated at 60° C. for 20 hr. The solvent was removed under vacuum at RT, and the residue was dissolved in DCM (100 mL), washed with water (2×15 mL) and concentrated to give 23B as a white solid (3 g).

Step 2: Synthesis of ethyl 2-(5-(((tert-butoxycarbonyl)amino)methyl)-4H-1,2,4-triazol-3-yl)acetate (23D)

DIPEA (0.77 g, 6 mmol) was added to a mixture of 23B (1 g, 5.3 mmol) and 23C (1 g, 5.3 mmol, Combi_Blocks) in 15 mL of toluene at RT. The mixture was heated at 80° C. for 6 hr and 100° C. for 15 hr. The reaction was cooled to RT, diluted with EtOAc (100 mL), and washed with water and brine. The solvent was removed under vacuum, then, titrated with DCM (15 mL). The solid was collected, washed with hexanes and dried to give 23D as white solid (0.6 g, 42%): $^1$H NMR (300 MHz, CDCl$_3$) δ 11.7 (br, 1H, —NH), 5.35 (br, 1H, NHBoc), 4.41 (br, 2H), 4.22-4.24 (m, 2H), 3.86 (s, 2H), 1.44 (s, 9H), 1.29 (br, 3H).

Step 3: Synthesis of 2-(5-(((tert-butoxycarbonyl)amino)methyl)-4H-1,2,4-triazol-3-yl)acetic Acid (23E)

The title compound was prepared from compound 23D following the procedure described in Step 2 of Example 19. ESI-MS m/z 257 (MH)$^+$ Step 4: Synthesis of tert-butyl 3-((R)-2-(2-(5-(((tert-butoxycarbonyl)amino)methyl)-4H-1,2,4-triazol-3-yl)acetamido)-2-((3aS,4S,6S,7aR)-3a,5,5-trimethyl-hexahydro-4,6-methanobenzo[d][1,3,2]dioxaborol-2-yl)ethyl)-2-methoxybenzoate (23F)

The title compound was prepared from 23E following the procedure described in Step 3 of Example 19. ESI-MS m/z 668 (MH)$^+$.

Step 5: Synthesis of (R)-3-(2-(5-(aminomethyl)-4H-1,2,4-triazol-3-yl)acetamido)-2-hydroxy-3,4-dihydro-2H-benzo[e][1,2]oxaborinine-8-carboxylic Acid (23)

The title compound was prepared from 23F and BCl$_3$ following the procedure described in step 4 of Example 1. The crude product was purified by reverse phase chromatography and dried using lyophilization. ESI-MS m/z 346 (MH)$^+$.

Example 24: (R)-3-(2-(2-(guanidinomethyl)thiazol-4-yl)acetamido)-2-hydroxy-3,4-dihydro-2H-benzo[e][1,2]oxaborinine-8-carboxylic Acid

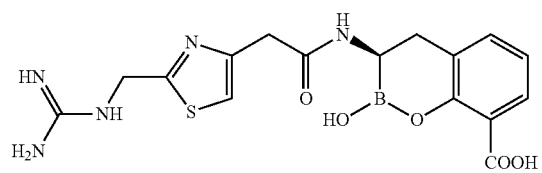 [SMILES: N=C(N)NCc1nc(CC(=O)N[C@H]2Cc3cccc(C(=O)O)c3OB2O)cs1]

Step 1: Synthesis of (R,Z)-3-(2-(2-((2,3-bis(tert-butoxycarbonyl)guanidino)methyl)thiazol-4-yl)acetamido)-2-hydroxy-3,4-dihydro-2H-benzo[e][1,2]oxaborinine-8-carboxylic Acid The title compound was prepared from compound 19 following the procedure described in Step 2 of Example 3.

Step 2: Synthesis of (R)-3-(2-(2-(guanidinomethyl)thiazol-4-yl)acetamido)-2-hydroxy-3,4-dihydro-2H-benzo[e][1,2]oxaborinine-8-carboxylic Acid (24)

The title compound was prepared from (R,Z)-3-(2-(2-((2,3-bis(tert-butoxycarbonyl)guanidino)methyl)thiazol-4-yl)acetamido)-2-hydroxy-3,4-dihydro-2H-benzo[e][1,2]oxaborinine-8-carboxylic acid and BCl$_3$ following the procedure described in Step 4 of Example 1. The crude product was purified by reverse phase chromatography and dried using lyophilization. ESI-MS m/z 404 (MH)$^+$.

Example 25: (R)-3-(2-(3-cyano-1H-1,2,4-triazol-1-yl)acetamido)-2-hydroxy-3,4-dihydro-2H-benzo[e][1,2]oxaborinine-8-carboxylic Acid

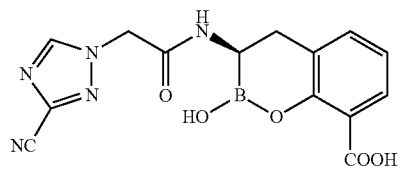 [SMILES: N#Cc1ncn(CC(=O)N[C@H]2Cc3cccc(C(=O)O)c3OB2O)n1]

Step 1: Synthesis of tert-butyl 3-((R)-2-(2-(3-cyano-1H-1,2,4-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate The title compound was prepared from compound 1C and 1H-1,2,4-triazole-5-carbonitrile following the procedure described in Step 1 of Example 18.

Step 2: Synthesis of (R)-3-(2-(3-cyano-1H-1,2,4-triazol-1-yl)acetamido)-2-hydroxy-3,4-dihydro-2H-benzo[e][1,2]oxaborinine-8-carboxylic Acid The title compound was prepared from tert-butyl 3-((R)-2-(2-(3-cyano-1H-1,2,4-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate and BCl$_3$ following the procedure described in step 4 of Example 1. The crude product was purified by reverse phase chromatography and dried using lyophilization. ESI-MS m/z 342 (MH)$^+$.

Example 26: (R)-2-hydroxy-3-(2-(4-((methylamino)methyl)-1H-1,2,3-triazol-1-yl)acetamido)-3,4-dihydro-2H-benzo[e][1,2]oxaborinine-8-carboxylic Acid

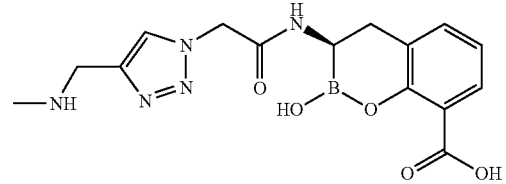 [SMILES: CNCc1cn(CC(=O)N[C@H]2Cc3cccc(C(=O)O)c3OB2O)nn1]

Compound 26 was prepared following similar procedure described in Example 2 (Steps 1 and 2) replacing tert-butyl prop-2-yn-1-ylcarbamate in step 1 with tert-butyl methyl (prop-2-yn-1-yl)carbamate. The title compound was purified by reverse phase chromatography and dried using lyophilization to afford the title product as white solid. ESI-MS m/z 360 (MH)$^+$.

Example 27: (R)-3-(2-(4-((diethylamino)methyl)-1H-1,2,3-triazol-1-yl)acetamido)-2-hydroxy-3,4-dihydro-2H-benzo[e][1,2]oxaborinine-8-carboxylic Acid

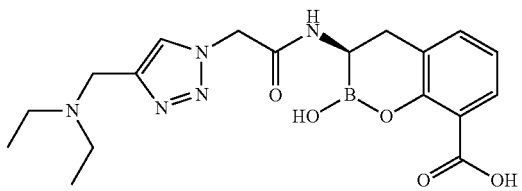 [SMILES: CCN(CC)Cc1cn(CC(=O)N[C@H]2Cc3cccc(C(=O)O)c3OB2O)nn1]

To (R)-3-(2-(4-(aminomethyl)-1H-1,2,3-triazol-1-yl)acetamido)-2-hydroxy-3,4-dihydro-2H-benzo[e][1,2]oxaborinine-8-carboxylic acid (Example 2, 0.035 g, 0.1 mmol)) in MeOH (5 mL) was added acetaldehyde (0.022 g, 0.5 mmol), followed by NaBH(OAc)$_3$ (0.21 g, 1 mmol). The resulting reaction mixture was stirred at RT overnight. Solvent was then removed and the residue was purified by reverse phase chromatography and dried using lyophilization to afford the title product as white solid. ESI-MS m/z 402 (MH)$^+$.

Example 28: (R)-2-hydroxy-3-(2-(4-(thiophen-2-yl)-1H-1,2,3-triazol-1-yl)acetamido)-3,4-dihydro-2H-benzo[e][1,2]oxaborinine-8-carboxylic Acid

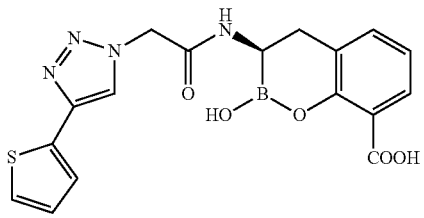 [SMILES: O=C(Cn1cc(-c2cccs2)nn1)N[C@H]1Cc2cccc(C(=O)O)c2OB1O]

Step 1: Synthesis of tert-butyl 2-methoxy-3-((R)-2-(2-(4-(thiophen-2-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate The title compound was prepared from compound 1D and 2-ethynylthiophene following the procedure described in Step 3 of Example 1.

Step 2: Synthesis of (R)-2-hydroxy-3-(2-(4-(thiophen-2-yl)-1H-1,2,3-triazol-1-yl)acetamido)-3,4-dihydro-2H-benzo[e][1,2]oxaborinine-8-carboxylic Acid The title compound was prepared from tert-butyl 2-methoxy-3-((R)-2-(2-(4-(thiophen-2-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate and BCl$_3$ following the procedure described in Step 4 of Example 1. The crude product was purified by reverse phase chromatography and dried using lyophilization. ESI-MS m/z 399 (MH)$^+$.

Example 29: (R)-2-hydroxy-3-(2-(4-(thiophen-3-yl)-1H-1,2,3-triazol-1-yl)acetamido)-3,4-dihydro-2H-benzo[e][1,2]oxaborinine-8-carboxylic Acid

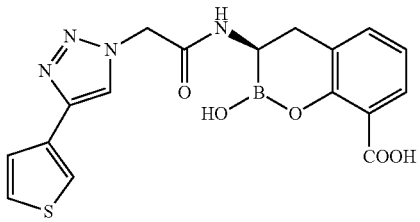 [SMILES: O=C(Cn1cc(-c2ccsc2)nn1)N[C@H]1Cc2cccc(C(=O)O)c2OB1O]

Step 1: Synthesis of tert-butyl 2-methoxy-3-((R)-2-(2-(4-(thiophen-3-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate The title compound was prepared from compound 1D and 3-ethynylthiophene following the procedure described in Step 3 of Example 1.

Step 2: Synthesis of (R)-2-hydroxy-3-(2-(4-(thiophen-3-yl)-1H-1,2,3-triazol-1-yl)acetamido)-3,4-dihydro-2H-benzo[e][1,2]oxaborinine-8-carboxylic Acid The title compound was prepared from tert-butyl 2-methoxy-3-((R)-2-(2-(4-(thiophen-3-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate and BCl$_3$ following the procedure described in Step 4 of Example 1. The crude product was purified by reverse phase chromatography and dried using lyophilization. ESI-MS m/z 399 (MH)$^+$.

Example 30: (R)-3-(3-(4-(aminomethyl)-1H-1,2,3-triazol-1-yl)propanamido)-2-hydroxy-3,4-dihydro-2H-benzo[e][1,2]oxaborinine-8-carboxylic Acid

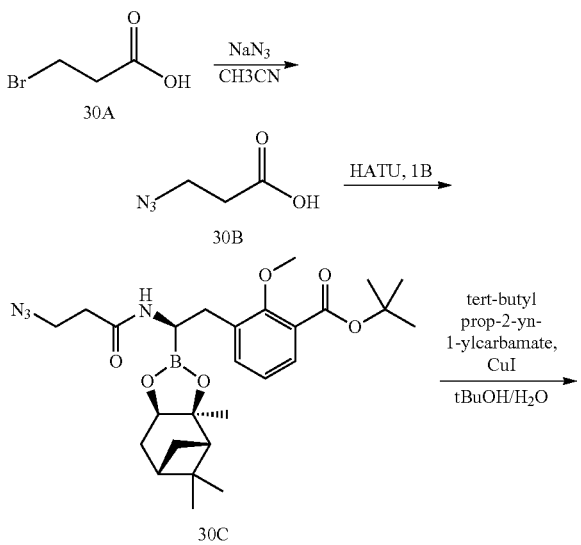

-continued

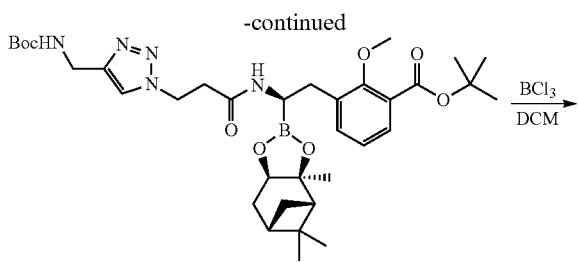

30D

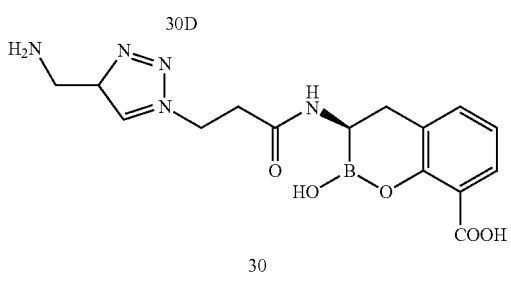

30

Step 1: Synthesis of 3-azidopropanoic Acid (30B)

A mixture of 30A (2 g, 13.2 mmol) and NaN₃ (2 g, 30 mmol) in 10 mL of CH₃CN was heated at 65° C. for 14 hr. After cooled to RT, the solvent was evaporated. The residue was suspended in EtOAc (20 mL), then, washed with 0.2N HCl and brine. The organic layer was concentrated to yield 30B as oil (0.5 g, 30%).

Step 2: Synthesis of tert-butyl 3-((R)-2-(3-azidopropanamido)-2-((3aS,4S,6S,7aR)-3a,5,5-trimethylhexahydro-4,6-methanobenzo[d][1,3,2]dioxaborol-2-yl)ethyl)-2-methoxybenzoate (30C)

The title compounds was prepared from 3B following the procedure described in step 3 of Example 19. ESI-MS m/z 527 (MH)⁺.

Step 3: Synthesis of tert-butyl 3-((R)-2-(3-(4-(((tert-butoxycarbonyl)amino)methyl)-1H-1,2,3-triazol-1-yl)propanamido)-2-((3aS,4S,6S,7aR)-3a,5,5-trimethylhexahydro-4,6-methanobenzo[d][1,3,2]dioxaborol-2-yl)ethyl)-2-methoxybenzoate (30D)

The title compound was prepared from tert-butyl prop-2-yn-1-ylcarbamate and 30C following the procedure described in Step 3 of Example 1.

Step 4: Synthesis of (R)-3-(3-(4-(aminomethyl)-1H-1,2,3-triazol-1-yl)propanamido)-2-hydroxy-3,4-dihydro-2H-benzo[e][1,2]oxaborinine-8-carboxylic Acid (30)

The title compound was prepared from 30D and BCl₃ following the procedure described in step 4 of Example 1. The crude product was purified by reverse phase chromatography and dried using lyophilization. ESI-MS m/z 360 (MH)⁺.

Example 31: (R)-3-(2-(2-(4-(aminomethyl)-1H-1,2,3-triazol-1-yl)acetamido)-2-boronoethyl)-2-methoxybenzoic Acid

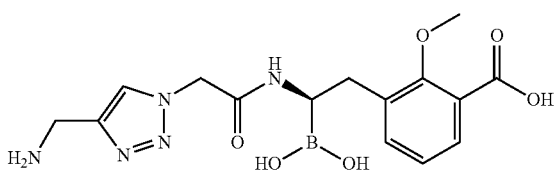 [SMILES: COc1c(C[C@H](NC(=O)Cn2cc(CN)nn2)B(O)O)cccc1C(=O)O]

To tert-butyl 3-((R)-2-(2-(4-(((tert-butoxycarbonyl)amino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (from step 1 in Example 2, 0.1 g) was added HCl (8 mL, 4N in dixoane). The reaction mixture was stirred at RT for 4 hr. Ethyl ether was added. The title compound was isolated from the residue using reverse phase HPLC and dried using lyophilization as white solid. ESI-MS m/z 378 (MH)⁺.

Example 32: (R)-3-(2-(4,5-bis(morpholinomethyl)-1H-1,2,3-triazol-1-yl)acetamido)-2-hydroxy-3,4-dihydro-2H-benzo[e][1,2]oxaborinine-8-carboxylic Acid

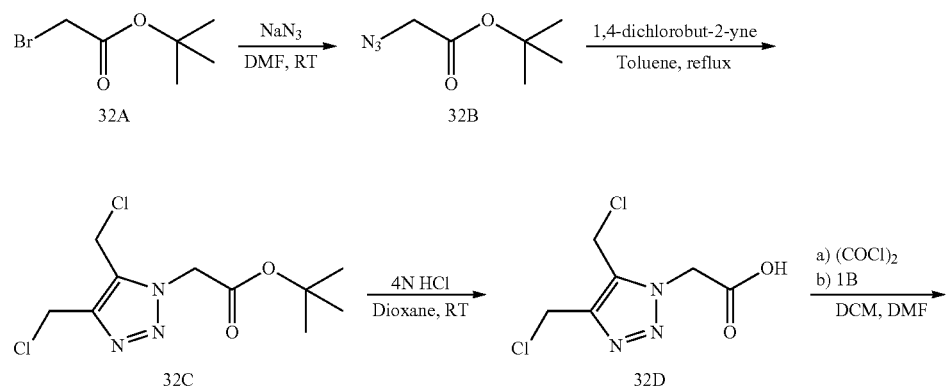

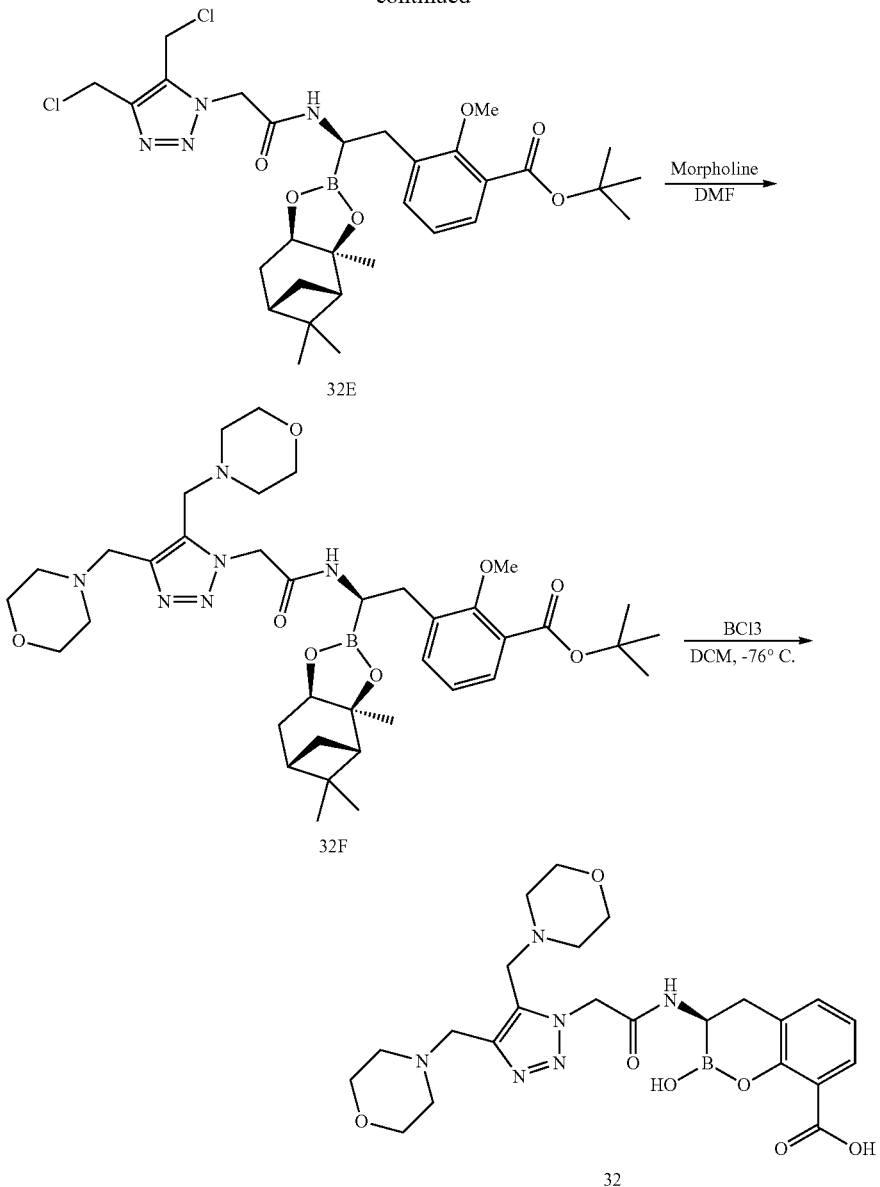

Step 1: Synthesis of tert-butyl 2-azidoacetate (32B)

tert-Butyl 2-bromoacetate (19.5 g, 100 mmol) was added dropwise to a suspension of sodium azide (7.2 g, 111 mmol) in DMF at RT. The reaction mixture was stirred overnight. Water was added and the aqueous phase was extracted with EtOAc. The organic phase was washed with brine, dried over Na$_2$SO$_4$, and concentrated in vacuo to afford the title compound as pale yellow oil (14.0 g)

Step 2: Synthesis of tert-butyl 2-(4,5-bis(chloromethyl)-1H-1,2,3-triazol-1-yl)acetate (32C)

A solution of tert-butyl 2-azidoacetate (0.78 g, 5 mmol) and 1,4-dichlorobut-2-yne (6.1 g, 50 mmol) in toluene (20 mL) was heated at reflux overnight. After removal of the solvent, the residue was purified by flash chromatography to afford the title compound (1.2 g).

Step 3: Synthesis of 2-(4,5-bis(chloromethyl)-1H-1,2,3-triazol-1-yl)acetic Acid (32D)

To tert-butyl 2-(4,5-bis(chloromethyl)-1H-1,2,3-triazol-1-yl)acetate (1.8 g) in a flask was added HCl (18 mL, 4N in dioxane). The resulting reaction mixture was stirred at RT for 1 hr. Ethyl ether was added and the precipitate was collected and dried to afford the title compound as a while solid (1.2 g).

Step 4: Synthesis of tert-butyl 3-((R)-2-(2-(4,5-bis(chloromethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (32E)

To a solution of 2-(4,5-bis(chloromethyl)-1H-1,2,3-triazol-1-yl)acetic acid (0.77 g, 3 mmol) in a DCM (10 mL) and DMF (4 mL) was added oxalyl chloride (0.42 g, 3.3 mmol) at 0° C. The reaction mixture was allowed to warm up to RT for 1 hr. The reaction mixture was cooled at 0° C. again. To this reaction mixture was added intermediate 1B solution (3 mmol in THF) slowly. The reaction mixture was allowed to warm up to RT and stirred for 1 hr. The reaction was quenched with sat. NaHCO$_3$, and extracted with EtOAc. The organic phase was dried over Na$_2$SO$_4$, filtered, and concentrated in vacuo. Flash chromatography on silica gel (EtOAc/Hexane, 10%-80%) afforded the title compound as light yellow foam (1.1 g).

Step 5: Synthesis of tert-butyl 3-((R)-2-(2-(4,5-bis(morpholinomethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (32F)

To tert-butyl 3-((R)-2-(2-(4,5-bis(chloromethyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (1.1 g, 1.7 mmol) in DMF (10 mL) was added morpholine (0.74 g, 8.5 mmol). The reaction mixture was stirred at RT for 3 hr. Water was added and extracted with EtOAc. The organic phase was dried over Na$_2$SO$_4$, filtered, and concentrated in vacuo to afford the title product without further purification. ESI-MS m/z 737 (MH)$^+$.

Step 6: Synthesis of (R)-3-(2-(4,5-bis(morpholinomethyl)-1H-1,2,3-triazol-1-yl)acetamido)-2-hydroxy-3,4-dihydro-2H-benzo[e][1,2]oxaborinine-8-carboxylic Acid (31)

To a solution of compound 32F (0.2 g, 0.27 mmol) in DCM (8 mL) at −76° C. was added BCl$_3$ (2.1 mL, 1 M in DCM) dropwise. The reaction mixture was stirred at same temperature for 20 min and was allowed to warm up to 0° C. Water (3 mL) was added slowly to the reaction mixture. Aqueous residue was purified by reverse phase chromatography (acetonitrile/H$_2$O, 0.1% TFA) and dried using lyophilization to afford the title compound as while solid. ESI-MS m/z 515 (MH)$^+$.

Example 33: (R)-3-(2-(4-(aminomethyl)-1H-1,2,3-triazol-1-yl)-2-methylpropanamido)-2-hydroxy-3,4-dihydro-2H-benzo[e][1,2]oxaborinine-8-carboxylic Acid

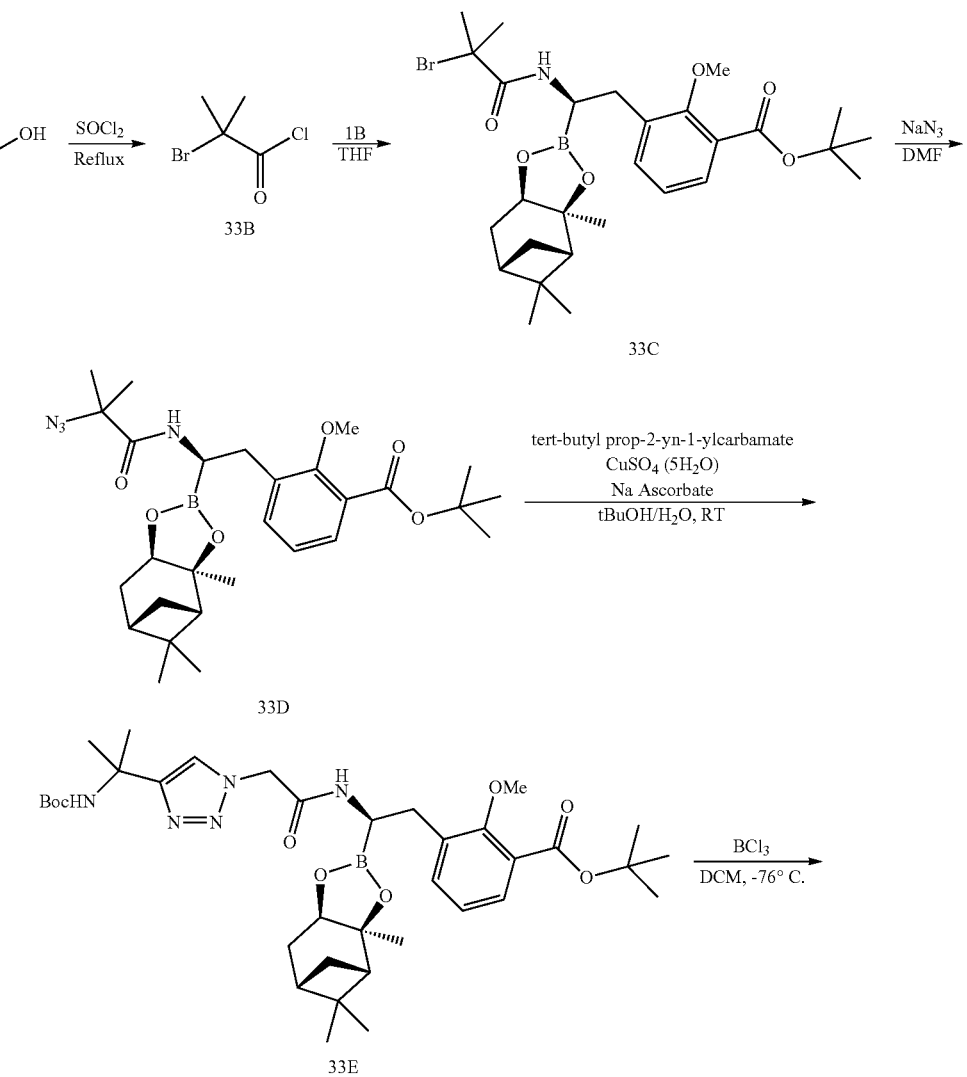

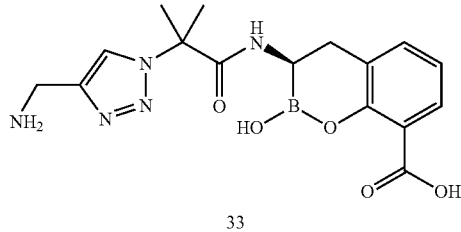

33

Step 1: Synthesis of 2-bromo-2-methylpropanoyl Chloride (33B)

A solution of 2-bromo-2-methylpropanoic acid (1.2 g) in $SOCl_2$ (10 mL) heated under reflux for 3 hr. The solvent was removed in vacuo to afford the product as a clear oil, which was used in the next step without further purification.

Step 2: Synthesis of tert-butyl 3-((R)-2-(2-bromo-2-methylpropanamido)-2-((3aS,4S,6S,7aR)-3a,5,5-trimethylhexahydro-4,6-methanobenzo[d][1,3,2]dioxaborol-2-yl)ethyl)-2-methoxybenzoate (33C)

To a solution of 2-bromo-2-methylpropanoyl chloride (0.250 g, 1.4 mmol) in DCM (10 mL) at 0° C. was added intermediate 1B solution (1.5 mmol in THF) slowly. The reaction mixture was allowed to warm up to RT and stirred for 1 hr. The reaction was quenched with sat. $NaHCO_3$ and extracted with EtOAc. The organic phase was dried over $Na_2SO_4$, filtered, and concentrated in vacuo to afford the title product, which was carried on to the next step.

Step 3: Synthesis of tert-butyl 3-((R)-2-(2-azido-2-methylpropanamido)-2-((3aS,4S,6S,7aR)-3a,5,5-trimethylhexahydro-4,6-methanobenzo[d][1,3,2]dioxaborol-2-yl)ethyl)-2-methoxybenzoate (33D)

To tert-butyl 3-((R)-2-(2-bromo-2-methylpropanamido)-2-((3aS,4S,6S,7aR)-3a,5,5-trimethylhexahydro-4,6-methanobenzo[d][1,3,2]dioxaborol-2-yl)ethyl)-2-methoxybenzoate from Step 2 in DMSO (5 mL) was added sodium azide (0.33 g, 4.5 mmol). The reaction mixture was stirred at RT overnight. Water was added and the aqueous phase was extracted with EtOAc. The organic phase was washed with brine, dried over $Na_2SO_4$, and concentrated in vacuo. The crude product was purified with flash chromatography on silica gel (EtOAc/Hexane, 10%-80%) afforded the title compound as yellow foam (0.25 g).

Step 4: Synthesis of tert-butyl 3-((R)-2-(2-(4-(2-((tert-butoxycarbonyl)amino)propan-2-yl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (33E)

To a mixture of tert-butyl 3-((R)-2-(2-azido-2-methylpropanamido)-2-((3aS,4S,6S,7aR)-3a,5,5-trimethylhexahydro-4,6-methanobenzo[d][1,3,2]dioxaborol-2-yl)ethyl)-2-methoxybenzoate (0.25 g, 0.46 mmol) and tert-butyl prop-2-yn-1-ylcarbamate (0.16 g, 1.0 mmol) in tBuOH (5 mL) and $H_2O$ (5 mL) was added $CuSO_4.5H_2O$ (0.025 g, 0.10 mmol) and Na Ascorbate (0.040 g, 0.20 mmol). The resulting reaction mixture was stirred at RT overnight. EtOAc was added and washed with brine, dried over $Na_2SO_4$, filtered and concentrated in vacuo. The crude product was purified with flash chromatography on silica gel (EtOAc/Hexane, 10%-80%) afforded the title compound as yellow foam (0.20 g). ESI-MS m/z 696 (MH)⁺.

Step 5: Synthesis of (R)-3-(2-(4-(aminomethyl)-1H-1,2,3-triazol-1-yl)-2-methylpropanamido)-2-hydroxy-3,4-dihydro-2H-benzo[e][1,2]oxaborinine-8-carboxylic Acid (33)

To a solution of compound 33E (0.1 g, 0.14 mmol) in DCM (8 mL) at −76° C. was added $BCl_3$ (1.0 mL, 1 M in DCM) dropwise. The reaction mixture was stirred at same temperature for 20 min and was allowed to warm up to 0° C. Water (3 mL) was added slowly to the reaction mixture. The aqueous residue was purified by reverse phase chromatography (acetonitrile/$H_2O$, 0.1% TFA) and dried using lyophilization to afford the title compound as while solid. ESI-MS m/z 374 (MH)⁺.

Example 34: (R)-3-(2-(4-((2-aminoethoxy)methyl)-1H-1,2,3-triazol-1-yl)acetamido)-2-hydroxy-3,4-dihydro-2H-benzo[e][1,2]oxaborinine-8-carboxylic Acid

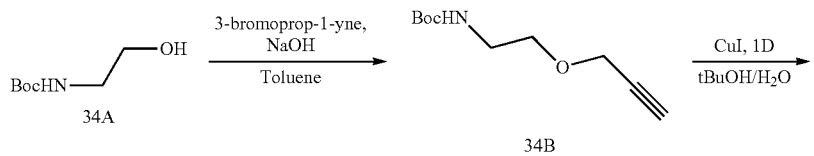

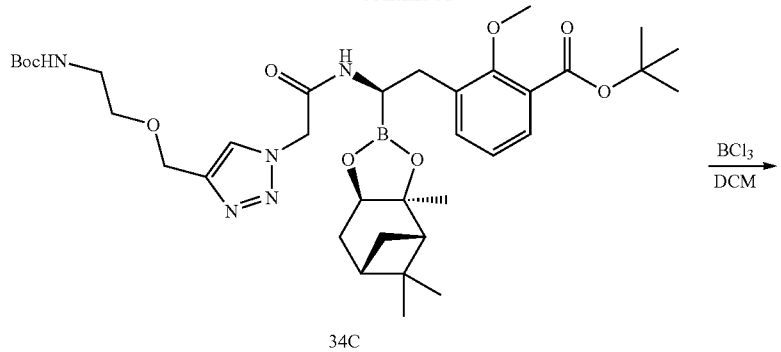

34C

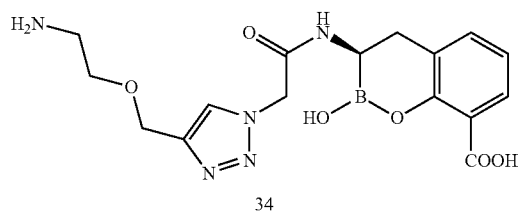

34

Step 1: Synthesis of tert-butyl (2-(prop-2-yn-1-yloxy)ethyl)carbamate (34B)

NaOH (1.5 g in 2 mL water, 60 mmol) was added to a solution of 34A (2 g, 12.4 mmol), 3-bromoprop-1-yne (2.2 g, 14.8 mmol) and TEBAC (0.2 g, 0.88 mmol) in 10 mL of toluene at RT. The mixture was stirred at RT for 24 hr. The organic layer was separated, washed with brine, concentrated and purified by flash chromatography (EtOAc/Hexanes 10% to 100%) to give 34B as colorless oil (2.0 g).

Step 2: Synthesis of tert-butyl 3-((R)-2-(2-(4-((2-((tert-butoxycarbonyl)amino)ethoxy)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (34C)

The title compound was prepared from compound 1D and 34B following the procedure described in Step 3 of Example 1.

Step 3: Synthesis of (R)-3-(2-(4-((2-aminoethoxy)methyl)-1H-1,2,3-triazol-1-yl)acetamido)-2-hydroxy-3,4-dihydro-2H-benzo[e][1,2]oxaborinine-8-carboxylic Acid (34)

The title compound was prepared from 34C and BCl₃ following the procedure described in Step 4 of Example 1. The crude product was purified by reverse phase chromatography and dried using lyophilization. ESI-MS m/z 390 (MH)⁺.

Example 35: (R)-3-(2-(3-carbamoyl-1H-1,2,4-triazol-1-yl)acetamido)-2-hydroxy-3,4-dihydro-2H-benzo[e][1,2]oxaborinine-8-carboxylic Acid

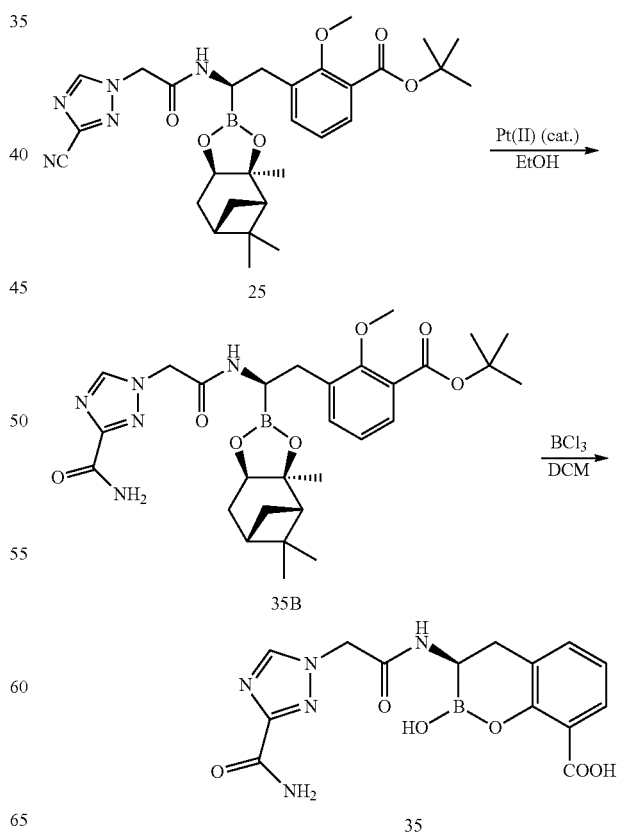

Step 1: Synthesis of tert-butyl 3-((R)-2-(2-(3-carbamoyl-1H-1,2,4-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (35B)

A mixture of 25 (50 mg, 0.09 mmol) and hydrido(dimethylphosphinous acid-kP)[hydrogen bis(dimethylphosphinito-kP)]platinum (II) (10 mg, 0.02 mmol) in 3 mL of water/EtOH (1:2) was flushed with argon, then, heated at 80° C. for 4 hr. After cooling to RT, the solvent was removed under vacuum, then, dried using lyophilization to give 35B as white solid. ESI-MS m/z 604 (MNa)+.

Step 2: Synthesis of (R)-3-(2-(3-carbamoyl-1H-1,2,4-triazol-1-yl)acetamido)-2-hydroxy-3,4-dihydro-2H-benzo[e][1,2]oxaborinine-8-carboxylic Acid (35)

The title compound was prepared from 35B and BCl₃ following the procedure described in Step 4 of Example 1. The crude product was purified by reverse phase chromatography and dried using lyophilization. ESI-MS m/z 360 (MH)+.

Example 36: (R)-3-(2-(4-(3-amino-1H-indazol-5-yl)-1H-1,2,3-triazol-1-yl)acetamido)-2-hydroxy-3,4-dihydro-2H-benzo[e][1,2]oxaborinine-8-carboxylic Acid

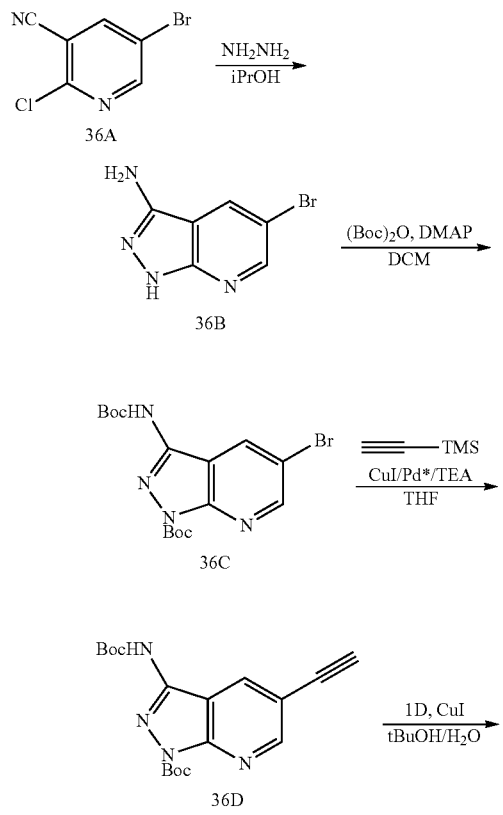

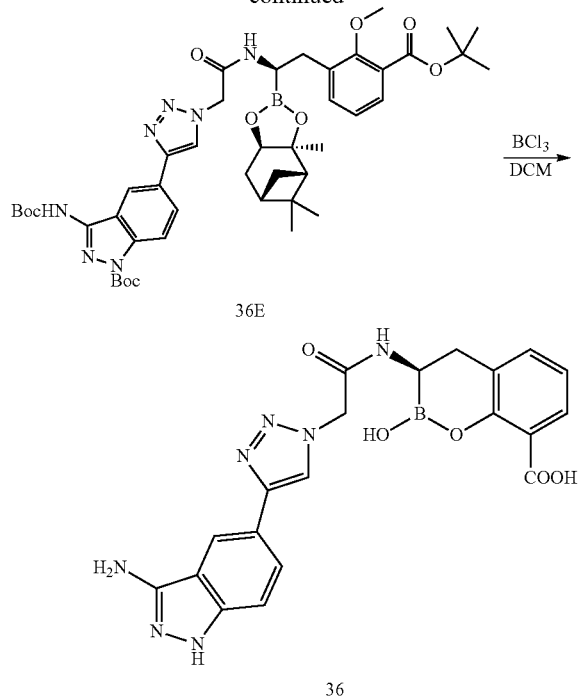

Step 1: Synthesis of 5-bromo-1H-pyrazolo[3,4-b]pyridin-3-amine (36B)

Hydrazine hydrate (4 ml) was added to a stirred solution of 5-bromo-2-chloronicotinonitrile (36A, 2 g) in i-PrOH (30 ml). The reaction mixture was stirred at 75° C. for 24 h. After cooling to RT, the solvent was removed under vacuum. The residue was washed with water (10 mL). The resulting solid was collected, washed with water, and dried to give 36B as yellow solid (1.8 g). ESI-MS m/z 212/214 (MH)+.

Step 2: Synthesis of tert-butyl 5-bromo-3-((tert-butoxycarbonyl)amino)-1H-pyrazolo[3,4-b]pyridine-1-carboxylate (36C)

(Boc)₂O (1.05 g, 4.8 mmol) was added to a solution of 36B (0.5 g, 2.4 mmol), TEA (0.5 g, 5 mmol) and DMAP (0.12 g, 1 mmol) in 20 mL of DCM at 0° C. The mixture was warmed to RT for 24 hr. The solvent was removed under vacuum, and the product was purified by flash chromatography (EtOAc/Hexane 2/5) to give 36C as colorless oil (0.7 g). ESI-MS m/z 413 & 415 (MH)+.

Step 3: Synthesis of tert-butyl 3-((tert-butoxycarbonyl)amino)-5-ethynyl-1H-pyrazolo[3,4-b]pyridine-1-carboxylate (36D)

A mixture of 36C (0.7 g, 1.7 mmol), Pd(PPh₃)₄ (0.14 g, 0.11 mmol) and CuI (40 mg, 0.2 mmol) in 10 mL of THF was flushed with argon, then, triethylamine (2 g, 20 mmol) and ethynyltrimethylsilane (0.4 g, 4.0 mmol) are added. The reaction mixture is stirred at 85° C. for 4 hr. The solvent was removed under vacuum at RT. The residues were dissolved in MeOH (20 mL) and treated with K₂CO₃ (0.2 g) at 60° C. for 24 hr. After cooling to RT, the reaction mixture was concentrated and purified by flash chromatography column to give 36D (0.3 g) as yellow solid: ¹H NMR (300 MHz, CDCl₃) δ 11.8 (s, 1H), 8.71 (s, 1H), 8.09 (s, 1H), 3.19 (s, 1H), 1.42-1.5 (m, 18H).

Step 4: Synthesis of tert-butyl 5-(1-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-2-oxoethyl)-1H-1,2,3-triazol-4-yl)-3-((tert-butoxycarbonyl)amino)-1H-indazole-1-carboxylate (36E)

The title compound was prepared from compound 1D and 36D following the procedure described in step 3 of Example 1. ESI-MS m/z 871 (MH)⁺.

Step 5: Synthesis of (R)-3-(2-(4-(3-amino-1H-indazol-5-yl)-1H-1,2,3-triazol-1-yl)acetamido)-2-hydroxy-3,4-dihydro-2H-benzo[e][1,2]oxaborinine-8-carboxylic Acid (36)

The title compound was prepared from 36D and BCl₃ following the procedure described in Step 4 of Example 1. The crude product was purified by reverse phase chromatography and dried using lyophilization. ESI-MS m/z 449 (MH)⁺.

Example 37: (R)-3-(2-(4-((2-aminoethyl)carbamoyl)-1H-1,2,3-triazol-1-yl)acetamido)-2-hydroxy-3,4-dihydro-2H-benzo[e][1,2]oxaborinine-8-carboxylic Acid

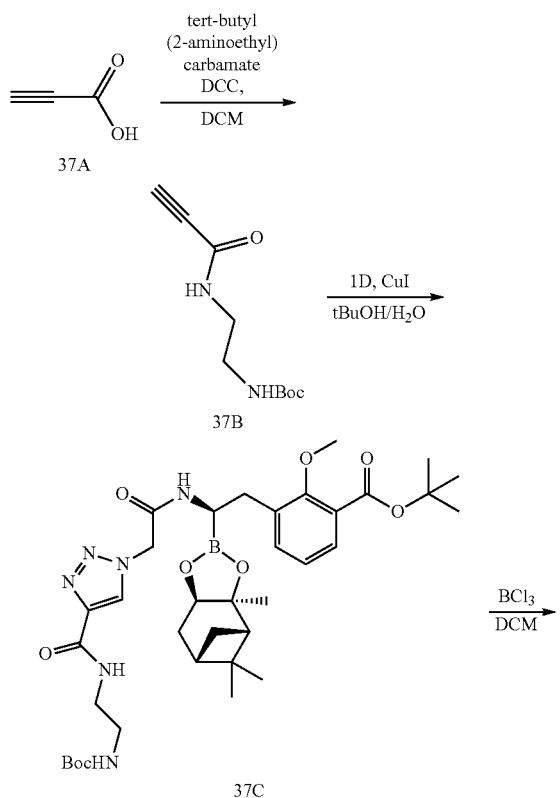

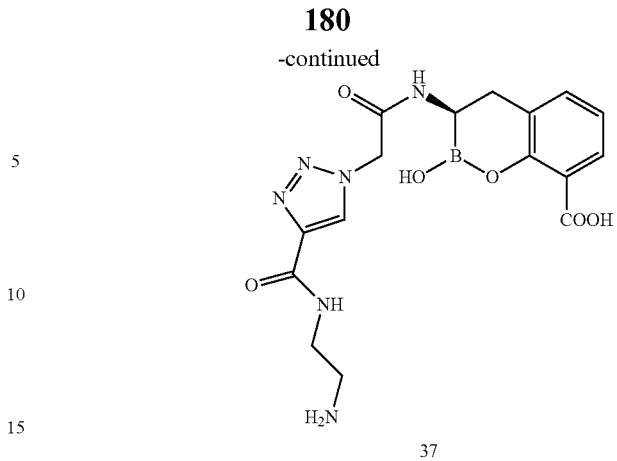

Step 1: Synthesis of tert-butyl (2-propiolamidoethyl) carbamate (37B)

Propynoic acid (1 g, 14.3 mmol) was added at 0° C. to a stirred solution of DCC (3.2 g, 15.7 mmol) in 100 mL of dichloromethane over 30 min. After 10 min, tert-butyl (2-aminoethyl)carbamate (2.4 g, 15 mmol, in 20 mL of DCM) was added over 1 hr. The reaction mixture stirred at 0° C. for 3 hr. The solid was filtered, the solvent was removed under vacuum and the residue was purified by flash chromatography (hexanes/AcOEt 2:1) to give 37B as yellow solid (1 g, 30%). ¹H NMR (300 MHz, CDCl3) δ 6.8 (br, 1H), 4.9 (br, 1H), 3.39-3.43 (m, 2H), 3.27-3.31 (m, 2H), 2.75-2.78 (m, 1H), 1.44 (s, 9H).

Step 2: tert-Butyl 3-((R)-2-(2-(4-((2-((tert-butoxycarbonyl)amino)ethyl)carbamoyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (37C)

The title compound was prepared from compound 1D and 37B following the procedure described in step 3 of Example 1. ESI-MS m/z 747 (MH)⁺.

Step 3: Synthesis of (R)-3-(2-(4-((2-aminoethyl)carbamoyl)-1H-1,2,3-triazol-1-yl)acetamido)-2-hydroxy-3,4-dihydro-2H-benzo[e][1,2]oxaborinine-8-carboxylic Acid (37)

The title compound was prepared from 37C and BCl₃ following the procedure described in step 4 of Example 1. The crude product was purified by reverse phase chromatography and dried using lyophilization. ESI-MS m/z 403 (MH)⁺.

Example 38: (R)-3-(2-(4,5-bis((dimethylamino)methyl)-1H-1,2,3-triazol-1-yl)acetamido)-2-hydroxy-3,4-dihydro-2H-benzo[e][1,2]oxaborinine-8-carboxylic Acid Compound 38 was prepared following a similar procedure as described in Example 31 replacing morpholine in Step 5 with dimethyl amine. The title compound was purified by reverse phase chromatography and dried using lyophilization to afford the title product as white solid. ESI-MS m/z 431 (MH)+.

Example 39: (R)-3-(2-(4-(guanidinomethyl)-1H-1,2,3-triazol-1-yl)-2-methylpropanamido)-2-hydroxy-3,4-dihydro-2H-benzo[e][1,2]oxaborinine-8-carboxylic Acid

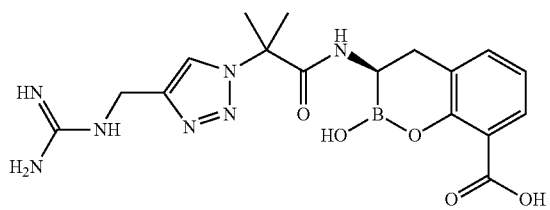 [SMILES: CC(C)(C(=O)N[C@H]1Cc2cccc(C(=O)O)c2OB1O)n1cc(CNC(=N)N)nn1]

Compound 39 was prepared following a similar procedure as described in Example 3, Steps 1 to 3. The title compound was purified by reverse phase chromatography and dried using lyophilization to afford the title product as white solid. ESI-MS m/z 416 (MH)+.

Example 40: (R)-3-(2-(1H-tetrazol-5-yl)acetamido)-2-hydroxy-3,4-dihydro-2H-benzo[e][1,2]oxaborinine-8-carboxylic Acid

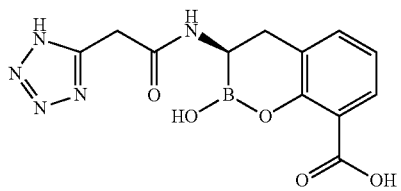 [SMILES: O=C(Cc1nnn[nH]1)N[C@H]1Cc2cccc(C(=O)O)c2OB1O]

Compound 40 was prepared following a similar procedure (Step 2 to Step 3) as described in Example 20 using 2-(1H-tetrazol-5-yl)acetic acid instead of 20B. The title compound was purified by reverse phase chromatography and dried using lyophilization to afford the title product as white solid. ESI-MS m/z 318 (MH)+.

Example 41: (R)-3-(2-(1-(2-aminoethyl)-1H-tetrazol-5-yl)acetamido)-2-hydroxy-3,4-dihydro-2H-benzo[e][1,2]oxaborinine-8-carboxylic Acid

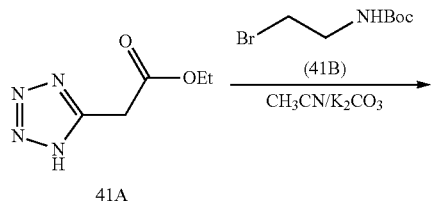

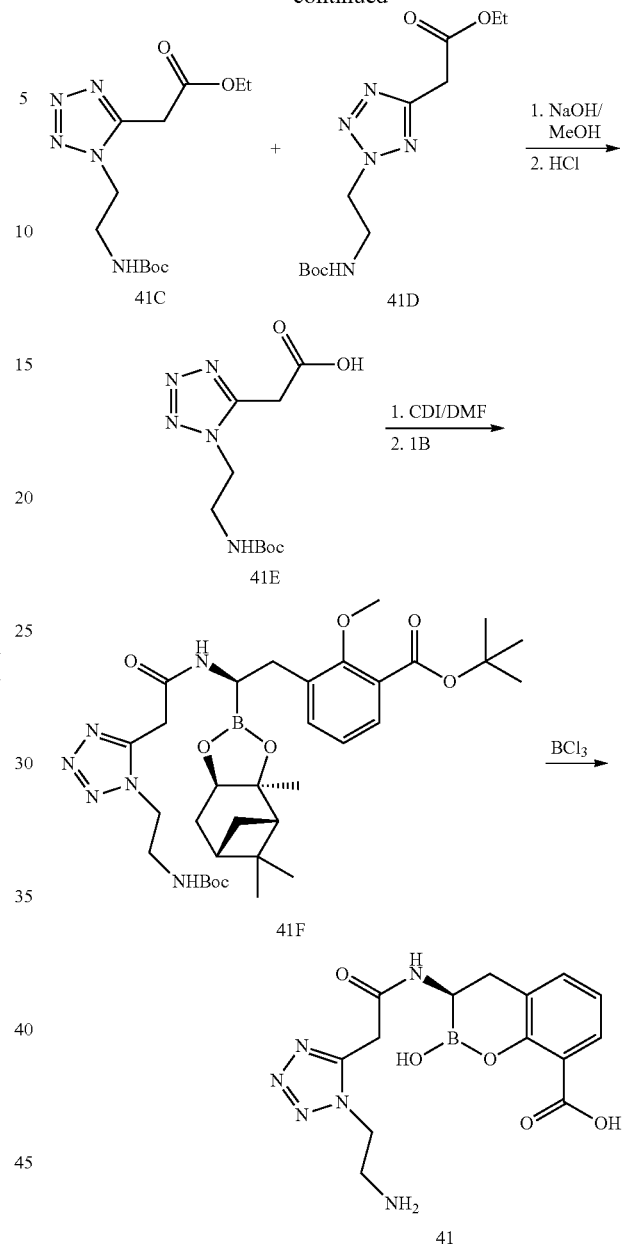

Step 1: Synthesis of ethyl 2-(1-(2-((tert-butoxycarbonyl)amino)ethyl)-1H-tetrazol-5-yl)acetate (41C)

A mixture of 41A (0.7 g, 4.5 mmol), 41B (1 g, 4.5 mmol) and $K_2CO_3$ (1.5 g, 11 mmol) in 20 mL of $CH_3CN$ was stirred at 40° C. for 2 days. After cooling to rt, the reaction mixture was quenched with water (20 mL), and extracted with EtOAc (150 mL). The organic layer was washed with brine, concentrated and purified by flash chromatograph on a silica gel column (EtOAc/Hexane 0~100%) to give 41C as white solid (0.4 g) and 41D as colorless oil (~0.8 g). 41C: ESI-MS m/z 300 (MH)+; $^1$H NMR (300 MHz, $CDCl_3$) 4.92 (br, 1H), 4.47 (t, 2H, J=6.0 Hz), 4.21 (q, 2H, J=6.9 Hz), 4.02 (s, 2H), 3.64-3.69 (m, 2H), 1.42 (s, 9H), 1.28 (t, 3H, J=6.0 Hz). 41D: ESI-MS m/z 300 (MH)+; $^1$H NMR (300 MHz, CDCl3) 4.95

(br, 1H, —NH), 4.70 (t, 2H, J=6.0 Hz), 4.19 (q, 2H, J=6.9 Hz), 3.95 (s, 2H), 3.69-3.72 (m, 2H), 1.40 (s, 9H), 1.27 (t, 3H, J=7.2 Hz).

Step 2: Synthesis of 2-(1-(2-((tert-butoxycarbonyl)amino)ethyl)-1H-tetrazol-5-yl)acetic Acid (41E)

NaOH (2 N in water, 1 mL) was added to a solution of 41C (0.2 g) in MeOH (4 mL) at 0° C. After 4 hr at 0° C., the mixture was warmed to RT for 4 hr. The reaction mixture was concentrated under vacuum at RT to remove most of MeOH, then added 4 mL of water/CH$_3$CN (1/1) and cooled with ice-water, neutralized with HCl (0.5 N) to pH ~2. The mixture was lyophilized to give crude 41E as white solid. ESI-MS m/z 272 (MH)$^+$.

Step 3: Synthesis of tert-butyl 3-((R)-2-(2-(1-(2-((tert-butoxycarbonyl)amino)ethyl)-1H-tetrazol-5-yl)acetamido)-2-((3aS,4S,6S,7aR)-3a,5,5-trimethyl-hexahydro-4,6-methanobenzo[d][1,3,2]dioxaborol-2-yl)ethyl)-2-methoxybenzoate (41F)

1,1'-Carbonyldiimidazole (CDI, 0.15 g, 0.9 mmol) was added to a solution of 41E (0.25 g, 0.92 mmol) in 4 mL of DMF at rt. The reaction mixture was stirred under argon for 1 hr at rt and 1 hr at 40° C. Then, added a solution of 1B (1.0 mmol in THF) at rt, and the mixture was stirred at rt for 20 hrs. The reaction was quenched with water (10 mL), and extracted with EtOAc (20 mL). The organic layer was washed with HCl (0.2 N aqu. 4 mL) and brine. The solvent was removed under vacuum, and the residue was purified by flash chromatograph (silica gel column, EtOAc/Hexane 0~100%) to give 41F as brown solid (0.25 g); ESI-MS m/z 683 (MH)$^+$.

Step 4: Synthesis of (R)-3-(2-(1-(2-aminoethyl)-1H-tetrazol-5-yl)acetamido)-2-hydroxy-3,4-dihydro-2H-benzo[e][1,2]oxaborinine-8-carboxylic Acid (41)

Compound 41 was prepared from 41F and BCl$_3$ following the procedure described in step 4 of Example 1. The crude product was purified by reverse phase chromatography and dried using lyophilization. ESI-MS m/z 361 (MH)$^+$.

Example 42: (R)-3-(2-(2-(2-aminoethyl)-2H-tetrazol-5-yl)acetamido)-2-hydroxy-3,4-dihydro-2H-benzo[e][1,2]oxaborinine-8-carboxylic Acid

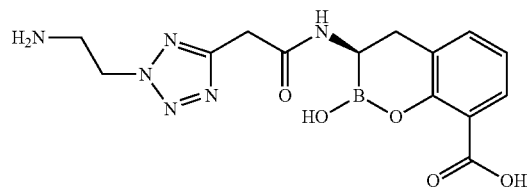 [SMILES: NCCn1nnc(CC(=O)N[C@H]2Cc3cccc(C(=O)O)c3OB2O)n1]

Compound 42 was prepared following the procedure (Step 2 to Step 4) described in Example 41 using compound 41D instead of 41C. The crude product was purified by reverse phase chromatography and dried using lyophilization to afford the title product as white solid. ESI-MS m/z 361 (MH)$^+$.

Example 43 and 44: (R)-2-hydroxy-3-(2-(1-(2-oxo-2-(((S)-pyrrolidin-3-yl)amino)ethyl)-1H-tetrazol-5-yl)acetamido)-3,4-dihydro-2H-benzo[e][1,2]oxaborinine-8-carboxylic Acid (43) and (R)-2-hydroxy-34 (2-oxo-2-(2-(2-oxo-2-(((S)-pyrrolidin-3-yl)amino)ethyl)-2H-tetrazol-5-yl)ethyl)amino)-3,4-dihydro-2H-benzo[e][1,2]oxaborinine-8-carboxylic Acid (44)

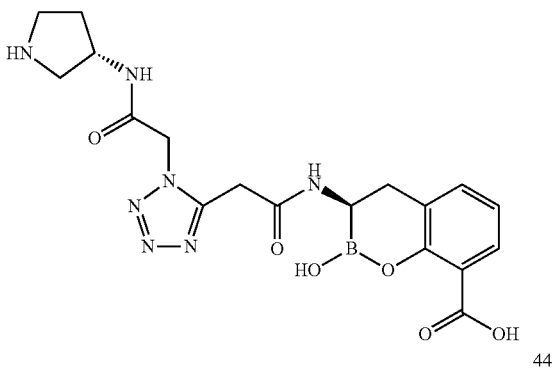

Step 1: Synthesis of compounds tert-butyl (S)-3-(2-chloroacetamido)pyrrolidine-1-carboxylate (43C)

43B (0.7 g) was added to a solution of 43A (1 g, 5.4 mmol) and TEA (1 g) in 20 mL of DCM at 0° C. The mixture was warmed to rt for 20 hr, then, quenched with water. The organic layer was concentrated and purified by flash chromatograph (silica gel column, EtOAc/Hexane 0~100%) to give 43C as white solid (1.0 g): $^1$H NMR (300 MHz, CDCl$_3$) δ 6.52 (br, 1H), 4.43-4.49 (m, 1H), 4.04 (s, 2H), 3.62-3.68 (m, 1H), 3.62-3.68 (m, 1H), 3.44 (br, 2H), 3.21 (br, 1H).2.15-2.22 (m, 1H), 1.88 (br, 1H), 1.46 (s, 9H).

Step 2: Synthesis of tert-butyl (S)-3-(2-(5-(2-ethoxy-2-oxoethyl)-1H-tetrazol-1-yl)acetamido)pyrrolidine-1-carboxylate (43E) and tert-butyl (S)-3-(2-(5-(2-ethoxy-2-oxoethyl)-2H-tetrazol-2-yl)acetamido)pyrrolidine-1-carboxylate (43F)

Compounds 43E and 43F were prepared following the procedure for compounds 41C and 41D, using 43C instead of 41B. ESI-MS m/z 405 (MH)$^+$ (LC/MS RT 4.747 min and 4.688 min).

Step 3: Synthesis of (R)-2-hydroxy-3-(2-(1-(2-oxo-2-(((S)-pyrrolidin-3-yl)amino)ethyl)-1H-tetrazol-5-yl)acetamido)-3,4-dihydro-2H-benzo[e][1,2]oxaborinine-8-carboxylic acid (43) and (R)-2-hydroxy-3-((2-oxo-2-(2-(2-oxo-2-(((S)-pyrrolidin-3-yl)amino)ethyl)-2H-tetrazol-5-yl)ethyl)amino)-3,4-dihydro-2H-benzo[e][1,2]oxaborinine-8-carboxylic Acid (44)

Compounds 43 and 44 were prepared following the similar procedure (step 2 to step 4) described in Example 41 using compound 43E and 43F instead of 41C. The title compound was purified by reverse phase chromatography and dried using lyophilization to afford the title product as white solid. ESI-MS m/z 444 (MH)$^+$ (LC/MS RT 2.804 min. and 2.825 min.).

Example 45 and 46: (R)-3-(2-(1-((2-aminothiazol-4-yl)methyl)-1H-tetrazol-5-yl)acetamido)-2-hydroxy-3,4-dihydro-2H-benzo[e][1,2]oxaborinine-8-carboxylic acid (45) and (R)-3-(2-(24(2-aminothiazol-4-yl)methyl)-2H-tetrazol-5-yl)acetamido)-2-hydroxy-3,4-dihydro-2H-benzo[e][1,2]oxaborinine-8-carboxylic Acid (46)

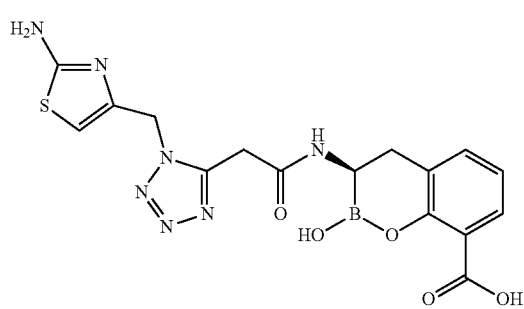

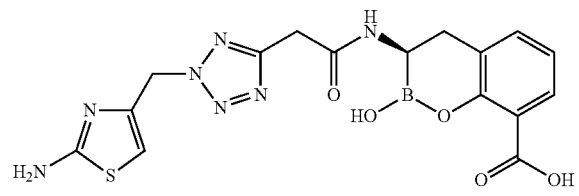

Compounds 45 and 46 were prepared following the procedure (Step 1 to Step 4) described in Example 41 using 4-(chloromethyl)thiazol-2-amine hydrochloride instead of 41B. The title compound was purified by reverse phase chromatography and dried using lyophilization (as a white solid mixture): ESI-MS m/z 430 (MH)$^+$.

Example 47: (R)-3-(2-(1-(2-guanidinoethyl)-1H-tetrazol-5-yl)acetamido)-2-hydroxy-3,4-dihydro-2H-benzo[e][1,2]oxaborinine-8-carboxylic Acid

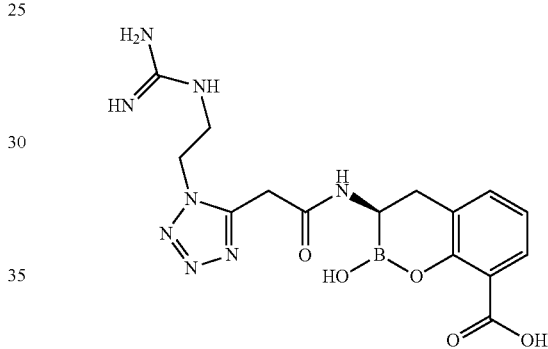

Compound 47 was prepared following a similar procedure as described in Example 3 (Steps 1 to 3) replacing compound 3A using compound 41F. The crude product was purified by reverse phase chromatography and dried using lyophilization to afford the title compound as white solid. ESI-MS m/z 403 (MH)$^+$.

Example 48: (R)-3-(2-(2-(2-guanidinoethyl)-2H-tetrazol-5-yl)acetamido)-2-hydroxy-3,4-dihydro-2H-benzo[e][1,2]oxaborinine-8-carboxylic Acid

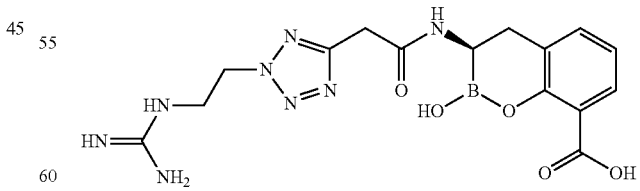

Compound 48 was prepared following a similar procedure as described in Example 47. The crude product was purified by reverse phase chromatography and dried using lyophilization to afford the title compound as white solid. ESI-MS m/z 403 (MH)$^+$.

Example 49: (R)-3-(2-(1-(2-(dimethylamino)ethyl)-1H-tetrazol-5-yl)acetamido)-2-hydroxy-3,4-dihydro-2H-benzo[e][1,2]oxaborinine-8-carboxylic Acid

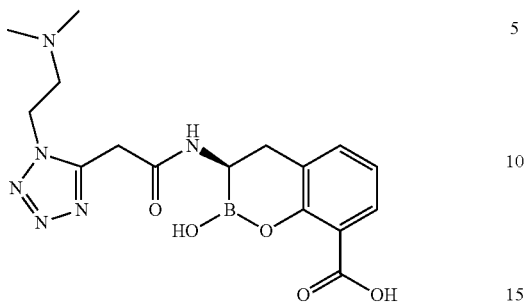

To a solution of (R)-3-(2-(1-(2-aminoethyl)-1H-tetrazol-5-yl)acetamido)-2-hydroxy-3,4-dihydro-2H-benzo[e][1,2]oxaborinine-8-carboxylic acid (Example 41, 0.020 g) in MeOH (5 mL) was added formaldehyde solution (37% in water, 0.1 mL) and Pd on Carbon (50 mg). The resulting reaction mixture was stirred at RT under hydrogen atmosphere (balloon) overnight. The catalyst was filtered and the solvent removed under reduced pressure. The crude product was purified by reverse phase HPLC to afford the title compound as white solid. ESI-MS m/z 389 (MH)+.

Example 50: (R)-3-(2-(1-(3-aminopropyl)-1H-tetrazol-5-yl)acetamido)-2-hydroxy-3,4-dihydro-2H-benzo[e][1,2]oxaborinine-8-carboxylic Acid

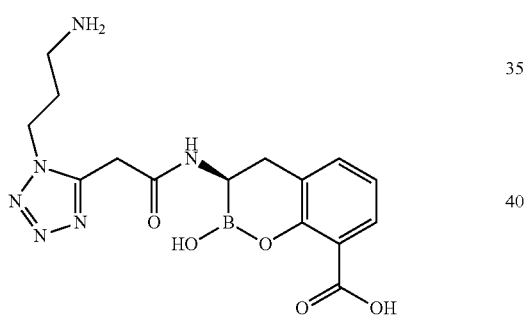

Compound 50 was prepared following a similar procedure as described in Example 41 (step 1 to 4) replacing 41B in step 1 with tert-butyl (3-bromopropyl)carbamate. The final product was purified by reverse phase chromatography and dried using lyophilization to afford the title compound as white solid. ESI-MS m/z 375 (MH)+.

Example 51: (3R)-3-(2-(2-(3-aminopropyl)tetrazolidin-5-yl)acetamido)-2-hydroxy-3,4-dihydro-2H-benzo[e][1,2]oxaborinine-8-carboxylic Acid

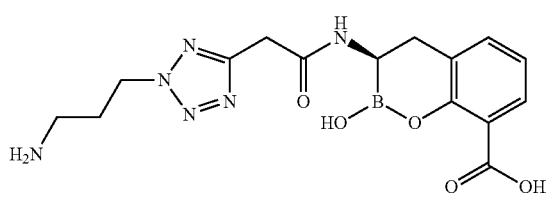 [SMILES: NCCCn1nnc(CC(=O)N[C@H]2Cc3cccc(C(=O)O)c3OB2O)n1]

Compound 51 was prepared following a similar procedure as described in Example 42. The final product was purified by reverse phase chromatography and dried using lyophilization to afford the title compound as white solid. ESI-MS m/z 375 (MH)+.

Example 52: (R)-2-hydroxy-3-(2-(1-(2-(isopropylamino)ethyl)-1H-tetrazol-5-yl)acetamido)-3,4-dihydro-2H-benzo[e][1,2]oxaborinine-8-carboxylic Acid

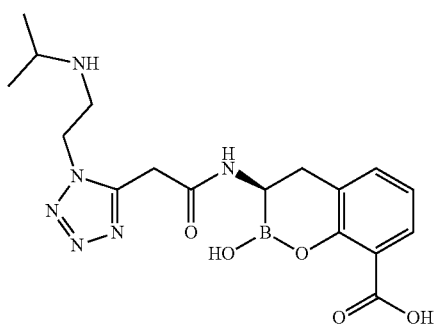 [SMILES: CC(C)NCCn1nnnc1CC(=O)N[C@H]1Cc2cccc(C(=O)O)c2OB1O]

Compound 52 was prepared from compound 41 following a similar procedure as described in Example 4. The crude product was purified by reverse phase chromatography and dried using lyophilization to afford the title compound as white solid. ESI-MS m/z 403 (MH)+.

Example 53: (R)-3-(2-(1-(3-guanidinopropyl)-1H-tetrazol-5-yl)acetamido)-2-hydroxy-3,4-dihydro-2H-benzo[e][1,2]oxaborinine-8-carboxylic Acid

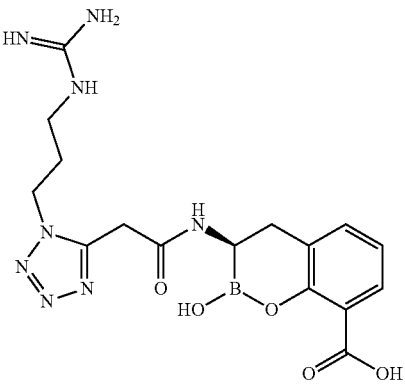 [SMILES: N=C(N)NCCCn1nnnc1CC(=O)N[C@H]1Cc2cccc(C(=O)O)c2OB1O]

Compound 53 was prepared following a similar procedure as described in Example 47. The final product was purified by reverse phase chromatography and dried using lyophilization to afford the title compound as white solid. ESI-MS m/z 417(MH)+.

Example 54: (R)-3-(2-(1-ethyl-1H-tetrazol-5-yl)acetamido)-2-hydroxy-3,4-dihydro-2H-benzo[e][1,2]oxaborinine-8-carboxylic Acid

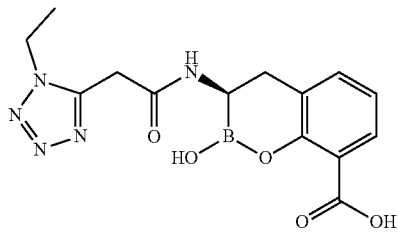 [SMILES: CCn1nnnc1CC(=O)N[C@H]1Cc2cccc(C(=O)O)c2OB1O]

Compound 54 was prepared following a similar procedure as described in Example 41. The final product was purified by reverse phase chromatography and dried using lyophilization to afford the title compound as white solid. ESI-MS m/z 346(MH)+.

Example 55: (R)-3-(2-(4-(5-(aminomethyl)thiophen-3-yl)-1H-1,2,3-triazol-1-yl)acetamido)-2-hydroxy-3,4-dihydro-2H-benzo[e][1,2]oxaborinine-8-carboxylic Acid

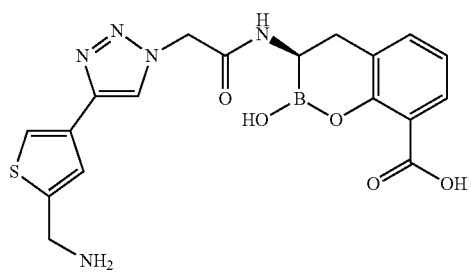 [SMILES: NCc1cc(-c2cn(CC(=O)N[C@H]3Cc4cccc(C(=O)O)c4OB3O)nn2)cs1]

Compound 55 was prepared following a similar procedure as described in Example 36 using tert-butyl ((4-bromothiophen-2-yl)methyl)carbamate instead of 36C. The final product was purified by reverse phase chromatography and dried using lyophilization to afford the title compound as white solid. ESI-MS m/z 428(MH)+.

Example 56: (R)-2-hydroxy-3-(2-(4-nitro-1H-pyrazol-1-yl)acetamido)-3,4-dihydro-2H-benzo[e][1,2]oxaborinine-8-carboxylic Acid

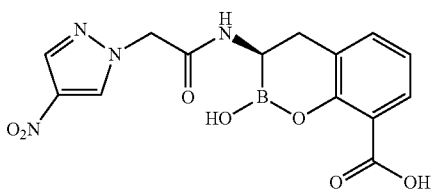 [SMILES: O=C(Cn1cc([N+](=O)[O-])cn1)N[C@H]1Cc2cccc(C(=O)O)c2OB1O]

Compound 56 was prepared following a similar procedure as described in Example 18, using 4-nitro-1H-pyrazole instead of 18A. The final product was purified by reverse phase chromatography and dried using lyophilization to afford the title compound as white solid. ESI-MS m/z 361(MH)+.

Example 57: (R)-3-(2-(5,6-dihydropyrrolo[3,4-c]pyrazol-2(4H)-yl)acetamido)-2-hydroxy-3,4-dihydro-2H-benzo[e][1,2]oxaborinine-8-carboxylic Acid

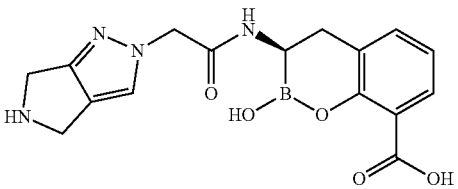 [SMILES: O=C(Cn1cc2c(n1)CNC2)N[C@H]1Cc2cccc(C(=O)O)c2OB1O]

Compound 57 was prepared following a similar procedure as described in Example 18 using tert-butyl 2,6-dihydropyrrolo[3,4-c]pyrazole-5(4H)-carboxylate instead of 18A. The final product was purified by reverse phase chromatography and dried using lyophilization to afford the title compound as white solid. ESI-MS m/z 357 (MH)+.

Example 58: (R)-3-(2-(4-amino-1H-pyrazol-1-yl)acetamido)-2-hydroxy-3,4-dihydro-2H-benzo[e][1,2]oxaborinine-8-carboxylic Acid

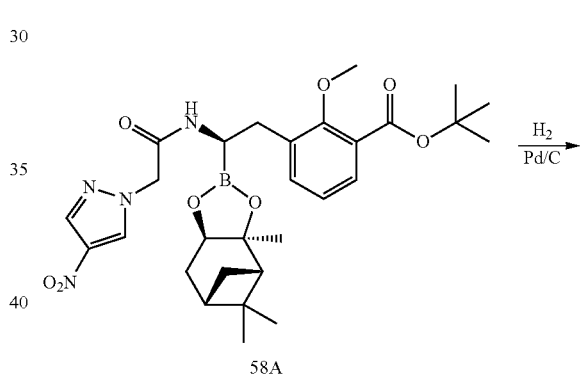

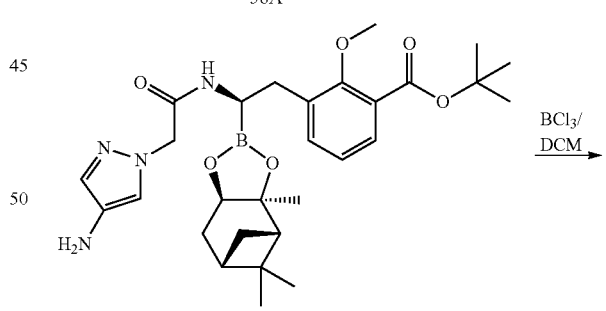

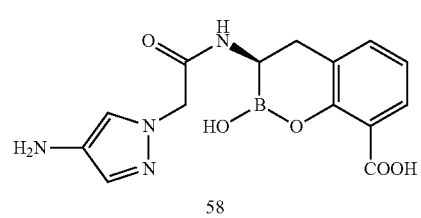

Step 1: Synthesis of tert-butyl 2-methoxy-3-((R)-2-(2-(4-nitro-1H-pyrazol-1-yl)acetamido)-2-((3aS,4S,6S,7aR)-3a,5,5-trimethylhexahydro-4,6-methanobenzo[d][1,3,2]dioxaborol-2-yl)ethyl)benzoate (58A)

Compound 58A was prepared following a similar procedure as described in Example 18 using 4-nitro-1H-pyrazole instead of 18A. ESI-MS m/z 583 (MH)⁺.

Step 2: Synthesis of tert-butyl 3-((R)-2-(2-(4-amino-1H-pyrazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (58B)

A mixture of 58A (20 mg) and Pd/C (10%, 20 mg) in 4 mL of DCM/EtOAc (1/1) was flushed with argon, then, stirred under hydrogen for 12 hrs at rt. The reaction was quenched with water, filtered and concentrated to give crude product 58B. ESI-MS m/z 583 (MH)⁺.

Step 3: Synthesis of (R)-3-(2-(4-amino-1H-pyrazol-1-yl)acetamido)-2-hydroxy-3,4-dihydro-2H-benzo[e][1,2]oxaborinine-8-carboxylic Acid Compound 58 was prepared following a similar procedure as described in Example 1 step 4 from the crude product 58B and BCl₃. The product was purified by reverse phase chromatography and dried using lyophilization to afford the title compound as white solid. ESI-MS m/z 331 (MH)⁺.

Example 59: (R)-3-(1-(2-aminoethyl)-1H-1,2,3-triazole-4-carboxamido)-2-hydroxy-3,4-dihydro-2H-benzo[e][1,2]oxaborinine-8-carboxylic Acid

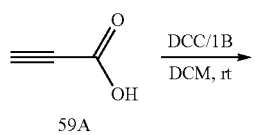

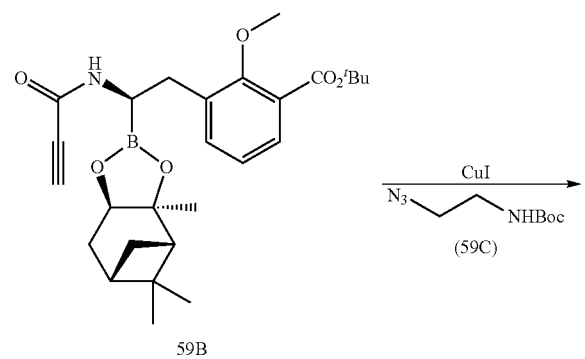

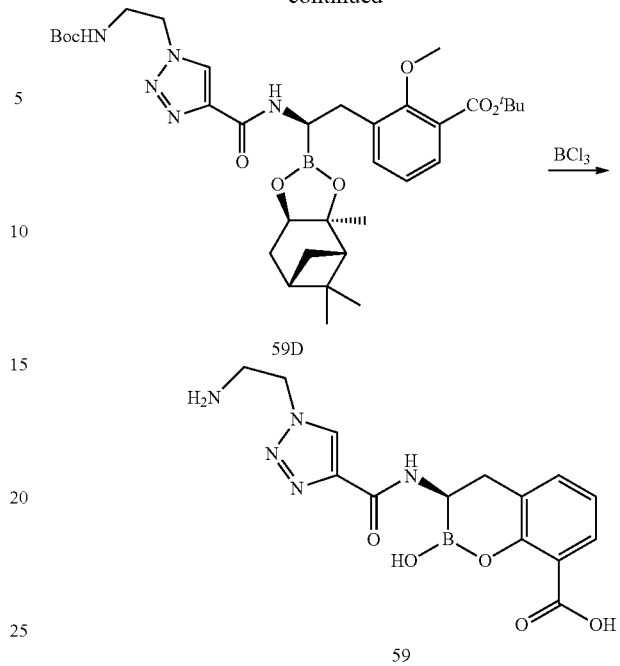

Step 1: Synthesis of tert-butyl 2-methoxy-3-((R)-2-propiolamido-2-((3aS,4S,6S,7aR)-3a,5,5-trimethylhexahydro-4,6-methanobenzo[d][1,3,2]dioxaborol-2-yl)ethyl)benzoate (59B)

Compound 59B was prepared following a similar procedure described in Example 37 (step 1) using 1B instead of tert-butyl (2-aminoethyl)carbamate. The product was purified by flash chromatograph (silica gel column, EtOAc/Hexane 0~100%) as yellow oil: ESI-MS m/z 504 (MNa)⁺.

Step 2: Synthesis of (R)-3-(1-(2-aminoethyl)-1H-1,2,3-triazole-4-carboxamido)-2-hydroxy-3,4-dihydro-2H-benzo[e][1,2]oxaborinine-8-carboxylic Acid Compound 59 was prepared following a similar procedure described in Example 37 (step 2 and 3) using 59B and 59C. The product was purified by reverse phase chromatography and dried using lyophilization to afford the title compound as white solid. ESI-MS m/z 346 (MH)⁺.

Example 60: (R)-3-(2-(4-(((2-aminoethyl)amino)methyl)-1H-1,2,3-triazol-1-yl)-2-methylpropanamido)-2-hydroxy-3,4-dihydro-2H-benzo[e][1,2]oxaborinine-8-carboxylic Acid

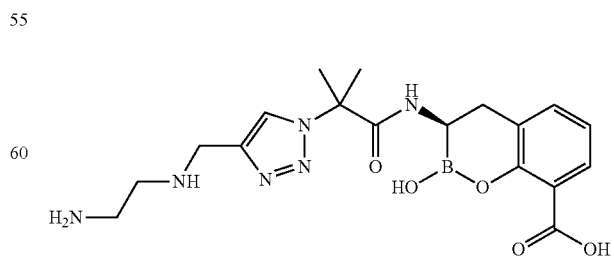

Compound 60 was prepared following a similar procedure as described in Example 21 (Step 1 and Step 2) from (R)-3-(2-(4-(aminomethyl)-1H-1,2,3-triazol-1-yl)-2-methylpropanamido)-2-hydroxy-3,4-dihydro-2H-benzo[e][1,2]oxaborinine-8-carboxylic acid (Example 33) and tert-butyl (2-oxoethyl)carbamate. The final product was purified by reverse phase chromatography and dried using lyophilization to afford the title compound as white solid. ESI-MS m/z 417 (MH)⁺.

Example 61: (R)-3-(2-(4-(((2-aminoethoxy)carbamoyl)-1H-1,2,3-triazol-1-yl)acetamido)-2-hydroxy-3,4-dihydro-2H-benzo[e][1,2]oxaborinine-8-carboxylic Acid

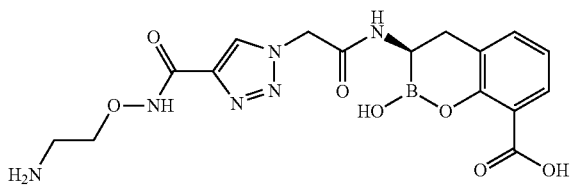 [SMILES: NCCONC(=O)c1cn(CC(=O)N[C@H]2Cc3cccc(C(=O)O)c3OB2O)nn1]

Compound 61 was prepared following a similar procedure as described in Example 37 using tert-butyl (2-(aminooxy)ethyl)carbamate instead of tert-butyl (2-aminoethyl)carbamate. The final product was purified by reverse phase chromatography and dried using lyophilization to afford the title compound as white solid. ESI-MS m/z 419 (MH)⁺.

Example 62: (R)-3-(2-(4-(2-aminopyridin-4-yl)-1H-1,2,3-triazol-1-yl)acetamido)-2-hydroxy-3,4-dihydro-2H-benzo[e][1,2]oxaborinine-8-carboxylic Acid

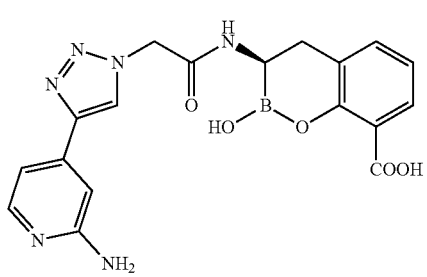 [SMILES: Nc1cc(-c2cn(CC(=O)N[C@H]3Cc4cccc(C(=O)O)c4OB3O)nn2)ccn1]

Compound 62 was prepared following a similar procedure as described in Example 36 using tert-butyl (4-bromopyridin-2-yl)carbamate instead of 36C. The final product was purified by reverse phase chromatography and dried using lyophilization to afford the title compound as white solid. ESI-MS m/z 409 (MH)⁺.

Example 63: (R)-3-(2-(4-(((2-aminoethyl)thio)methyl)-1H-1,2,3-triazol-1-yl)acetamido)-2-hydroxy-3,4-dihydro-2H-benzo[e][1,2]oxaborinine-8-carboxylic Acid

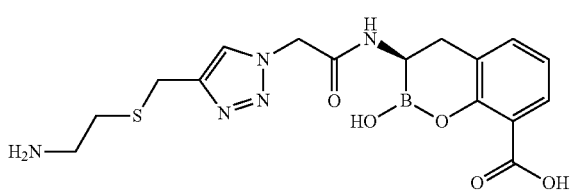 [SMILES: NCCSCc1cn(CC(=O)N[C@H]2Cc3cccc(C(=O)O)c3OB2O)nn1]

Compound 63 was prepared following a similar procedure as described in Example 34 using tert-butyl (2-mercaptoethyl)carbamate instead of 34A. The final product was purified by reverse phase chromatography and dried using lyophilization to afford the title compound as white solid. ESI-MS m/z 406(MH)⁺.

Example 64: (R)-3-(2-(4-((2,6-diamino-4-oxo-1,4-dihydropyrimidin-5-yl)methyl)-1H-1,2,3-triazol-1-yl)acetamido)-2-hydroxy-3,4-dihydro-2H-benzo[e][1,2]oxaborinine-8-carboxylic Acid

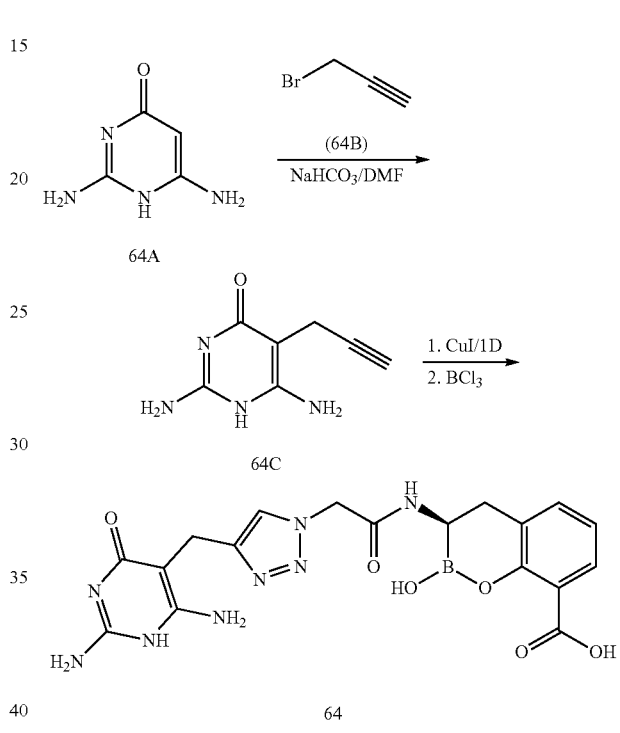

Step 1: Synthesis of 2,6-diamino-5-(prop-2-yn-1-yl)pyrimidin-4(1H)-one (64C)

64B (0.5 g, 4.2 mmol) was added to a mixture of 64A (0.5 g, 4 mmol) and NaHCO₃ (0.5 g, 6 mmol) in 2 mL of DMF at rt. The mixture was stirred at rt for 72 hrs. Then, added water (10 mL), and filtered. The solid was washed with water and dried to give 64C as white solid (0.3 g): ¹H NMR (300 MHz, DMSO-d6) δ 6.2 (s, 2H, NH₂), 5.81 (s, 2H, —NH₂), 3.06 (d, 2H, J=2.4 Hz), 2.76 (s, 1H), 2.55 (t, 1H, J=2.2 Hz); ESI-MS m/z 165(MH)⁺.

Step 2: Synthesis of (R)-3-(2-(4-((2,6-diamino-4-oxo-1,4-dihydropyrimidin-5-yl)methyl)-1H-1,2,3-triazol-1-yl)acetamido)-2-hydroxy-3,4-dihydro-2H-benzo[e][1,2]oxaborinine-8-carboxylic Acid Compound 64 was prepared following a similar procedure as described in Example 37 using 64C instead of 37B. The final product was purified by reverse phase chromatography and dried using lyophilization to afford the title compound as white solid. ESI-MS m/z 455(MH)⁺.

Example 65: (R)-3-(2-(4-((3-aminopropyl)carbamoyl)-1H-1,2,3-triazol-1-yl)acetamido)-2-hydroxy-3,4-dihydro-2H-benzo[e][1,2]oxaborinine-8-carboxylic Acid

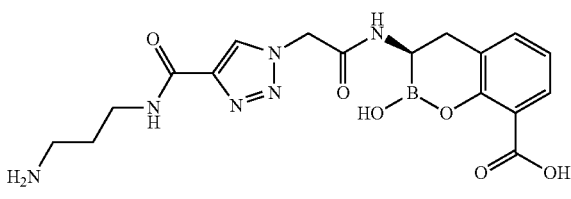 [SMILES: NCCCNC(=O)c1cn(CC(=O)N[C@H]2Cc3cccc(C(=O)O)c3OB2O)nn1]

Compound 65 was prepared following a similar procedure as described in Example 37 using tert-butyl (3-aminopropyl)carbamate instead of tert-butyl (2-aminoethyl)carbamate. The final product was purified by reverse phase chromatography and dried using lyophilization to afford the title compound as white solid. ESI-MS m/z 417 (MH)+.

Example 66: (R)-3-(2-(4-(S)-3-aminopyrrolidine-1-carbonyl)-1H-1,2,3-triazol-1-yl)acetamido)-2-hydroxy-3,4-dihydro-2H-benzo[e][1,2]oxaborinine-8-carboxylic Acid

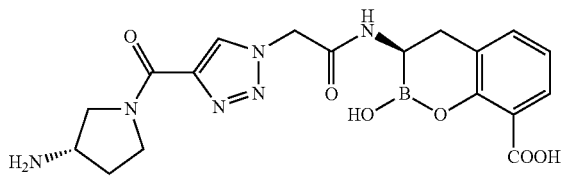 [SMILES: N[C@H]1CCN(C(=O)c2cn(CC(=O)N[C@H]3Cc4cccc(C(=O)O)c4OB3O)nn2)C1]

Compound 66 was prepared following a similar procedure as described in Example 37 using tert-butyl (S)-pyrrolidin-3-ylcarbamate instead of tert-butyl (2-aminoethyl)carbamate. The final product was purified by reverse phase chromatography and dried using lyophilization to afford the title compound as white solid. ESI-MS m/z 429 (MH)+.

Example 67: (R)-3-(2-(5-(aminomethyl)-1,3,4-thiadiazol-2-yl)acetamido)-2-hydroxy-3,4-dihydro-2H-benzo[e][1,2]oxaborinine-8-carboxylic Acid

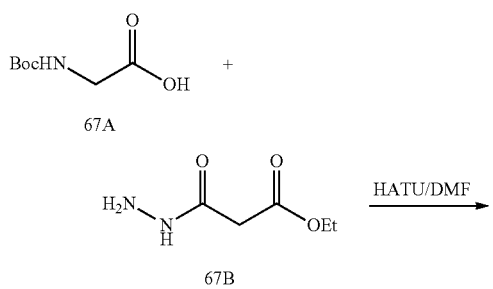

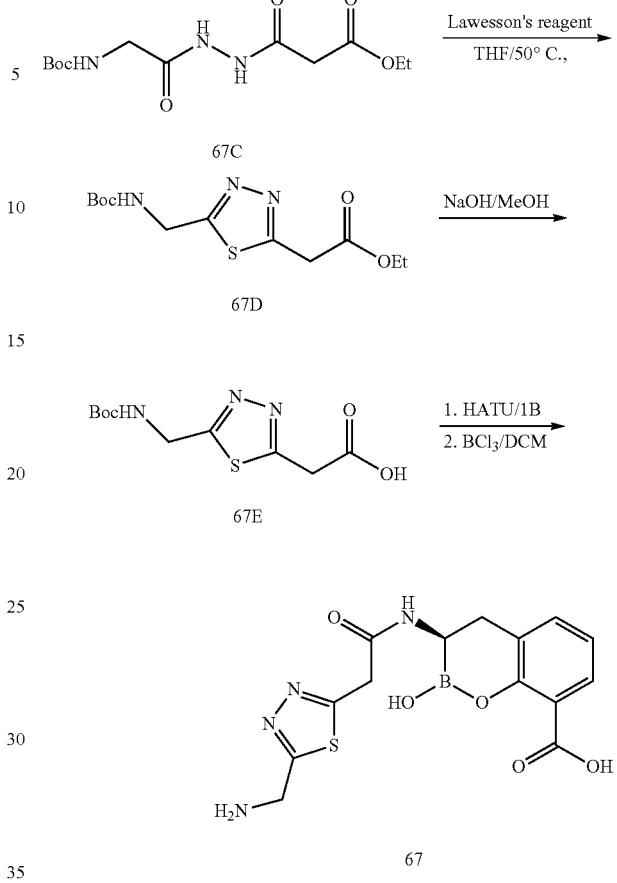

Step 1: Synthesis of ethyl 3-(2-((tert-butoxycarbonyl)glycyl)hydrazinyl)-3-oxopropanoate (67C)

DIPEA was added to a mixture of 67A (1.2 g, 6.8 mmol) and HATU (3 g, 7.8 mmol) in 10 mL of DMF at 0° C. The mixture was warmed to rt for 30 min., followed by the addition of 67B (1 g, 6.8 mmol). The reaction mixture was stirred at rt for 20 hr. The reaction was quenched with water (10 mL) and EtOAc (30 mL). The EtOAc layer was washed with water (2×10 mL)/brine (10 mL) and concentrated purified by flash chromatograph (silica gel column, EtOAc/Hexane 0~100%) to give 67C as colorless oil (1.0 g): ESI-MS m/z 326 (MNa)+.

Step 2: Synthesis of ethyl 2-(5-(((tert-butoxycarbonyl)amino)methyl)-1,3,4-thiadiazol-2-yl)acetate (67D)

A mixture of 67C (0.4 g) and lawesson's reagent (1.2 g) in 20 mL of THF was heated at 50° C. for 20 hrs. After cooling to rt, EtOAc (20 mL) was added. The reaction mixture was washed with 1N NaOH (5 mL) and brine, and purified by flash chromatograph (silica gel column, EtOAc/Hexane 0~100%) to give 67D as white solid (0.2 g): $^1$H NMR (300 MHz, CDCl$_3$) δ 7.8 (br, 1H), 4.7 (d, 2H, J=5.4 Hz), 4.23 (q, 2H, J=6.6 Hz), 4.14 (s, 2H), 1.46 (s, 9H), 1.29 (t, 3H, J=7.5 Hz); ESI-MS m/z 302 (MH)+.

Step 3: Synthesis of (R)-3-(2-(5-(aminomethyl)-1,3,4-thiadiazol-2-yl)acetamido)-2-hydroxy-3,4-dihydro-2H-benzo[e][1,2]oxaborinine-8-carboxylic Acid Compound 67 was prepared following a similar procedure as described in Example 41 using 67D instead of 41C. The final product was purified by reverse phase chromatography and dried using lyophilization to afford the title compound as white solid. ESI-MS m/z 363 (MH)+.

Example 68: (R)-3-(2-(4-(aminomethyl)-1H-pyrazol-1-yl)acetamido)-2-hydroxy-3,4-dihydro-2H-benzo[e][1,2]oxaborinine-8-carboxylic Acid

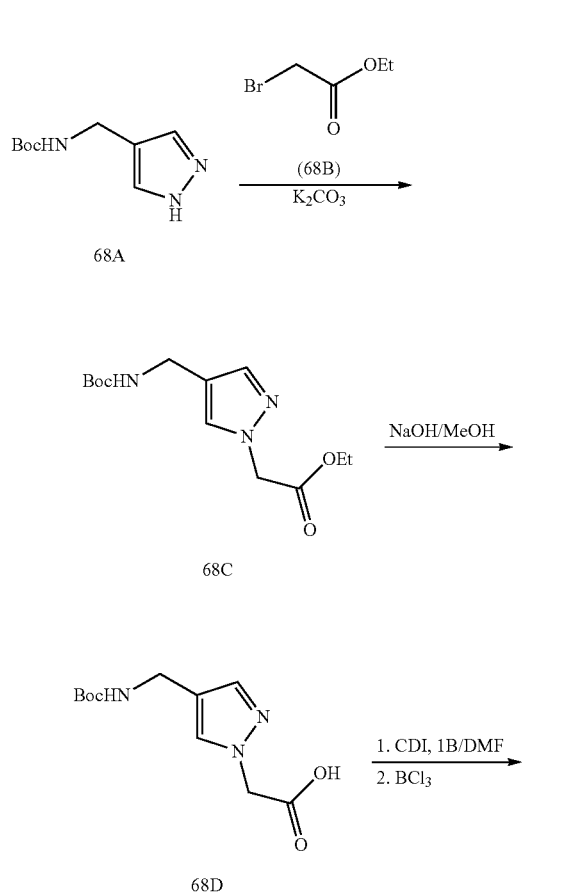

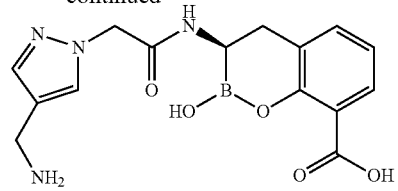
68

Step 1: Synthesis of ethyl 2-(4-(((tert-butoxycarbonyl)amino)methyl)-1H-pyrazol-1-yl)acetate (68C)

68B (0.4 g, 2.4 mmol) was added to a mixture of 68A (0.4 g, 2 mmol) and K$_2$CO$_3$ (0.5 g, 3.6 mmol) in 15 mL of CH$_3$CN at rt. The mixture was heated at 50° C. for 20 hrs. After cooled to rt, the reaction mixture was diluted with EtOAc (80 mL), washed with water/brine, concentrated and purified by flash chromatograph (silica gel column, EtOAc/Hexane 0~100%) to give 68C as colorless oil (0.6 g): $^1$H NMR (300 MHz, CDCl$_3$) δ 7.46 (s, 1H), 7.41 (s, 1H), 4.84 (s, 2H), 4.8 (br, 1H), 4.16-4.22 (m, 4H), 1.43 (s, 9H), 1.24-1.28 (m, 3H).

Step 2: Synthesis of (R)-3-(2-(4-(aminomethyl)-1H-pyrazol-1-yl)acetamido)-2-hydroxy-3,4-dihydro-2H-benzo[e][1,2]oxaborinine-8-carboxylic Acid Compound 68 was prepared following a similar procedure as described in Example 41 using 68C instead of 41C. The final product was purified by reverse phase chromatography and dried using lyophilization to afford the title compound as white solid. ESI-MS m/z 345 (MH)+.

Example 69: (R)-3-(2-(4-4(2-aminoethyl)sulfonamido)methyl)-1H-1,2,3-triazol-1-yl)acetamido)-2-hydroxy-3,4-dihydro-2H-benzo[e][1,2]oxaborinine-8-carboxylic Acid

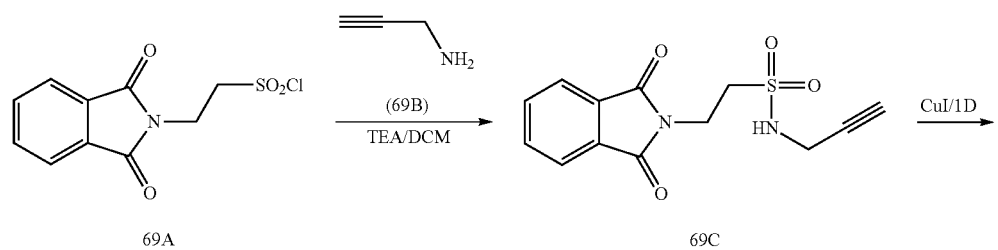

-continued

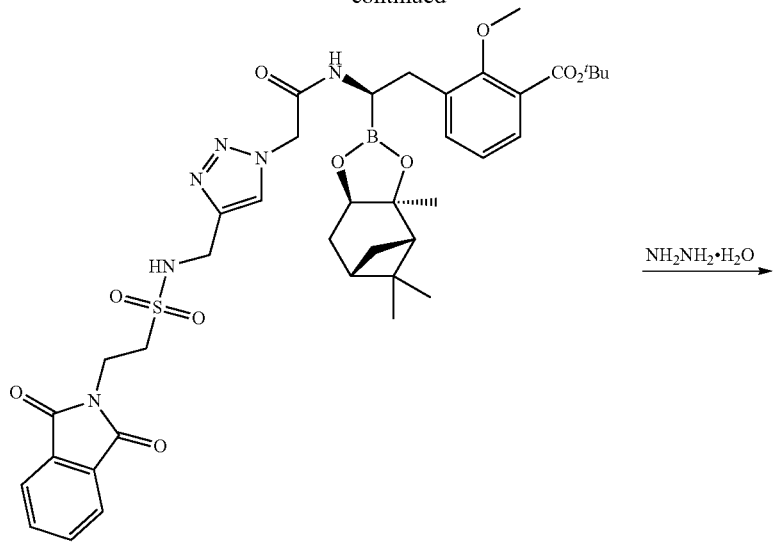

69D

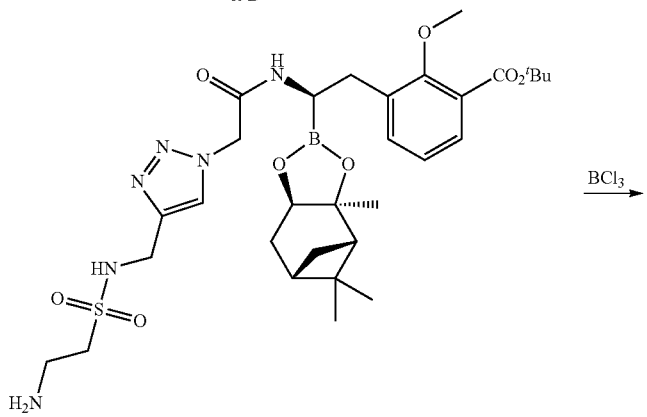

69E

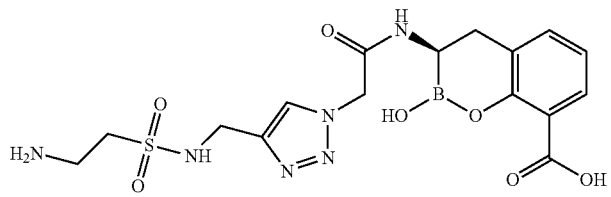

69

Step 1: Synthesis of 2-(1,3-dioxoisoindolin-2-yl)-N-(prop-2-yn-1-yl)ethane-1-sulfonamide (69C)

Compound 69A (0.2 g, 3.6 mmol in 10 mL of DCM) was added to a solution of 69B (1 g, 3.6 mmol), TEA and DMAP (0.1 g) in 10 mL of DCM at 0° C. The reaction mixture was stirred at 0° C. rt for 2 hrs. The reaction was quenched with water, and washed with 0.2N HCl and brine. The organic layer was concentrated and purified by a silica gel flash chromatograph to give 69C as white solid. ESI-MS m/z 293 (MH)+.

Step 2: Synthesis of tert-butyl 3-((R)-2-(2-(4-(((2-(1,3-dioxoisoindolin-2-yl)ethyl)sulfonamido)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (69D)

Compound 69D was prepared following a similar procedure as described in Example 37 using 69C instead of 37B. ESI-MS m/z 805(MH)+.

Step 3: Synthesis of tert-butyl 3-((R)-2-(2-(4-(((2-aminoethyl)sulfonamido)methyl)-1H-1,2,3-triazol-1-yl)acetamido)-2-((3aS,4S,6S,7aR)-3a,5,5-trimethyl-hexahydro-4,6-methanobenzo[d][1,3,2]dioxaborol-2-yl)ethyl)-2-methoxybenzoate (69E)

NH$_2$NH.H$_2$O (40 µL, 50% aqueous, 0.4 mmol) was added to a solution of 69D (0.1 g, 0.12 mmol) and n-Bu$_4$NHSO$_4$ (0.2 g) in 4 mL of THF at rt. After 30 min, the reaction was quenched with 0.2N HCl (4 mL), and the solid was filtered. The solvent was removed under vacuum to give crude 69E: ESI-MS m/z 675 (MH)$^+$.

Step 4: Synthesis of (R)-3-(2-(4-(((2-aminoethyl)sulfonamido)methyl)-1H-1,2,3-triazol-1-yl)acetamido)-2-hydroxy-3,4-dihydro-2H-benzo[e][1,2]oxaborinine-8-carboxylic Acid Compound 69 was prepared following a similar procedure as described in Example 41 using 69E instead of 41C. The final product was purified by reverse phase chromatography and dried using lyophilization to afford the title compound as white solid. ESI-MS m/z 453 (MH)$^+$.

Example 70: (R)-3-(2-(4-(((4-aminophenyl)sulfonamido)methyl)-1H-1,2,3-triazol-1-yl)acetamido)-2-hydroxy-3,4-dihydro-2H-benzo[e][1,2]oxaborinine-8-carboxylic Acid

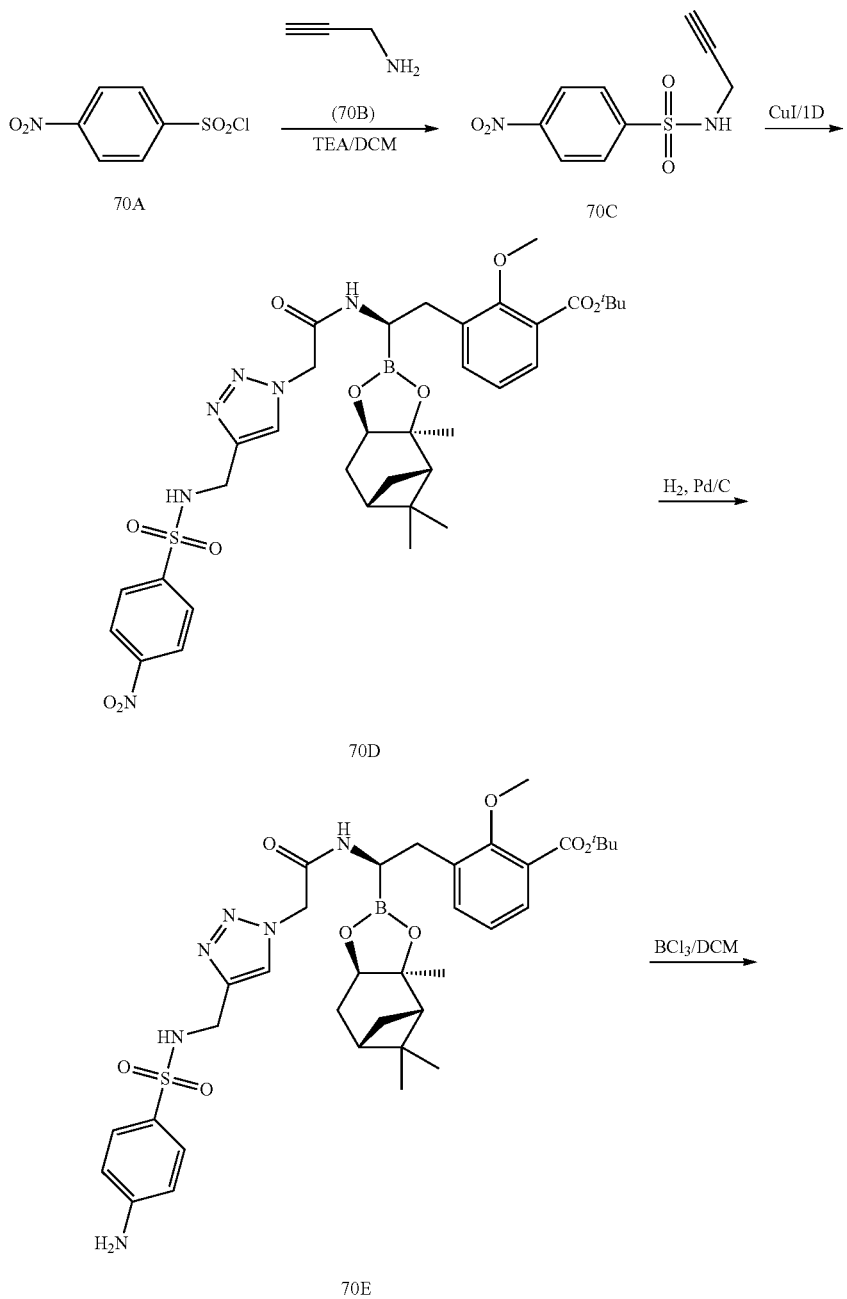

-continued

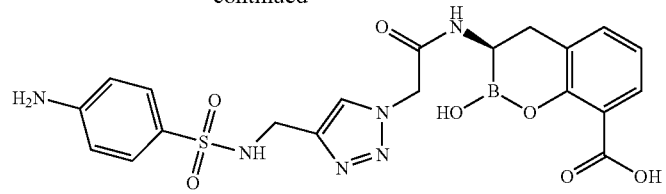

70

Step 1: Preparation of 4-nitro-N-(prop-2-yn-1-yl)benzenesulfonamide (70C) and tert-butyl 2-methoxy-3-((R)-2-(2-(4-(((4-nitrophenyl)sulfonamido)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)benzoate (70D)

Compound 70C [ESI-MS m/z 241 (MH)$^+$] and 70D [ESI-MS m/z 753 (MH)$^+$] were prepared following a similar procedure as described in Example 69 using 70A instead of 69A.

Step 2: Synthesis of tert-butyl 3-((R)-2-(2-(4-(((4-aminophenyl)sulfonamido)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (70E)

A mixture of 70D (40 mg) and Pd/C (10%, 50 mg) in 4 mL of THF and 0.04 mL (0.2 N HCl) was stirred under H$_2$ at rt for 2 hr. The reaction was quenched with 0.2 N HCl (2 mL), filtered the catalyst and removed the solvent under vacuum to give crude 70E. ESI-MS m/z 723 (MH)$^+$1.

Step 3: Synthesis of (R)-3-(2-(4-(((4-aminophenyl)sulfonamido)methyl)-1H-1,2,3-triazol-1-yl)acetamido)-2-hydroxy-3,4-dihydro-2H-benzo[e][1,2]oxaborinine-8-carboxylic Acid Compound 70 was prepared following a similar procedure as described in Example 41 using 70E instead of 41C. The final product was purified by reverse phase chromatography and dried using lyophilization to afford the title compound as white solid. ESI-MS m/z 501 (MH)$^+$.

Example 71: (R)-3-(1-(2-aminoethyl)-1H-1,2,4-triazole-3-carboxamido)-2-hydroxy-3,4-dihydro-2H-benzo[e][1,2]oxaborinine-8-carboxylic Acid

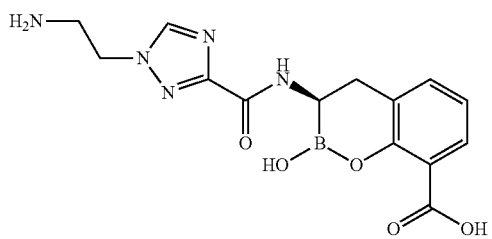 [SMILES: NCCn1cnc(C(=O)N[C@H]2Cc3cccc(C(=O)O)c3OB2O)n1]

Compound 71 was prepared following a similar procedure as described in Example 41 using methyl 4H-1,2,4-triazole-3-carboxylate instead of 41A. The final product was purified by reverse phase chromatography and dried using lyophilization to afford the title compound as white solid. ESI-MS m/z 346 (MH)$^+$.

Examples 72 and 73: (R)-3-(1-(2-aminoethyl)-1H-imidazole-4-carboxamido)-2-hydroxy-3,4-dihydro-2H-benzo[e][1,2]oxaborinine-8-carboxylic acid (72) and (R)-3-(1-(2-aminoethyl)-1H-imidazole-5-carboxamido)-2-hydroxy-3,4-dihydro-2H-benzo[e][1,2]oxaborinine-8-carboxylic Acid (73)

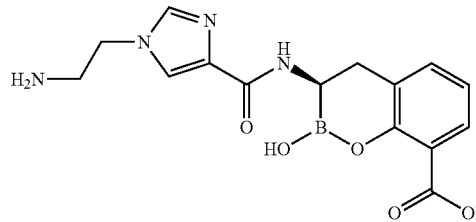

72

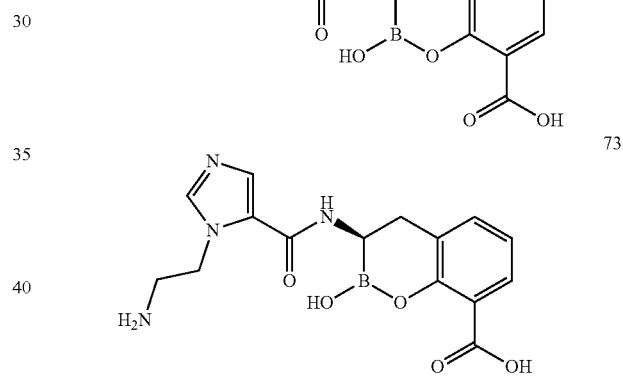

73

Compounds 72 and 73 (two regioisomers, the relative structures were not assigned) were prepared following a similar procedure as described in Example 41 using methyl 1H-imidazole-5-carboxylate instead of 41A. The final product was purified by reverse phase chromatography and dried using lyophilization to afford the title compound as white solid: ESI-MS m/z 345 (MH)$^+$.

Example 74: (R)-3-(2-(4-(6-aminopyridin-3-yl)-1H-1,2,3-triazol-1-yl)acetamido)-2-hydroxy-3,4-dihydro-2H-benzo[e][1,2]oxaborinine-8-carboxylic Acid

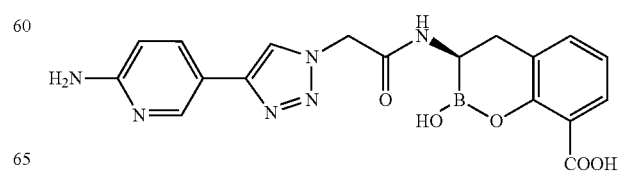

Compound 74 was prepared following a similar procedure as described in Example 36 using tert-butyl (5-bromopyridin-2-yl)carbamate instead of 36C. The final product was purified by reverse phase chromatography and dried using lyophilization to afford the title compound as white solid. ESI-MS m/z 409 (MH)$^+$.

Example 75: (R)-3-(2-(4-(6-(aminomethyl)pyridin-3-yl)-1H-1,2,3-triazol-1-yl)acetamido)-2-hydroxy-3,4-dihydro-2H-benzo[e][1,2]oxaborinine-8-carboxylic Acid

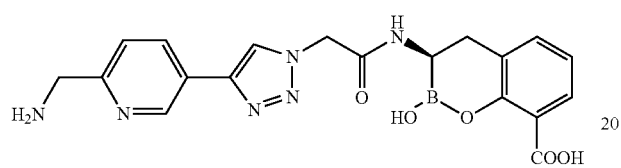

Compound 75 was prepared following a similar procedure as described in Example 36 using tert-butyl ((5-bromopyridin-2-yl)methyl)carbamate instead of 36C. The final product was purified by reverse phase chromatography and dried using lyophilization to afford the title compound as white solid. ESI-MS m/z 423 (MH)$^+$.

Example 76: (R)-3-(2-(4-((2-aminoacetamido)methyl)-1H-1,2,3-triazol-1-yl)acetamido)-2-hydroxy-3,4-dihydro-2H-benzo[e][1,2]oxaborinine-8-carboxylic Acid

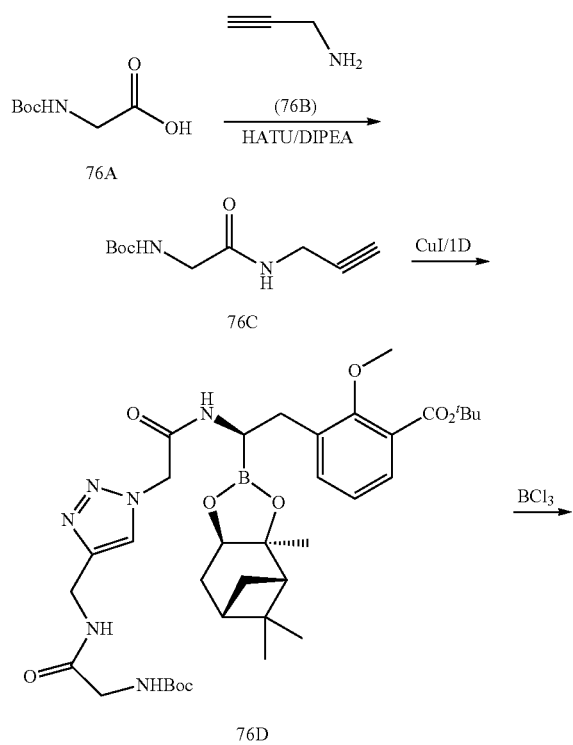

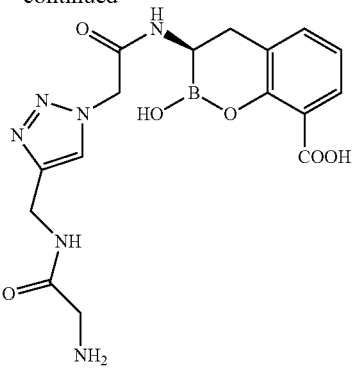

76

Step 1: Synthesis of tert-butyl (2-oxo-2-(prop-2-yn-1-ylamino)ethyl)carbamate (76C)

DIPEA (0.5 g, 3.8 mmol) was added to a solution of 76A (0.5 g, 2.9 mmol) and HATU (1.3 g, 3.3 mmol) in 4 mL of DMF at rt, followed by the addition of added 76B (0.2 g, 3.6 mmol in 2 mL of DCM). The mixture was stirred at rt for 20 hr. The reaction was quenched with water and extracted with EtOAc. The organic layer was washed with 0.2 N HCl and brine, concentrated and purified by by a silica gel flash chromatograph to give 76C as white solid (0.4 g). $^1$H NMR (300 MHz, CD$_3$Cl) δ 6.38 (br, 1H), 5.05 (br, 1H), 4.06 (s, 2H), 3.81 (s, 2H), 2.23 (s, 1H), 1.60 (s, 9H).

Step 2: Synthesis of (R)-3-(2-(4-((2-aminoacetamido)methyl)-1H-1,2,3-triazol-1-yl)acetamido)-2-hydroxy-3,4-dihydro-2H-benzo[e][1,2]oxaborinine-8-carboxylic Acid Compound 76 was prepared following a similar procedure as described in Example 36 using 76C instead of 36D. The final product was purified by reverse phase chromatography and dried using lyophilization to afford the title compound as white solid. ESI-MS m/z 403 (MH)$^+$.

Example 77: (R)-3-(2-(4-((2-(aminooxy)acetamido)methyl)-1H-1,2,3-triazol-1-yl)acetamido)-2-hydroxy-3,4-dihydro-2H-benzo[e][1,2]oxaborinine-8-carboxylic Acid

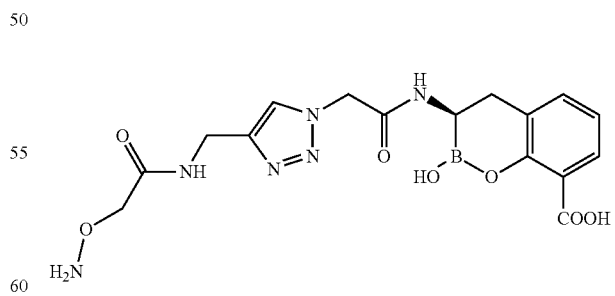

Compound 77 was prepared following a similar procedure as described in Example 76 using 2-(((tert-butoxycarbonyl)amino)oxy)acetic acid instead of 76A. The final product was purified by reverse phase chromatography and dried using lyophilization to afford the title compound as white solid. ESI-MS m/z 419 (MH)$^+$.

Example 78: (R)-2-hydroxy-3-(2-(imidazo[2,1-b]thiazol-6-yl)acetamido)-3,4-dihydro-2H-benzo[e][1,2]oxaborinine-8-carboxylic Acid

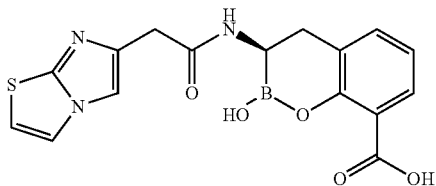 [SMILES: O=C(Cc1cn2ccsc2n1)N[C@H]1Cc2cccc(C(=O)O)c2OB1O]

Compound 78 was prepared following similar procedure (step 2 to step 3) described in Example 20 using compound 2-(imidazo[2,1-b]thiazol-6-yl)acetic acid instead of 20B. The title compound was purified by reverse phase chromatography and dried using lyophilization to afford the title product as white solid. ESI-MS m/z 372 (MH)+.

Example 79: (R)-2-hydroxy-3-(2-(4-(methylcarbamoyl)-1H-1,2,3-triazol-1-yl)acetamido)-3,4-dihydro-2H-benzo[e][1,2]oxaborinine-8-carboxylic Acid

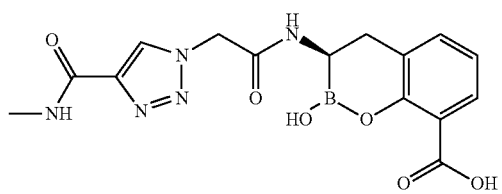 [SMILES: CNC(=O)c1cn(CC(=O)N[C@H]2Cc3cccc(C(=O)O)c3OB2O)nn1]

Compound 79 was prepared following a similar procedure as described in Example 37 using methylamine instead of tert-butyl (2-aminoethyl)carbamate. The final product was purified by reverse phase chromatography and dried using lyophilization to afford the title compound as white solid. ESI-MS m/z 374 (MH)+.

Example 80: (R)-3-(2-(4-(3-aminoazetidine-1-carbonyl)-1H-1,2,3-triazol-1-yl)acetamido)-2-hydroxy-3,4-dihydro-2H-benzo[e][1,2]oxaborinine-8-carboxylic Acid

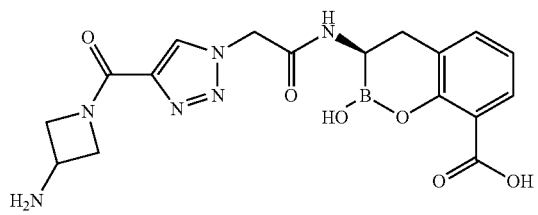 [SMILES: NC1CN(C(=O)c2cn(CC(=O)N[C@H]3Cc4cccc(C(=O)O)c4OB3O)nn2)C1]

Compound 80 was prepared following a similar procedure as described in Example 37 using tert-butyl azetidin-3-ylcarbamate instead of tert-butyl (2-aminoethyl)carbamate. The final product was purified by reverse phase chromatography and dried using lyophilization to afford the title compound as white solid. ESI-MS m/z 415 (MH)+.

Example 81: (R)-2-hydroxy-3-(2-(4-(((S)-pyrrolidin-3-yl)carbamoyl)-1H-1,2,3-triazol-1-yl)acetamido)-3,4-dihydro-2H-benzo[e][1,2]oxaborinine-8-carboxylic Acid

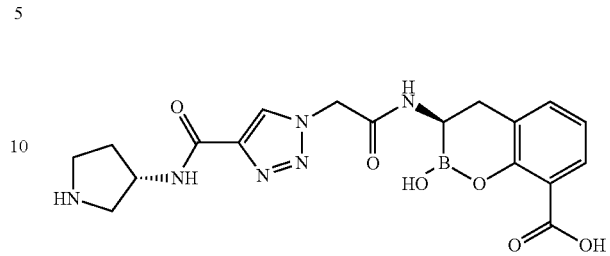

Compound 81 was prepared following a similar procedure as described in Example 37 using tert-butyl (S)-3-aminopyrrolidine-1-carboxylate instead of tert-butyl (2-aminoethyl)carbamate. The final product was purified by reverse phase chromatography and dried using lyophilization to afford the title compound as white solid. ESI-MS m/z 429 (MH)+.

Example 82: (R)-3-(2-(4-(4-aminopiperidine-1-carbonyl)-1H-1,2,3-triazol-1-yl)acetamido)-2-hydroxy-3,4-dihydro-2H-benzo[e][1,2]oxaborinine-8-carboxylic Acid

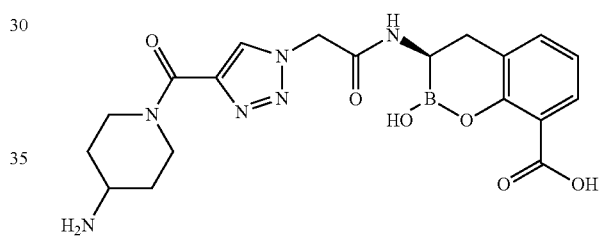

Compound 82 was prepared following a similar procedure as described in Example 37 using tert-butyl piperidin-4-ylcarbamate instead of tert-butyl (2-aminoethyl)carbamate. The final product was purified by reverse phase chromatography and dried using lyophilization to afford the title compound as white solid. ESI-MS m/z 443 (MH)+.

Example 83: (R)-2-hydroxy-3-(2-(4-(piperidin-4-ylcarbamoyl)-1H-1,2,3-triazol-1-yl)acetamido)-3,4-dihydro-2H-benzo[e][1,2]oxaborinine-8-carboxylic Acid

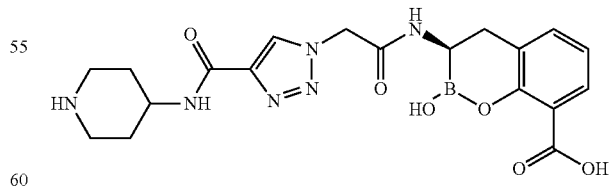

Compound 83 was prepared following a similar procedure as described in Example 37 using tert-butyl 4-aminopiperidine-1-carboxylate instead of tert-butyl (2-aminoethyl)carbamate. The final product was purified by reverse phase chromatography and dried using lyophilization to afford the title compound as white solid. ESI-MS m/z 443 (MH)+.

Example 84: (R)-2-hydroxy-3-(2-(4-(((R)-pyrrolidin-3-yl)carbamoyl)-1H-1,2,3-triazol-1-yl)acetamido)-3,4-dihydro-2H-benzo[e][1,2]oxaborinine-8-carboxylic Acid

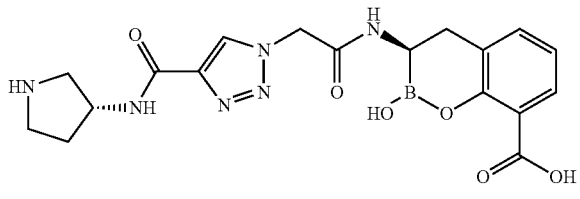 [SMILES: O=C(Cn1cc(C(=O)N[C@@H]2CCNC2)nn1)N[C@H]1Cc2cccc(C(=O)O)c2OB1O]

Compound 84 was prepared following a similar procedure as described in Example 37 using tert-butyl (R)-3-aminopyrrolidine-1-carboxylate instead of tert-butyl (2-aminoethyl)carbamate. The final product was purified by reverse phase chromatography and dried using lyophilization to afford the title compound as white solid. ESI-MS m/z 429 (MH)$^+$.

Example 85: (R)-3-(2-(4-(R)-3-aminopyrrolidine-1-carbonyl)-1H-1,2,3-triazol-1-yl)acetamido)-2-hydroxy-3,4-dihydro-2H-benzo[e][1,2]oxaborinine-8-carboxylic Acid

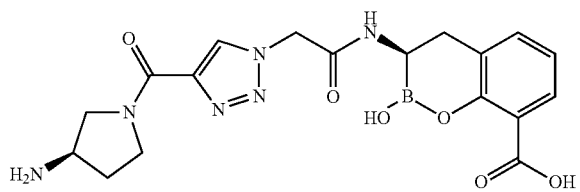 [SMILES: N[C@@H]1CCN(C(=O)c2cn(CC(=O)N[C@H]3Cc4cccc(C(=O)O)c4OB3O)nn2)C1]

Compound 85 was prepared following a similar procedure as described in Example 37 using tert-butyl (R)-pyrrolidin-3-ylcarbamate instead of tert-butyl (2-aminoethyl)carbamate. The final product was purified by reverse phase chromatography and dried using lyophilization to afford the title compound as white solid. ESI-MS m/z 429 (MH)$^+$.

Example 86: (R)-3-(2-(4-((3-amino-2,2-dimethylpropyl)carbamoyl)-1H-1,2,3-triazol-1-yl)acetamido)-2-hydroxy-3,4-dihydro-2H-benzo[e][1,2]oxaborinine-8-carboxylic Acid

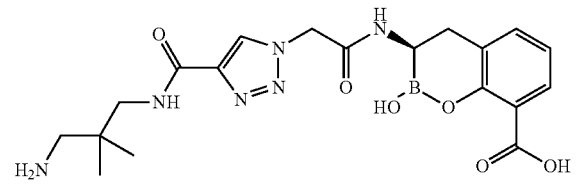 [SMILES: CC(C)(CN)CNC(=O)c1cn(CC(=O)N[C@H]2Cc3cccc(C(=O)O)c3OB2O)nn1]

Compound 86 was prepared following a similar procedure as described in Example 37 using tert-butyl (3-amino-2,2-dimethylpropyl)carbamate instead of tert-butyl (2-aminoethyl)carbamate. The final product was purified by reverse phase chromatography and dried using lyophilization to afford the title compound as white solid. ESI-MS m/z 445 (MH)$^+$.

Example 87: (R)-2-hydroxy-3-(2-(4-((2-(methylamino)ethyl)carbamoyl)-1H-1,2,3-triazol-1-yl)acetamido)-3,4-dihydro-2H-benzo[e][1,2]oxaborinine-8-carboxylic Acid

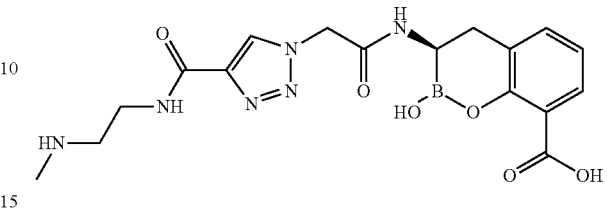

Compound 87 was prepared following a similar procedure as described in Example 37 using tert-butyl (2-aminoethyl)(methyl)carbamate instead of tert-butyl (2-aminoethyl)carbamate. The final product was purified by reverse phase chromatography and dried using lyophilization to afford the title compound as white solid. ESI-MS m/z 417 (MH)$^+$.

Example 88: (R)-3-(2-(4-(azetidin-3-ylcarbamoyl)-1H-1,2,3-triazol-1-yl)acetamido)-2-hydroxy-3,4-dihydro-2H-benzo[e][1,2]oxaborinine-8-carboxylic Acid

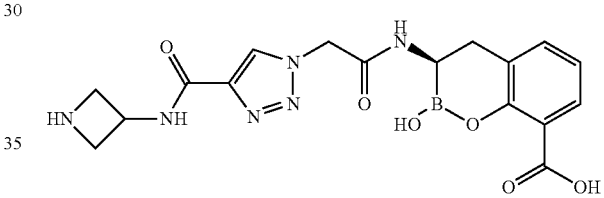

Compound 88 was prepared following a similar procedure as described in Example 37 using tert-butyl 3-aminoazetidine-1-carboxylate instead of tert-butyl (2-aminoethyl)carbamate. The final product was purified by reverse phase chromatography and dried using lyophilization to afford the title compound as white solid. ESI-MS m/z 415 (MH)$^+$.

Example 89: (3R)-2-hydroxy-3-(2-(4-(pyrrolidin-3-yl)-1H-1,2,3-triazol-1-yl)acetamido)-3,4-dihydro-2H-benzo[e][1,2]oxaborinine-8-carboxylic Acid

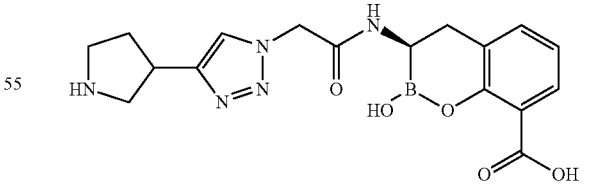

Compound 89 was prepared following a similar procedure as described in Example 1 (Steps 3 and 4) replacing prop-2-yn-1-ol in step 3 with tert-butyl 3-ethynylpyrrolidine-1-carboxylate. The crude product was purified by reverse phase chromatography and dried using lyophilization to afford the title compound as white solid. ESI-MS m/z 386 (MH)$^+$.

Example 90: (R)-3-(2-(4-(azetidin-3-yl)-1H-1,2,3-triazol-1-yl)acetamido)-2-hydroxy-3,4-dihydro-2H-benzo[e][1,2]oxaborinine-8-carboxylic Acid

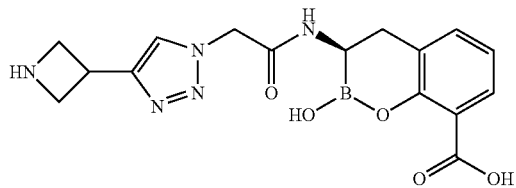

Compound 90 was prepared following a similar procedure as described in Example 1 (Steps 3 and 4) replacing prop-2-yn-1-ol in step 3 with tert-butyl 3-ethynylazetidine-1-carboxylate. The crude product was purified by reverse phase chromatography and dried using lyophilization to afford the title compound as white solid. ESI-MS m/z 372 (MH)$^+$.

Example 91: (R)-3-(2-(4-(1-carbamimidoylazetidin-3-yl)-1H-1,2,3-triazol-1-yl)acetamido)-2-hydroxy-3,4-dihydro-2H-benzo[e][1,2]oxaborinine-8-carboxylic Acid

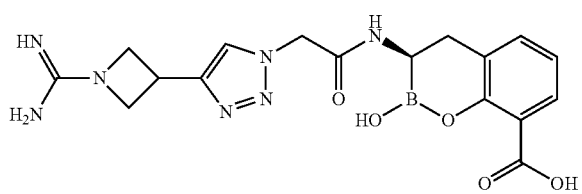 [SMILES: N=C(N)N1CC(c2cn(CC(=O)N[C@H]3Cc4cccc(C(=O)O)c4OB3O)nn2)C1]

Compound 91 was prepared following a similar procedure as described in Example 3. The crude product was purified by reverse phase chromatography and dried using lyophilization to afford the title compound as white solid. ESI-MS m/z 414 (MH)$^+$.

Example 92: (3R)-3-(2-(4-(3-amino-2-hydroxypropyl)-1H-1,2,3-triazol-1-yl)acetamido)-2-hydroxy-3,4-dihydro-2H-benzo[e][1,2]oxaborinine-8-carboxylic Acid

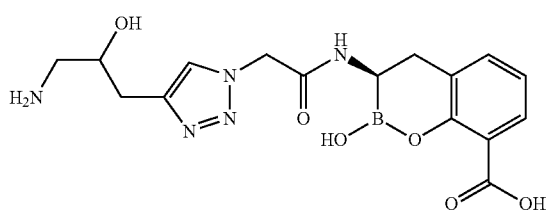 [SMILES: NCC(O)Cc1cn(CC(=O)N[C@H]2Cc3cccc(C(=O)O)c3OB2O)nn1]

Compound 92 was prepared following a similar procedure as described in Example 1 (Steps 3 and 4) replacing prop-2-yn-1-ol in step 3 with tert-butyl (2-hydroxybut-3-yn-1-yl)carbamate. The crude product was purified by reverse phase chromatography and dried using lyophilization to afford the title compound as white solid. ESI-MS m/z 390 (MH)$^+$.

Example 93: (3R)-3-(2-(4-(3-guanidino-2-hydroxypropyl)-1H-1,2,3-triazol-1-yl)acetamido)-2-hydroxy-3,4-dihydro-2H-benzo[e][1,2]oxaborinine-8-carboxylic Acid

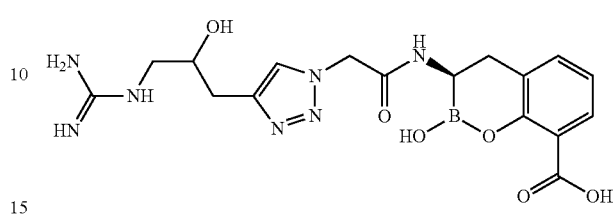

Compound 93 was prepared following a similar procedure as described in Example 3. The crude product was purified by reverse phase chromatography and dried using lyophilization to afford the title compound as white solid. ESI-MS m/z 432 (MH)$^+$.

Example 94 and 95: (R)-2-hydroxy-3-(1-(2-oxo-2-(((S)-pyrrolidin-3-yl)amino)ethyl)-1H-tetrazole-5-carboxamido)-3,4-dihydro-2H-benzo[e][1,2]oxaborinine-8-carboxylic Acid (94) and (R)-2-hydroxy-3-(2-(2-oxo-2-(((S)-pyrrolidin-3-yl)amino)ethyl)-2H-tetrazole-5-carboxamido)-3,4-dihydro-2H-benzo[e][1,2]oxaborinine-8-carboxylic Acid (95)

94

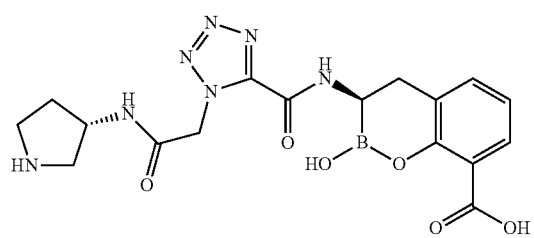

95

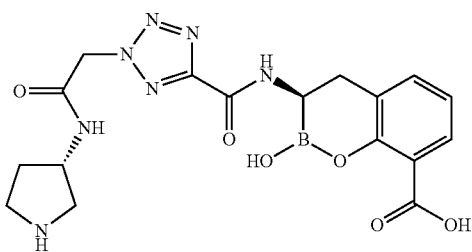

Compound 94 and 95 were prepared as a mixture of two regioisomers following a similar procedure as described in Example 41 using 43C and ethyl 2-oxo-2-(1H-tetrazol-5-yl)acetate instead of 41A and 41B. The final product was purified by reverse phase chromatography and dried using lyophilization to afford the title compound as white solid. ESI-MS m/z 430 (MH)$^+$.

Example 96: (R)-3-(2-(2-(2-hydrazinyl-2-oxoethyl)-2H-tetrazol-5-yl)acetamido)-2-hydroxy-3,4-dihydro-2H-benzo[e][1,2]oxaborinine-8-carboxylic Acid

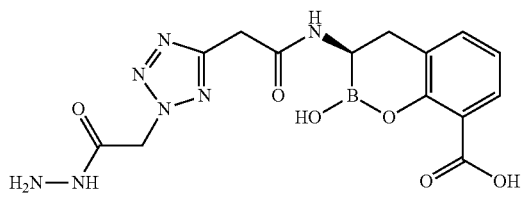 [SMILES: NNC(=O)Cn1nnc(CC(=O)N[C@H]2Cc3cccc(C(=O)O)c3OB2O)n1]

Compound 96 were prepared following a similar procedure as described in Example 43 using tert-butyl hydrazinecarboxylate instead of 43A. The final product was purified by reverse phase chromatography and dried using lyophilization to afford the title compound as white solid. ESI-MS m/z 390 (MH)+.

Example 97: (R)-3-(2-(1H-tetrazol-1-yl)acetamido)-2-hydroxy-3,4-dihydro-2H-benzo[e][1,2]oxaborinine-8-carboxylic Acid

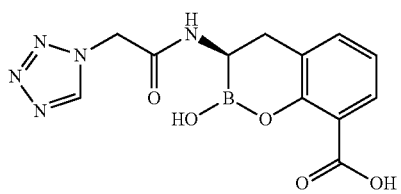 [SMILES: O=C(Cn1cnnn1)N[C@H]1Cc2cccc(C(=O)O)c2OB1O]

Compound 97 was prepared following similar procedure (step 2 to step 3) described in Example 20 using 2-(1H-tetrazol-1-yl)acetic acid instead of 20B. The title compound was purified by reverse phase chromatography and dried using lyophilization to afford the title product as white solid. ESI-MS m/z 318 (MH)+.

Example 98: (R)-2-hydroxy-3-(2-(1-(piperidin-4-ylmethyl)-1H-tetrazol-5-yl)acetamido)-3,4-dihydro-2H-benzo[e][1,2]oxaborinine-8-carboxylic Acid

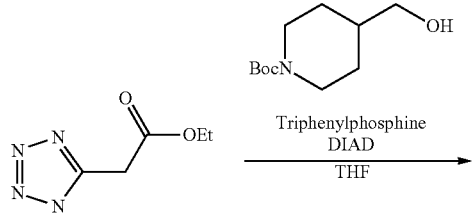

41A

-continued

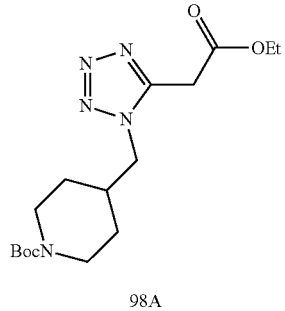

98A

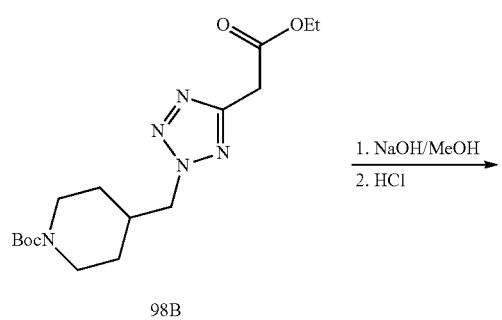

98B

1. NaOH/MeOH
2. HCl

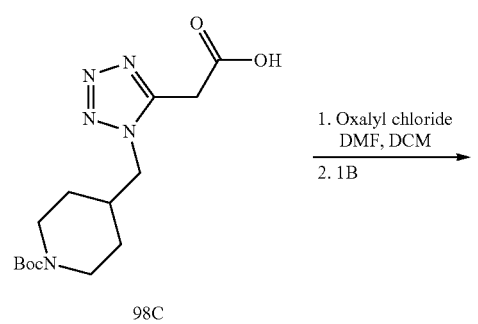

98C

1. Oxalyl chloride DMF, DCM
2. 1B

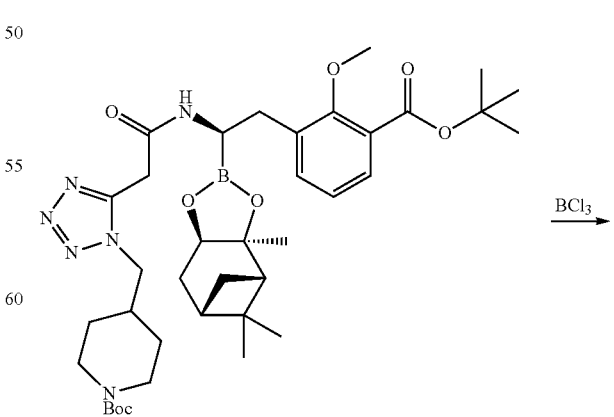

98D

BCl₃

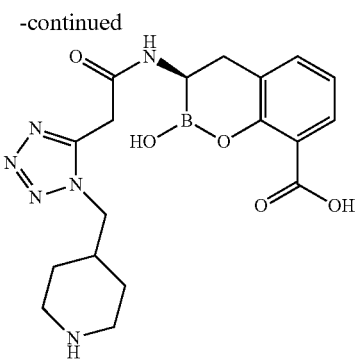

98

Step 1: Synthesis of tert-butyl 4-((5-(2-ethoxy-2-oxoethyl)-1H-tetrazol-1-yl)methyl)piperidine-1-carboxylate (98A)

To a mixture of 41A (0.78 g, 5 mmol), tert-butyl 4-(hydroxymethyl)piperidine-1-carboxylate (1.08 g, 5 mmol) and PPh$_3$ (144 g, 5.5 mmol) in 20 mL of THF was added DIAD (1.1 mL, 5.5 mmol) at 0° C. slowly. The resulting reaction mixture was allowed to warm to room temperature overnight. The solvent was removed and the two isomers was isolated and purified by column chromatography to afford the titled compound as colorless oil (0.4 g).

Step 2: Synthesis of 2-(1-((1-(tert-butoxycarbonyl)piperidin-4-yl)methyl)-1H-tetrazol-5-yl)acetic Acid (98C)

2-(1-((1-(tert-butoxycarbonyl)piperidin-4-yl)methyl)-1H-tetrazol-5-yl)acetic acid was synthesized using same procedure described in step 2, Example 41.

Step 3: Synthesis of tert-butyl 4-((5-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-2-oxoethyl)-1H-tetrazol-1-yl)methyl)piperidine-1-carboxylate (98D)

To compound 98C (0.33 g, 1 mmol) in DCM (10 mL) and DMF (1 mL) at 0° C. was added oxalyl chloride (0.5 mL, 2 M in DCM) slowly. The resulting reaction mixture was stirred at same temperature for 30 mins, at which time a solution of 1B (1 mmol) was added. The reaction mixture was then stirred at RT for 30 min. Water was added and extracted with EtOAc. The organic phase was dried over Na$_2$SO$_4$, concentrated and purified by flash chromatography to afford the compound 98D as yellow oil.

Step 4: Synthesis of (R)-2-hydroxy-3-(2-(1-(piperidin-4-ylmethyl)-1H-tetrazol-5-yl)acetamido)-3,4-dihydro-2H-benzo[e][1,2]oxaborinine-8-carboxylic Acid (98)

Compound 98 was prepared from 98D and BCl$_3$ following the procedure described in step 4 of Example 1. The crude product was purified by reverse phase chromatography and dried using lyophilization. ESI-MS m/z 415 (MH)$^+$.

Example 99: (R)-2-hydroxy-3-(2-(2-(piperidin-4-ylmethyl)-2H-tetrazol-5-yl)acetamido)-3,4-dihydro-2H-benzo[e][1,2]oxaborinine-8-carboxylic Acid

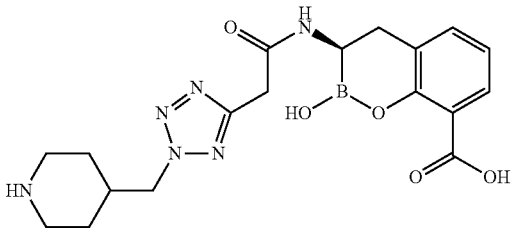 [SMILES: O=C(Cc1nnn(CC2CCNCC2)n1)N[C@H]1Cc2cccc(C(=O)O)c2OB1O]

Compound 99 was prepared following the procedure (Step 2 to Step 4) described in Example 98 using compound 98B instead of 98A. The crude product was purified by reverse phase chromatography and dried using lyophilization to afford the title product as white solid. ESI-MS m/z 415 (MH)$^+$.

Example 100: (R)-3-(2-(2-(azetidin-3-yl)-2H-tetrazol-5-yl)acetamido)-2-hydroxy-3,4-dihydro-2H-benzo[e][1,2]oxaborinine-8-carboxylic Acid

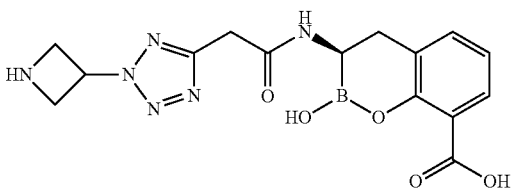 [SMILES: O=C(Cc1nnn(C2CNC2)n1)N[C@H]1Cc2cccc(C(=O)O)c2OB1O]

Compound 100 was prepared following the procedure (Step 1 to Step 4) described in Example 98. The crude product was purified by reverse phase chromatography and dried using lyophilization to afford the title product as white solid. ESI-MS m/z 373 (MH)$^+$.

Example 101: (R)-3-(2-(1-(2-fluoroethyl)-1H-tetrazol-5-yl)acetamido)-2-hydroxy-3,4-dihydro-2H-benzo[e][1,2]oxaborinine-8-carboxylic Acid

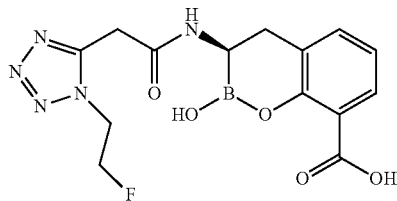 [SMILES: O=C(Cc1nnnn1CCF)N[C@H]1Cc2cccc(C(=O)O)c2OB1O]

Compound 101 was prepared following the procedure (Step 3 to Step 4) described in Example 98 from 2-(1-(2-fluoroethyl)-1H-tetrazol-5-yl)acetic acid. The crude product was purified by reverse phase chromatography and dried using lyophilization to afford the title product as white solid. ESI-MS m/z 364 (MH)$^+$.

Example 102: (R)-3-(2-(5-(2-aminoethyl)-1H-tetrazol-1-yl)acetamido)-2-hydroxy-3,4-dihydro-2H-benzo[e][1,2]oxaborinine-8-carboxylic Acid

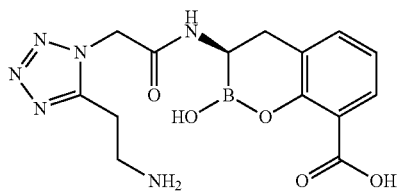

Compound 102 was prepared following the procedure (Step 3 to Step 4) described in Example 98 from 2-(5-(2-((tert-butoxycarbonyl)amino)ethyl)-1H-tetrazol-1-yl)acetic acid. The crude product was purified by reverse phase chromatography and dried using lyophilization to afford the title product as white solid. ESI-MS m/z 361 (MH)⁺.

Example 103: (R)-3-(2-(5-(2-aminoethyl)-2H-tetrazol-2-yl)acetamido)-2-hydroxy-3,4-dihydro-2H-benzo[e][1,2]oxaborinine-8-carboxylic Acid

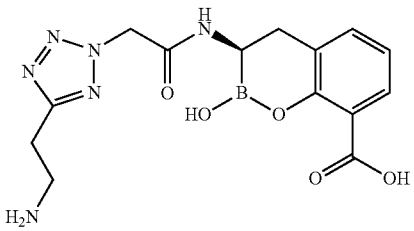 [SMILES: NCCc1nnn(CC(=O)N[C@H]2Cc3cccc(C(=O)O)c3OB2O)n1]

Compound 103 was prepared following the procedure (Step 3 to Step 4) described in Example 98 from 2-(5-(2-((tert-butoxycarbonyl)amino)ethyl)-2H-tetrazol-2-yl)acetic acid. The crude product was purified by reverse phase chromatography and dried using lyophilization to afford the title product as white solid. ESI-MS m/z 361 (MH)⁺.

Example 104: (R)-3-(2-(1-(2-formimidamidoethyl)-1H-tetrazol-5-yl)acetamido)-2-hydroxy-3,4-dihydro-2H-benzo[e][1,2]oxaborinine-8-carboxylic Acid

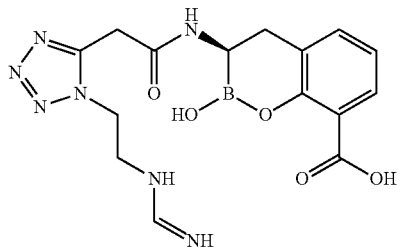 [SMILES: N=CNCCn1nnnc1CC(=O)N[C@H]1Cc2cccc(C(=O)O)c2OB1O]

Compound 104 was prepared following the procedure described in Example 22 from (R)-3-(2-(5-(2-aminoethyl)-1H-tetrazol-1-yl)acetamido)-2-hydroxy-3,4-dihydro-2H-benzo[e][1,2]oxaborinine-8-carboxylic acid. The crude product was purified by reverse phase chromatography and dried using lyophilization to afford the title product as white solid. ESI-MS m/z 388 (MH)⁺.

Example 105: (R)-3-(2-(4-(aminomethyl)-5-iodo-1H-1,2,3-triazol-1-yl)acetamido)-2-hydroxy-3,4-dihydro-2H-benzo[e][1,2]oxaborinine-8-carboxylic Acid

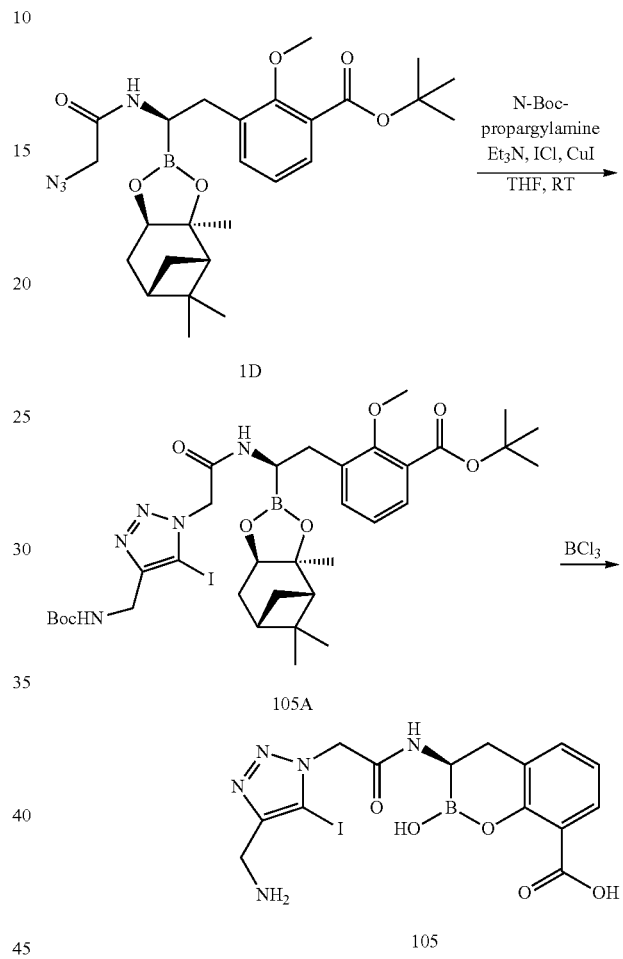

Step 1: Synthesis of 105A

To a mixture of compound 1D (0.5 mmol), N-Boc-propargylamine (0.5 mmol), ICl (1 mmol), and CuI (1 mmol) in THF (10 mL) was added TEA (0.7 mmol). The reaction mixture was stirred at RT under argon for 4 hr. The solvent was removed under reduced pressure. The residue was purified by column chromatography (5%-100% EtOAc in hexane) to afford compound 105A.

Step 2: Synthesis of (R)-3-(2-(4-(aminomethyl)-5-iodo-1H-1,2,3-triazol-1-yl)acetamido)-2-hydroxy-3,4-dihydro-2H-benzo[e][1,2]oxaborinine-8-carboxylic Acid (105)

Compound 105 was prepared from 105A and BCl₃ following the procedure described in Step 4 of Example 1. The crude product was purified by reverse phase chromatography and dried using lyophilization. ESI-MS m/z 472 (MH)⁺.

Example 106: (R)-3-(2-(4-(aminomethyl)-5-methyl-1H-1,2,3-triazol-1-yl)acetamido)-2-hydroxy-3,4-dihydro-2H-benzo[e][1,2]oxaborinine-8-carboxylic Acid

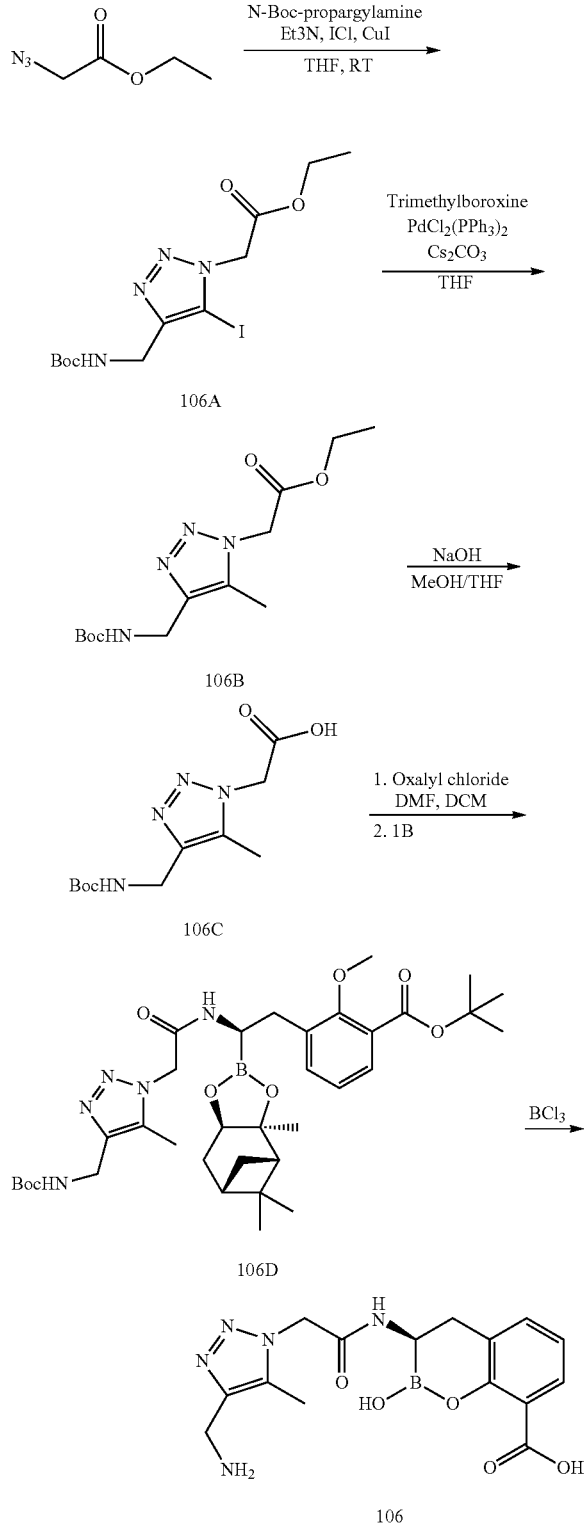

Step 1: Synthesis of ethyl 2-(4-(((tert-butoxycarbonyl)amino)methyl)-5-iodo-1H-1,2,3-triazol-1-yl)acetate (106A)

Compound 106 was prepared from ethyl 2-azidoacetate following the procedure described in Step 1 of Example 105.

Step 2: Synthesis of ethyl 2-(4-(((tert-butoxycarbonyl)amino)methyl)-5-methyl-1H-1,2,3-triazol-1-yl)acetate (106B)

A mixture of compound 106A (0.5 mmol), $PdCl_2(PPh_3)_2$ (0.05 mmol), Trimethylboroxine (1 mmol) and $Cs_2CO_3$ (1 mmol) in THF (5 mL) was heated at 70° C. for 4 h. The solvent was removed under reduced pressure and the residue purified by chromatography (5%-100% EtOAc in hexane) to afford compound 106B.

Step 3: Synthesis of 2-(4-(((tert-butoxycarbonyl)amino)methyl)-5-methyl-1H-1,2,3-triazol-1-yl)acetic Acid (106C)

2-(4-(((tert-Butoxycarbonyl)amino)methyl)-5-methyl-1H-1,2,3-triazol-1-yl)acetic acid was synthesized using same procedure described in Step 2, Example 41.

Step 4: Synthesis of tert-butyl 3-((R)-2-(2-(4-(((tert-butoxycarbonyl)amino)methyl)-5-methyl-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (106D)

tert-Butyl 3-((R)-2-(2-(4-(((tert-butoxycarbonyl)amino)methyl)-5-methyl-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was synthesized using same procedure described in Step 3, Example 98.

Step 5: Synthesis of (R)-3-(2-(4-(aminomethyl)-5-methyl-1H-1,2,3-triazol-1-yl)acetamido)-2-hydroxy-3,4-dihydro-2H-benzo[e][1,2]oxaborinine-8-carboxylic Acid (106)

Compound 106 was prepared from 106D and $BCl_3$ following the procedure described in Step 4 of Example 1. The crude product was purified by reverse phase chromatography and dried using lyophilization. ESI-MS m/z 360 $(MH)^+$.

Example 107: (R)-3-(2-(4-(aminomethyl)-5-chloro-1H-1,2,3-triazol-1-yl)acetamido)-2-hydroxy-3,4-dihydro-2H-benzo[e][1,2]oxaborinine-8-carboxylic Acid

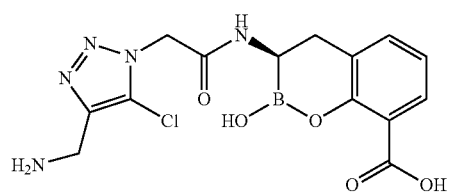

Step 1: Synthesis of ethyl 2-(4-(((tert-butoxycarbonyl)amino)methyl)-5-chloro-1H-1,2,3-triazol-1-yl)acetate In a manner similar to Example 106, a mixture of ethyl 2-azidoacetate (10 mmol), N-Boc-propargylamine (10 mmol), NCS (30 mmol), CuCl (10 mmol) in DCM (100 mL) was treated with DIEA (30 mmol). The reaction mixture was stirred at RT under argon overnight. The solvent was removed under reduced pressure. The residue was purified by column chromatography (5%-100% EtOAc in hexane) to afford the triazole intermediate.

Step 2: Synthesis of 2-(4-(((tert-butoxycarbonyl)amino)methyl)-5-chloro-1H-1,2,3-triazol-1-yl)acetic Acid 2-(4-(((tert-Butoxycarbonyl)amino)methyl)-5-chloro-1H-1,2,3-triazol-1-yl)acetic acid was synthesized using same procedure described in Step 2, Example 41.

Step 3: Synthesis of (R)-3-(2-(4-(aminomethyl)-5-chloro-1H-1,2,3-triazol-1-yl)acetamido)-2-hydroxy-3,4-dihydro-2H-benzo[e][1,2]oxaborinine-8-carboxylic Acid (107)

Compound 107 was synthesized from 2-(4-(((tert-butoxycarbonyl)amino)methyl)-5-chloro-1H-1,2,3-triazol-1-yl)acetic acid following the same procedure described in Step 4 and Step 5 from Example 106. The product was purified by reverse phase chromatography and dried using lyophilization. ESI-MS m/z 380 (MH)$^+$.

Example 108: (R)-3-(2-(4-(aminomethyl)-5-(thiophen-3-yl)-1H-1,2,3-triazol-1-yl)acetamido)-2-hydroxy-3,4-dihydro-2H-benzo[e][1,2]oxaborinine-8-carboxylic Acid

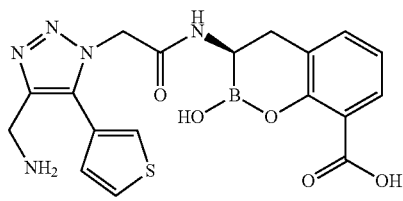 [SMILES: NCc1nnn(CC(=O)N[C@H]2Cc3cccc(C(=O)O)c3OB2O)c1-c1ccsc1]

Step 1: Synthesis of ethyl 2-(4-(((tert-butoxycarbonyl)amino)methyl)-5-(thiophen-3-yl)-1H-1,2,3-triazol-1-yl)acetate A mixture of 106B (0.5 mmol), thiophen-3-ylboronic acid (1 mmol), Pd(PPh$_3$)$_4$ (0.05 mmol), Cs$_2$CO$_3$ (2 mmol) in dixoane (10 mL) was heated at 80° C. for 4 h. The solvent was removed under reduced pressure. The residue was purified by column chromatography (5%-100% EtOAc in Hexane) to afford the titled compound.

Step 2: Synthesis of 2-(4-(((tert-butoxycarbonyl)amino)methyl)-5-(thiophen-3-yl)-1H-1,2,3-triazol-1-yl)acetic Acid 2-(4-(((tert-butoxycarbonyl)amino)methyl)-5-(thiophen-3-yl)-1H-1,2,3-triazol-1-yl)acetic acid was synthesized using same procedure described in Step 2, Example 41.

Step 3: Synthesis of (R)-3-(2-(4-(aminomethyl)-5-(thiophen-3-yl)-1H-1,2,3-triazol-1-yl)acetamido)-2-hydroxy-3,4-dihydro-2H-benzo[e][1,2]oxaborinine-8-carboxylic Acid (108)

Compound 108 was synthesized from 2-(4-(((tert-butoxycarbonyl)amino)methyl)-5-(thiophen-3-yl)-1H-1,2,3-triazol-1-yl)acetic acid following the same procedure described in Step 4 and Step 5 from Example 106. The product was purified by reverse phase chromatography and dried using lyophilization. ESI-MS m/z 428 (MH)$^+$.

Example 109: (R)-3-(2-(4-(aminomethyl)-5-(3-aminoprop-1-yn-1-yl)-1H-1,2,3-triazol-1-yl)acetamido)-2-hydroxy-3,4-dihydro-2H-benzo[e][1,2]oxaborinine-8-carboxylic Acid

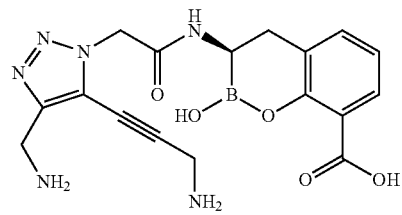 [SMILES: NCC#Cc1c(CN)nnn1CC(=O)N[C@H]1Cc2cccc(C(=O)O)c2OB1O]

Compound 109 was prepared following the procedure (Step 3 to Step 4) described in Example 98 from 2-(4-(((tert-butoxycarbonyl)amino)methyl)-5-(3-((tert-butoxycarbonyl)amino)prop-1-yn-1-yl)-1H-1,2,3-triazol-1-yl)acetic acid. The crude product was purified by reverse phase chromatography and dried using lyophilization to afford the title product as white solid. ESI-MS m/z 399 (MH)$^+$.

Example 110: (R)-3-(2-(4-(aminomethyl)-5-(3-aminopropyl)-1H-1,2,3-triazol-1-yl)acetamido)-2-hydroxy-3,4-dihydro-2H-benzo[e][1,2]oxaborinine-8-carboxylic Acid

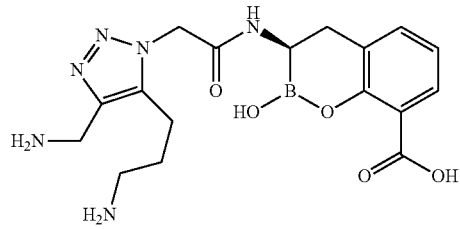 [SMILES: NCCCc1c(CN)nnn1CC(=O)N[C@H]1Cc2cccc(C(=O)O)c2OB1O]

Compound 110 was prepared following the procedure (Step 3 to Step 4) described in Example 98, utilizing 2-(4-(aminomethyl)-5-(3-aminopropyl)-1H-1,2,3-triazol-1-yl)acetic acid. The crude product was purified by reverse phase chromatography and dried using lyophilization to afford the title product as white solid. ESI-MS m/z 403 (MH)$^+$.

Example 111: (R)-3-(2-(4-(fluoromethyl)-1H-1,2,3-triazol-1-yl)acetamido)-2-hydroxy-3,4-dihydro-2H-benzo[e][1,2]oxaborinine-8-carboxylic Acid

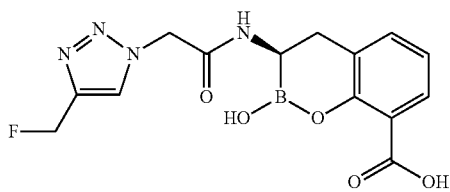 [SMILES: O=C(Cn1cc(CF)nn1)N[C@H]1Cc2cccc(C(=O)O)c2OB1O]

Compound 111 was prepared following the procedure (Step 3 to Step 4) described in Example 98, utilizing 2-(4-(fluoromethyl)-1H-1,2,3-triazol-1-yl)acetic acid. The crude product was purified by reverse phase chromatography and dried using lyophilization to afford the title product as white solid. ESI-MS m/z 349 (MH)$^+$.

Example 112: (R)-2-hydroxy-3-(2-(4-(((4,4,4-trifluorobutyl)amino)methyl)-1H-1,2,3-triazol-1-yl)acetamido)-3,4-dihydro-2H-benzo[e][1,2]oxaborinine-8-carboxylic Acid

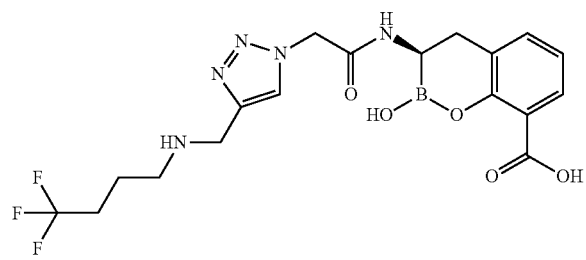 [SMILES: O=C(Cn1cc(CNCCCC(F)(F)F)nn1)N[C@H]1Cc2cccc(C(=O)O)c2OB1O]

Step 1: Synthesis of 2-(4-(((tert-butoxycarbonyl)(4,4,4-trifluorobutyl)amino)methyl)-1H-1,2,3-triazol-1-yl)acetic Acid

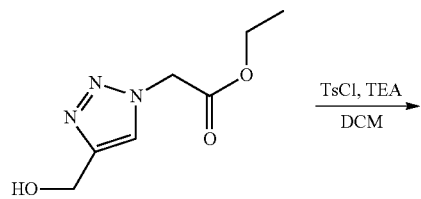

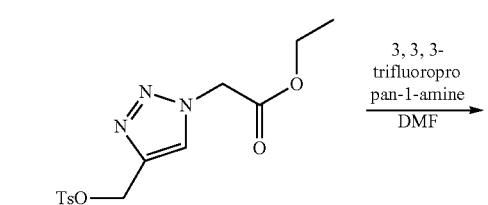

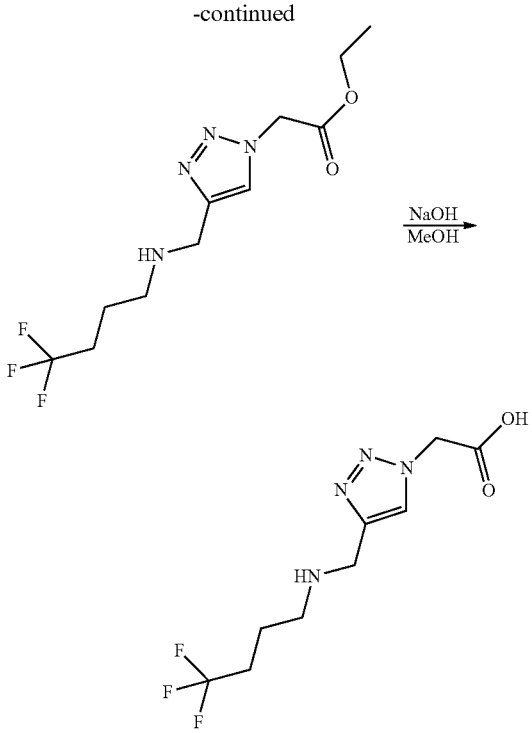

Step 1-A. Synthesis of ethyl 2-(4-((tosyloxy)methyl)-1H-1,2,3-triazol-1-yl)acetate To ethyl 2-(4-(hydroxymethyl)-1H-1,2,3-triazol-1-yl)acetate (600 mg) in DCM (10 mL) was added TsCl (0.5 mL) and TEA (1 mL) at 0° C. The reaction mixture was warmed to RT while stirring. The organic phase was washed with water and brine, concentrated and dried over anhydrous Na$_2$SO$_4$. Removal of the solvents afforded ethyl 2-(4-((tosyloxy)methyl)-1H-1,2,3-triazol-1-yl)acetate (800 mg).

Step 1-B. Synthesis of ethyl 2-(4-(((4,4,4-trifluorobutyl)amino)methyl)-1H-1,2,3-triazol-1-yl)acetate To ethyl 2-(4-((tosyloxy)methyl)-1H-1,2,3-triazol-1-yl)acetate (400 mg) in DMF (5 mL) was added 3,3,3-trifluoropropan-1-amine (381 mg). The reaction mixture was stirred at 80° C. overnight. Water was added and the mixture was extracted with EtOAc. The organic phase was washed with water and brine, concentrated and dried over anhydrous Na$_2$SO$_4$. After removal of the solvents the crude product was dissolved in DCM (10 mL), this solution was then treated with (Boc)$_2$O (660 mg) and TEA (0.5 mL). The resulting reaction mixture was stirred at RT overnight. The reaction mixture was concentrated and the residue purified by chromatography to affored ethyl 2-(4-(((4,4,4-trifluorobutyl)amino)methyl)-1H-1,2,3-triazol-1-yl)acetate (450 mg).

Step 1-C. Synthesis of 2-(4-(((tert-butoxycarbonyl)(4,4,4-trifluorobutyl)amino)methyl)-1H-1,2,3-triazol-1-yl)acetic Acid The ester was dissolved in MeOH (5 mL) and 1 N NaOH (3 mL) was added. After stirring at RT for 3 h, 1 N HCl (4 mL) was added and the mixture was extracted with EtOAc. The organic phase was washed with brine, concentrated and dried over anhydrous Na₂SO₄. Removal of the solvents afforded the titled acid (350 mg)

Step 2: Synthesis of (R)-2-hydroxy-3-(2-(4-(((4,4,4-trifluorobutyl)amino)methyl)-1H-1,2,3-triazol-1-yl)acetamido)-3,4-dihydro-2H-benzo[e][1,2]oxaborinine-8-carboxylic Acid Compound 112 was prepared following the procedure (Step 3 to Step 4) described in Example 98, utilizing 2-(4-(((tert-butoxycarbonyl)(4,4,4-trifluorobutyl)amino)methyl)-1H-1,2,3-triazol-1-yl)acetic acid. The crude product was purified by reverse phase chromatography and dried using lyophilization to afford the title product as white solid. ESI-MS m/z 456 (MH)⁺.

Example 113: (R)-3-((S)-6-amino-2-(4-(aminomethyl)-1H-1,2,3-triazol-1-yl)hexanamido)-2-hydroxy-3,4-dihydro-2H-benzo[e][1,2]oxaborinine-8-carboxylic Acid

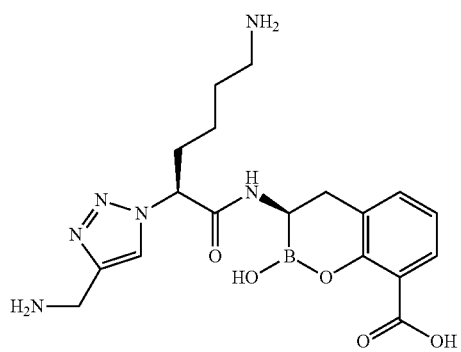 [SMILES: NCCCC[C@@H](C(=O)N[C@H]1Cc2cccc(C(=O)O)c2OB1O)n1cc(CN)nn1]

Step 1: Synthesis of (S)-6-((tert-butoxycarbonyl)amino)-2-(4-(((tert-butoxycarbonyl)amino)methyl)-1H-1,2,3-triazol-1-yl)hexanoic Acid To a mixture of (S)-(−)-2-Azido-6-(Boc-amino)hexanoic acid (dicyclohexylammonium) salt (1 mmol), N-Boc propargyl amine (1.5 mmol), CuS0.5H₂O (0.2 mmol), sodium ascorbate (0.4 mol) in ᵗBuOH/H₂O (16 mL, 1:1) in a flask was stirred at RT for 4 hr. EtOAc was the added and the organic phase was washed with 1 N HCl, water and brine. The organic phase was dried and concentrated. The product was then purified by chromatography on silica gel.

Step 2: Synthesis of (R)-3-((S)-6-amino-2-(4-(aminomethyl)-1H-1,2,3-triazol-1-yl)hexanamido)-2-hydroxy-3,4-dihydro-2H-benzo[e][1,2]oxaborinine-8-carboxylic Acid Compound 113 was prepared following the procedure (Step 3 to Step 4) described in Example 98, utilizing (S)-6-((tert-butoxycarbonyl)amino)-2-(4-(((tert-butoxycarbonyl)amino)methyl)-1H-1,2,3-triazol-1-yl)hexanoic acid. The crude product was purified by reverse phase chromatography and dried using lyophilization to afford the title product as white solid. ESI-MS m/z 417 (MH)⁺.

Example 114: (R)-3-((S)-2-amino-3-(4-(aminomethyl)-1H-1,2,3-triazol-1-yl)propanamido)-2-hydroxy-3,4-dihydro-2H-benzo[e][1,2]oxaborinine-8-carboxylic Acid

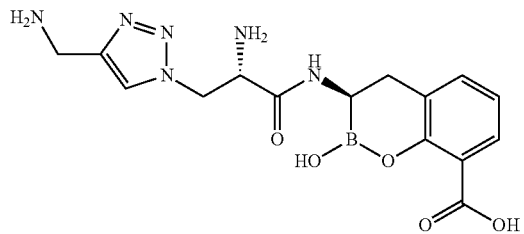 [SMILES: NCc1cn(C[C@H](N)C(=O)N[C@H]2Cc3cccc(C(=O)O)c3OB2O)nn1]

Step 1: Synthesis of (S)-2-((tert-butoxycarbonyl)amino)-3-(4-(((tert-butoxycarbonyl)amino)methyl)-1H-1,2,3-triazol-1-yl)propanoic Acid (S)-2-((tert-butoxycarbonyl)amino)-3-(4-(((tert-butoxycarbonyl)amino)methyl)-1H-1,2,3-triazol-1-yl)propanoic acid was synthesized following the same procedure from step 1 in Example 114.

Step 2: Synthesis of (R)-3-((S)-2-amino-3-(4-(aminomethyl)-1H-1,2,3-triazol-1-yl)propanamido)-2-hydroxy-3,4-dihydro-2H-benzo[e][1,2]oxaborinine-8-carboxylic Acid Compound 114 was prepared following the procedure (Step 3 to Step 4) described in Example 98, utilizing (S)-2-((tert-butoxycarbonyl)amino)-3-(4-(((tert-butoxycarbonyl)amino)methyl)-1H-1,2,3-triazol-1-yl)propanoic acid. The crude product was purified by reverse phase chromatography and dried using lyophilization to afford the title product as white solid. ESI-MS m/z 375 (MH)⁺.

Example 115: (R)-3-((S)-2-(4-(aminomethyl)-1H-1,2,3-triazol-1-yl)-4-(methylthio)butanamido)-2-hydroxy-3,4-dihydro-2H-benzo[e][1,2]oxaborinine-8-carboxylic Acid

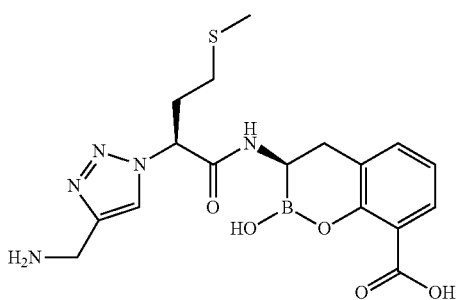 [SMILES: CSCC[C@@H](C(=O)N[C@H]1Cc2cccc(C(=O)O)c2OB1O)n1cc(CN)nn1]

Step 1: Synthesis of (S)-2-(4-(aminomethyl)-1H-1,2,3-triazol-1-yl)-4-(methylthio)butanoic Acid (S)-2-(4-(aminomethyl)-1H-1,2,3-triazol-1-yl)-4-(methylthio)butanoic acid was synthesized following the same procedure from Step 1 in Example 114.

Step 2: Synthesis of (R)-3-((S)-2-(4-(aminomethyl)-1H-1,2,3-triazol-1-yl)-4-(methylthio)butanamido)-2-hydroxy-3,4-dihydro-2H-benzo[e][1,2]oxaborinine-8-carboxylic Acid Compound 115 was prepared following the procedure (Step 3 to Step 4) described in Example 98, utilizing (S)-2-(4-(aminomethyl)-1H-1,2,3-triazol-1-yl)-4-(methylthio)butanoic acid. The crude product was purified by reverse phase chromatography and dried using lyophilization to afford the title product as white solid. ESI-MS m/z 420 (MH)+.

Example 116: (R)-3-(2-(3-borono-1H-pyrazol-1-yl)acetamido)-2-hydroxy-3,4-dihydro-2H-benzo[e][1,2]oxaborinine-8-carboxylic Acid

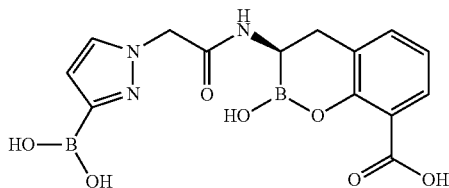 [SMILES: O=C(Cn1ccc(B(O)O)n1)N[C@H]1Cc2cccc(C(=O)O)c2OB1O]

Compound 116 was prepared following the procedure (Step 3 to Step 4) described in Example 98, utilizing 2-(3-(4,4,5,5-tetramethyl-1,3,2-dioxaborolan-2-yl)-1H-pyrazol-1-yl)acetic acid. The crude product was purified by reverse phase chromatography and dried using lyophilization to afford the title product as white solid. ESI-MS m/z 359 (MH)+.

Example 117: (R)-3-(2-(4-(2-aminoethyl)-4H-1,2,4-triazol-3-yl)acetamido)-2-hydroxy-3,4-dihydro-2H-benzo[e][1,2]oxaborinine-8-carboxylic Acid

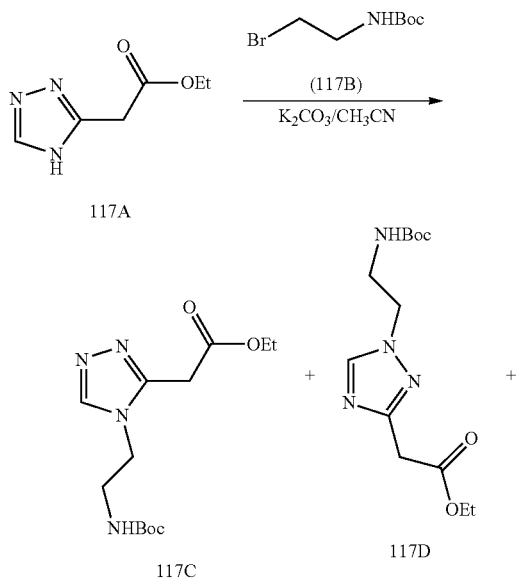

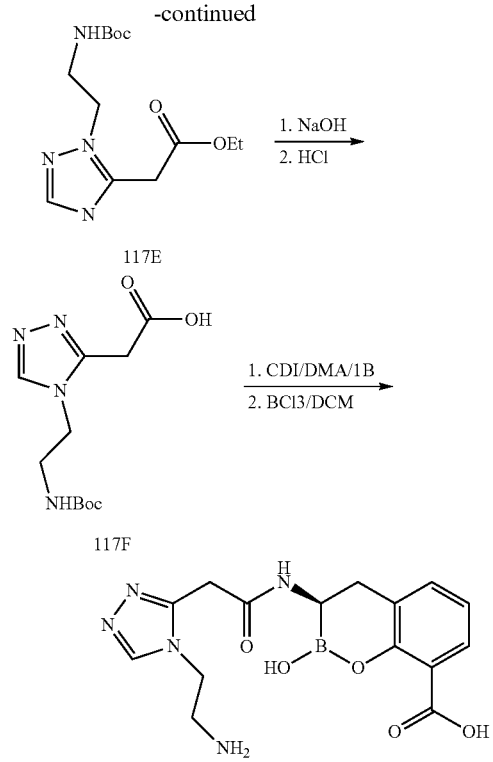

Step 1: Synthesis of Ethyl 2-(4-(2-((tert-butoxycarbonyl)amino)ethyl)-4H-1,2,4-triazol-3-yl)acetate (117C), ethyl 2-(1-(2-((tert-butoxycarbonyl)amino)ethyl)-1H-1,2,4-triazol-3-yl)acetate (17D), and Ethyl 2-(1-(2-((tert-butoxycarbonyl)amino)ethyl)-1H-1,2,4-triazol-5-yl)acetate (117E)

A mixture of 117A (1.0 g, 6.4 mmol), K₂CO₃ (1.5 g, 10.8 mmol), ᵗBu₄NHSO₄ (0.1 g) and 117B (1.5 g) in 10 mL of CH₃CN was stirred at rt for 20 hr, then, heated at 40° C. for 3 hr. After cooling to RT, the reaction mixture was quenched with water and extracted with EtOAc. The organic layer was washed with brine, concentrated under vacuum, and purified by flash chromatograph on a silica gel column (EtOAc/Hexane 0~100%) to give 117C (0.4 g), 117D (0.5 g) and 117E (0.4 g) as white solid. ESI-MS m/z 299 (MH)+.

Step 2: Synthesis of 2-(4-(2-((tert-butoxycarbonyl)amino)ethyl)-4H-1,2,4-triazol-3-yl)acetic Acid Compound 117F was prepared following the procedure Step 2 described in Example 41 from 117C, ESI-MS m/z 271 (MH)+.

Step 3: Synthesis of (R)-3-(2-(4-(2-aminoethyl)-4H-1,2,4-triazol-3-yl)acetamido)-2-hydroxy-3,4-dihydro-2H-benzo[e][1,2]oxaborinine-8-carboxylic Acid Compound 117 was prepared following the procedure (Step 3 and Step 4) described in Example 41, from 117F. ESI-MS m/z 360 (MH)+.

Example 118: (R)-3-(2-(1-(2-aminoethyl)-1H-1,2,4-triazol-3-yl)acetamido)-2-hydroxy-3,4-dihydro-2H-benzo[e][1,2]oxaborinine-8-carboxylic Acid

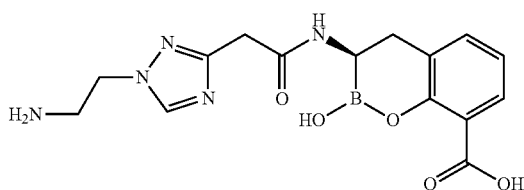 [SMILES: NCCn1cnc(CC(=O)N[C@H]2Cc3cccc(C(=O)O)c3OB2O)n1]

Compound 118 was prepared following the procedure described in Example 117, from 117D. ESI-MS m/z 360 (MH)+.

Example 119: (R)-3-(2-(1-(2-aminoethyl)-1H-1,2,4-triazol-5-yl)acetamido)-2-hydroxy-3,4-dihydro-2H-benzo[e][1,2]oxaborinine-8-carboxylic Acid

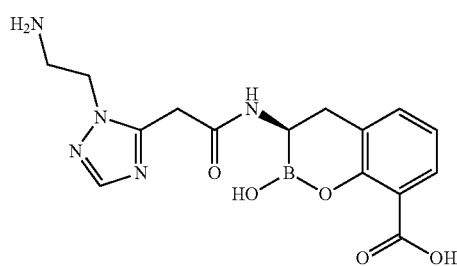 [SMILES: NCCn1ncnc1CC(=O)N[C@H]1Cc2cccc(C(=O)O)c2OB1O]

Compound 119 was prepared following the procedure (Step 2 and Step 3) described in Example 117, utilizing 117E. ESI-MS m/z 360 (MH)+.

Example 120: (R)-3-(2-(5-(aminomethyl)-4-methyl-1H-1,2,3-triazol-1-yl)acetamido)-2-hydroxy-3,4-dihydro-2H-benzo[e][1,2]oxaborinine-8-carboxylic Acid

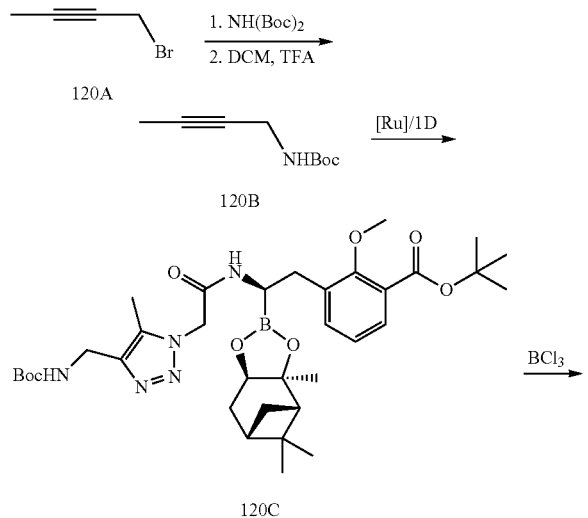

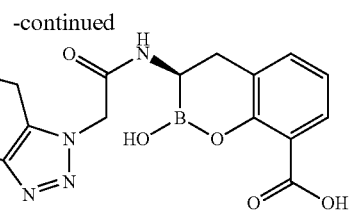

Step 1: Synthesis of tert-butyl but-2-yn-1-ylcarbamate (120B)

Compound 120B was prepared following the literature procedure (Anderson, James C., et al., *J. Org. Chem.* 2000, 65(26), 9152).

Step 2: Synthesis of tert-butyl 3-((R)-2-(2-(4-(((tert-butoxycarbonyl)amino)methyl)-5-methyl-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (120C)

Compound 120C was prepared following the procedure (Step 1) described in Example 13, from 120B and 1D using pentamethylcyclopentadienylbis(triphenylphosphine)ruthenium(II) chloride [Cp*RuCl(PPh$_3$)$_2$] as catalyst. ESI-MS m/z 682 (MH)+.

Step 3: Synthesis of (R)-3-(2-(5-(aminomethyl)-4-methyl-1H-1,2,3-triazol-1-yl)acetamido)-2-hydroxy-3,4-dihydro-2H-benzo[e][1,2]oxaborinine-8-carboxylic Acid Compound 120 was prepared following the procedure described in Example 13, Step 2, utilizing 120C. ESI-MS m/z 360 (MH)+.

Example 121: (R)-3-(2-(5-(2-aminoethyl)-1H-1,2,3-triazol-1-yl)acetamido)-2-hydroxy-3,4-dihydro-2H-benzo[e][1,2]oxaborinine-8-carboxylic Acid

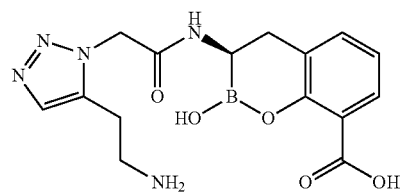

Compound 121 was prepared following the procedure described in Example 13 (Step 1 and Step 2), using tert-butyl but-3-yn-1-ylcarbamate instead of tert-butyl prop-2-yn-1-ylcarbamate. ESI-MS m/z 360 (MH)+.

Example 122: (R)-3-(2-(1-(2-aminoethyl)-1H-1,2,3-triazol-4-yl)acetamido)-2-hydroxy-3,4-dihydro-2H-benzo[e][1,2]oxaborinine-8-carboxylic Acid

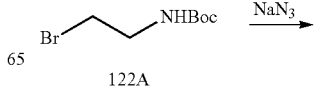

231
-continued

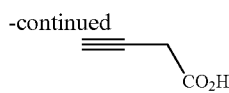

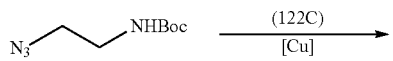

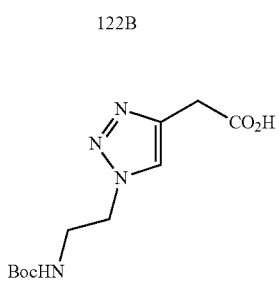

Step 1: Synthesis of tert-butyl (2-azidoethyl)carbamate (122B)

A mixture of N-(tert-butyloxycarbonyl)-2-bromoethylamine (122A, 0.2 g, 0.89 mmol) and NaN$_3$ (0.2 g, 3 mmol) in dry DMF (2 mL) was stirred at rt for 72 hr. The reaction mixture was diluted with EtOAc (6 mL), washed with water (2×3 mL) and brine. The solvent was removed under vacuum at RT to give crude 122B as colorless oil. ESI-MS m/z 209 (MNa)$^+$.

Step 2: Synthesis of 2-(1-(2-((tert-butoxycarbonyl)amino)ethyl)-1H-1,2,3-triazol-4-yl)acetic Acid A mixture of the crude 122B (0.4 g, 2.2 mmol), 122C (0.25 g, 3 mmol), CuSO$_4$.5H$_2$O (20 mg) and sodium ascorbate (0.1 g) in 5 mL of $^t$-BuOH/water (1/1) was stirred at 50° C. for 24 h. The reaction mixture was cooled to rt, concentrated and under purified by reverse Phase HPLC to give 122D as off-white solid (0.2 g). ESI-MS m/z 271 (MH)$^+$.

Step 3: Synthesis of (R)-3-(2-(1-(2-aminoethyl)-1H-1,2,3-triazol-4-yl)acetamido)-2-hydroxy-3,4-dihydro-2H-benzo[e][1,2]oxaborinine-8-carboxylic Acid Compound 122 was prepared following the procedure (Step 3 and Step 4) described in Example 41 from 122D. ESI-MS m/z 360 (MH)$^+$.

232

Example 123: (R)-3-(2-(1-((1-(2-aminoethyl)-1H-1,2,3-triazol-4-yl)methyl)-1H-tetrazol-5-yl)acetamido)-2-hydroxy-3,4-dihydro-2H-benzo[e][1,2]oxaborinine-8-carboxylic Acid

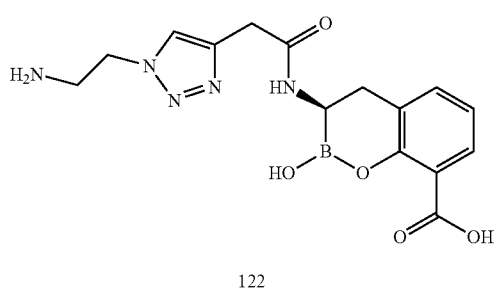

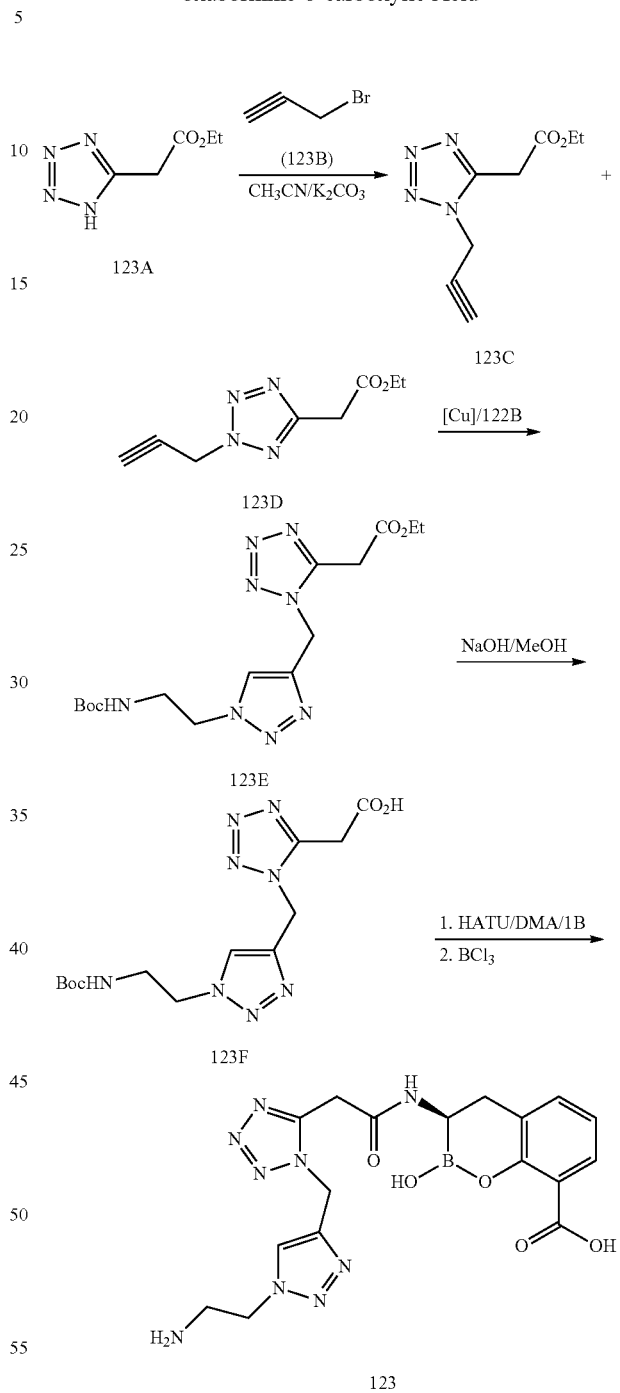

Step 1: Synthesis of ethyl 2-(1-(prop-2-yn-1-yl)-1H-tetrazol-5-yl)acetate (123C), and ethyl 2-(2-(prop-2-yn-1-yl)-2H-tetrazol-5-yl)acetate (123D)

Propargyl bromide 123B (2.5 g~80% in toluene) was added to a mixture of 123A (2.0 g) and K$_2$CO$_3$ (2.5 g) in 30 mL CH$_3$CN/DMA (25/5 V/V) at rt. The mixture was warmed to 40° C. for 24 hr. After the mixture was cooled to rt, the reaction was quenched with water, extracted with EtOAc and purified by flash chromatography on a silica gel column (EtOAc/Hexane 0~100%) to give 123C (0.7 g) and 123D (0.8 g) as colorless oil. ESI-MS m/z 195 (MH)⁺.

Step 2: Synthesis of ethyl 2-(1-((1-(2-((tert-butoxycarbonyl)amino)ethyl)-1H-1,2,3-triazol-4-yl)methyl)-1H-tetrazol-5-yl)acetate Compound 123E was prepared following the procedure described in Example 122 (Step 2), from 122B and 123C. The product was purified by flash chromatograph on a silica gel column (EtOAc/Hexane 0~100%) as colorless oil. ESI-MS m/z 381 (MH)⁺.

Step 3: Synthesis of 2-(1-((1-(2-((tert-butoxycarbonyl)amino)ethyl)-1H-1,2,3-triazol-4-yl)methyl)-1H-tetrazol-5-yl)acetic Acid Compound 123F was prepared following the procedure (Step 2) described in Example 41 from 123E. ESI-MS m/z 353 (MH)⁺.

Step 4: Synthesis of (R)-3-(2-(1-((1-(2-aminoethyl)-1H-1,2,3-triazol-4-yl)methyl)-1H-tetrazol-5-yl)acetamido)-2-hydroxy-3,4-dihydro-2H-benzo[e][1,2]oxaborinine-8-carboxylic Acid Compound 123 was prepared following the procedure described in Example 41 (Step 3 and Step 4), from 123F. ESI-MS m/z 442 (MH)⁺.

Example 124: (R)-3-(2-(2-((1-(2-aminoethyl)-1H-1,2,3-triazol-4-yl)methyl)-2H-tetrazol-5-yl)acetamido)-2-hydroxy-3,4-dihydro-2H-benzo[e][1,2]oxaborinine-8-carboxylic Acid

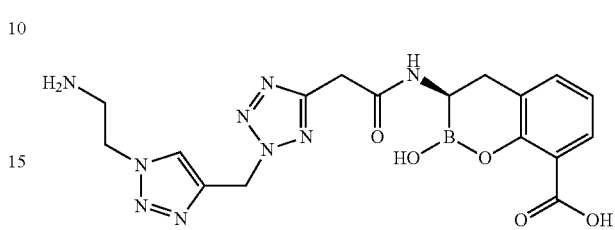

Compound 124 was prepared following the procedure described in Example 123 (Step 2 to Step 4), using 123D. ESI-MS m/z 442 (MH)⁺.

Table 1 illustrates the structures and analytical data for Example compounds.

TABLE 1

| Ex. | Structure | MW | ESI-MS (m/z) for [MH]⁺ |
|---|---|---|---|
| 1 | 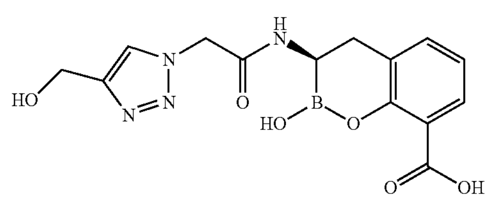 [SMILES: O=C(Cn1cc(CO)nn1)N[C@H]1Cc2cccc(C(=O)O)c2OB1O] | 346 | 347 |
| 2 | 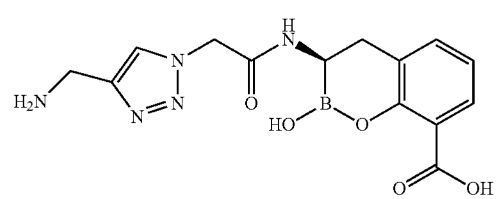 [SMILES: NCc1cn(CC(=O)N[C@H]2Cc3cccc(C(=O)O)c3OB2O)nn1] | 345 | 346 |
| 3 | 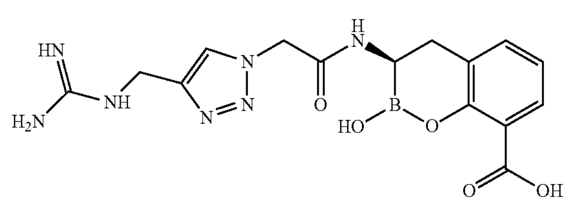 [SMILES: N=C(N)NCc1cn(CC(=O)N[C@H]2Cc3cccc(C(=O)O)c3OB2O)nn1] | 387 | 388 |

TABLE 1-continued

Example compounds 1-124

| Ex. | Structure | MW | ESI-MS (m/z) for [MH]+ |
|---|---|---|---|
| 4 | 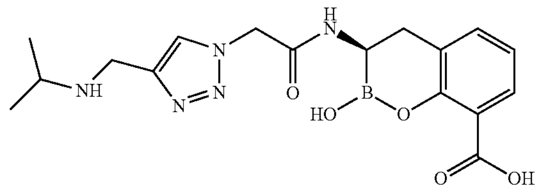 [SMILES: CC(C)NCc1cn(CC(=O)N[C@H]2Cc3cccc(C(=O)O)c3OB2O)nn1] | 387 | 388 |
| 5 | 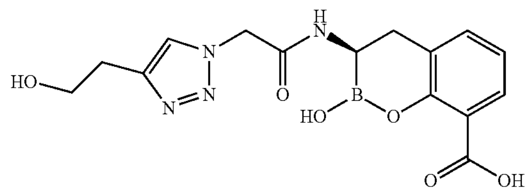 [SMILES: O=C(Cn1cc(CCO)nn1)N[C@H]1Cc2cccc(C(=O)O)c2OB1O] | 360 | 361 |
| 6 | 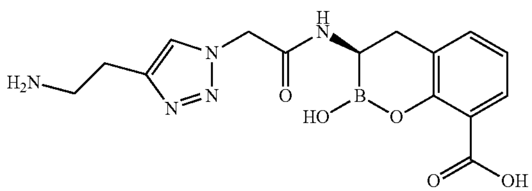 [SMILES: NCCc1cn(CC(=O)N[C@H]2Cc3cccc(C(=O)O)c3OB2O)nn1] | 359 | 360 |
| 7 | 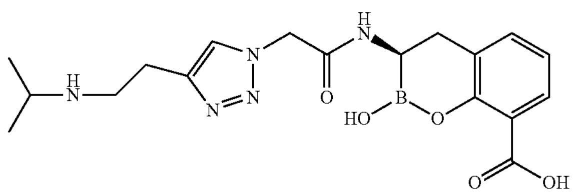 [SMILES: CC(C)NCCc1cn(CC(=O)N[C@H]2Cc3cccc(C(=O)O)c3OB2O)nn1] | 401 | 402 |
| 8 | 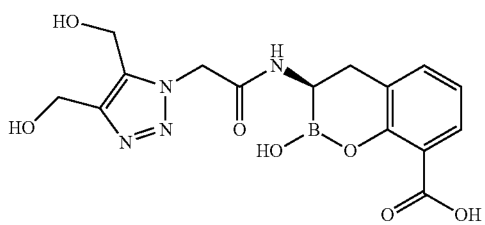 [SMILES: O=C(Cn1nnc(CO)c1CO)N[C@H]1Cc2cccc(C(=O)O)c2OB1O] | 376 | 377 |
| 9 | 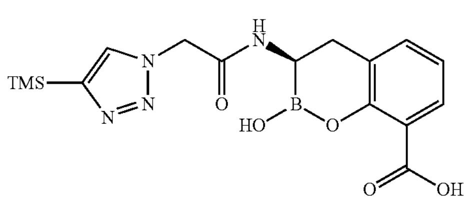 [SMILES: C[Si](C)(C)c1cn(CC(=O)N[C@H]2Cc3cccc(C(=O)O)c3OB2O)nn1] | 388 | 389 |
| 10 | 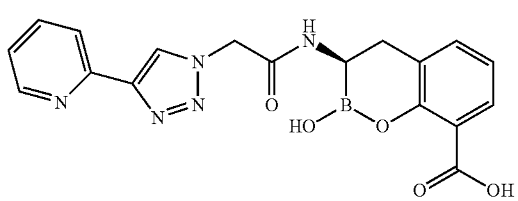 [SMILES: O=C(Cn1cc(-c2ccccn2)nn1)N[C@H]1Cc2cccc(C(=O)O)c2OB1O] | 393 | 394 |

TABLE 1-continued

Example compounds 1-124

| Ex. | Structure | MW | ESI-MS (m/z) for [MH]+ |
|---|---|---|---|
| 11 | 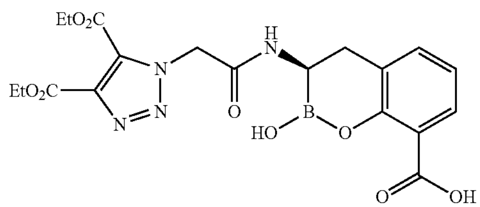 [SMILES: CCOC(=O)c1nnn(CC(=O)N[C@H]2Cc3cccc(C(=O)O)c3OB2O)c1C(=O)OCC] | 460 | 461 |
| 12 | 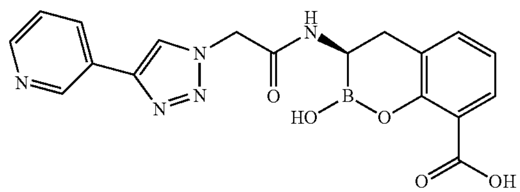 [SMILES: O=C(Cn1cc(-c2cccnc2)nn1)N[C@H]1Cc2cccc(C(=O)O)c2OB1O] | 393 | 394 |
| 13 | 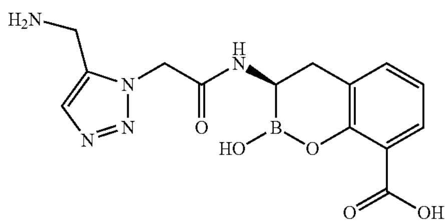 [SMILES: NCc1cnnn1CC(=O)N[C@H]1Cc2cccc(C(=O)O)c2OB1O] | 345 | 346 |
| 14 | 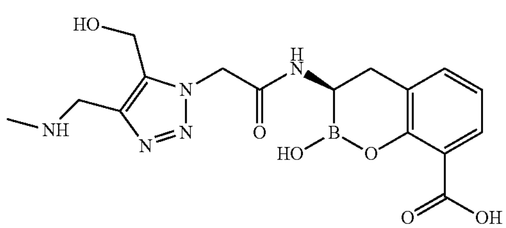 [SMILES: CNCc1nnn(CC(=O)N[C@H]2Cc3cccc(C(=O)O)c3OB2O)c1CO] | 389 | 390 |
| 15 | 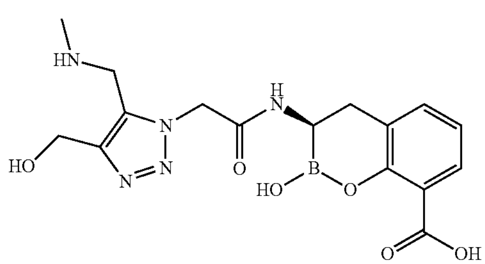 [SMILES: CNCc1c(CO)nnn1CC(=O)N[C@H]1Cc2cccc(C(=O)O)c2OB1O] | 389 | 390 |
| 16 | 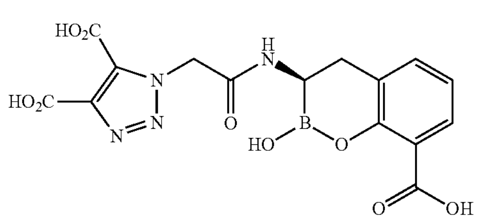 [SMILES: O=C(Cn1nnc(C(=O)O)c1C(=O)O)N[C@H]1Cc2cccc(C(=O)O)c2OB1O] | 404 | 405 |

TABLE 1-continued

Example compounds 1-124

| Ex. | Structure | MW | ESI-MS (m/z) for [MH]+ |
|---|---|---|---|
| 17 | 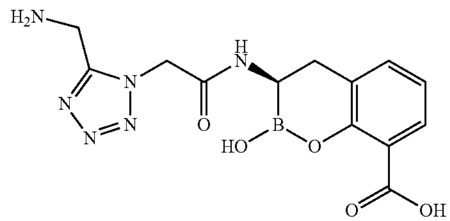 [SMILES: NCc1nnnn1CC(=O)N[C@H]1Cc2cccc(C(=O)O)c2OB1O] | 346 | 347 |
| 18 | 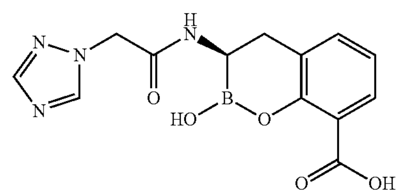 [SMILES: O=C(Cn1cncn1)N[C@H]1Cc2cccc(C(=O)O)c2OB1O] | 316 | 317 |
| 19 | 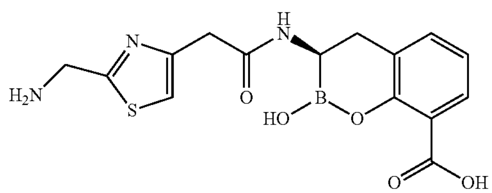 | 361 | 362 |
| 20 | 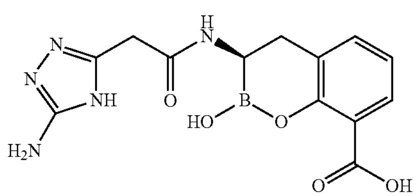 [SMILES: Nc1nnc(CC(=O)N[C@H]2Cc3cccc(C(=O)O)c3OB2O)[nH]1] | 331 | 332 |
| 21 | 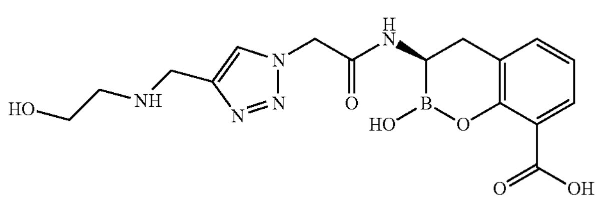 [SMILES: O=C(Cn1cc(CNCCO)nn1)N[C@H]1Cc2cccc(C(=O)O)c2OB1O] | 389 | 390 |
| 22 | 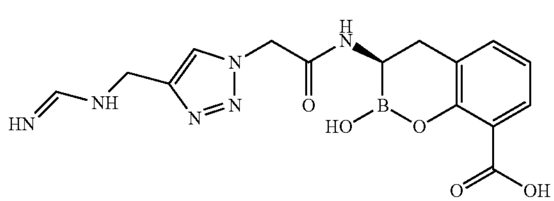 [SMILES: N=CNCc1cn(CC(=O)N[C@H]2Cc3cccc(C(=O)O)c3OB2O)nn1] | 372 | 373 |
| 23 | 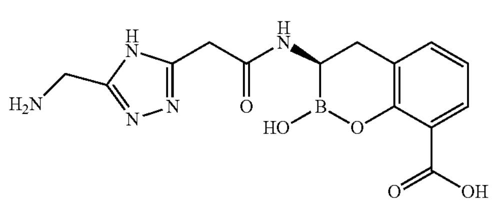 [SMILES: NCc1nnc(CC(=O)N[C@H]2Cc3cccc(C(=O)O)c3OB2O)[nH]1] | 345 | 346 |

TABLE 1-continued

Example compounds 1-124

| Ex. | Structure | MW | ESI-MS (m/z) for [MH]+ |
|---|---|---|---|
| 24 | 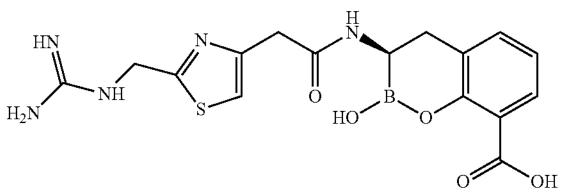 [SMILES: N=C(N)NCc1nc(CC(=O)N[C@H]2Cc3cccc(C(=O)O)c3OB2O)cs1] | 403 | 404 |
| 25 | 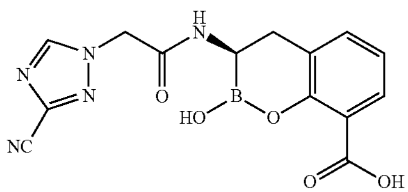 [SMILES: N#Cc1ncn(CC(=O)N[C@H]2Cc3cccc(C(=O)O)c3OB2O)n1] | 341 | 342 |
| 26 | 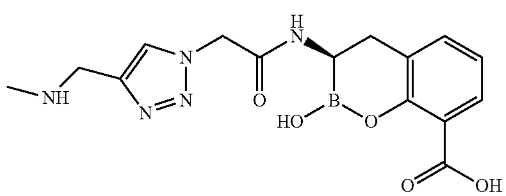 [SMILES: CNCc1cn(CC(=O)N[C@H]2Cc3cccc(C(=O)O)c3OB2O)nn1] | 359 | 360 |
| 27 | 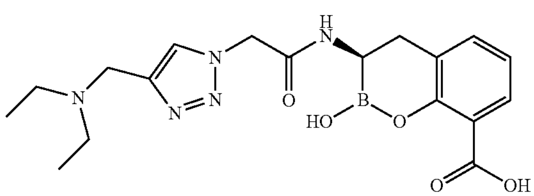 [SMILES: CCN(CC)Cc1cn(CC(=O)N[C@H]2Cc3cccc(C(=O)O)c3OB2O)nn1] | 401 | 402 |
| 28 | 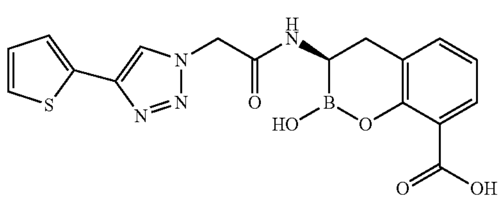 [SMILES: O=C(Cn1cc(-c2cccs2)nn1)N[C@H]1Cc2cccc(C(=O)O)c2OB1O] | 398 | 399 |
| 29 | 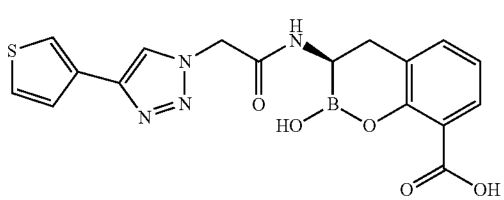 [SMILES: O=C(Cn1cc(-c2ccsc2)nn1)N[C@H]1Cc2cccc(C(=O)O)c2OB1O] | 398 | 399 |
| 30 | 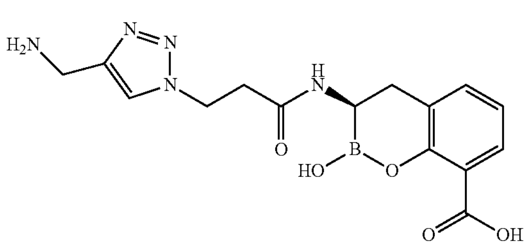 [SMILES: NCc1cn(CCC(=O)N[C@H]2Cc3cccc(C(=O)O)c3OB2O)nn1] | 359 | 360 |

TABLE 1-continued

Example compounds 1-124

| Ex. | Structure | MW | ESI-MS (m/z) for [MH]+ |
|---|---|---|---|
| 31 | 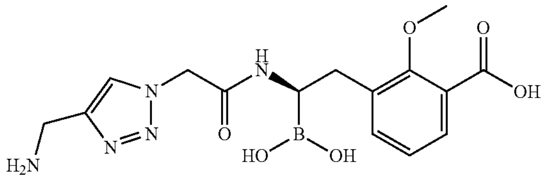 [SMILES: COc1c(C[C@H](NC(=O)Cn2cc(CN)nn2)B(O)O)cccc1C(=O)O] | 377 | 378 |
| 32 | 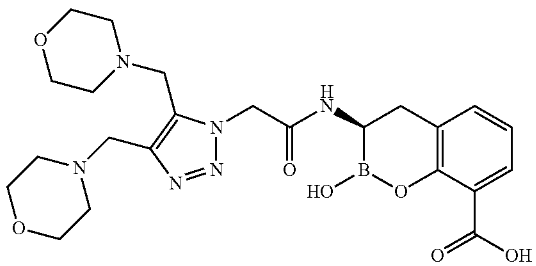 [SMILES: O=C(Cn1nnc(CN2CCOCC2)c1CN1CCOCC1)N[C@H]1Cc2cccc(C(=O)O)c2OB1O] | 514 | 515 |
| 33 | 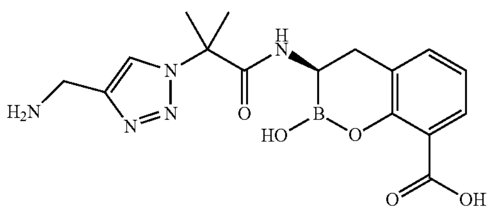 [SMILES: CC(C)(C(=O)N[C@H]1Cc2cccc(C(=O)O)c2OB1O)n1cc(CN)nn1] | 373 | 374 |
| 34 | 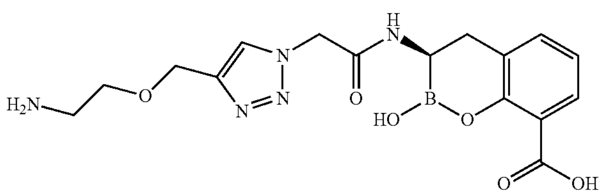 | 389 | 390 |
| 35 | 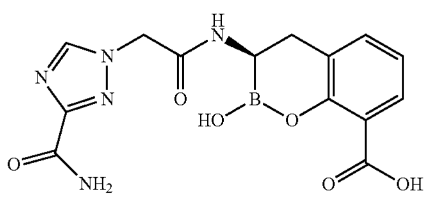 [SMILES: NC(=O)c1ncn(CC(=O)N[C@H]2Cc3cccc(C(=O)O)c3OB2O)n1] | 359 | 360 |
| 36 | 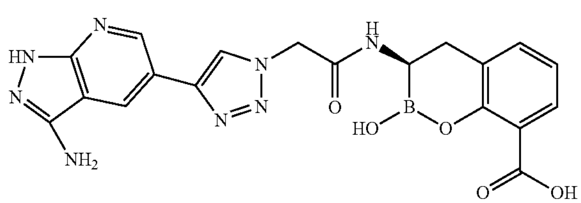 [SMILES: Nc1n[nH]c2ncc(-c3cn(CC(=O)N[C@H]4Cc5cccc(C(=O)O)c5OB4O)nn3)cc12] | 448 | 449 |
| 37 | 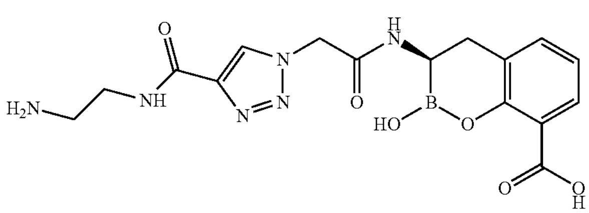 [SMILES: NCCNC(=O)c1cn(CC(=O)N[C@H]2Cc3cccc(C(=O)O)c3OB2O)nn1] | 402 | 403 |

TABLE 1-continued
Example compounds 1-124
| Ex. | Structure | MW | ESI-MS (m/z) for [MH]+ |
|---|---|---|---|
| 38 | 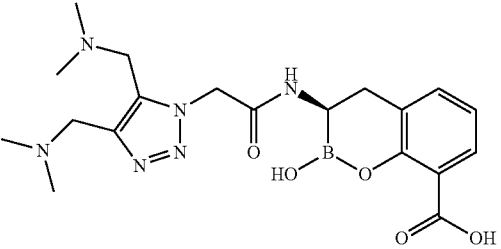 [SMILES: CN(C)Cc1nnn(CC(=O)N[C@H]2Cc3cccc(C(=O)O)c3OB2O)c1CN(C)C] | 430 | 431 |
| 39 | 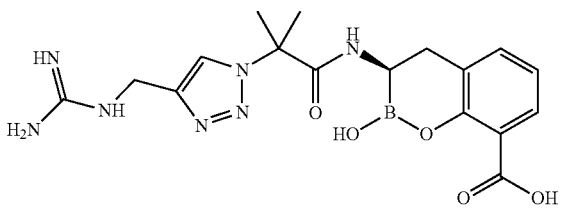 [SMILES: CC(C)(C(=O)N[C@H]1Cc2cccc(C(=O)O)c2OB1O)n1cc(CNC(=N)N)nn1] | 415 | 416 |
| 40 | 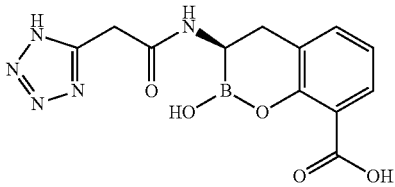 [SMILES: O=C(Cc1nnn[nH]1)N[C@H]1Cc2cccc(C(=O)O)c2OB1O] | 317 | 318 |
| 41 | 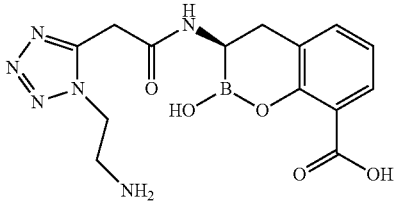 | 360 | 361 |
| 42 | 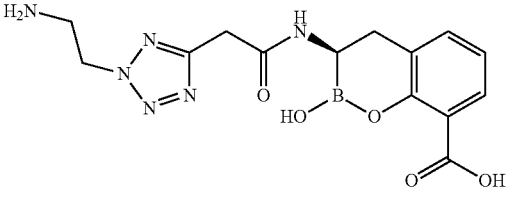 [SMILES: NCCn1nnc(CC(=O)N[C@H]2Cc3cccc(C(=O)O)c3OB2O)n1] | 360 | 361 |
| 43 | 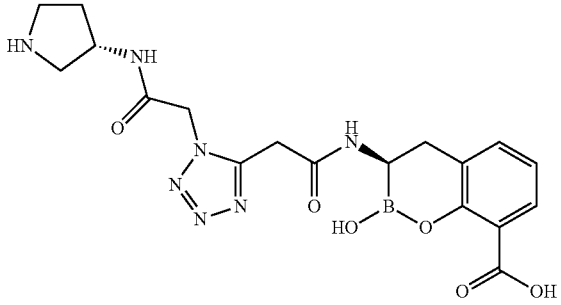 [SMILES: O=C(Cn1nnnc1CC(=O)N[C@H]1Cc2cccc(C(=O)O)c2OB1O)N[C@H]1CCNC1] | 443 | 444 |

TABLE 1-continued

Example compounds 1-124

| Ex. | Structure | MW | ESI-MS (m/z) for [MH]+ |
|---|---|---|---|
| 44 | 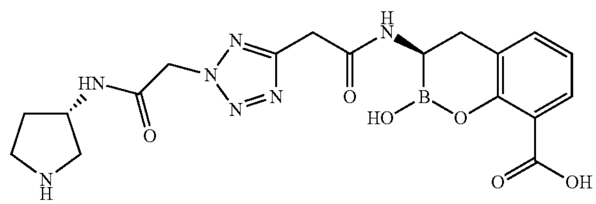 [SMILES: O=C(Cn1nnc(CC(=O)N[C@H]2Cc3cccc(C(=O)O)c3OB2O)n1)N[C@H]1CCNC1] | 443 | 444 |
| 45 | 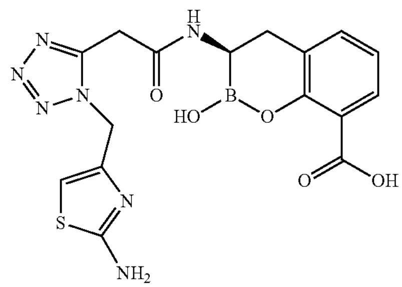 [SMILES: Nc1nc(Cn2nnnc2CC(=O)N[C@H]2Cc3cccc(C(=O)O)c3OB2O)cs1] | 429 | 430 |
| 46 | 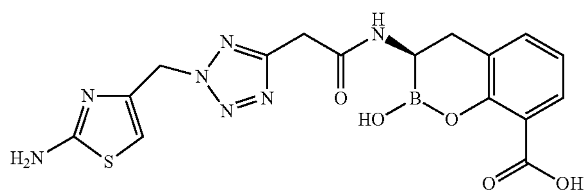 [SMILES: Nc1nc(Cn2nnc(CC(=O)N[C@H]3Cc4cccc(C(=O)O)c4OB3O)n2)cs1] | 429 | 430 |
| 47 | 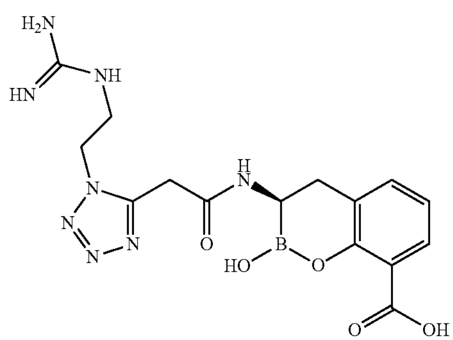 [SMILES: N=C(N)NCCn1nnnc1CC(=O)N[C@H]1Cc2cccc(C(=O)O)c2OB1O] | 402 | 403 |
| 48 | 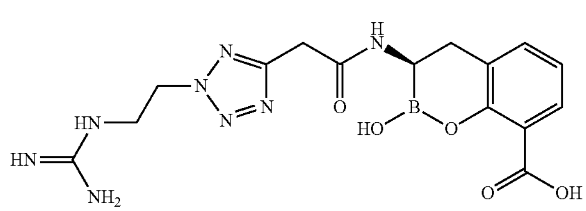 [SMILES: N=C(N)NCCn1nnc(CC(=O)N[C@H]2Cc3cccc(C(=O)O)c3OB2O)n1] | 402 | 403 |

TABLE 1-continued
Example compounds 1-124
| Ex. | Structure | MW | ESI-MS (m/z) for [MH]+ |
|---|---|---|---|
| 49 | 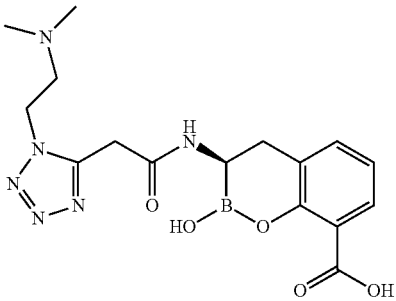 [SMILES: CN(C)CCn1nnnc1CC(=O)N[C@H]1Cc2cccc(C(=O)O)c2OB1O] | 388 | 389 |
| 50 | 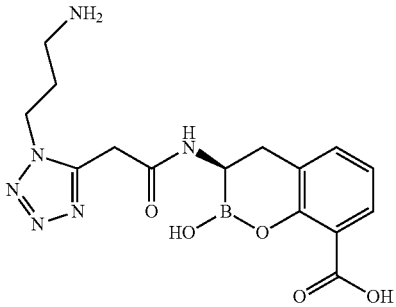 [SMILES: NCCCn1nnnc1CC(=O)N[C@H]1Cc2cccc(C(=O)O)c2OB1O] | 374 | 375 |
| 51 | 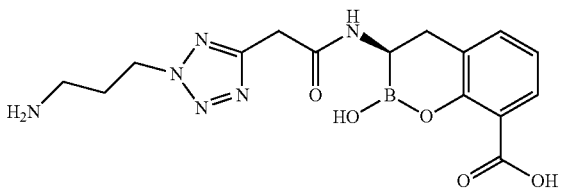 [SMILES: NCCCn1nnc(CC(=O)N[C@H]2Cc3cccc(C(=O)O)c3OB2O)n1] | 374 | 375 |
| 52 | 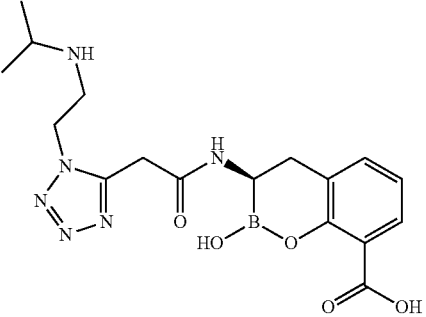 [SMILES: CC(C)NCCn1nnnc1CC(=O)N[C@H]1Cc2cccc(C(=O)O)c2OB1O] | 402 | 403 |
| 53 | 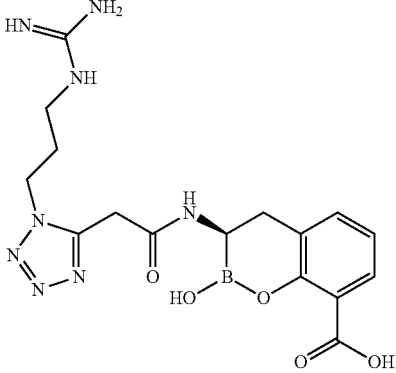 [SMILES: N=C(N)NCCCn1nnnc1CC(=O)N[C@H]1Cc2cccc(C(=O)O)c2OB1O] | 416 | 417 |

TABLE 1-continued

Example compounds 1-124

| Ex. | Structure | MW | ESI-MS (m/z) for [MH]+ |
|---|---|---|---|
| 54 | 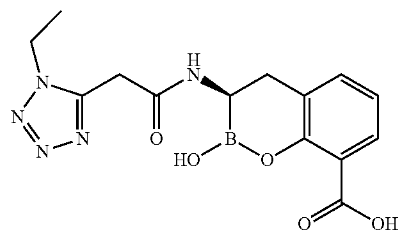 [SMILES: CCn1nnnc1CC(=O)N[C@H]1Cc2cccc(C(=O)O)c2OB1O] | 345 | 346 |
| 55 | 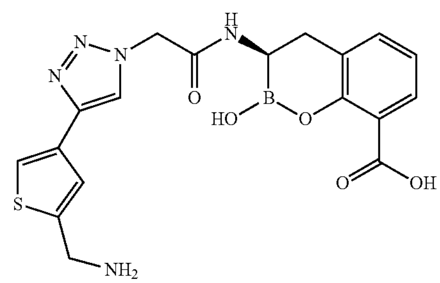 [SMILES: NCc1cc(-c2cn(CC(=O)N[C@H]3Cc4cccc(C(=O)O)c4OB3O)nn2)cs1] | 427 | 428 |
| 56 | 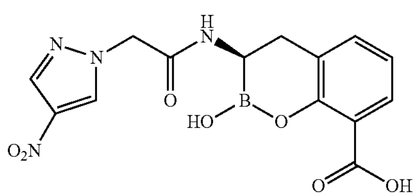 [SMILES: O=C(Cn1cc([N+](=O)[O-])cn1)N[C@H]1Cc2cccc(C(=O)O)c2OB1O] | 360 | 361 |
| 57 | 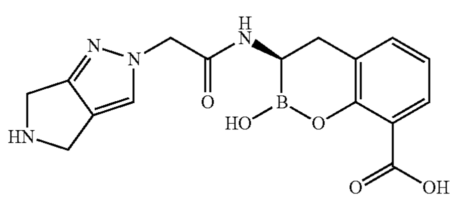 [SMILES: O=C(Cn1cc2c(n1)CNC2)N[C@H]1Cc2cccc(C(=O)O)c2OB1O] | 356 | 357 |
| 58 | 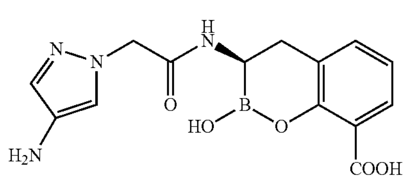 [SMILES: Nc1cnn(CC(=O)N[C@H]2Cc3cccc(C(=O)O)c3OB2O)c1] | 330 | 331 |
| 59 | 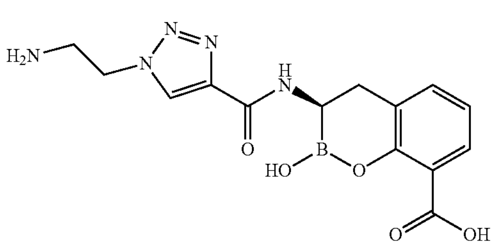 [SMILES: NCCn1cc(C(=O)N[C@H]2Cc3cccc(C(=O)O)c3OB2O)nn1] | 345 | 346 |

TABLE 1-continued

Example compounds 1-124

| Ex. | Structure | MW | ESI-MS (m/z) for [MH]+ |
|---|---|---|---|
| 60 | 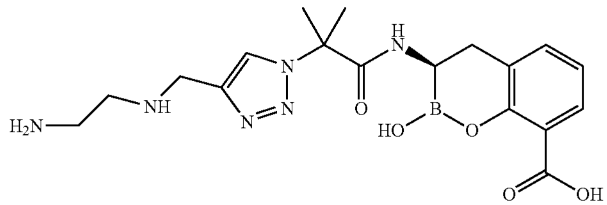 [SMILES: CC(C)(C(=O)N[C@H]1Cc2cccc(C(=O)O)c2OB1O)n1cc(CNCCN)nn1] | 416 | 417 |
| 61 | 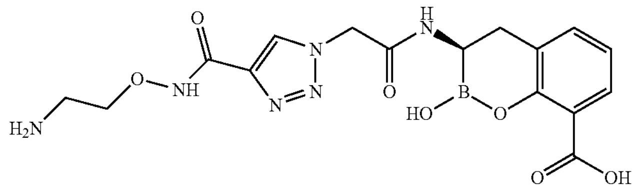 [SMILES: NCCONC(=O)c1cn(CC(=O)N[C@H]2Cc3cccc(C(=O)O)c3OB2O)nn1] | 418 | 419 |
| 62 | 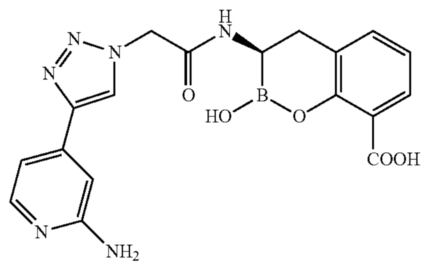 [SMILES: Nc1cc(-c2cn(CC(=O)N[C@H]3Cc4cccc(C(=O)O)c4OB3O)nn2)ccn1] | 408 | 409 |
| 63 | 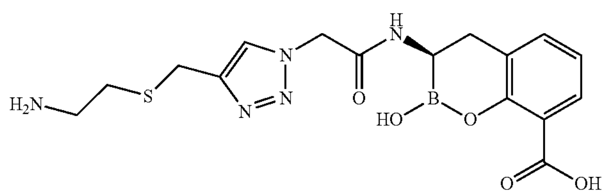 [SMILES: NCCSCc1cn(CC(=O)N[C@H]2Cc3cccc(C(=O)O)c3OB2O)nn1] | 405 | 406 |
| 64 | 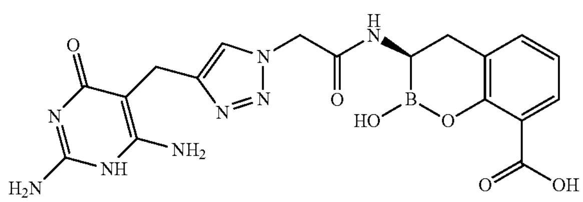 [SMILES: Nc1nc(=O)c(Cc2cn(CC(=O)N[C@H]3Cc4cccc(C(=O)O)c4OB3O)nn2)c(N)[nH]1] | 454 | 455 |
| 65 | 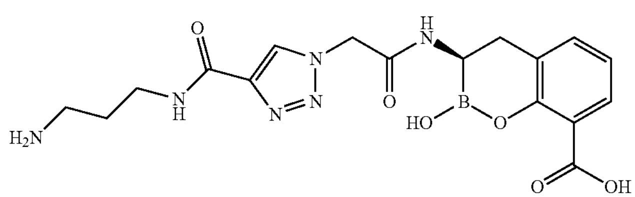 [SMILES: NCCCNC(=O)c1cn(CC(=O)N[C@H]2Cc3cccc(C(=O)O)c3OB2O)nn1] | 416 | 417 |
| 66 | 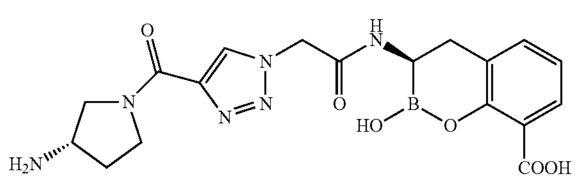 [SMILES: N[C@H]1CCN(C(=O)c2cn(CC(=O)N[C@H]3Cc4cccc(C(=O)O)c4OB3O)nn2)C1] | 428 | 429 |

TABLE 1-continued
Example compounds 1-124
| Ex. | Structure | MW | ESI-MS (m/z) for [MH]+ |
|---|---|---|---|
| 67 | 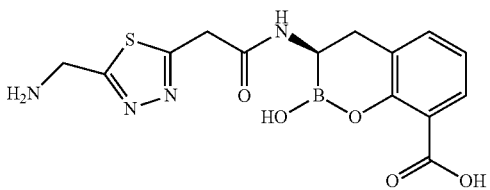 | 362 | 363 |
| 68 | 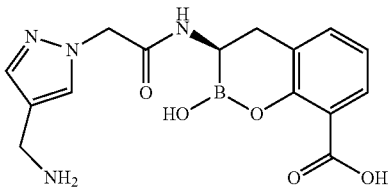 [SMILES: NCc1cnn(CC(=O)N[C@H]2Cc3cccc(C(=O)O)c3OB2O)c1] | 344 | 345 |
| 69 | 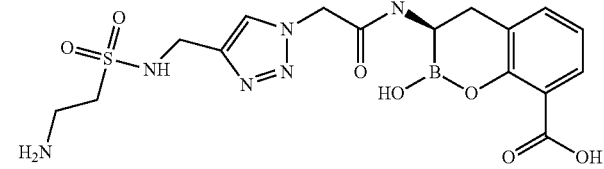 | 452 | 453 |
| 70 | 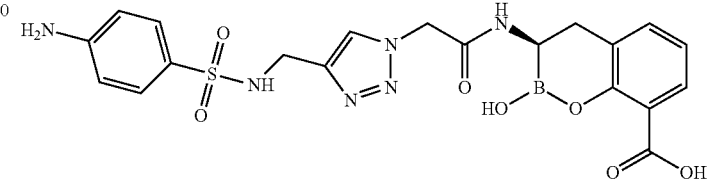 | 500 | 501 |
| 71 | 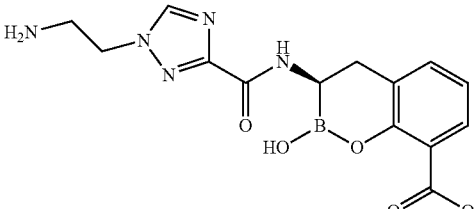 | 345 | 346 |
| 72 | 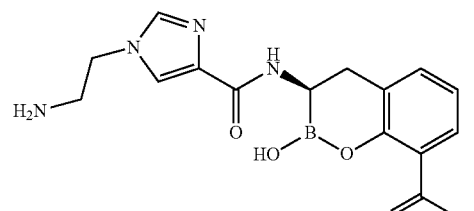 | 345 | 346 |
| 73 | 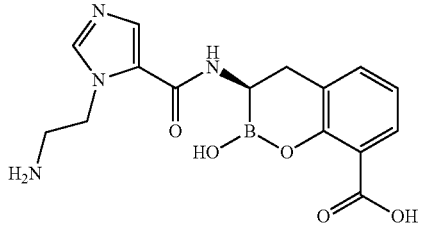 [SMILES: NCCn1cncc1C(=O)N[C@H]1Cc2cccc(C(=O)O)c2OB1O] | 345 | 346 |

TABLE 1-continued

Example compounds 1-124

| Ex. | Structure | MW | ESI-MS (m/z) for [MH]+ |
|---|---|---|---|
| 74 | 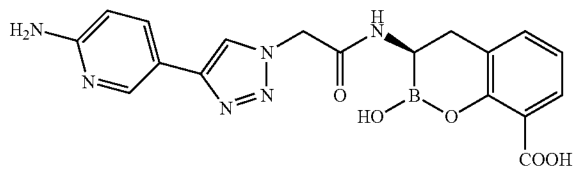 [SMILES: Nc1ccc(-c2cn(CC(=O)N[C@H]3Cc4cccc(C(=O)O)c4OB3O)nn2)cn1] | 408 | 409 |
| 75 | 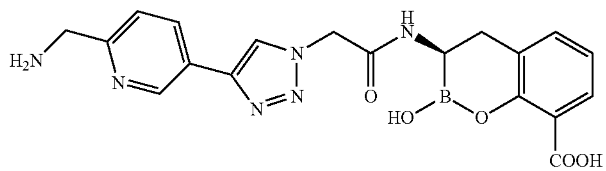 [SMILES: NCc1ccc(-c2cn(CC(=O)N[C@H]3Cc4cccc(C(=O)O)c4OB3O)nn2)cn1] | 422 | 423 |
| 76 | 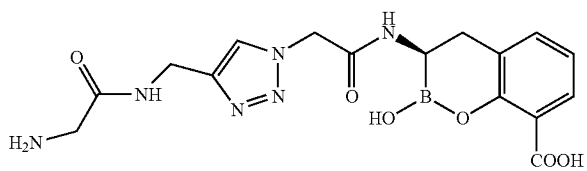 [SMILES: NCC(=O)NCc1cn(CC(=O)N[C@H]2Cc3cccc(C(=O)O)c3OB2O)nn1] | 402 | 403 |
| 77 | 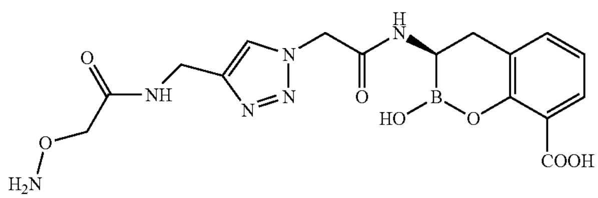 [SMILES: NOCC(=O)NCc1cn(CC(=O)N[C@H]2Cc3cccc(C(=O)O)c3OB2O)nn1] | 418 | 419 |
| 78 | 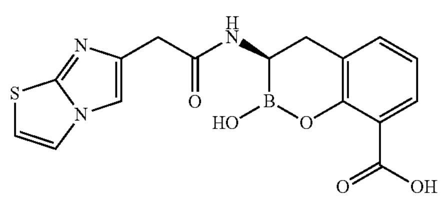 [SMILES: O=C(Cc1cn2ccsc2n1)N[C@H]1Cc2cccc(C(=O)O)c2OB1O] | 371 | 372 |
| 79 | 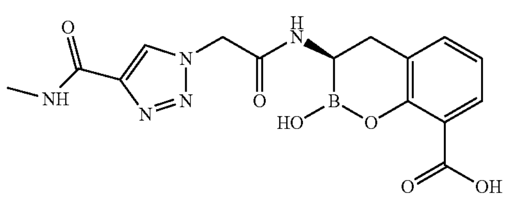 [SMILES: CNC(=O)c1cn(CC(=O)N[C@H]2Cc3cccc(C(=O)O)c3OB2O)nn1] | 373 | 374 |
| 80 | 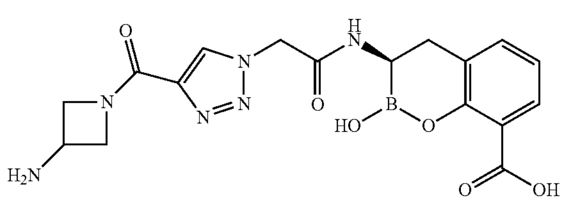 [SMILES: NC1CN(C(=O)c2cn(CC(=O)N[C@H]3Cc4cccc(C(=O)O)c4OB3O)nn2)C1] | 414 | 415 |
| 81 | 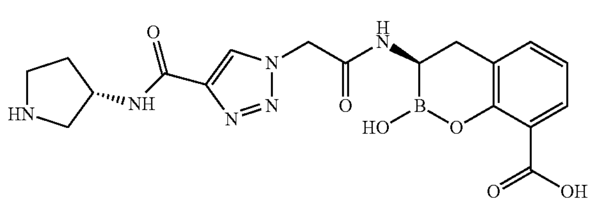 [SMILES: O=C(Cn1cc(C(=O)N[C@H]2CCNC2)nn1)N[C@H]1Cc2cccc(C(=O)O)c2OB1O] | 428 | 429 |

TABLE 1-continued

Example compounds 1-124

| Ex. | Structure | MW | ESI-MS (m/z) for [MH]+ |
|---|---|---|---|
| 82 | 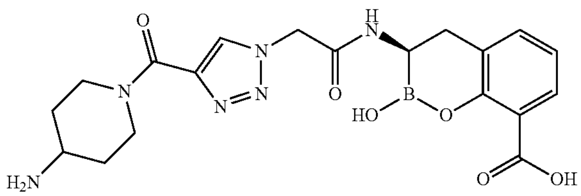 [SMILES: NC1CCN(C(=O)c2cn(CC(=O)N[C@H]3Cc4cccc(C(=O)O)c4OB3O)nn2)CC1] | 442 | 443 |
| 83 | 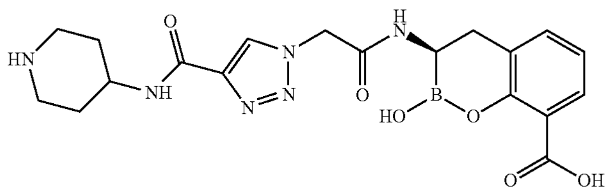 [SMILES: O=C(Cn1cc(C(=O)NC2CCNCC2)nn1)N[C@H]1Cc2cccc(C(=O)O)c2OB1O] | 442 | 443 |
| 84 | 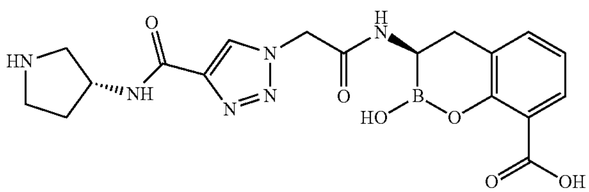 [SMILES: O=C(Cn1cc(C(=O)N[C@@H]2CCNC2)nn1)N[C@H]1Cc2cccc(C(=O)O)c2OB1O] | 428 | 429 |
| 85 | 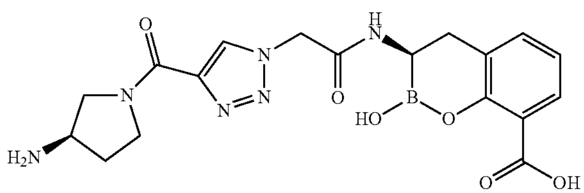 [SMILES: N[C@@H]1CCN(C(=O)c2cn(CC(=O)N[C@H]3Cc4cccc(C(=O)O)c4OB3O)nn2)C1] | 428 | 429 |
| 86 | 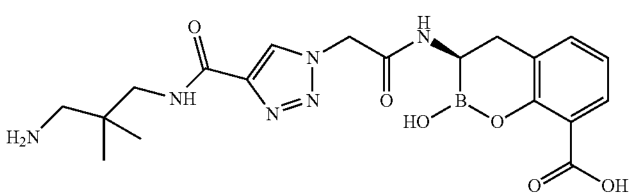 [SMILES: CC(C)(CN)CNC(=O)c1cn(CC(=O)N[C@H]2Cc3cccc(C(=O)O)c3OB2O)nn1] | 444 | 445 |
| 87 | 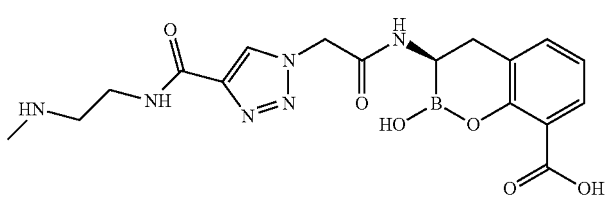 [SMILES: CNCCNC(=O)c1cn(CC(=O)N[C@H]2Cc3cccc(C(=O)O)c3OB2O)nn1] | 416 | 417 |
| 88 | 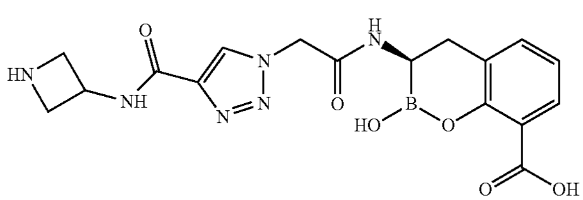 [SMILES: O=C(Cn1cc(C(=O)NC2CNC2)nn1)N[C@H]1Cc2cccc(C(=O)O)c2OB1O] | 414 | 415 |

TABLE 1-continued

Example compounds 1-124

| Ex. | Structure | MW | ESI-MS (m/z) for [MH]+ |
|---|---|---|---|
| 89 | 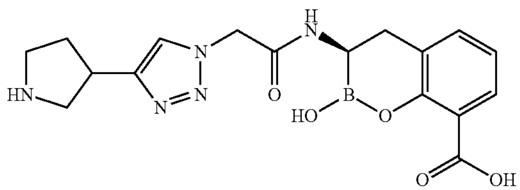 [SMILES: O=C(Cn1cc(C2CCNC2)nn1)N[C@H]1Cc2cccc(C(=O)O)c2OB1O] | 385 | 386 |
| 90 | 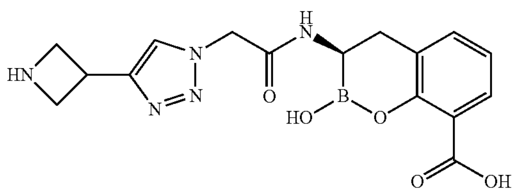 [SMILES: O=C(Cn1cc(C2CNC2)nn1)N[C@H]1Cc2cccc(C(=O)O)c2OB1O] | 371 | 372 |
| 91 | 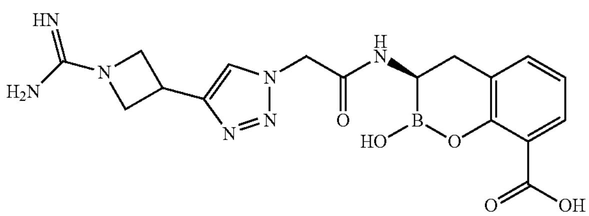 [SMILES: N=C(N)N1CC(c2cn(CC(=O)N[C@H]3Cc4cccc(C(=O)O)c4OB3O)nn2)C1] | 413 | 414 |
| 92 | 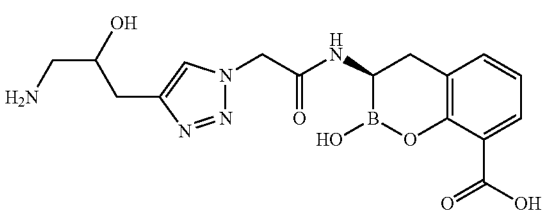 [SMILES: NCC(O)Cc1cn(CC(=O)N[C@H]2Cc3cccc(C(=O)O)c3OB2O)nn1] | 389 | 390 |
| 93 | 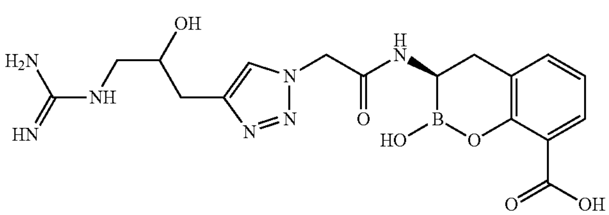 [SMILES: N=C(N)NCC(O)Cc1cn(CC(=O)N[C@H]2Cc3cccc(C(=O)O)c3OB2O)nn1] | 431 | 432 |
| 94 | 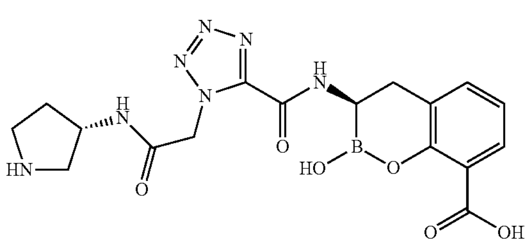 [SMILES: O=C(Cn1nnnc1C(=O)N[C@H]1Cc2cccc(C(=O)O)c2OB1O)N[C@H]1CCNC1] | 429 | 430 |

TABLE 1-continued

Example compounds 1-124

| Ex. | Structure | MW | ESI-MS (m/z) for [MH]+ |
|---|---|---|---|
| 95 | 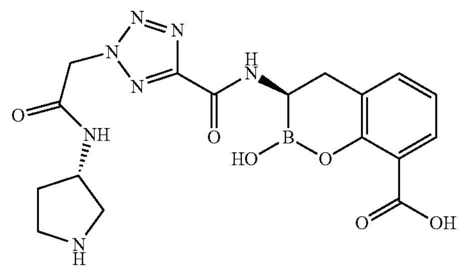 [SMILES: O=C(Cn1nnc(C(=O)N[C@H]2Cc3cccc(C(=O)O)c3OB2O)n1)N[C@H]1CCNC1] | 429 | 430 |
| 96 | 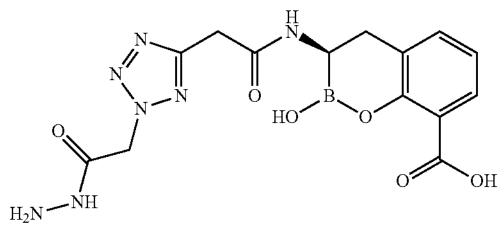 [SMILES: NNC(=O)Cn1nnc(CC(=O)N[C@H]2Cc3cccc(C(=O)O)c3OB2O)n1] | 389 | 390 |
| 97 | 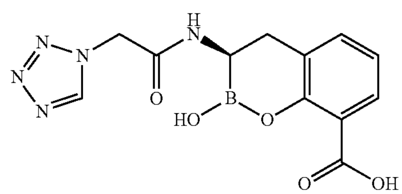 [SMILES: O=C(Cn1cnnn1)N[C@H]1Cc2cccc(C(=O)O)c2OB1O] | 317 | 318 |
| 98 | 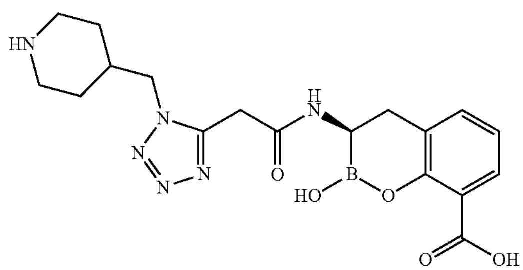 [SMILES: O=C(Cc1nnnn1CC1CCNCC1)N[C@H]1Cc2cccc(C(=O)O)c2OB1O] | 414 | 415 |
| 99 | 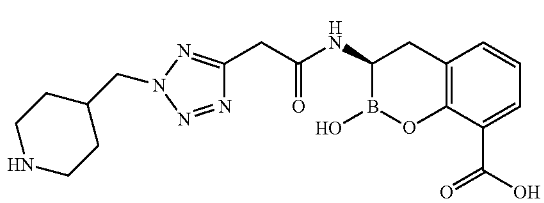 [SMILES: O=C(Cc1nnn(CC2CCNCC2)n1)N[C@H]1Cc2cccc(C(=O)O)c2OB1O] | 414 | 415 |
| 100 | 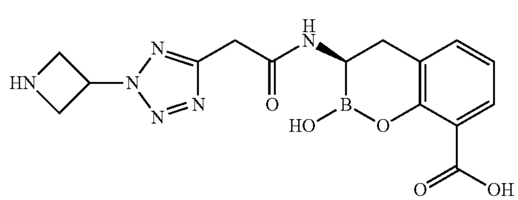 [SMILES: O=C(Cc1nnn(C2CNC2)n1)N[C@H]1Cc2cccc(C(=O)O)c2OB1O] | 372 | 373 |

TABLE 1-continued

Example compounds 1-124

| Ex. | Structure | MW | ESI-MS (m/z) for [MH]+ |
|---|---|---|---|
| 101 | 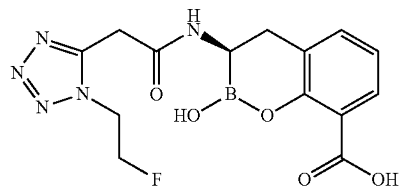 [SMILES: O=C(Cc1nnnn1CCF)N[C@H]1Cc2cccc(C(=O)O)c2OB1O] | 363 | 364 |
| 102 | 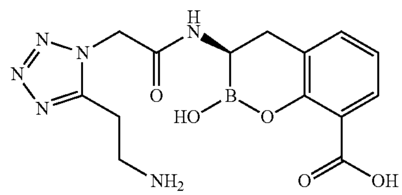 [SMILES: NCCc1nnnn1CC(=O)N[C@H]1Cc2cccc(C(=O)O)c2OB1O] | 360 | 361 |
| 103 | 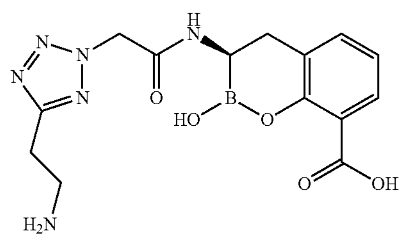 [SMILES: NCCc1nnn(CC(=O)N[C@H]2Cc3cccc(C(=O)O)c3OB2O)n1] | 360 | 361 |
| 104 | 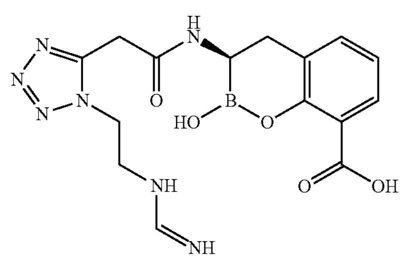 [SMILES: N=CNCCn1nnnc1CC(=O)N[C@H]1Cc2cccc(C(=O)O)c2OB1O] | 387 | 388 |
| 105 | 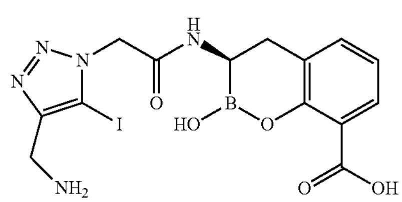 [SMILES: NCc1nnn(CC(=O)N[C@H]2Cc3cccc(C(=O)O)c3OB2O)c1I] | 471 | 472 |
| 106 | 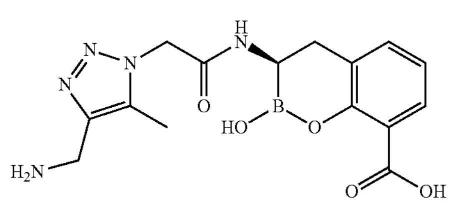 [SMILES: Cc1c(CN)nnn1CC(=O)N[C@H]1Cc2cccc(C(=O)O)c2OB1O] | 359 | 360 |
| 107 | 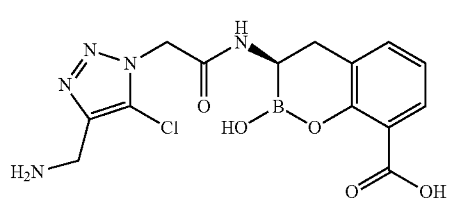 [SMILES: NCc1nnn(CC(=O)N[C@H]2Cc3cccc(C(=O)O)c3OB2O)c1Cl] | 379 | 380 |

TABLE 1-continued

Example compounds 1-124

| Ex. | Structure | MW | ESI-MS (m/z) for [MH]+ |
|---|---|---|---|
| 108 | 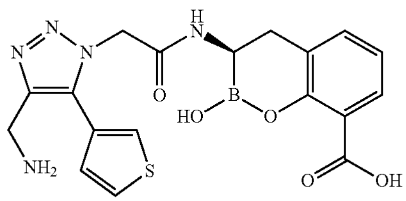 [SMILES: NCc1nnn(CC(=O)N[C@H]2Cc3cccc(C(=O)O)c3OB2O)c1-c1ccsc1] | 426 | 427 |
| 109 | 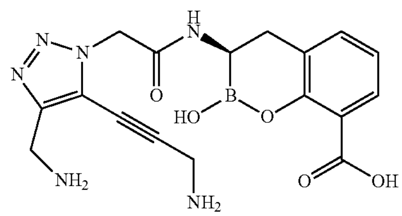 [SMILES: NCC#Cc1c(CN)nnn1CC(=O)N[C@H]1Cc2cccc(C(=O)O)c2OB1O] | 398 | 399 |
| 110 | 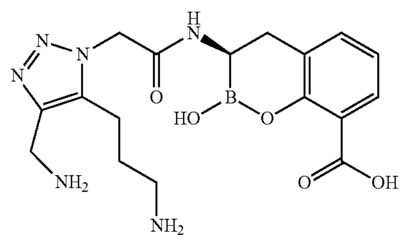 [SMILES: NCCCc1c(CN)nnn1CC(=O)N[C@H]1Cc2cccc(C(=O)O)c2OB1O] | 402 | 403 |
| 111 | 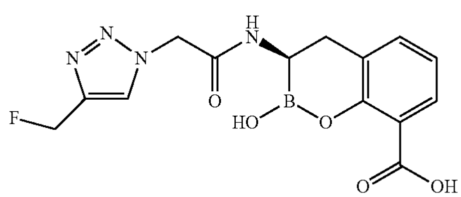 [SMILES: O=C(Cn1cc(CF)nn1)N[C@H]1Cc2cccc(C(=O)O)c2OB1O] | 348 | 349 |
| 112 | 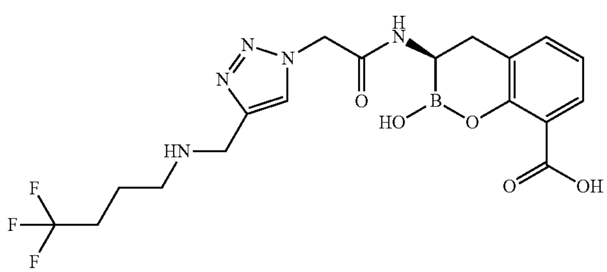 [SMILES: O=C(Cn1cc(CNCCCC(F)(F)F)nn1)N[C@H]1Cc2cccc(C(=O)O)c2OB1O] | 455 | 456 |
| 113 | 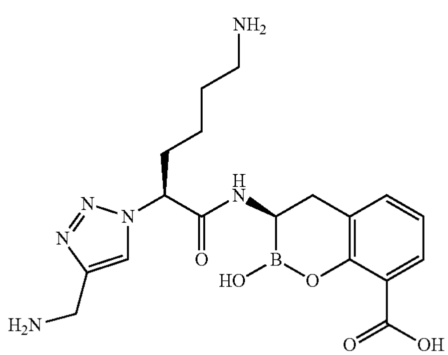 [SMILES: NCCCC[C@@H](C(=O)N[C@H]1Cc2cccc(C(=O)O)c2OB1O)n1cc(CN)nn1] | 416 | 417 |

TABLE 1-continued

Example compounds 1-124

| Ex. | Structure | MW | ESI-MS (m/z) for [MH]+ |
|---|---|---|---|
| 114 | 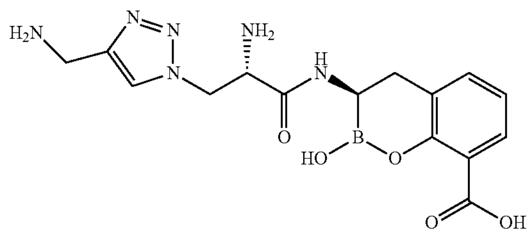 [SMILES: NCc1cn(C[C@H](N)C(=O)N[C@H]2Cc3cccc(C(=O)O)c3OB2O)nn1] | 374 | 375 |
| 115 | 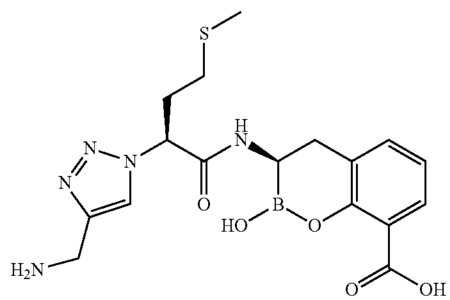 [SMILES: CSCC[C@@H](C(=O)N[C@H]1Cc2cccc(C(=O)O)c2OB1O)n1cc(CN)nn1] | 419 | 420 |
| 116 | 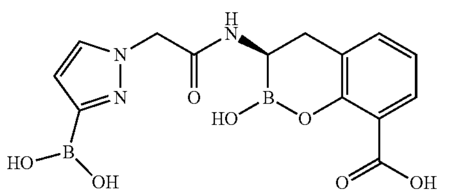 [SMILES: O=C(Cn1ccc(B(O)O)n1)N[C@H]1Cc2cccc(C(=O)O)c2OB1O] | 358 | 359 |
| 117 | 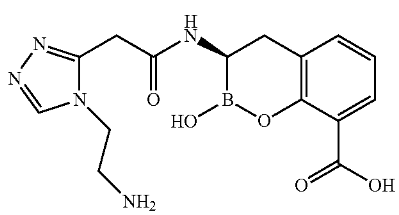 [SMILES: NCCn1cnnc1CC(=O)N[C@H]1Cc2cccc(C(=O)O)c2OB1O] | 359 | 360 |
| 118 | 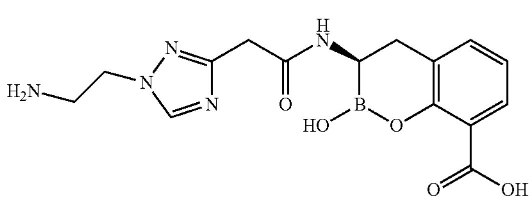 [SMILES: NCCn1cnc(CC(=O)N[C@H]2Cc3cccc(C(=O)O)c3OB2O)n1] | 359 | 360 |
| 119 | 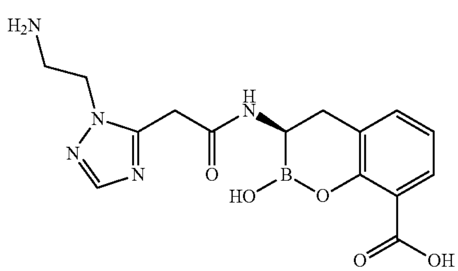 [SMILES: NCCn1ncnc1CC(=O)N[C@H]1Cc2cccc(C(=O)O)c2OB1O] | 359 | 360 |

271 272

TABLE 1-continued

Example compounds 1-124

| Ex. | Structure | MW | ESI-MS (m/z) for [MH]+ |
|---|---|---|---|
| 120 | 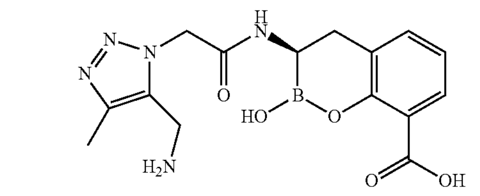 [SMILES: Cc1nnn(CC(=O)N[C@H]2Cc3cccc(C(=O)O)c3OB2O)c1CN] | 359 | 360 |
| 121 | 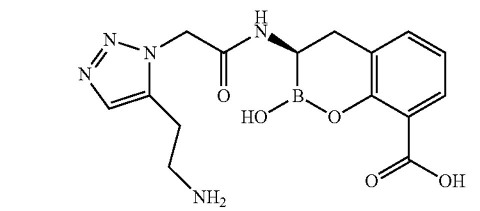 [SMILES: NCCc1cnnn1CC(=O)N[C@H]1Cc2cccc(C(=O)O)c2OB1O] | 359 | 360 |
| 122 | 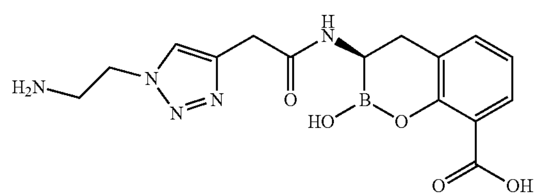 [SMILES: NCCn1cc(CC(=O)N[C@H]2Cc3cccc(C(=O)O)c3OB2O)nn1] | 359 | 360 |
| 123 | 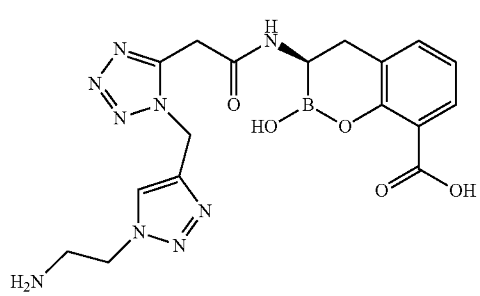 [SMILES: NCCn1cc(Cn2nnnc2CC(=O)N[C@H]2Cc3cccc(C(=O)O)c3OB2O)nn1] | 380 | 381 |
| 124 | 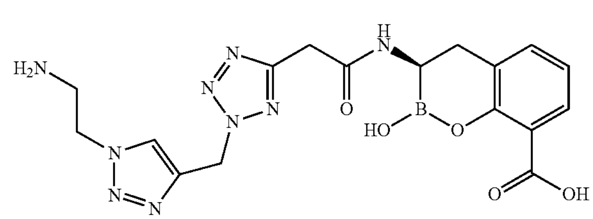 [SMILES: NCCn1cc(Cn2nnc(CC(=O)N[C@H]3Cc4cccc(C(=O)O)c4OB3O)n2)nn1] | 441 | 442 |

Examples 125-141 in Table 2 are synthesized as described for Examples 1-124.

TABLE 2
Examples 125-141
| Ex. | Structure |
|---|---|
| 125 | 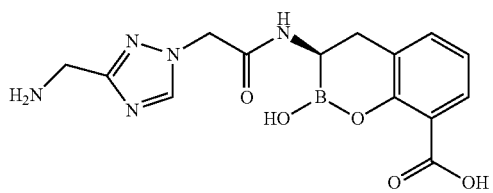 |
| 126 | 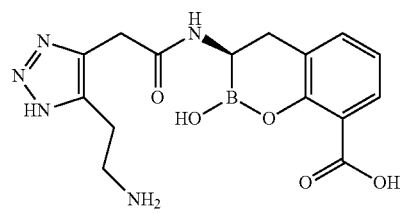 [SMILES: NCCc1[nH]nnc1CC(=O)N[C@H]1Cc2cccc(C(=O)O)c2OB1O] |
| 127 | 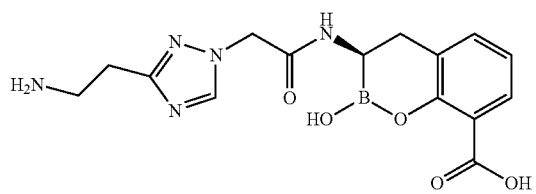 [SMILES: NCCc1ncn(CC(=O)N[C@H]2Cc3cccc(C(=O)O)c3OB2O)n1] |
| 128 | 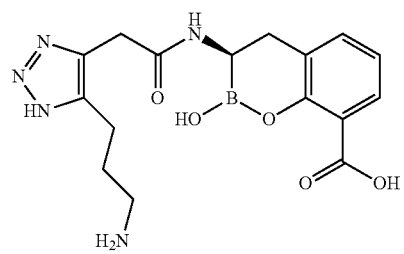 [SMILES: NCCCc1[nH]nnc1CC(=O)N[C@H]1Cc2cccc(C(=O)O)c2OB1O] |
| 129 | 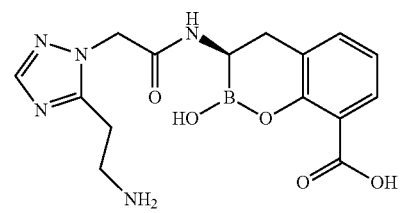 [SMILES: NCCc1ncnn1CC(=O)N[C@H]1Cc2cccc(C(=O)O)c2OB1O] |
| 130 | 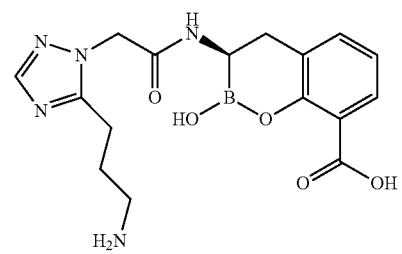 [SMILES: NCCCc1ncnn1CC(=O)N[C@H]1Cc2cccc(C(=O)O)c2OB1O] |

TABLE 2-continued
Examples 125-141
| Ex. | Structure |
|---|---|
| 131 | 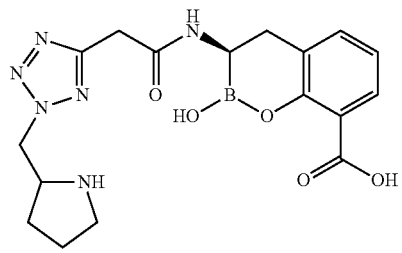 [SMILES: O=C(Cc1nnn(CC2CCCN2)n1)N[C@H]1Cc2cccc(C(=O)O)c2OB1O] |
| 132 | 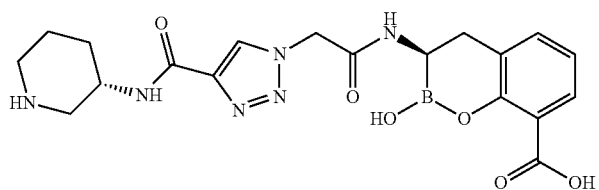 [SMILES: O=C(Cn1cc(C(=O)N[C@H]2CCCNC2)nn1)N[C@H]1Cc2cccc(C(=O)O)c2OB1O] |
| 133 | 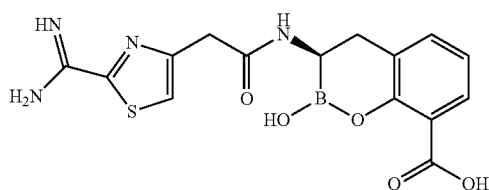 [SMILES: N=C(N)c1nc(CC(=O)N[C@H]2Cc3cccc(C(=O)O)c3OB2O)cs1] |
| 134 | 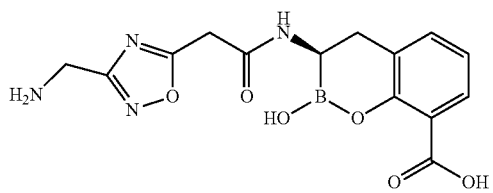 [SMILES: NCc1noc(CC(=O)N[C@H]2Cc3cccc(C(=O)O)c3OB2O)n1] |
| 135 | 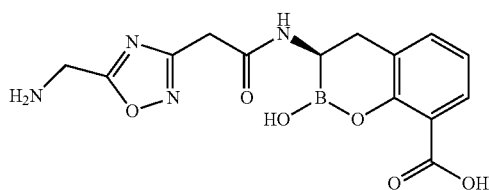 |
| 136 | 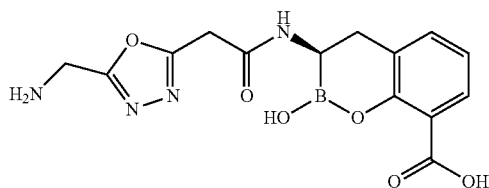 |
| 137 | 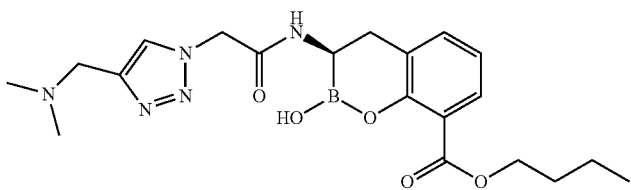 [SMILES: CCCCOC(=O)c1cccc2c1OB(O)[C@@H](NC(=O)Cn1cc(CN(C)C)nn1)C2] |

TABLE 2-continued
Examples 125-141
| Ex. | Structure |
|---|---|
| 138 | 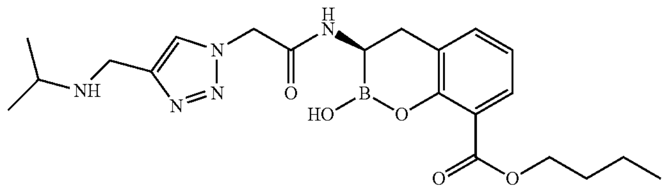 [SMILES: CCCCOC(=O)c1cccc2c1OB(O)[C@@H](NC(=O)Cn1cc(CNC(C)C)nn1)C2] |
| 139 | 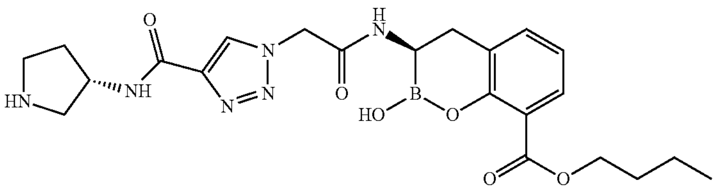 [SMILES: CCCCOC(=O)c1cccc2c1OB(O)[C@@H](NC(=O)Cn1cc(C(=O)N[C@H]3CCNC3)nn1)C2] |
| 140 | 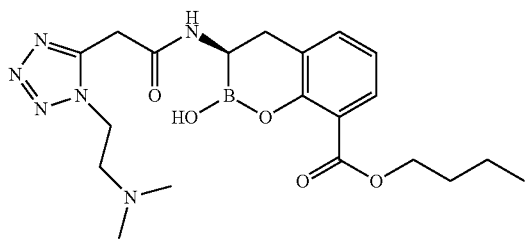 [SMILES: CCCCOC(=O)c1cccc2c1OB(O)[C@@H](NC(=O)Cc1nnnn1CCN(C)C)C2] |
| 141 | 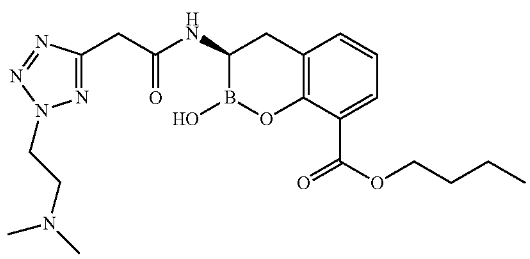 [SMILES: CCCCOC(=O)c1cccc2c1OB(O)[C@@H](NC(=O)Cc1nnn(CCN(C)C)n1)C2] |
Example 142: (R)-3-(2-(1-((1-(2-aminoethyl)-1H-1,
2,3-triazol-4-yl)methyl)-1H-tetrazol-5-yl)acet-
amido)-2-hydroxy-3,4-dihydro-2H-benzo[e][1,2]
oxaborinine-8-carboxylic Acid
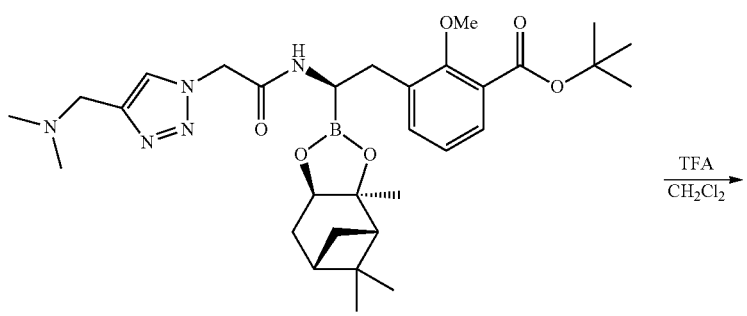

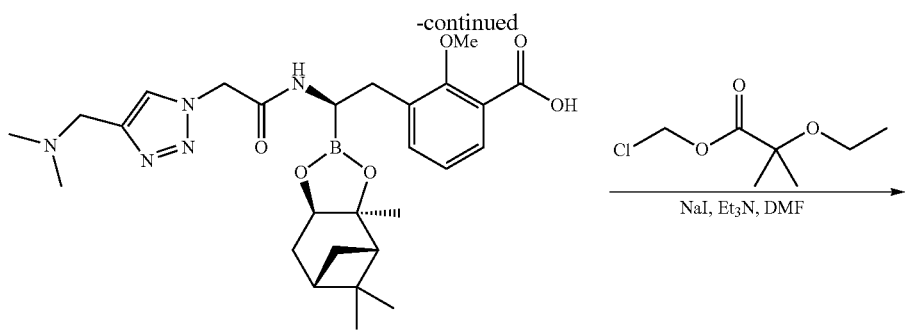

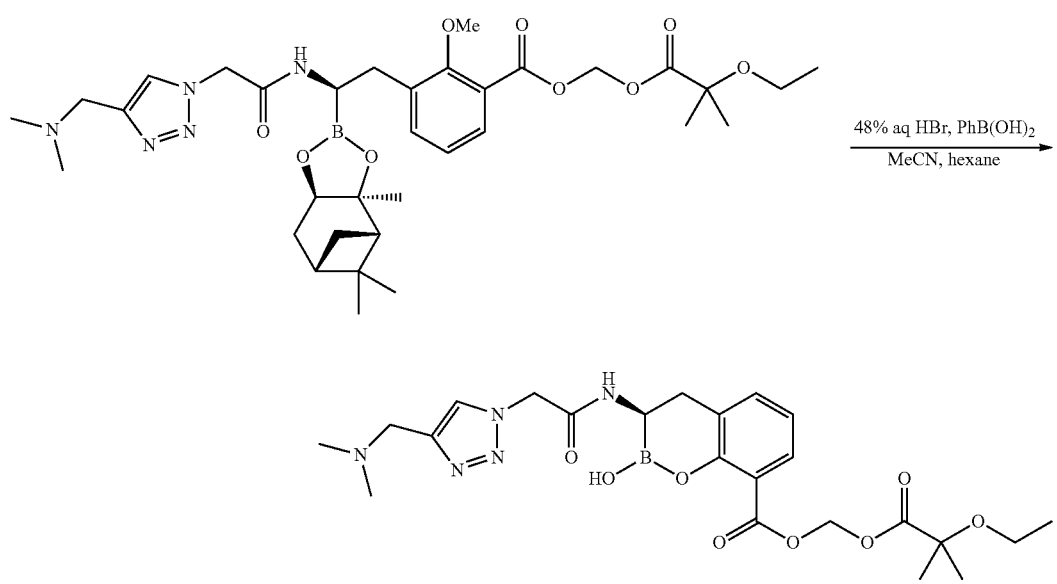

Step 1: Synthesis of 3-((R)-2-(2-(4-((dimethyl-amino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoic Acid (R)-3-(2-(4-((diethylamino)methyl)-1H-1,2,3-triazol-1-yl)acetamido)-2-hydroxy-3,4-dihydro-2H-benzo[e][1,2]oxaborinine-8-carboxylic acid is prepared according to the method of Example 27, and treated with 4 N HCl/dioxane overnight to provide the title carboxylic acid.

Step 2: Synthesis of ((2-ethoxy-2-methylpropanoyl)oxy)methyl 3-((R)-2-(2-(4-((dimethylamino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate To a solution of 3-((R)-2-(2-(4-((dimethylamino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoic acid (1 mmol), sodium iodide (1.1 mmol), and DMF (5 mL) is added chloromethyl 2-methyl-2-ethoxypropanoate (3 mmol) and triethylamine (3.5 mmol) under argon. The reaction is heated to 45-60° C. for 16 h. The reaction is quenched with water and extracted with ethyl acetate, and the combined organic layers are washed with brine, dried over MgSO₄, filtered, and concentrated. The crude product is purified by flash chromatography on silica gel to provide the title compound.

Step 3: Synthesis of ((2-ethoxy-2-methylpropanoyl)oxy)methyl (R)-3-(2-(4-((dimethylamino)methyl)-1H-1,2,3-triazol-1-yl)acetamido)-2-hydroxy-3,4-dihydro-2H-benzo[e][1,2]oxaborinine-8-carboxylate To a solution of ((2-ethoxy-2-methylpropanoyl)oxy)methyl 3-((R)-2-(2-(4-((dimethylamino)methyl)-1H-1,2,3-triazol-1-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.6 mmol) and acetonitrile (6 mL) under argon is added phenylboronic acid (0.8 mmol), hexane (6.0 mL), and hydrobromic acid (0.3 g, 48% in H₂O, 1.8 mmol). The reaction is stirred for 5 h with the hexane layer being removed and replaced at 1.5 h and 3 h. The reaction is quenched with water, layers separated, and the aqueous layer concentrated to remove acetonitrile. The crude product is purified by reverse phase preparative HPLC and dried using lyophilization to give the title compound.

Examples 143-156 in Table 2 are synthesized as described for Example 142.

TABLE 3

Example 143-156

| Ex. | Structure |
|---|---|
| 143 | 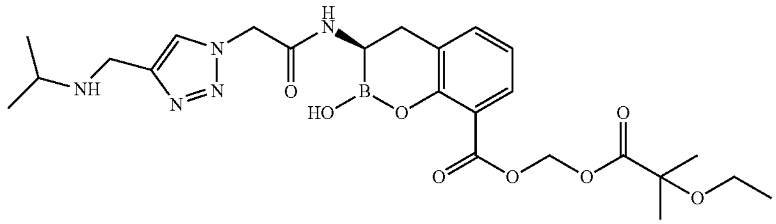 [SMILES: CCOC(C)(C)C(=O)OCOC(=O)c1cccc2c1OB(O)[C@@H](NC(=O)Cn1cc(CNC(C)C)nn1)C2] |
| 144 | 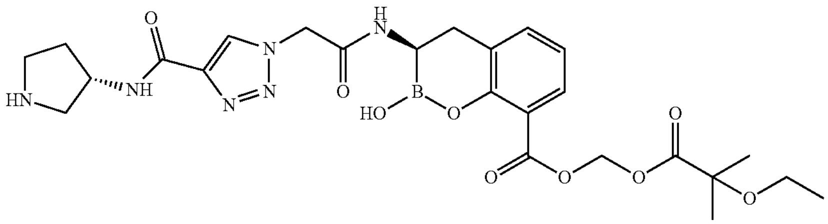 [SMILES: CCOC(C)(C)C(=O)OCOC(=O)c1cccc2c1OB(O)[C@@H](NC(=O)Cn1cc(C(=O)N[C@H]3CCNC3)nn1)C2] |
| 145 | 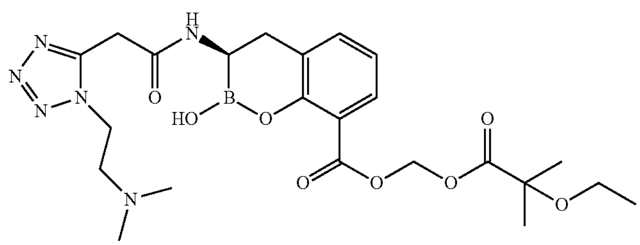 [SMILES: CCOC(C)(C)C(=O)OCOC(=O)c1cccc2c1OB(O)[C@@H](NC(=O)Cc1nnnn1CCN(C)C)C2] |
| 146 | 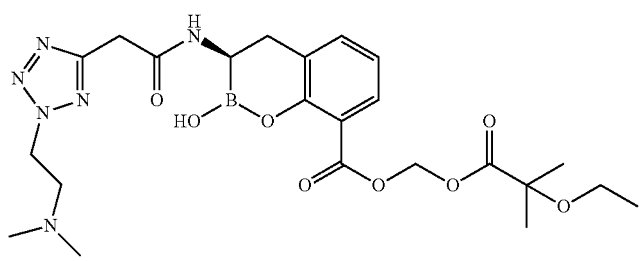 [SMILES: CCOC(C)(C)C(=O)OCOC(=O)c1cccc2c1OB(O)[C@@H](NC(=O)Cc1nnn(CCN(C)C)n1)C2] |
| 147 | 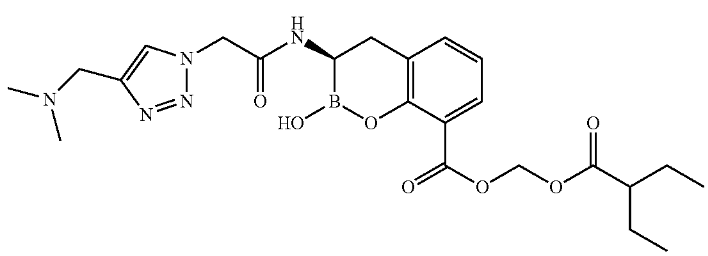 [SMILES: CCC(CC)C(=O)OCOC(=O)c1cccc2c1OB(O)[C@@H](NC(=O)Cn1cc(CN(C)C)nn1)C2] |
| 148 | 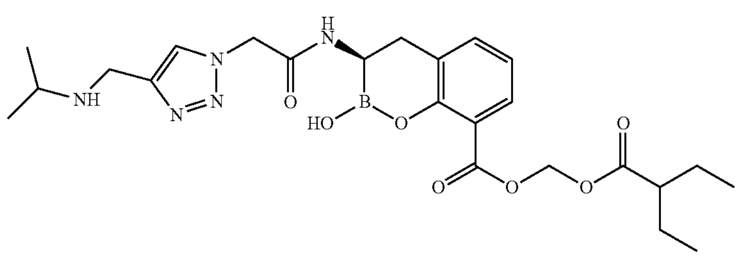 [SMILES: CCC(CC)C(=O)OCOC(=O)c1cccc2c1OB(O)[C@@H](NC(=O)Cn1cc(CNC(C)C)nn1)C2] |

TABLE 3-continued
Example 143-156
| Ex. | Structure |
|---|---|
| 149 | 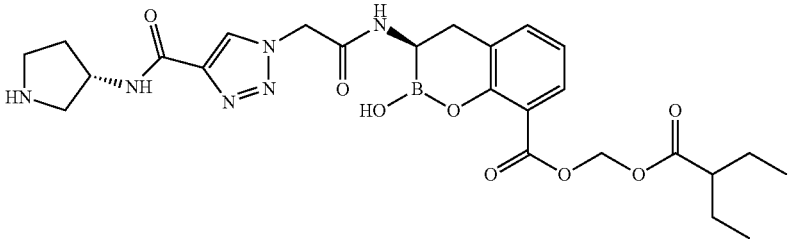 [SMILES: CCC(CC)C(=O)OCOC(=O)c1cccc2c1OB(O)[C@@H](NC(=O)Cn1cc(C(=O)N[C@H]3CCNC3)nn1)C2] |
| 150 | 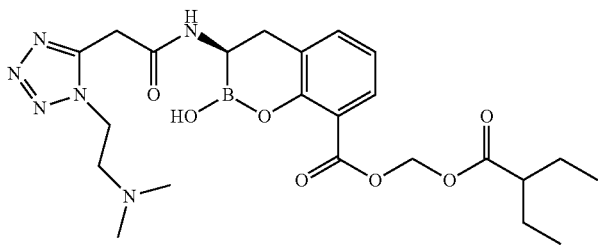 [SMILES: CCC(CC)C(=O)OCOC(=O)c1cccc2c1OB(O)[C@@H](NC(=O)Cc1nnnn1CCN(C)C)C2] |
| 151 | 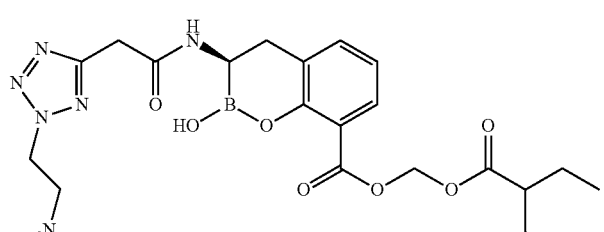 |
| 152 | 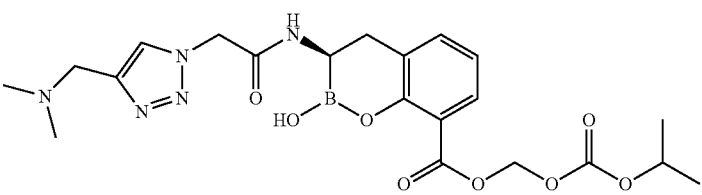 [SMILES: CC(C)OC(=O)OCOC(=O)c1cccc2c1OB(O)[C@@H](NC(=O)Cn1cc(CN(C)C)nn1)C2] |
| 153 | 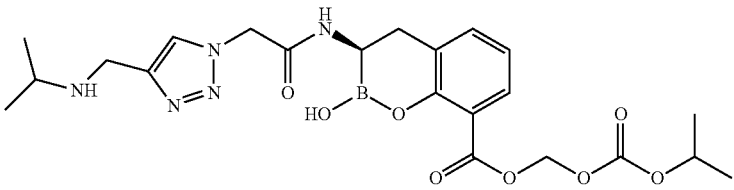 [SMILES: CC(C)NCc1cn(CC(=O)N[C@H]2Cc3cccc(C(=O)OCOC(=O)OC(C)C)c3OB2O)nn1] |
| 154 | 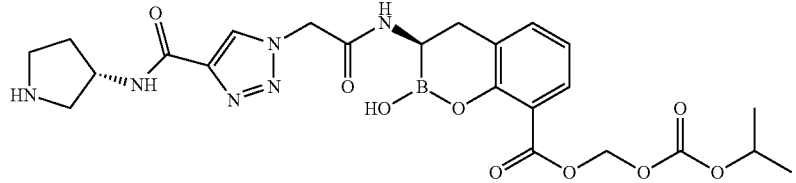 [SMILES: CC(C)OC(=O)OCOC(=O)c1cccc2c1OB(O)[C@@H](NC(=O)Cn1cc(C(=O)N[C@H]3CCNC3)nn1)C2] |

TABLE 3-continued

Example 143-156

| Ex. | Structure |
|---|---|
| 155 | (structure: tetrazole-CH2-C(O)-NH-chroman-boronate with HO-B-O, benzoate ester -C(O)-O-CH2-O-C(O)-O-isopropyl; tetrazole N-CH2CH2-N(CH3)2) |
| 156 | (structure: tetrazole-CH2-C(O)-NH-chroman-boronate with HO-B-O, benzoate ester -C(O)-O-CH2-O-C(O)-O-isopropyl; tetrazole N-CH2CH2-N(CH3)2, regioisomer) |

Example 157: Parenteral Composition of a Compounds of Formula (I) or Formula (II)

To prepare a parenteral pharmaceutical composition suitable for administration by injection, 100 mg of a compound of Formula (I) or Formula (II), or a water soluble pharmaceutically acceptable salt thereof, is dissolved in DMSO and then mixed with 10 ml of 0.9% sterile saline solution. The mixture is incorporated into a dosage unit suitable for administration by injection.

Example 158: Oral Composition of a Compounds of Formula (I) or Formula (II)

To prepare a pharmaceutical composition for oral delivery, 400 mg of compound of Formula (I) or Formula (II) and the following ingredients are mixed intimately and pressed into single scored tablets.

Tablet Formulation

| Ingredient | Quantity per tablet mg |
|---|---|
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

Capsule Formulation

| Ingredient | Quantity per capsule mg |
|---|---|
| compound | 200 |
| lactose spray dried | 148 |
| magnesium stearate | 2 |

BIOLOGICAL EXAMPLES

Example I: Experimental Method for β-Lactamase Enzyme Assays

Isolation of β-Lactamases.

For SHV-5, Kpc-2, p99AmpC and OXA-1 β-lactamases, *E. coli* BL21(DE3) bacterial cells carrying expression plasmids (expressed as native untagged proteins) for the individual β-lactamases were grown in 1 L of Superbroth (Teknova Inc. Hollister, Calif.) supplemented with 100 µg/ml kanamycin selection and 1×5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 µm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled concentrated, quantitated by BCA protein determination (Thermo Scientific, Rockford, Ill.), dialyzed into PBS and frozen at −80° C. in 20% glycerol until use.

For Vim-2 metallo β-lactamase, the procedure was identical with the following exceptions, first the protein was not pH adjusted to pH 5 with 50 mM sodium acetate, second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run ($3^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 µM in 96-well microtiter plates. An equal volume of diluted enzyme stock was added, and the plates were incubated at 37° C. for 15 min. Nitrocefin was used as substrate for p99 AmpC, VIM-2 and OXA-1 and dispensed into each well at a final concentration of 100 µM. Absorbance at 486 nm was immediately monitored for 10 min using a Biotek Powerwave XS2 microplate spectrophotometer using the GENS software package (Biotek Instruments, Winooski Vt.). In an analogous fashion, imipenem was used as substrate for Kpc-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II: Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 4 for representative enzymes across different subtypes (note SHV-5 represents an Ambler Class A Extended Spectrum β-Lactamases, KPC-2 exemplifies a Class A carbapenemase, AmpC represents a chromosomal Class C, OXA-48 represents a Class D oxacillinase and VIM-2 represents a class B zinc-dependent metallo-β-lactamase also possessing carbapenemase activity), where A represents an $IC_{50}$ of 10-100 µM, B represents an $IC_{50}$ of 1 to 10 µM, C represents an $IC_{50}$ of 0.1 to 1 µM, and D represents an $IC_{50}$ of <0.1 µM. NT=Not tested.

TABLE 4

Inhibition of Diverse β-Lactamases by Exemplary Compounds

| EXAMPLE | Class A SHV-5 | Class A KPC-2 | Class B VIM-2 | Class C AmpC | Class D OXA-48 |
|---|---|---|---|---|---|
| 1 | D | D | B | D | C |
| 2 | D | D | D | D | C |
| 3 | D | D | D | D | D |
| 4 | C | C | D | D | D |
| 5 | D | D | A | D | C |
| 6 | C | D | B | D | B |
| 7 | C | B | B | D | B |
| 8 | D | C | B | B | C |
| 9 | D | D | B | D | C |
| 10 | D | D | B | D | D |
| 11 | D | D | B | D | D |
| 12 | D | D | B | D | C |
| 13 | C | D | C | D | C |
| 14 | C | C | C | D | C |
| 15 | C | C | D | D | C |
| 16 | D | D | B | D | D |
| 17 | NT | D | D | NT | C |
| 18 | NT | D | C | NT | B |
| 19 | D | D | C | D | D |
| 20 | D | D | C | C | C |
| 21 | D | D | D | D | C |
| 22 | C | C | C | D | B |
| 23 | D | D | C | D | C |
| 24 | D | D | C | D | C |
| 25 | D | D | C | D | C |
| 26 | D | C | D | D | C |
| 27 | D | D | C | D | C |
| 28 | D | D | C | D | C |
| 29 | D | D | C | D | C |
| 30 | D | D | C | D | C |
| 31 | D | D | C | C | B |
| 32 | D | D | C | D | C |
| 33 | D | D | D | D | D |
| 34 | D | D | C | D | B |
| 35 | D | D | B | D | B |
| 36 | D | D | B | D | C |
| 37 | D | D | D | D | B |
| 38 | C | D | C | D | C |
| 39 | D | D | D | D | C |
| 40 | D | D | B | D | C |
| 41 | D | D | D | D | C |
| 42 | D | D | D | D | C |
| 43 | D | D | D | D | C |
| 44 | D | D | D | D | C |
| 45 + 46 | D | D | C | D | C |
| 47 | D | D | D | D | B |
| 48 | D | D | D | D | B |
| 49 | D | D | C | D | C |
| 50 | D | D | D | D | B |
| 51 | D | D | D | D | B |
| 52 | D | D | D | D | B |
| 53 | D | D | D | D | B |
| 54 | D | D | C | D | B |
| 55 | D | D | C | D | C |
| 56 | D | D | C | D | C |
| 57 | D | D | C | D | B |
| 58 | D | D | C | D | C |
| 59 | D | D | D | D | B |
| 60 | D | C | D | D | D |
| 61 | D | D | C | D | C |
| 62 | D | D | C | D | D |
| 63 | D | D | C | D | C |
| 64 | D | D | C | D | D |
| 65 | D | D | D | D | C |
| 66 | D | D | D | D | C |
| 67 | D | D | C | D | C |
| 68 | C | D | C | D | C |
| 69 | D | D | C | D | B |
| 70 | D | D | B | D | C |
| 71 | C | C | C | D | A |
| 72 | D | D | C | D | C |
| 73 | D | D | C | D | C |
| 74 | D | D | B | D | C |
| 75 | D | C | C | D | C |
| 76 | D | C | D | D | C |
| 77 | D | C | C | D | C |
| 78 | D | D | C | D | D |
| 79 | D | D | C | D | C |
| 80 | D | D | C | D | C |
| 81 | D | D | D | D | C |

TABLE 4-continued

Inhibition of Diverse β-Lactamases by Exemplary Compounds

| EXAMPLE | Class A SHV-5 | KPC-2 | Class B VIM-2 | Class C AmpC | Class D OXA-48 |
|---|---|---|---|---|---|
| 82 | D | D | C | D | C |
| 83 | C | C | D | D | C |
| 84 | C | D | D | D | C |
| 85 | C | C | C | D | C |
| 86 | C | D | D | C | B |
| 87 | C | D | D | D | B |
| 88 | C | D | D | D | B |
| 89 | C | C | C | D | B |
| 90 | C | D | C | D | B |
| 91 | D | D | C | D | B |
| 92 | C | D | D | D | B |
| 93 | D | D | C | D | B |
| 94 + 95 | D | D | D | D | A |
| 96 | D | D | C | D | D |
| 97 | D | D | C | D | D |
| 98 | D | D | D | D | C |
| 99 | D | D | C | D | C |
| 100 | D | C | D | D | D |
| 101 | D | D | C | D | D |
| 102 | C | D | D | D | C |
| 103 | C | D | C | D | C |
| 104 | D | D | C | D | C |
| 105 | C | D | D | D | D |
| 106 | C | D | D | D | D |
| 107 | C | D | D | D | D |
| 108 | C | D | D | D | D |
| 109 | C | C | D | C | D |
| 110 | B | C | D | C | C |
| 111 | D | D | B | D | C |
| 112 | C | C | C | D | C |
| 113 | B | C | D | D | C |
| 114 | A | C | B | D | B |
| 115 | C | C | C | D | B |
| 116 | D | D | B | D | C |
| 117 | D | C | C | D | C |
| 118 | C | C | B | D | C |
| 119 | D | C | C | D | C |
| 120 | C | D | D | D | D |
| 121 | D | D | C | D | D |
| 122 | D | D | C | D | C |
| 123 | D | C | B | D | C |
| 124 | D | D | B | D | C |
| 125 | C | D | D | D | B |

Example III: In Vitro Antibacterial Assays of β-Lactamase Inhibition

To determine the ability of test compounds to potentiate the inhibition of the growth of bacterial strains that produce beta-lactamase enzymes in the presence of a β-lactam antibiotic, classic cell based broth microdilution MIC assays were employed. Six bacteria strains producing beta-lactamase enzymes were used: *E. coli* expressing the Class A Extended Spectrum Beta-Lactamase (ESBL) CTX-M-15, *E. cloacae* expressing the Class C P99, *K. pneumoniae* expressing the Class A carbapenemase KPC-2, *P. aeruginosa* expressing the Class B carbapenemase VIM-2, *K. pneumoniae* expressing the class A carbapenemase KPC-2 and the class B carbapenemase VIM-4, and *K. pneumoniae* producing the Class D carbapenemase OXA-48. The assay was conducted in Cation Adjusted Mueller Hinton Broth (CAMHB, BD #212322, BD Diagnostic Systems, Sparks, Md.). Bacteria strains were grown for 3-5 hours in CAMBH broth. Test compounds (Examples 1-94) were added to a microtiter plate in 2-fold serial dilutions in CAMHB in a final concentration range of 16 μg/mL to 0.125 μg/ml. An overlay of CAMHB containing a Beta-lactam was added to the compounds at a final static concentration of 4 μg/ml. Ceftazidime (CAZ, Sigma# C3809-1 G, Sigma-Aldrich, St. Louis, Mo.) was used as the partner antibiotic for *E. coli* expressing Ambler Class A ESBL CTX-M-15 (MIC alone >128 μg/ml), and *E. cloacae* expressing Class C P99 (MIC alone=128 μg/mL). Meropenem (Mero, USP #1392454, U.S. Pharmacopeia, Rockville, Md.) was used as the partner antibiotic for *K. pneumoniae* expressing Ambler Class A carbapenemase KPC-2 (MIC alone >128 μg/mL), *P. aeruginosa* expressing Class A carbapenemase VIM-2 (MIC alone=16 μg/mL), *K. pneumoniae* expressing the Ambler Class A carbapenemase KPC-2 and Ambler Class B carbapenemase VIM-4 (MIC alone=64 μg/mL), and *K. pneumoniae* expressing the Ambler Class D carbapenemase OXA-48 (MIC alone=128 μg/mL). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C. then the Minimal Inhibitory Concentration (MIC) of the test compound is determined visually.

Using the methodology described above, examples of the current invention were evaluated for their ability to inhibit the growth of β-lactamase-producing bacteria in the presence of a β-lactam antibiotic.

Representative results are shown in Table 5 where A represents an MIC >16 μg/mL, B represents an MIC between 1 and 16 μg/mL inclusive, and C represents an MIC of <1 μg/mL of a β-lactamase inhibitor of Examples 1-94. NT=Not Tested.

TABLE 5

Broad spectrum inhibition of bacterial growth. MIC of example compounds of Formula (I) or Formula (II) in the presence of a fixed amount (4 μg/mL) of designated β-lactam antibiotics ceftazidime (CAZ) or meropenem (Mero).

MIC (μg/mL) of Exemplary Compounds in presence of fixed β-lactams

| | Fixed CAZ | | Fixed Mero Carbapenemases (Classes A, B and D) | | | |
|---|---|---|---|---|---|---|
| | ESBLs (Class A and C) | | | | *K. p.* | |
| EXAMPLE | *E. coli* ESBL4 CTX-M-15 | *E. cl.* 144200 p99 AmpC | *K. p.* 156319 KPC-3 | *P. aerug.* 2775 VIM-2 | A-1797 KPC-2 VIM-4 | *K. p.* 11978 OXA-48 |
| 1 | C | C | B | B | B | B |
| 2 | C | C | C | C | C | B |

TABLE 5-continued

Broad spectrum inhibition of bacterial growth. MIC of example compounds of Formula (I) or Formula (II) in the presence of a fixed amount (4 µg/mL) of designated β-lactam antibiotics ceftazidime (CAZ) or meropenem (Mero).

MIC (µg/mL) of Exemplary Compounds in presence of fixed β-lactams

| | Fixed CAZ | | Fixed Mero Carbapenemases (Classes A, B and D) | | | |
|---|---|---|---|---|---|---|
| | ESBLs (Class A and C) | | | | *K. p.* | |
| EXAMPLE | *E. coli* ESBL4 CTX-M-15 | *E. cl.* 144200 p99 AmpC | *K. p.* 156319 KPC-3 | *P. aerug.* 2775 VIM-2 | A-1797 KPC-2 VIM-4 | *K. p.* 11978 OXA-48 |
| 3 | C | C | C | C | C | C |
| 4 | C | C | B | C | C | B |
| 5 | C | NT | B | B | B | B |
| 6 | C | NT | C | C | B | B |
| 7 | C | C | C | C | B | B |
| 8 | C | C | B | B | B | B |
| 9 | B | NT | A | NT | A | A |
| 10 | C | C | B | NT | A | B |
| 11 | B | NT | B | NT | B | A |
| 12 | C | C | B | B | A | B |
| 13 | B | C | B | B | B | B |
| 14 | B | C | B | B | B | B |
| 15 | C | C | B | C | B | B |
| 16 | B | C | B | B | B | B |
| 17 | C | C | B | C | B | B |
| 18 | C | C | C | B | B | B |
| 19 | C | C | B | C | B | B |
| 20 | C | C | B | B | B | B |
| 21 | C | C | B | B | B | B |
| 22 | C | C | C | C | B | B |
| 23 | C | C | C | C | B | B |
| 24 | C | C | B | B | B | B |
| 25 | C | C | B | B | A | B |
| 26 | C | C | B | B | C | B |
| 27 | C | C | B | B | B | B |
| 28 | C | C | B | B | A | B |
| 29 | C | C | B | B | B | B |
| 30 | C | C | C | B | B | B |
| 31 | B | C | B | C | B | A |
| 32 | B | A | B | B | A | A |
| 33 | C | C | B | C | C | B |
| 34 | C | C | B | C | B | B |
| 35 | C | C | B | B | A | B |
| 36 | C | C | B | B | A | B |
| 37 | C | C | B | C | C | B |
| 38 | B | C | B | B | B | B |
| 39 | C | C | B | C | B | B |
| 40 | C | C | C | B | B | B |
| 41 | C | C | C | C | C | B |
| 42 | C | C | C | C | C | B |
| 43 | C | C | C | C | B | B |
| 44 | C | C | B | C | B | B |
| 45 + 46 | C | C | B | B | B | B |
| 47 | C | C | C | C | B | C |
| 48 | C | C | B | C | B | B |
| 49 | C | C | C | B | B | B |
| 50 | C | C | C | C | C | B |
| 51 | C | C | C | C | B | B |
| 52 | C | C | C | C | B | B |
| 53 | C | C | C | C | C | B |
| 54 | C | C | B | B | B | B |
| 55 | C | C | C | B | B | B |
| 56 | C | C | B | B | B | B |
| 57 | C | C | C | B | B | B |
| 58 | C | C | B | B | B | B |
| 59 | C | C | B | C | B | A |
| 60 | B | C | B | C | C | B |
| 61 | C | C | B | C | B | B |
| 62 | C | C | C | B | A | B |
| 63 | C | C | C | C | B | B |
| 64 | C | C | C | B | B | B |
| 65 | C | C | C | B | B | B |
| 66 | C | C | C | C | B | B |
| 67 | C | C | B | C | B | B |
| 68 | C | C | C | C | B | B |

TABLE 5-continued

Broad spectrum inhibition of bacterial growth. MIC of example compounds of Formula (I) or Formula (II) in the presence of a fixed amount (4 µg/mL) of designated β-lactam antibiotics ceftazidime (CAZ) or meropenem (Mero).

MIC (µg/mL) of Exemplary Compounds in presence of fixed β-lactams

| | Fixed CAZ | | Fixed Mero Carbapenemases (Classes A, B and D) | | | |
|---|---|---|---|---|---|---|
| | ESBLs (Class A and C) | | | | K. p. | |
| EXAMPLE | E. coli ESBL4 CTX-M-15 | E. cl. 144200 p99 AmpC | K. p. 156319 KPC-3 | P. aerug. 2775 VIM-2 | A-1797 KPC-2 VIM-4 | K. p. 11978 OXA-48 |
| 69 | C | C | B | C | B | B |
| 70 | C | C | B | B | B | B |
| 71 | C | C | C | C | B | A |
| 72 | C | C | C | B | B | B |
| 73 | C | C | B | C | B | B |
| 74 | C | C | B | B | A | B |
| 75 | C | C | C | B | B | B |
| 76 | C | C | C | C | B | B |
| 77 | C | C | C | C | B | B |
| 78 | C | C | B | B | A | B |
| 79 | C | C | C | C | B | C |
| 80 | C | C | B | C | B | B |
| 81 | C | C | C | C | C | C |
| 82 | C | C | C | C | B | C |
| 83 | C | C | C | C | B | B |
| 84 | C | C | B | C | C | B |
| 85 | C | C | C | C | B | B |
| 86 | C | C | C | C | C | B |
| 87 | C | C | C | C | C | B |
| 88 | C | C | B | C | C | B |
| 89 | C | C | C | C | B | B |
| 90 | C | C | B | C | B | B |
| 91 | C | C | C | B | B | B |
| 92 | C | C | C | C | B | B |
| 93 | C | C | B | C | B | B |
| 94 + 95 | C | C | B | C | B | B |
| 96 | C | C | B | C | B | B |
| 97 | C | C | C | B | B | C |
| 98 | C | C | C | C | B | B |
| 99 | C | C | C | C | B | B |
| 100 | C | C | C | C | B | C |
| 101 | C | C | B | C | B | C |
| 102 | C | C | B | C | B | B |
| 103 | C | C | C | C | B | B |
| 104 | C | C | C | C | C | C |
| 105 | C | C | C | C | C | C |
| 106 | C | C | C | C | C | B |
| 107 | C | B | C | C | C | B |
| 108 | C | B | B | C | C | B |
| 109 | C | NT | B | C | C | B |
| 110 | C | NT | C | C | C | B |
| 111 | C | NT | B | B | B | B |
| 112 | C | NT | B | C | B | A |
| 113 | C | C | B | C | C | A |
| 114 | C | C | C | C | B | B |
| 115 | C | C | B | B | B | B |
| 116 | C | NT | B | C | B | B |
| 117 | C | C | C | C | B | B |
| 118 | C | C | C | C | B | B |
| 119 | C | C | C | C | B | B |
| 120 | C | C | B | NT | B | B |
| 121 | C | C | C | C | B | B |
| 122 | C | NT | B | C | B | B |
| 123 | C | C | C | A | B | B |
| 124 | C | C | B | A | B | B |
| 125 | C | C | C | C | C | B |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I) or Formula (II) or pharmaceutically acceptable salts, solvates, stereoisomers, tautomers, or N-oxides thereof:

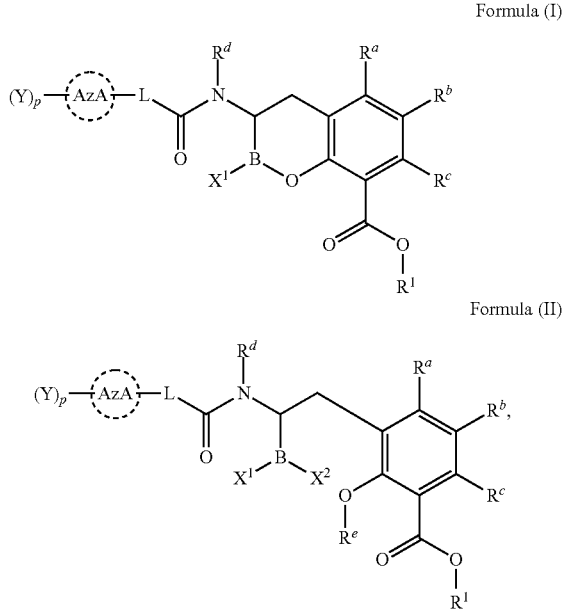

wherein:
L is —(CR$^2$R$^3$)—;
n is 0, 1, 2, 3, 4, 5, or 6;
p is 1 or 2;
X$^1$ and X$^2$ are independently selected from —OH, —OR$^x$, and F;
AzA is a five-membered heteroaromatic ring system bearing at least three N heteroatoms;
Y is selected from the group consisting of fluoro, chloro, bromo, iodo, optionally substituted C$_1$-C$_6$ alkyl, optionally substituted C$_2$-C$_6$ alkynyl, optionally substituted aryl, optionally substituted heteroaryl, and —(CR$^9$R$^{10}$)$_v$NR$^6$R$^7$, wherein at least one Y is —(CR$^9$R$^{10}$)$_v$NR$^6$R$^7$
v is 1-4;
R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{11}$, —NR$^6$R$^7$, and —SR$^{11}$;
R$^e$ is hydrogen, optionally substituted C$_1$-C$_6$ alkyl, or optionally substituted C$_3$-C$_6$ cycloalkyl;
each R$^x$ is independently optionally substituted C$_1$-C$_6$ alkyl, optionally substituted C$_3$-C$_6$ cycloalkyl, optionally substituted alkoxyalkyl, optionally substituted hydroxyalkyl, optionally substituted aminoalkyl, optionally substituted heterocycle, optionally substituted aryl, optionally substituted heteroaryl, optionally substituted cycloalkylalkyl, optionally substituted heterocyclealkyl, optionally substituted aralkyl, optionally substituted heteroaralkyl, (poly ethylene glycol) ethyl, or an optionally substituted saccharide;
or two R$^x$ taken together with the atoms to which they are attached form an optionally substituted heterocycle;

R$^1$ is hydrogen, R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;
each q is independently 2, 3, 4, 5, or 6;
each R$^{30}$ is independently —CH$_2$—, —CH(CH$_3$)—, —C(CH$_3$)$_2$—, or optionally substituted 1,1'-cyclopropylene;
each R$^{31}$ is optionally substituted C$_1$-C$_{12}$ alkyl, optionally substituted C$_2$-C$_{12}$ alkenyl, optionally substituted C$_2$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl; or
two R$^{31}$ are taken together with the nitrogen to which they are attached to form a C$_3$-C$_8$ heterocyclyl;
each R$^2$ and R$^3$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{11}$, —SR$^{11}$, —NR$^6$R$^7$, —(CR$^9$R$^{10}$)$_v$C(O)NR$^6$R$^7$, —(CR$^9$R$^{10}$)$_v$C(O)OH, —(CR$^9$R$^{10}$)$_v$OH, —(CR$^9$R$^{10}$)$_v$NR$^6$R$^7$, and —(CR$^9$R$^{10}$)$_v$N(R$^6$)C(=NR$^8$)NR$^6$R$^7$;
or R$^2$ and R$^3$ on the same carbon are taken together to form an oxo or optionally substituted oxime;
or R$^2$ and R$^3$ on the same carbon are taken together to form an optionally substituted spiro-carbocycle or optionally substituted spiro-heterocycle with the carbon to which they are attached;
or when n is at least 2, two R$^2$ on different carbons are taken together form an optionally substituted carbocycle or optionally substituted heterocycle with the carbons to which they are attached;
or when n is at least 2, two R$^2$ on adjacent carbons are taken together to form a double bond; or two R$^2$ and two R$^3$ on adjacent carbons are taken together to form a triple bond;
each R$^d$, R$^6$ and R$^7$ are independently selected from the group consisting of hydrogen, —CN, —OH, —S(O)$_2$R$^{11}$, —S(O)$_2$NH$_2$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or R$^6$ and R$^7$ taken together form an optionally substituted heterocycle with the nitrogen to which they are attached;
each R$^8$ is independently hydrogen, —OH, —OR$^{11}$, —CN, —NO$_2$, —NR$^6$, or optionally substituted C$_1$-C$_6$ alkyl;
each R$^9$ and R$^{10}$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{11}$, —SR$^{11}$, —NR$^6$R$^7$, —NR$^6$C(O)R$^{11}$, —(CR$^a$R$^b$)$_v$NR$^6$R$^7$, —(CR$^a$R$^b$)$_v$C(O)NR$^6$R$^7$, —C(O)NR$^6$R$^7$, —C(O)OR$^{11}$, —C(O)OH, —NR$^6$SO$_2$R$^{11}$, optionally substituted heterocyclyl, optionally substituted aryl, and optionally substituted heteroaryl;

or R$^9$ and R$^{10}$ taken together with the carbon atom to which they are attached form an optionally substituted oxime, an optionally substituted carbocycle, or an optionally substituted heterocycle; and each R$^{11}$ is independently optionally substituted C$_1$-C$_6$ alkyl, optionally substituted C$_3$-C$_6$ cycloalkyl, optionally substituted heteroaryl, optionally substituted heterocyclyl, or optionally substituted aryl.

2. The compound of claim 1, wherein R$^a$, R$^b$, and R$^c$ are independently selected from the group consisting of hydrogen, fluoro, chloro, —OH, and —OCH$_3$.

3. The compound of claim 1, wherein X$^1$ is —OH and X$^2$ is —OH when present.

4. The compound of claim 1, wherein R$^d$ is hydrogen.

5. The compound of claim 1, wherein n is 1, 2, or 3.

6. The compound of claim 1, wherein each R$^2$ and R$^3$ are hydrogen.

7. The compound of claim 1, wherein R$^1$ is hydrogen, R$^{31}$, —R$^{30}$OC(O)R$^{31}$, or —R$^{30}$OC(O)OR$^{31}$; each R$^{30}$ is independently —CH$_2$—, —CH(CH$_3$)—, or —C(CH$_3$)$_2$—; and each R$^{31}$ is optionally substituted C$_1$-C$_{12}$ alkyl, optionally substituted C$_2$-C$_{12}$ alkenyl, optionally substituted C$_2$-C$_{12}$ alkynyl, C$_3$-C$_8$ cycloalkyl, C$_3$-C$_8$ heterocyclyl, optionally substituted aryl, optionally substituted heteroaryl, optionally substituted alkylcycloalkyl, optionally substituted alkylheterocyclyl, optionally substituted alkylaryl, or optionally substituted alkylheteroaryl.

8. The compound of claim 1, wherein R$^1$ is hydrogen.

9. The compound of claim 1, wherein (Y)$_p$-AzA is selected from:

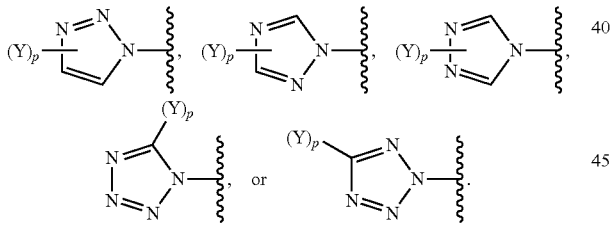

10. The compound of claim 1, wherein (Y)$_p$-AzA is selected from:

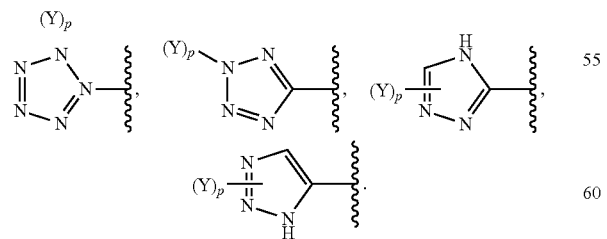

11. The compound of claim 1, wherein p is 1 or 2.

12. The compound of claim 1, wherein each R$^6$ and R$^7$ are independently selected from the group consisting of hydrogen and optionally substituted C$_1$-C$_6$ alkyl.

13. The compound of claim 1, wherein R$^9$ and R$^{10}$ are hydrogen and v is 1 or 2.

14. The compound of claim 1 that is selected from the group consisting of:

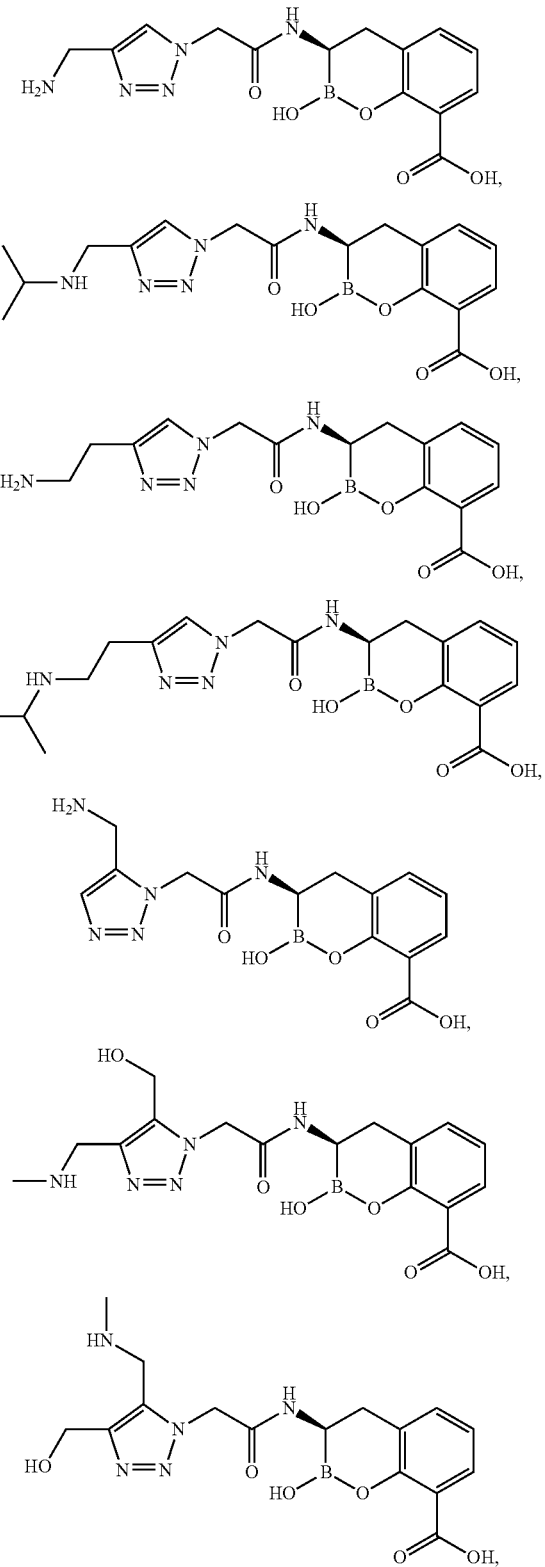

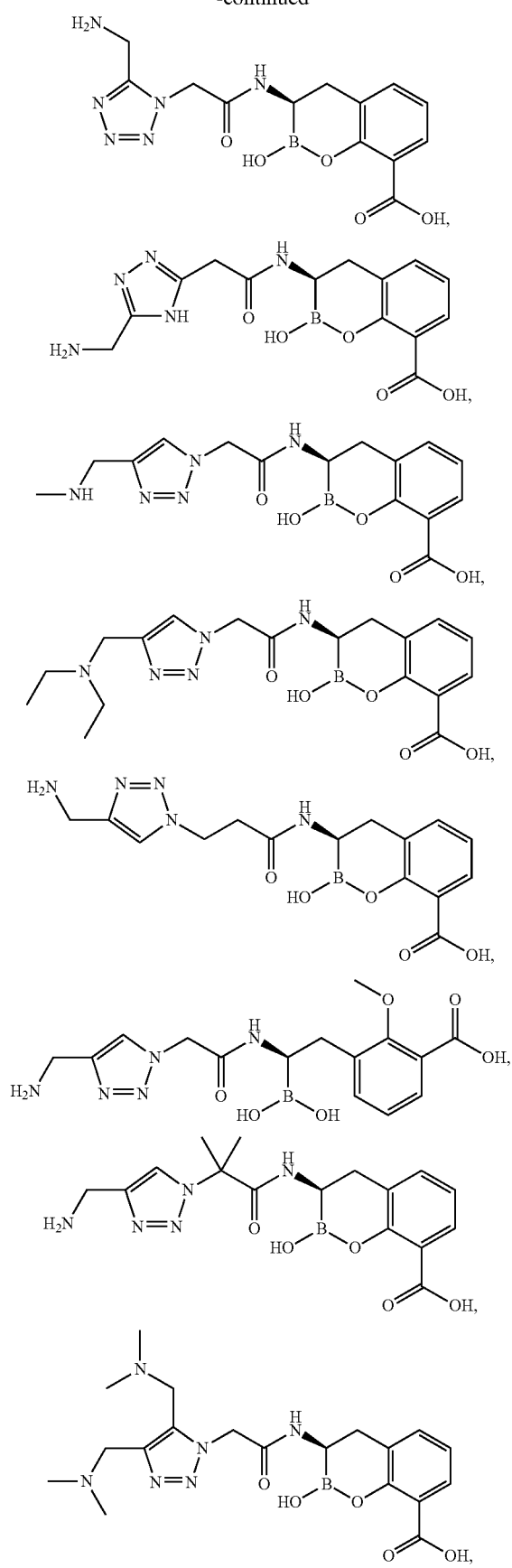
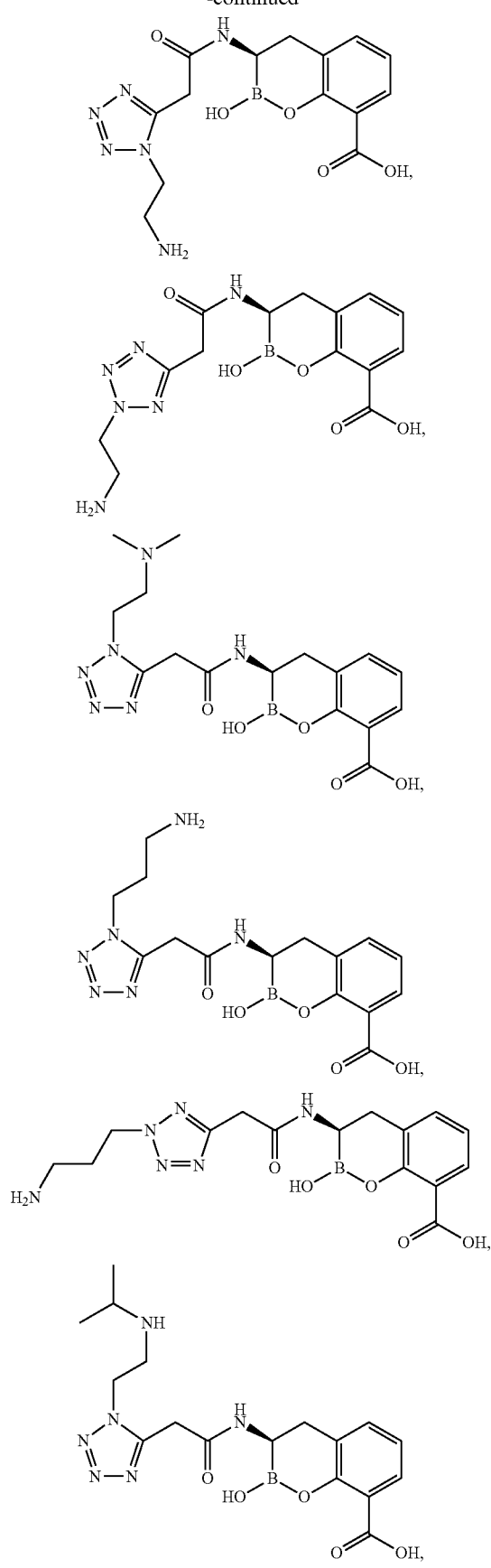

301
-continued
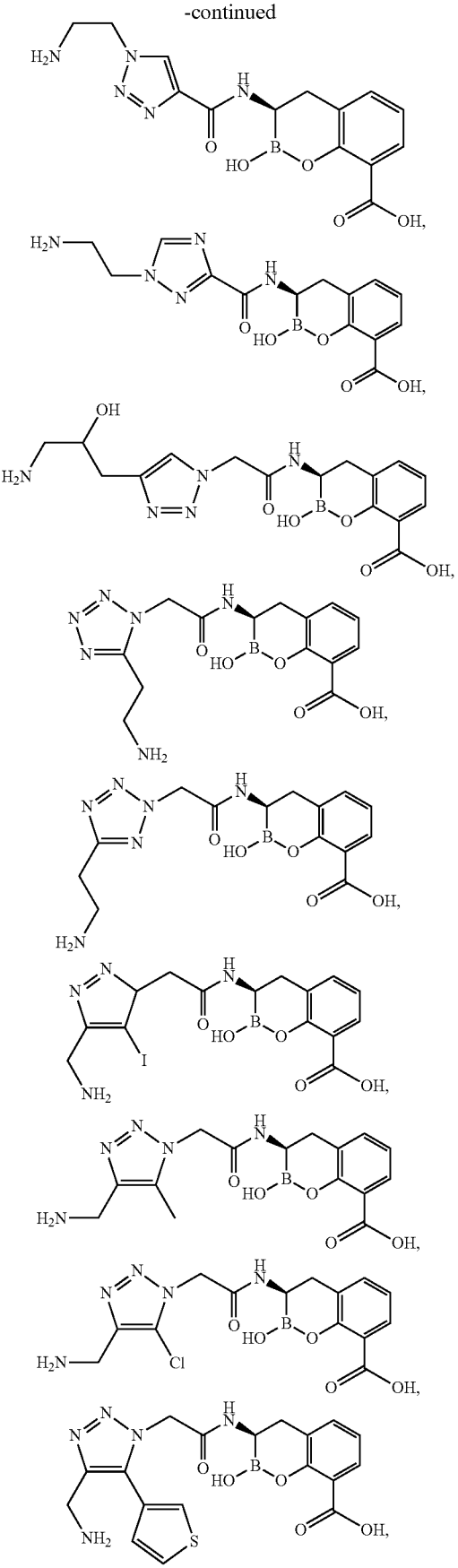
302
-continued
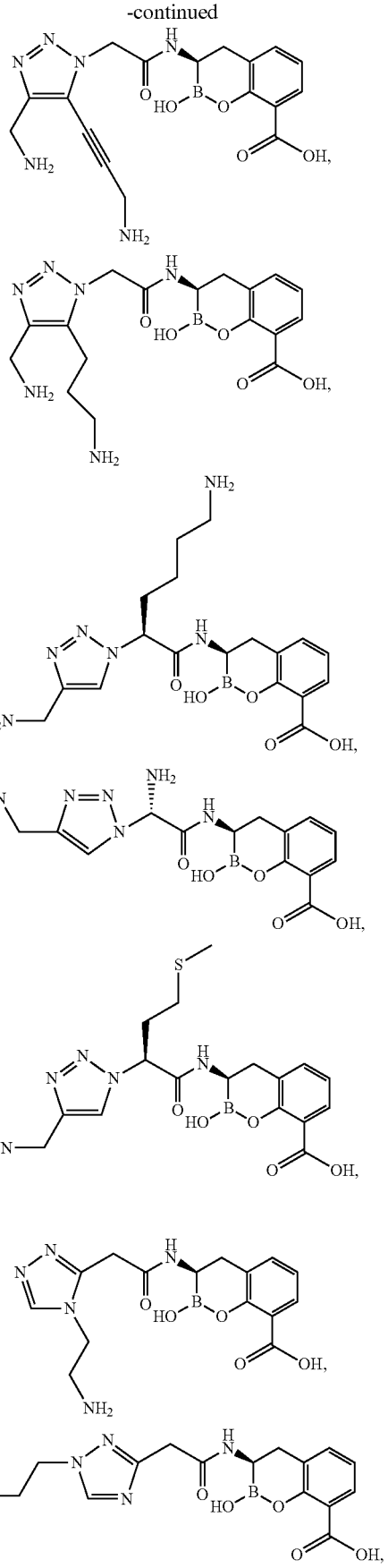

303
-continued
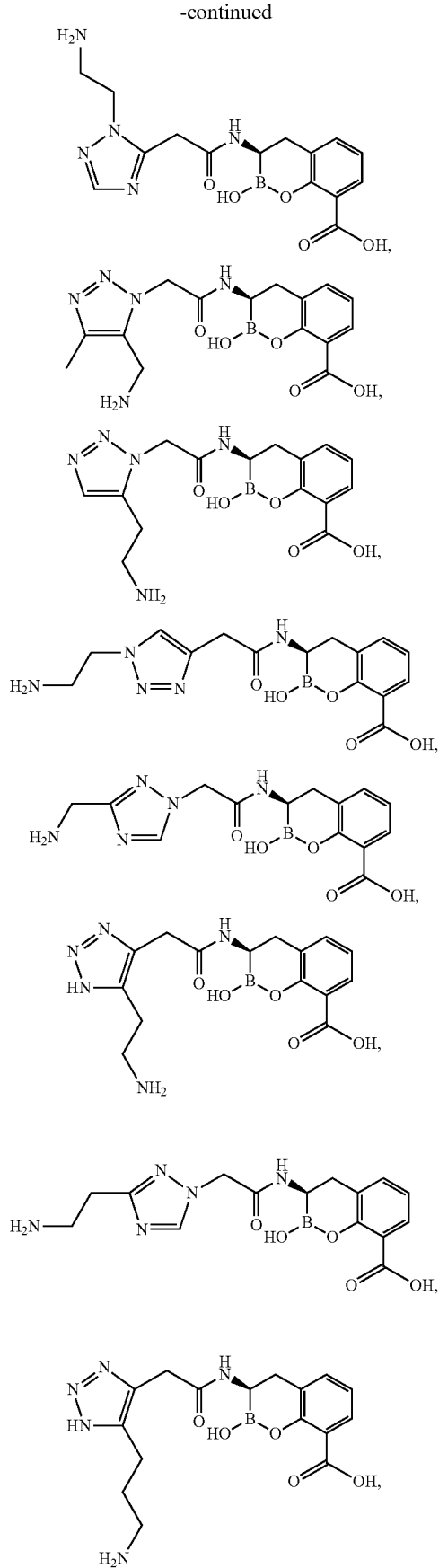
304
-continued
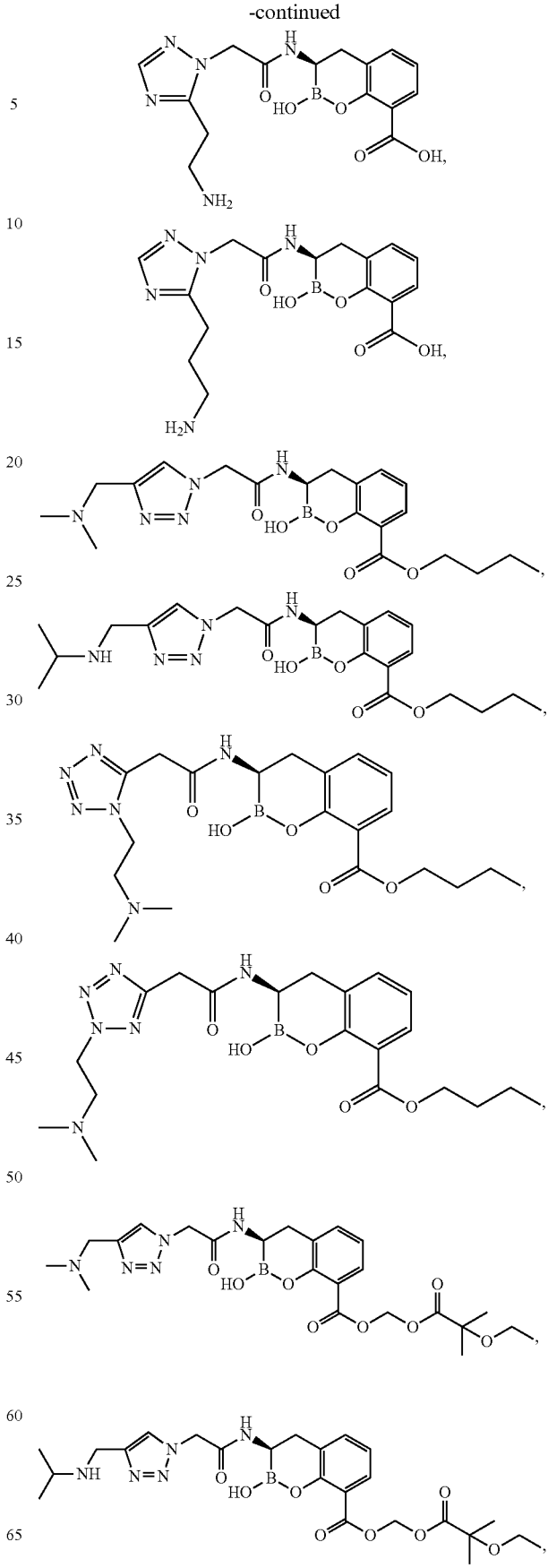

-continued

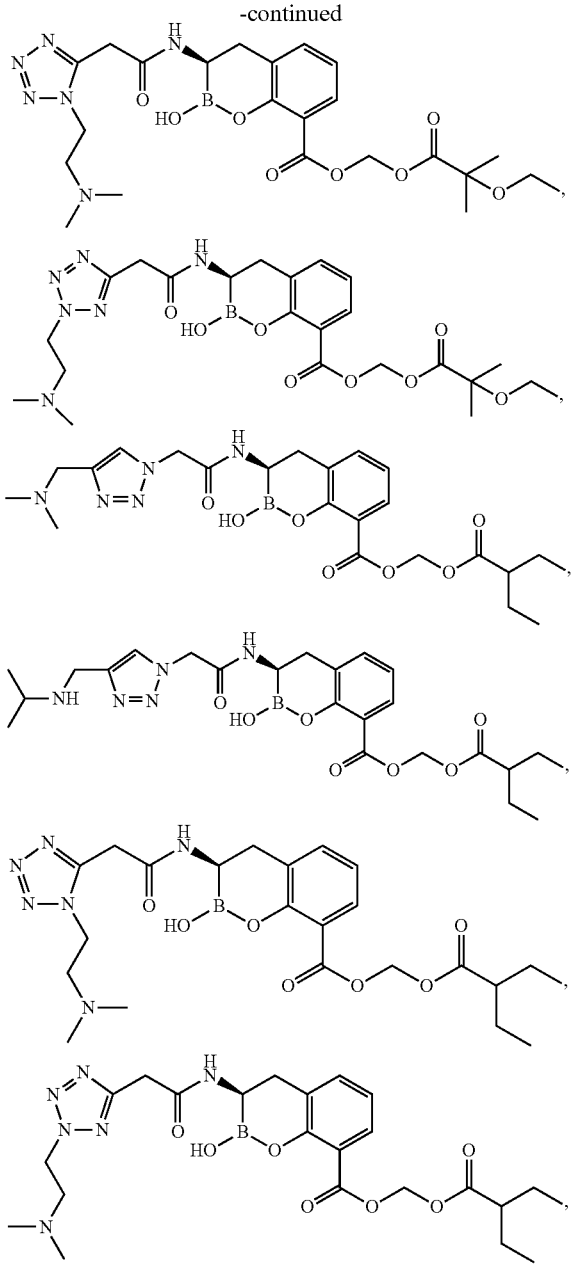

-continued

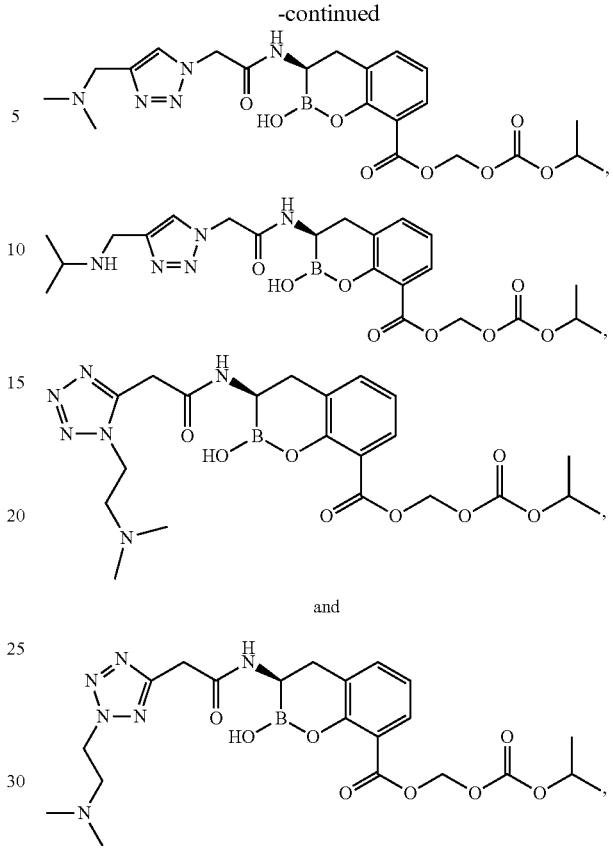

and or a pharmaceutically acceptable salt, solvate, stereoisomer, tautomer, or N-oxide thereof.

15. A pharmaceutical composition comprising a compound of claim 1 or a pharmaceutically acceptable salt, solvate, stereoisomer, tautomer, or N-oxide thereof, and a pharmaceutically acceptable excipient.

16. The pharmaceutical composition of claim 15, further comprising a beta-lactam antibiotic.

17. A method of treating a bacterial infection in a subject, comprising administering to the subject a compound of claim 1, optionally in combination with a beta-lactam antibiotic.

* * * * *

UNITED STATES PATENT AND TRADEMARK OFFICE
CERTIFICATE OF CORRECTION

PATENT NO. : 10,399,996 B2
APPLICATION NO. : 15/261359
DATED : September 3, 2019
INVENTOR(S) : Burns et al.

Page 1 of 1

It is certified that error appears in the above-identified patent and that said Letters Patent is hereby corrected as shown below:

In the Claims

Claim 1; Column 295; Line 33: delete "–(CR$^2$R$^3$)–" and replace with -- –(CR$^2$R$^3$)$_n$– --

Claim 1; Column 295; Line 45: delete "–(CR$^9$R$^{10}$)$_v$NR$^6$R$^7$" and replace with -- –(CR$^9$R$^{10}$)$_v$NR$^6$R$^7$;--

Claim 1; Column 295; Line 60: delete "heterocycle" and replace with --heterocyclyl--

Claim 1; Column 295; Lines 62-63: delete "heterocyclealkyl" and replace with --heterocyclylalkyl--

Claim 10; Column 297; Lines 54-58: delete " 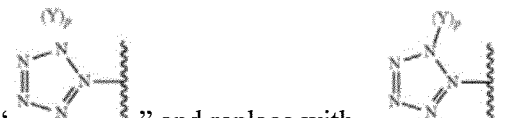 " and replace with --  --

Claim 14; Column 302; Lines 33-39: delete " 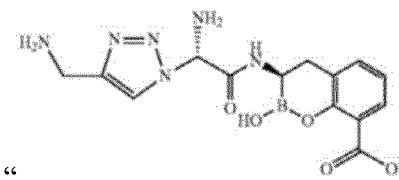 " and replace with 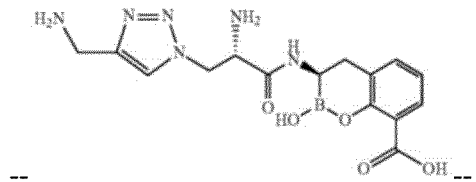 --

Signed and Sealed this
Twenty-ninth Day of October, 2019

Andrei Iancu
*Director of the United States Patent and Trademark Office*